United States Patent
Breuer et al.

(10) Patent No.: US 10,717,973 B2
(45) Date of Patent: Jul. 21, 2020

(54) METHOD FOR THE BIOCATALYTIC CYCLIZATION OF TERPENES AND CYCLASE MUTANTS EMPLOYABLE THEREIN

(71) Applicant: BASF SE, Ludwigshafen (DE)

(72) Inventors: Michael Breuer, Darmstadt (DE); Bernhard Hauer, Fußgönheim (DE); Dieter Jendrossek, Tübingen (DE); Gabriele Siedenburg, Stuttgart (DE); Juergen Pleiss, Asperg (DE); Demet Sirim, Stuttgart (DE); Silvia Fadenrecht, Stuttgart (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/212,287

(22) Filed: Dec. 6, 2018

(65) Prior Publication Data

US 2019/0119665 A1    Apr. 25, 2019

Related U.S. Application Data

(62) Division of application No. 15/234,529, filed on Aug. 11, 2016, now Pat. No. 10,190,112, which is a division of application No. 14/560,263, filed on Dec. 4, 2014, now Pat. No. 9,447,404, which is a division of application No. 13/297,798, filed on Nov. 16, 2011, now Pat. No. 8,932,839.

(60) Provisional application No. 61/540,028, filed on Sep. 28, 2011, provisional application No. 61/499,228, filed on Jun. 21, 2011, provisional application No. 61/414,434, filed on Nov. 17, 2010.

(51) Int. Cl.
| | |
|---|---|
| *C12P 7/22* | (2006.01) |
| *C12P 7/02* | (2006.01) |
| *C12N 9/88* | (2006.01) |
| *C12N 9/90* | (2006.01) |
| *C12P 5/00* | (2006.01) |

(52) U.S. Cl.
CPC ............... *C12N 9/88* (2013.01); *C12N 9/90* (2013.01); *C12P 5/007* (2013.01); *C12P 7/02* (2013.01); *C12P 7/22* (2013.01); *C12Y 406/01* (2013.01); *C12Y 504/99017* (2013.01); *Y02P 20/52* (2015.11)

(58) Field of Classification Search
CPC ... C12N 9/88; C12N 9/90; C12P 5/007; C12P 7/22; C12Y 504/9901; C12Y 406/01; Y02P 20/52

USPC ............ 435/233, 252, 254.2, 320.1
See application file for complete search history.

(56) References Cited

U.S. PATENT DOCUMENTS

| | | |
|---|---|---|
| 8,759,043 B2 | 6/2014 | Breuer et al. |
| 8,932,839 B2 | 1/2015 | Breuer et al. |
| 9,447,404 B2 | 9/2016 | Breuer et al. |
| 2016/0340666 A1 | 11/2016 | Breuer et al. |

FOREIGN PATENT DOCUMENTS

WO    WO-2010139719 A2    12/2010

OTHER PUBLICATIONS

"Nomenclature Committee of the International Union of Biochemistry and Molecular Biology (NC-IUBMB)", Eur. J. Biochem., 1999, vol. 264, pp. 610-650.
Daum et al., "Genes and Enzymes Involved in Bacterial Isoprenoid Biosynthesis", Current Opinion in Chemical Biology, 2009, vol. 13, pp. 180-188.
Devos et al., "Practical Limits of Function Prediction," Proteins: Structure, Function and Genetics, vol. 41, (2000), pp. 98-107.
Kisselev, L., "Polypeptide Release Factors in Prokaryotes and Eukaryotes: Same Function, Different Structure," Structure, 2002, vol. 10, pp. 8-9.
Neumann et al, "Purification, Partial Characterization and Substrate Specificity of a Squalene Cyclase from *Bacillus acidocaldarius*," Biol Chem., 1986, vol. 367, pp. 723-729.
Seo et al., "The Genome Sequence of the Ethanologenic Bacterium *Zymomonas mobilis* ZM4" Nature Biotechnology, 2005, vol. 23, No. 1, pp. 63-68.
Whisstock et al., "Prediction of Protein Function From Protein Sequence and Structure," Quarterly Reviews of Biophysics, 2003, vol. 36, No. 3, pp. 307-340.
Witkowski, et al., ., "Conversion of a β-Ketoacyl Synthase to a Malonyl Decarboxylase by Replacement of the Active-Site Cysteine with Glutamine," Biochemistry, 1999, vol. 38, pp. 11643-11650.

*Primary Examiner* — Robert B Mondesi
*Assistant Examiner* — Mohammad Y Meah
(74) *Attorney, Agent, or Firm* — Faegre Drinker Biddle & Reath LLP

(57) ABSTRACT

The present invention relates to novel mutants with cyclase activity and use thereof in a method for biocatalytic cyclization of terpenes, such as in particular for the production of isopulegol by cyclization of citronellal; a method for the preparation of menthol and methods for the biocatalytic conversion of further compounds with structural motifs similar to terpene.

12 Claims, 4 Drawing Sheets
Specification includes a Sequence Listing.

```
  1 MGIDRMNSLS RLLMKKIFGA EKTSYKPASD TIIGTDTLKR PNRRPEPTAK
 51 VDKTIFKTMG NSLNNTLVSA CDWLIGQQKP DGHWVGAVES NASMEAEWCL
101 ALWFLGLEDH PLRPRLGNAL LEMQREDGSW GVYFGAGNGD INATVEAYAA
151 LRSLGYSADN PVLKKAAAWI AEKGGLKNIR VFTRYWLALI GEWPWEKTPN
201 LPPEIIWFPD NFVFSIYNFA QWARATMVPI AILSARRPSR PLRPQDRLDE
251 LFPEGRARFD YELPKKEGID LWSQFFRTTD RGLHWVQSNL LKRNSLREAA
301 IRHVLEWIIR HQDADGGWGG IQPPWVYGLM ALHGEGYQLY HPVMAKALSA
351 LDDPGWRHDR GESSWIQATN SPVWDTMLAL MALKDAKAED RFTPEMDKAA
401 DWLLARQVKV KGDWSIKLPD VEPGGWAFEY ANDRYPDTDD TAVALIALSS
451 YRDKEEWQKK GVEDAITRGV NWLIAMQSEC GGWGAFDKDN NRSILSKIPF
501 CDFGESIDPP SVDVTAHVLE AFGTLGLSRD MPVIQKAIDY VRSEQEAEGA
551 WFGRWGVNYI YGTGAVLPAL AAIGEDMTQP YITKACDWLV AHQQEDGGWG
601 ESCSSYMEID SIGKGPTTPS QTAWALMGLI AANRPEDYEA IAKGCHYLID
651 RQEQDGSWKE EEFTGTGFPG YGVGQTIKLD DPALSKRLLQ GAELSRAFML
701 RYDFYRQFFP IMALSRAERL IDLNN
```

Fig. 1a

```
   1 atgggtattg acagaatgaa tagcttaagt cgcttgttaa tgaagaagat
  51 tttcggggct gaaaaaacct cgtataaacc ggcttcgat accataatcg
 101 gaacggatac cctgaaaaga ccgaaccggc ggcctgaacc gacggcaaaa
 151 gtcgacaaaa cgatattcaa gactatgggg aatagtctga ataataccct
 201 tgtttcagcc tgtgactggt tgatcggaca acaaaagccc gatggtcatt
 251 gggtcggtgc cgtggaatcc aatgcttcga tggaagcaga atggtgtctg
 301 gccttgtggt ttttgggtct ggaagatcat ccgcttcgtc caagattggg
 351 caatgctctt ttggaaatgc agcgggaaga tggctcttgg ggagtctatt
 401 tcggcgctgg aaatggcgat atcaatgcca cggttgaagc ctatgcggcc
 451 ttgcggtctt ggggtattc tgccgataat cctgttttga aaaagcggc
 501 agcatggatt gctgaaaaag gcggattaaa aaatatccgt gtctttaccc
 551 gttattggct ggcgttgatc ggggaatggc cttgggaaaa gacccctaac
 601 cttccccctg aaattatctg gttccctgat aattttgtct tttcgattta
 651 taattttgcc aatgggcgc gggcaaccat ggtgccgatt gctattctgt
 701 ccgcgagacg accaagccgc ccgctgcgcc ctcaagaccg attggatgaa
 751 ctgtttccag aaggccgcgc tcgctttgat tatgaattgc cgaaaaaaga
 801 aggcatcgat ctttggtcgc aattttccg aaccactgac cgtggattac
 851 attgggttca gtccaatctg ttaaagcgca atagcttgcg tgaagccgct
 901 atccgtcatg ttttggaatg gattatccgg catcaggatg ccgatggcgg
 951 ttggggtgga attcagccac cttgggtcta tggtttgatg gcgttacatg
1001 gtgaaggcta tcagctttat catccggtga tggccaagc tttgtcggct
1051 ttggatgatc ccggttggcg acatgacaga ggcgagtctt cttggataca
1101 ggccaccaat agtccggtat gggatacaat gttggccttg atggcgttaa
1151 aagacgccaa ggccgaggat cgttttacgc cggaaatgga taaggccgcc
1201 gattggcttt tggctcgaca ggtcaaagtc aaaggcgatt ggtcaatcaa
1251 actgcccgat gttgaaccg gtggatgggc attgaatat gccaatgatc
1301 gctatcccga taccgatgat accgccgtcg cttgatcgc cctttcctct
1351 tatcgtgata aggaggagtg gcaaaagaaa ggcgttgagg acgccattac
1401 ccgtggggtt aattggttga tcgccatgca aagcgaatgt ggcggttggg
1451 gagcctttga taaggataat aacagaagta tccttccaa aattcctttt
1501 tgtgatttcg gagaatctat tgatccgcct tcagtcgatg taacggcgca
1551 tgtttagag gccttttgga ccttgggact gtcccgcgat atgccggtca
1601 tccaaaaagc gatcgactat gtccgttccg aacaggaagc cgaaggcgcg
1651 tggtttggtc gttggggcgt taattatatc tatggcaccg gtgcggttct
1701 gcctgctttg cggcgatcg gtgaagatat gacccagcct acatcacca
1751 aggcttgcga ttggctggtc gcacatcagc aggaagacgg cggttggggc
1801 gaaagctgct cttcctatat ggagattgat tccattggga agggcccaac
1851 cacgccgtcc cagactgctt gggctttgat ggggttgatc gcggccaatc
1901 gtcccgaaga ttatgaagcc attgccaagg gatgccatta tctgattgat
1951 cgccaagagc aggatggtag ctggaaagaa gaagaattca ccggcaccgg
2001 attccccggt tatggcgtgg tcagacgat caagttggat gatccggctt
2051 tatcgaaacg attgcttcaa ggcgctgaac tgtcacgggc gtttatgctg
2101 cgttatgatt tttatcggca attcttcccg attatggcgt taagtcgggc
2151 agagagactg attgatttga ataattga
```

Fig. 1b

METHOD FOR THE BIOCATALYTIC CYCLIZATION OF TERPENES AND CYCLASE MUTANTS EMPLOYABLE THEREIN

RELATED APPLICATIONS

This application is a divisional of U.S. application Ser. No. 15/234,529, filed Aug. 11, 2016, now U.S. Pat. No. 10,190,112, which is a divisional of U.S. application Ser. No. 14/560,263, filed Dec. 4, 2014, now U.S. Pat. No. 9,447,404, which is a divisional of U.S. application Ser. No. 13/297,798, filed Nov. 16, 2011, now U.S. Pat. No. 8,932,839, which claims the benefit under 35 U.S.C. § 119(e) of U.S. Provisional Application No. 61/414,434, filed Nov. 17, 2010, U.S. Provisional Application No. 61/499,228, filed Jun. 21, 2011, and U.S. Provisional Application No. 61/540,028, filed Sep. 28, 2011. The entire content of each aforementioned application is hereby incorporated by reference in its entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 074012_0194_03_583523_ST25. The size of the text file is 1,590 KB, and the text file was created on Nov. 9, 2018.

BRIEF DESCRIPTION OF THE INVENTION

The present invention relates to novel methods for cyclizing terpenes using cyclases and to novel mutants with cyclase activity and use thereof in a method for biocatalytic cyclization of terpenes, such as in particular for the production of isopulegol by cyclization of citronellal; a method for the preparation of menthol and methods for the biocatalytic conversion of further compounds with structural motifs similar to terpene.

BACKGROUND OF THE INVENTION

Isopulegol of formula (II) (2-isopropenyl-5-methyl-cyclohexanol) is a terpene that is used as an aroma compound, to generate "flower notes". Moreover, it is an intermediate in the synthesis of menthol from citral.

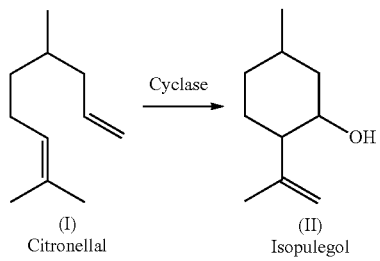

(I) Citronellal        (II) Isopulegol

Isopulegol isomers occur in nature in a large number of essential oils. As isopulegol is formed relatively easily from citronellal, the compound of formula (I) (3,7-dimethyloct-6-en-1-al), it often occurs accompanying citronellal or is formed during extraction of the essential oil. Isopulegol, which is produced industrially from (+)-citronellal, is as a rule a mixture of different isomers with a high proportion of (−)-isopulegol.

The industrial production of isopulegol is mainly carried out by the chemical cyclization of (+)-citronellal. Originally 80-85% pure raw material obtained from citronella oil was used. Since the 1990s this has increasingly been replaced with the optically purer (+)-citronellal (97.5%) from the so-called Takasago process. Here, geranyldiethyldiamine is isomerized asymmetrically to (+)-citronellal using an Rh-BINAP-complex catalyst (Rh-complex with 2,2'-bis(diphenylphosphino)-1,1'-binaphthyl). The chemical synthesis of isopulegol starting from citronellal has been described many times. (+)-Citronellal can be cyclized using a copper-chromium catalyst, zinc bromide, alkylaluminum chloride, a rhodium complex, a solid acid-base catalyst, zeolite or silica gel. In recent times the silica gel method has increasingly been superseded by the method with zinc bromide, as the latter has higher selectivity.

The cyclization of terpenes with the aid of special cyclases is generally known. For example, in nature squalene is cyclized by a squalene-hopene cyclase (SHC) to the pentacyclic hopene.

The gene and protein sequences of squalene-hopene cyclase derived from the bacterium *Zymomonas mobilis* (Zm-SHC) are known (Genpept Accession No AAV90172 2004 and Nat Biotechnol 2005, 23:63-68, cf. SEQ ID NO: 1 and 2).

In international application PCT/EP2010/057696 (WO2010139719 A2), to the complete disclosure of which reference is expressly made herein, polypeptides are proposed as biocatalysts for the cyclization of homofarnesol to ambroxan.

The biosynthesis of numerous monoterpenes in the corresponding production organisms has already been elucidated. Frequently this involves cyclization of linear precursor molecules by highly specific biocatalysts. The precursors are generally esters of linear terpene alcohols and diphosphoric acid. One typical example of such a precursor is geranyl pyrophosphate. The pyrophosphate group is eliminated from the molecule enzymatically, and is subsequently hydrolyzed into two phosphate ions.

On the other side, a carbocation is formed, which is then able to undergo further intramolecular reaction and which recombines to form a cyclic monoterpene, with elimination of a proton, for example (Curr. Opin. Chem. Biol. 2009, 13: 180-188).

A problem to be solved by the present invention, furthermore, was to find an alternative to the known chemical cyclization methods for terpenes, allowing terpene compounds to be cyclized by means of enzymatic catalysis, such as the linear citronellal to be cyclized to isopulegol, for example. The problem to be solved by the present invention was furthermore to provide novel biocatalysts that can be used for the cyclization of terpenes, for example of citronellal with formation of isopulegol.

SUMMARY OF THE INVENTION

The above first problem is solved by a method of production of isopulegol of general formula (I)

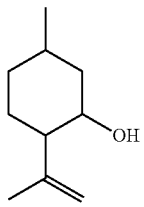

(I)

comprising one reaction step,
wherein citronellal of general formula (II)

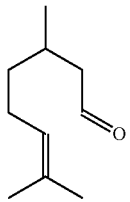

(II)

is cyclized biocatalytically to the corresponding isopulegol of formula (I) by means of an enzyme having the activity of citronellal-isopulegol cyclase.

The above second problem could, surprisingly, be solved by providing mutants of wild-type enzymes, such as Zm-SHC-1 (SEQ ID NO:2). In particular it was in fact found that through targeted introduction of mutations in at least one highly conserved sequence position in said cyclases, in particular squalene-hopene cyclases (cf. alignment of SEQ ID NOs. 2 to 326, below) the enzymatic activity can be influenced in the desired manner.

DESCRIPTION OF THE FIGURES

FIG. 1a shows the wild-type amino acid sequence (SEQ ID NO: 2) of squalene-hopene cyclase 1 from *Zymomonas mobilis* (Zm-SHC-1). Position 486 of saturation mutagenesis is marked.

FIG. 1b shows the wild-type nucleic acid sequence (SEQ ID NO: 1) of Zm-SHC-1. Positions 1456-1458 of saturation mutagenesis are marked.

DETAILED DESCRIPTION OF THE INVENTION

A. General Definitions

Figure 2:
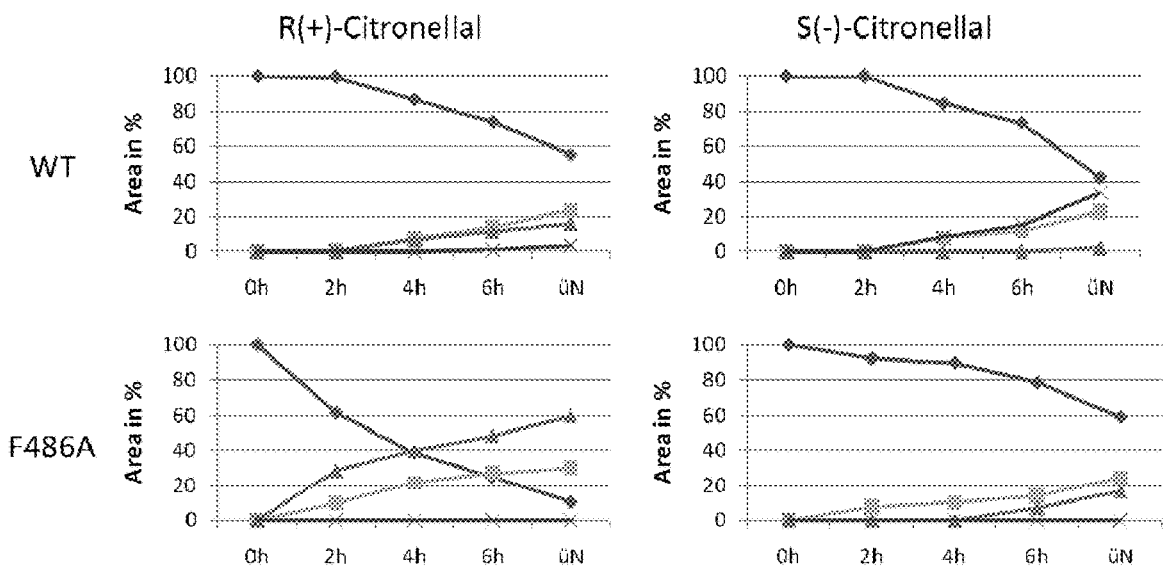
FIG. 2 shows the turnover of the SHC_1 WT protein compared with the F486A mutant as a function of time with 10 mM R(+)- and S(−)-citronellal as substrate. The percentage distribution of substrate and isopulegol product isomers after incubation for various times at 30° C. is shown in each case. Citronellal (diamonds), isopulegol I (squares), isopulegol II (triangles) and isopulegol III (crosses).

"Cyclases" in the sense of the present invention are generally enzymes or enzyme mutants, which in particular display the activity of a citronellal-isopulegol cyclase. Intramolecular transferases from the isomerase subclass are suitable as enzymes with the activity of a citronellal-isopulegol cyclase; i.e. proteins with the EC number EC 5.4. (Enzyme code according to Eur. J. Biochem. 1999, 264, 610-650). In particular they are representatives of EC 5.4.99.17. Suitable enzymes with the activity of a citronellal-isopulegol cyclase are in particular those cyclases that also bring about the cyclization of homofarnesol to ambroxan or of squalene to hopene (hence sometimes also designated "SHC": squalene hopene cyclase) and which are described in detail in international application PCT/EP2010/057696, to which reference is expressly made here. In particular, cyclases according to the invention are those that are derived by mutation of SHCs.

On the basis of the reversibility of enzymatic reactions, the present invention relates to the enzymatic reactions described herein in both directions of reaction.

"Functional mutants" of a "cyclase" include the "functional equivalents" of such enzymes defined below.

The term "biocatalytic process" refers to any process carried out in the presence of catalytic activity of a "cyclase" according to the invention or of an enzyme with "cyclase activity", i.e. processes in the presence of raw, or purified, dissolved, dispersed or immobilized enzyme, or in the presence of whole microbial cells, which have or express such enzyme activity. Biocatalytic processes therefore include both enzymatic and microbial processes.

The term "stereospecific" means that one of several possible stereoisomers of a compound produced according to the invention is produced with at least one asymmetry center by the action of an enzyme according to the invention in high "enantiomeric excess" or high "enantiomeric purity", for example at least 90% ee, in particular at least 95% ee, or at least 98% ee, or at least 99% ee. The ee % value is calculated from the following formula:

$$ee \% = [X_A - X_B]/[X_A + X_B] * 100,$$

in which $X_A$ and $X_B$ stand for the mole fraction of enantiomers A and B respectively.

"First sphere residues" and "second sphere residues" are amino acid residues which, based on structural analyses of the protein, are assigned a special proximity to the reactive center of the cyclase. The criterion for the first sphere is the distance from the ligand 2-azasqualene, which is given in a published x-ray structure (pdb: lump). These residues were determined automatically with a computer program (ligin-.weizmann.ac.il/cgi-bin/lpccsu/LpcCsu.cgi; Sobolev V, Sorokine A, Prilusky J, Abola E E, Edelman M. Automated analysis of interatomic contacts in proteins. Bioinformatics 1999; 15(4):327-332.). This program assumes that two molecules are in contact with each other when the distance between their atoms corresponds to the sum of their van der Waals radii±1 Å. The second sphere includes all amino acids that are located in a radius of 5 Å to each residue of the first sphere. Such residues therefore appear to be especially suitable for undertaking directed mutation, for further targeted modification of the enzyme activity.

"Cyclase activity", determined with a "reference substrate under standard conditions", is e.g. an enzyme activity that describes the formation of a cyclic product from a noncyclic substrate. Standard conditions are e.g. substrate concentrations from 10 mM to 0.2 M, in particular 15 to 100 mM, for example about 20 to 25 mM; at pH 4 to 8, and at temperatures of e.g. 15 to 30 or 20 to 25° C. It can be determined with recombinant cyclase-expressing cells, lysed cyclase-expressing cells, fractions thereof or enriched or purified cyclase enzyme. In particular the reference substrate is a citronellal of formula (II); in particular R(+)-citronellal, or a citronellal racemate, in a concentration from 15 to 100 mM or about 20 to 25 mM, at 20 to 25° C. and pH 4-6, such as 4.5; as is also described in more detail in the examples.

An "F486-analog" position corresponds to position F486 according to SEQ ID NO:2 from the functional standpoint and can be determined by sequence alignment of SHCs from organisms other than *Zymomonas mobilis* as explained herein. For example the F486-analog position of SEQ ID NO:3 is position F449 and of SEQ ID NO:4 position F481 and of SEQ ID NO:5 position F447 and of SEQ ID NO:6 position F438. Corresponding analogies apply to the other sequence positions described concretely for SEQ ID NO: 2 herein, such as the so-called "first sphere residues" and "second sphere residues" or of the DXDD motif and their analogous positions in SEQ ID NO:3 to 326).

"Terpenes" are hydrocarbons that are made up of isoprene units (C5 units), in particular noncyclic terpenes, for example squalene, the carbon number of which is divisible by 5.

"Terpenoids" are substances that are derived from terpenes, in particular noncyclic terpenes, e.g. by additional insertion of carbon atoms and/or heteroatoms, for example citronellal.

"Terpene-like" compounds for the purposes of the present invention comprise in particular those compounds which fall within the general structural formula (IV) as defined below.

Generally encompassed in accordance with the invention are all isomeric forms of the compounds described herein, such as constitutional isomers and more particularly stereoisomers and mixtures thereof, such as optical isomers or geometric isomers, such as E- and Z-isomers, and also combinations thereof. Where there are two or more centers of asymmetry in a molecule, the invention encompasses all combinations of different conformations of these centers of asymmetry, such as pairs of enantiomers, for example.

"Menthol" encompasses all stereoisomeric forms such as (+)-menthol, (+)-isomenthol, (+)-neomenthol, (+)-neoisomentol, (−)-menthol, (−)-isomenthol, (−)-neomenthol, (−)-neoisomenthol and any desired mixtures thereof.

Citronellal of formula (II) is commercially available both as R(+)-citronellal of formula (R-Ill) and as S(−)-citronellal of formula (S-Ill) and as racemate of formula (II).

(R-II)

(S-II)

Isopulegol of Formula (I)

(I)

has in positions 1, 3 and 6 in each case an optically active center, so that in principle 4 different diastereomers with in each case 2 enantiomers, thus altogether 8 stereoisomers, are conceivable, starting from the racemate of citronellal of formula (I).

1R, 3R, 6S     1S, 3S, 6R

Isopulegol 1S, 3R, 6S     1R, 3S, 6R

Neo-Isopulegol

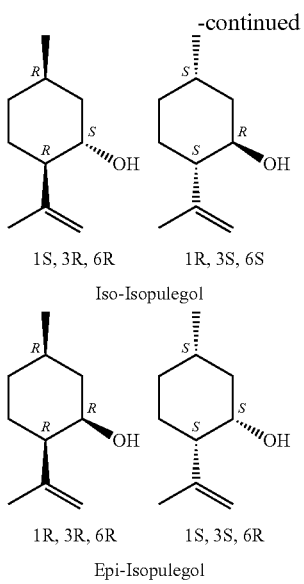

1S, 3R, 6R     1R, 3S, 6S

Iso-Isopulegol 1R, 3R, 6R     1S, 3S, 6R

Epi-Isopulegol

Isopulegol is also called isopulegol I, neo-isopulegol is also called isopulegol II; iso-isopulegol is also called isopulegol III; epi-isopulegol or neo-iso-isopulegol is also called isopulegol IV.

Unless indicated otherwise, the general chemical definitions that apply herein are as follows: Alkyl and also all alkyl moieties in radicals derived therefrom, such as hydroxyalkyl, for example: saturated, straight-chain or branched hydrocarbon radicals having 1 to 4, 1 to 6, 1 to 8 or 1 to 10 carbon atoms, e.g.

$C_1$-$C_6$-alkyl: such as methyl, ethyl, propyl, 1-methylethyl, butyl, 1-methylpropyl, 2-methylpropyl and 1,1-dimethylethyl as exemplary representatives of $C_1$-$C_4$-alkyl; and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Hydroxy-$C_1$-$C_6$-alkyl, comprising hydroxy-$C_1$-$C_4$-alkyl, such as e.g. hydroxymethyl, 1- or 2-hydroxyethyl, 1-, 2- or 3-hydroxypropyl, 1-hydroxymethylethyl, 1-, 2-, 3- or 4-hydroxybutyl, 1-hydroxymethylpropyl and 2-hydroxymethylpropyl.

Alkenyl stands for mono- or polyunsaturated, more particularly monounsaturated, straight-chain or branched hydrocarbon radicals having 2 to 4, 2 to 6, 2 to 8, 2 to 10 or 2 to 20 carbon atoms and one double bond in any desired position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Oxo", for example, is a radical which together with the C atom to which it is bonded forms a keto group (C=O).

"Methylene" (=$CH_2$), for example, is a radical which together with the C atom to which it is bonded forms a vinyl radical (—CH=$CH_2$).

B. Special Embodiments of the Invention

The present invention relates in particular to the following special embodiments:

1. Enzyme mutant with cyclase activity, selected from mutants of a wild-type enzyme, which comprises an amino acid sequence, selected from SEQ ID NO: 2 to 326 or a partial sequence thereof; wherein the mutant catalyzes at least the cyclization of at least one citronellal isomer (or a mixture of isomers, for example racemate) according to the above definition to at least one isopulegol isomer (or to a pair of diastereomers I to IV, for example I and/or II) according to the above definition, wherein the partial sequence or short form of the cyclase comprises e.g. at least 50, 100, 150, 200, 250, 300, 350, 400, 450, 500, 550, 600, 650 or 700 continuous amino acid residues of one of these sequences, and is accessible e.g. by N- and/or C-terminal shortening of the concrete sequences.

2. Enzyme mutant according to embodiment 1, comprising
   a) a mutation in position F486 of SEQ ID NO: 2 or
   b) a mutation in a sequence selected from SEQ ID NO: 3 to 326, wherein the mutated position corresponds to position F486 of SEQ ID NO: 2 (i.e. is an "F486-analog" position);
   wherein at least the cyclization of at least one citronellal isomer to at least one isopulegol isomer is made possible by the mutation (i.e. the corresponding original or wild-type protein did not catalyze this reaction) or is modified (i.e. the corresponding original or wild-type protein catalyzed this reaction, but e.g. at lower product yield, turnover rate and/or stereospecificity). Moreover, the partial sequence or short form of the cyclase also has this cyclase-typical mutation in a position corresponding to F486 from SEQ ID NO: 2. For example, an N-terminally shortened version of the cyclase according to SEQ ID NO: 2 is an example of said short version. This is characterized by the following N-terminus: (M)KIFGAEKTSYKPASDTIIGTDTLKRPN . . . wherein the N-terminal K corresponds to position 16 of SEQ ID NO:2.

3. Enzyme mutant according to one of the preceding embodiments in which up to 25% or up to 20, 15, 10, 9, 8, 7, 6, 5, 4, 3, 2 or 1% of the amino acid residues, for example 1 to 30, 2 to 25, 3 to 20 or 4 to 15 or 5 to 10 of the amino acid residues, are in each case altered relative to the unmutated wild-type sequence according to SEQ ID NO: 2 to 326, by deletion, insertion, substitution, addition, inversion or a combination thereof.

4. Enzyme mutant according to one of the preceding embodiments, in which the mutation in position F486 of SEQ ID NO:2 or in a position corresponding to this position in one of the sequences according to SEQ ID NO: 3 to 326, is a substitution selected from F486N, F486Q, F486L, F486M, F486E, F486G, F486S, F486V, F486T, F486C, F486I and F486A or optionally selected from F486H, F486Y, F486W and F486D.

5. Enzyme mutant according to one of the preceding embodiments, in which additionally (or alternatively, but in particular additionally) at least one, for example 1, 2, 3, 4, 5, 6, 7, or 8, mutations in one of the positions W374, D437, D440, F428, W555, Y561, Y702, Y705 (the so-called "first sphere residues") of SEQ ID NO: 2 or in at least one corresponding position selected from these positions, is present in one of the sequences according to SEQ ID NO: 3 to 326.

6. Enzyme mutant according to one of the preceding embodiments, in which there is no mutation in position D437 and/or D439 and/or D440 of SEQ ID NO: 2 (DXDD motif) or the respective corresponding position in one of the sequences according to SEQ ID NO: 3 to 326.

7. Enzyme mutant according to one of the preceding embodiments, in which there is no mutation in position Y702 of SEQ ID NO: 2 or in the corresponding position in one of the sequences according to SEQ ID NO: 3 to 326, or if a mutation is present, this is a substitution Y702F or optionally Y702E or Y702D or corresponding substitution.

8. Enzyme mutant according to one of the preceding embodiments, which optionally is further mutated in at least one, for example 1 to 15, 1 to 10 or 1 to 5, such as 1, 2, 3 or 4, of positions P229, D439, D508, E601, G553, G556, N432, P436, P499, R224, S371, T376, T563, W414 or W624 (the so-called "second sphere residues") of SEQ ID NO: 2 or in at least one corresponding position selected from these positions, in one of the sequences according to SEQ ID NO: 3 to 326; and optionally a further mutation in position E429, L700 and R554 of SEQ ID NO: 2 or the analogous positions of SEQ ID NO: 3 to 326.

9. Enzyme mutant according to one of the preceding embodiments, selected from
   a) the single mutants
      F486X with X=N, Q, L, M, E, G, S, V, T, C, I or A according to SEQ ID NO: 2 or a short version thereof;
      Y702X with X=F, A, C or S according to SEQ ID NO: 2 or a short version thereof;
      Y561X with X=A or S according to SEQ ID NO: 2 or a short version thereof;
      wherein the short version comprises e.g. the following N-terminal sequence: (M)KIFGAEKTSYKPAS-DTIIGTDTLKRPN . . .
   b) the multiple mutants F486A/Y702A, F486A/Y561A or F486A/Y705A according to SEQ ID NO: 2
   c) the mutants corresponding to a) or b), derived from one of SEQ ID NO: 3 to 325.

10. Enzyme mutant according to one of the preceding embodiments, which comprises at least 50%, for example 50 to 100% or more than 100%, for example >100 to 1000%, in each case determined under standard conditions using a reference substrate that displays citronellal-isopulegol cyclase activity of an enzyme, which has an amino acid sequence according to SEQ ID NO: 2 from position 1 to 725, 2 to 725 or 16 to 725, optionally extended N-terminally with a methionine residue.

11. Enzyme mutant according to embodiment 10, wherein the citronellal-isopulegol cyclase activity is determined under standard conditions using a citronellal, for example the racemate or the R(+) form, as reference substrate.

12. Enzyme mutant according to one of the preceding embodiments, wherein the mutation takes place in an enzyme, and comprises an amino acid sequence according to SEQ ID NO: 2 from position 1 to 725, 2 to 725 or 16 to 725, optionally extended N-terminally with a methionine residue.

13. Nucleic acid sequence coding for a mutant according to one of the preceding embodiments.

14. Expression cassette, comprising a nucleic acid sequence according to embodiment 13.

15. Recombinant vector, comprising, under the control of at least one regulatory element, at least one nucleic acid sequence according to embodiment 13 or at least one expression cassette according to embodiment 14.

16. Recombinant microorganism, comprising at least one nucleic acid sequence according to embodiment 13 or at least one expression cassette according to embodiment 14 or at least one vector according to embodiment 15.

17. Biocatalytic process for producing isopulegol of general formula (I)

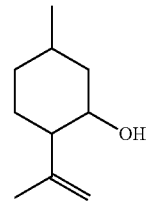

(I)

wherein citronellal of general formula (II)

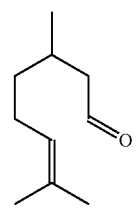

(II)

is cyclized to isopulegol of formula (I) by means of an enzyme of EC class EC 5.4.99, in particular of EC class EC 5.4.99.17, or in the presence of a microorganism expressing this enzyme.

18. Biocatalytic process for producing isopulegol of general formula (I)

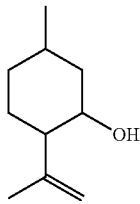

wherein citronellal of general formula (II)

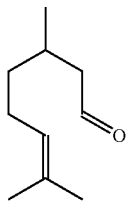

is cyclized to isopulegol of formula (I) by means of an enzyme mutant according to one of embodiments 1 to 12, or in the presence of a microorganism expressing this enzyme mutant according to embodiment 16.

19. A method of production of menthol of formula III

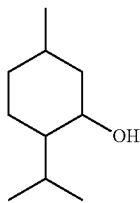

by
a) cyclizing citronellal to isopulegol by a method according to embodiment 17 or 18, and
b) catalytically hydrogenating isopulegol to menthol.

20. The method according to embodiment 19, where the hydrogenation takes place in the presence of hydrogen and a catalyst comprising
   30% to 70% by weight of oxygen-containing compounds of nickel, calculated as NiO,
   15% to 45% by weight of oxygen-containing compounds of zirconium, calculated as $ZrO_2$,
   5% to 30% by weight of oxygen-containing compounds of copper, calculated as CuO, and
   0.1% to 10% by weight of oxygen-containing compounds of molybdenum, calculated as $MoO_3$,
   the % by weight figures being based on the dry, unreduced catalyst.

21. A method for enzymatic or biocatalytic conversions of compounds of general formula IV

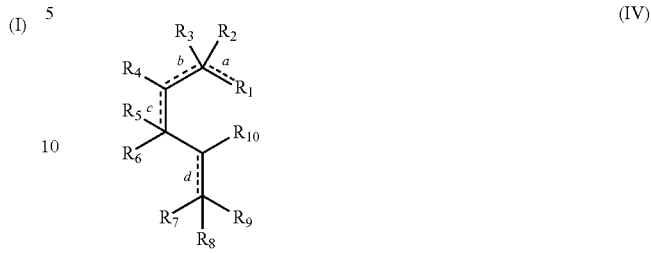

in which
"a", "b", "c" and "d", in each case independently of one another, represent a single or double C—C bond, with the proviso that cumulative double bonds are excluded; and with the following provisos:
$R_1$ possesses the following definitions:
   (1) when "a" is a double bond:
      $R_1$ is selected from
         oxo (=O), or
         CH—$(CH_2)_n$—Z,
            in which n is 0, 1 or 2 and
            Z is OH, CHO, C(O)alkyl, such as $C(O)C_1$-$C_4$-alkyl, in particular C(O)—$CH_3$ or C(O)—$CH_2CH_3$; COOH, $C(CH_2)$—CH=$CH_2$; $C(OH)(CH_3)$—CH=$CH_2$; $C(CH_3)$=CH—CH=$CH_2$; or a radical of the formula $C(CH_3)$=CH—$CH_2$Y
            in which
            Y is OH, $CH_2OH$, COOH, or $CH_2C(O)CH_3$; or
   (2) when "a" is a single bond:
      $R_1$ is selected from
         $CH_3$; CHO; $CH_2CH_2OH$; CH=$CH_2$; $CH_2C(O)OH$; $CH_2CHO$ or $C_3H_6CH(CH_3)CHO$;
   wherein, when "a" is a double bond, it has E or Z configuration;
$R_2$ and $R_3$ possess the following definitions:
   (1) when "a" and "b" are each a single bond:
      $R_2$ and $R_3$ independently of one another are H, alkyl, such as $C_1$-$C_4$-alkyl or OH, or
      $R_2$ and $R_3$ together are a methylene (=$CH_2$) or oxo (=O) group; or
   (2) when "a" or "b" is a double bond, one of the radicals $R_2$ and $R_3$ is absent and the other of the two radicals is H, $C_1$-$C_4$-alkyl, in particular methyl, or OH;
$R_4$ is H or hydroxy-$C_1$-$C_4$-alkyl, in particular Hydroxymethyl;
$R_5$ and $R_6$ possess the following definitions:
   (1) when "c" is a single bond:
      $R_5$ and $R_6$ are each H, or $R_5$ and $R_6$ together are an oxo (=O) group; or
   (2) when "c" is a double bond, one of the radicals $R_5$ and $R_6$ is absent and the other of the two radicals is H;
$R_7$, $R_8$ and $R_9$ possess the following definitions:
   (1) when "d" is a single bond:
      two of the radicals $R_7$, $R_8$ and $R_9$ in each case independently of one another are H or alkyl, such as $C_1$-$C_4$-alkyl, in particular methyl or ethyl, and the other of the radicals is OH; or
   (2) when "d" is a double bond, one of the radicals $R_7$, $R_8$ and $R_9$ is absent and the other of the two radicals in each case independently of one another are H or alkyl, such as $C_1$-$C_4$-alkyl, in particular methyl or ethyl;

$R_{10}$ is H or hydroxy-$C_1$-$C_6$-alkyl, such as hydroxy-$C_1$-$C_4$-alkyl, or mono- or polyunsaturated $C_2$-$C_6$-alkenyl, such as, in particular, H or CH=CH—C(CH$_3$)=CH$_2$;

where a compound of the formula IV in stereoisomerically pure form, or a stereoisomer mixture thereof, is reacted using an enzyme of class EC 5.4.99, in particular of class EC 5.4.99.17, or an enzyme mutant according to one of embodiments 1 to 12 or in the presence of a microorganism according to embodiment 16 expressing these enzymes or enzyme mutants.

22. The method according to embodiment 21, in which a compound is converted which is selected from compounds of the formula IVa

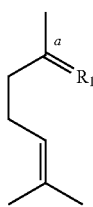
(IVa)

in which $R_1$ possesses the definitions indicated above and in particular is the radical CH—(CH$_2$)$_n$—Z in which
n=0 and Z=CHO, or COOH; or
n=1 and Z=OH; or
n=2 and Z=C(O)CH$_3$; COOH, C(CH$_2$)—CH=CH$_2$; C(CH$_3$)=CH—CH=CH$_2$;
or is a radical of the formula C(CH$_3$)=CH—CH$_2$Y in which Y is OH, CH$_2$OH, COOH, or CH$_2$C(O)CH$_3$;

and "a" optionally has E or Z configuration;
or of the formula IVb

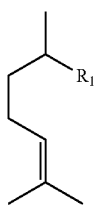
(IVb)

in which $R_1$ possesses the definitions indicated above and in particular is CH$_2$CHO;
or of the formula IVc

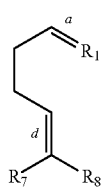
(IVc)

in which
$R_1$ possesses the definitions indicated above, and in particular is CH—CHO; and one of the radicals $R_7$ and $R_8$ is H and the other is $C_1$-$C_4$-alkyl, where in particular $R_7$ is ethyl and the double bonds "a" and "d" have Z configuration.

23. The method according to one of embodiments 20 to 22, in which the compound of the formula IV is selected from citronellal; citral; farnesol; homofarnesol; homofarnesol derivatives, such as homofarnesylic acid; geranylacetone, melonal; nonadienal; and trimethyldecatetraene.

24. Use of an enzyme from EC class EC 5.4.99, in particular from EC class EC 5.4.99.17 for the cyclization of terpenes and/or terpenoids, in particular for the conversion of citronellal to isopulegol.

25. Use of an enzyme mutant according to one of embodiments 1 to 12, a nucleic acid according to embodiment 13, an expression construct according to embodiment 14, a recombinant vector according to embodiment 15 or a recombinant microorganism according to embodiment 1 for the cyclization of terpenes and/or terpenoids, and for the conversion of compounds of the general formula IV according to the definition in one of the embodiments 20 to 23.

25. Use according to embodiment 25 for the conversion of citronellal to isopulegol; or for the conversion of squalene to hopene.

26. A method of production of isopulegol of general formula (I)

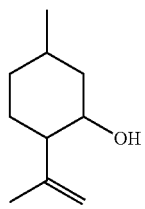
(I)

comprising one reaction step,
wherein citronellal of general formula (II)

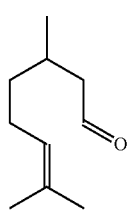
(II)

is cyclized biocatalytically to the corresponding isopulegol of formula (I) by means of an enzyme having the activity of a citronellal-isopulegol cyclase.

27. The method according to embodiment 26, wherein the enzyme possesses a polypeptide sequence which either
a) is SEQ ID NO: 2, or
b) in which up to 25%, such as, for example, up to 20, 15, 10, 9, 8, 7, 6, 5, 4, 3, 2 or 1% of the amino acid residues are altered relative to SEQ ID NO: 2 by deletion, insertion, substitution or a combination thereof, and which still has at least 50%, such as, for example, at least 60, 65, 70, 75, 80, 85, 90 or 95%, of the enzymatic activity of SEQ ID NO: 2.

28. The method according to embodiment 26 or 27, wherein the enzyme is encoded by a nucleic acid sequence according to SEQ ID NO: 1 or a functional equivalent thereof.
29. The method according to one of embodiments 26 to 28, wherein the enzyme is encoded by a nucleic acid sequence according to SEQ ID NO: 1 or a functional equivalent thereof, the nucleic acid sequence being part of a gene construct or vector.
30. The method according to one of embodiments 26 to 29, wherein the enzyme is encoded by a nucleic acid sequence according to SEQ ID NO: 1 or a functional equivalent thereof, the nucleic acid sequence being part of a gene construct or vector which are present in a host cell.
31. The method according to one of embodiments 26 to 30, wherein the enzyme is present in a form selected from the group consisting of:
   a) free, optionally purified or partly purified polypeptide having the activity of a citronellal-isopulegol cyclase;
   b) immobilized polypeptide having the activity of a citronellal-isopulegol cyclase;
   c) polypeptide according to a) or b) which is isolated from cells;
   d) whole cell, optionally resting or digested cells, comprising at least one polypeptide having the activity of a citronellal-isopulegol cyclase;
   e) cell lysate or cell homogenate of the cells described under d).
32. The method according to embodiment 31, wherein the cells are microorganisms, preferably transgenic microorganisms expressing at least one heterologous nucleic acid molecule coding for a polypeptide having the activity of a citronellal-isopulegol cyclase.
33. The method according to one of embodiments 26 to 32, wherein the production of isopulegol takes place in one-phase aqueous systems or in two-phase systems.
34. The method according to one of embodiments 26 to 33, in which the reaction of citronellal to isopulegol takes place at a temperature in the range from 20 to 40° C. and/or at a pH in the range from 4 to 8.
35. The method according to one of embodiments 26 to 34, wherein the enzyme having the activity of a citronellal-isopulegol cyclase is encoded by a gene which has been isolated from a microorganism selected from the group of microorganisms consisting of *Zymomonas mobilis, Methylococcus capsulatus, Rhodopseudomonas palustris, Bradyrhizobium japonicum, Frankia* spec. and *Streptomyces coelicolor*, in particular *Zymomonas mobilis*.
36. The method according to one of embodiments 26 to 35, wherein the enzyme having the activity of a citronellal-isopulegol cyclase has been produced by a microorganism which overproduces the enzyme having the activity of a citronellal-isopulegol cyclase and which has been selected from the group of microorganisms consisting of the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.
37. The method according to one of embodiments 26 to 36, wherein the enzyme having the activity of a citronellal-isopulegol cyclase has been produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis* which overproduce the enzyme having the activity of a citronellal-isopulegol cyclase.
38. Use of an enzyme having the activity of a citronellal-isopulegol cyclase for the biocatalytic conversion of citronellal to isopulegol.
39. Use according to embodiment 38, wherein the enzyme possesses a polypeptide sequence which either
   a) is SEQ ID NO: 2, or
   b) in which up to 25%, such as, for example, up to 20, 15, 10, 9, 8, 7, 6, 5, 4, 3, 2 or 1% of the amino acid residues are altered relative to SEQ ID NO: 2 by deletion, insertion, substitution or a combination thereof, and which still has at least 50%, such as, for example, at least 60, 65, 70, 75, 80, 85, 90 or 95%, of the enzymatic activity of SEQ ID NO: 2.
40. Use according to embodiment 38 or 39, wherein the enzyme is encoded by a nucleic acid sequence according to SEQ ID NO: 1 or a functional equivalent thereof.
41. Use of a gene construct or vector comprising a nucleic acid sequence according to SEQ ID NO: 1 or a functional equivalent thereof, which encode a polypeptide having the activity of a citronellal-isopulegol cyclase, which serves for the biocatalytic conversion of citronellal to isopulegol, in a method of production of isopulegol by cyclization of citronellal.
42. Use of a host cell which comprises a gene construct or a vector comprising a nucleic acid sequence according to SEQ ID NO: 1 or a functional equivalent thereof, for preparing an enzyme having the activity of a citronellal-isopulegol cyclase for the biocatalytic conversion of citronellal to isopulegol.

C. Further Embodiments of the Invention

1. Especially Suitable Wild-Type Sequences

SHC wild-type sequences usable according to the invention, whose SEQ ID NO, source organism, GenBank reference number, the amino acid residue "corresponding" to position F486 of SEQ ID NO:2, i.e. F486-analog ("Aa") and whose sequence position are presented in the following table. The information is based on a sequence alignment, which was set up as follows:

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
| --- | --- | --- | --- | --- | --- |
| s1 | seq_ID 2 | *Zymomonas mobilis* | AAV90172.1 | F | 486 |
| s20 | seq_ID 3 | *Streptomyces coelicolor* | CAB39697.1 | F | 449 |
| s911 | seq_ID 4 | *Acetobacter pasteurianus* | BAH99456.1 | F | 481 |

-continued

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
|---|---|---|---|---|---|
| s2 | seq_ID 5 | *Bradyrhizobium* sp. | ABQ33590.1 | F | 447 |
| s940 | seq_ID 6 | *Zymomonas mobilis* | EER62728.1 | F | 438 |
| s949 | seq_ID 7 | *Acidithiobacillus caldus* | EET25937.1 | Y | 432 |
| s167 | seq_ID 8 | *Acidithiobacillus ferrooxidans* | ACH84004.1 | Y | 429 |
| s41 | seq_ID 9 | *Acidobacterium capsulatum* | ACO34244.1 | F | 458 |
| s36 | seq_ID 10 | *Acidothermus cellulolyticus* | ABK53469.1 | F | 426 |
| s83 | seq_ID 11 | *Adiantum capillus-veneris* | BAF93209.1 | Y | 436 |
| s143 | seq_ID 12 | *Ajellomyces capsulatus* | EDN09769.1 | F | 496 |
| s995 | seq_ID 13 | *Ajellomyces capsulatus* | EER40510.1 | — | 432 |
| s163 | seq_ID 14 | *Ajellomyces capsulatus* | EEH02950.1 | F | 429 |
| s13 | seq_ID 15 | *Alicyclobacillus acidocaldarius* | EED08231.1 | Y | 420 |
| s14 | seq_ID 16 | *Alicyclobacillus acidocaldarius* | P33247.4 | Y | 420 |
| s1193 | seq_ID 17 | *Alicyclobacillus acidocaldarius* | AAT70690.1 | Y | 116 |
| s21 | seq_ID 18 | *Alicyclobacillus acidoterrestris* | CAA61950.1 | Y | 420 |
| s1189 | seq_ID 19 | *Alicyclobacillus acidoterrestris* | AAT70691.1 | Y | 121 |
| s51 | seq_ID 20 | *Anabaena variabilis* | ABA24268.1 | F | 423 |
| s76 | seq_ID 21 | *Anaeromyxobacter* sp. | ABS28257.1 | F | 440 |
| s159 | seq_ID 22 | *Aspergillus clavatus* | EAW07713.1 | F | 446 |
| s131 | seq_ID 23 | *Aspergillus flavus* | EED48353.1 | F | 444 |
| s176 | seq_ID 24 | *Aspergillus fumigatus* | EDP50814.1 | F | 502 |
| s126 | seq_ID 25 | *Aspergillus fumigatus* | EAL84865.1 | F | 449 |
| s178 | seq_ID 26 | *Aspergillus fumigatus* | EAL86291.2 | F | 406 |
| s121 | seq_ID 27 | *Aspergillus niger* | CAK43501.1 | F | 441 |
| s115 | seq_ID 28 | *Aspergillus niger* | CAK45506.1 | F | 440 |
| s124 | seq_ID 29 | *Aspergillus oryzae* | BAE63941.1 | F | 444 |
| s119 | seq_ID 30 | *Azotobacter vinelandii* | EAM07611.1 | F | 442 |
| s223 | seq_ID 31 | *Bacillus amyloliquefaciens* | ABS74269.1 | F | 413 |
| s221 | seq_ID 32 | *Bacillus anthracis* | AAP27368.1 | F | 409 |
| s976 | seq_ID 33 | *Bacillus cereus* | EEK66523.1 | F | 423 |
| s225 | seq_ID 34 | *Bacillus cereus* | EAL12758.1 | F | 423 |
| s972 | seq_ID 35 | *Bacillus cereus* | EEL44583.1 | F | 412 |
| s977 | seq_ID 36 | *Bacillus cereus* | EEK43841.1 | F | 412 |
| s985 | seq_ID 37 | *Bacillus cereus* | EEK82938.1 | F | 412 |
| s988 | seq_ID 38 | *Bacillus cereus* | EEK99528.1 | F | 412 |
| s981 | seq_ID 39 | *Bacillus cereus* | EEK77935.1 | F | 412 |
| s987 | seq_ID 40 | *Bacillus cereus* | EEL81079.1 | F | 412 |
| s960 | seq_ID 41 | *Bacillus cereus* | EEK88307.1 | F | 412 |
| s979 | seq_ID 42 | *Bacillus cereus* | EEL63943.1 | F | 412 |
| s974 | seq_ID 43 | *Bacillus cereus* | EEL59884.1 | F | 412 |
| s956 | seq_ID 44 | *Bacillus cereus* | EEL69857.1 | F | 412 |
| s951 | seq_ID 45 | *Bacillus cereus* | EEL92663.1 | F | 412 |
| s986 | seq_ID 46 | *Bacillus cereus* | EEL49968.1 | F | 411 |
| s227 | seq_ID 47 | *Bacillus cereus* | AAU16998.1 | F | 409 |
| s224 | seq_ID 48 | *Bacillus cereus* | AAS42477.1 | F | 409 |
| s212 | seq_ID 49 | *Bacillus cereus* | ACK95843.1 | F | 409 |
| s289 | seq_ID 50 | *Bacillus coahuilensis* | 205373680 | F | 276 |
| s219 | seq_ID 51 | *Bacillus cytotoxicus* | ABS22481.1 | F | 411 |
| s230 | seq_ID 52 | *Bacillus licheniformis* | AAU23777.1 | F | 414 |
| s955 | seq_ID 53 | *Bacillus mycoides* | EEL98438.1 | F | 412 |
| s990 | seq_ID 54 | *Bacillus mycoides* | EEM04821.1 | F | 411 |
| s989 | seq_ID 55 | *Bacillus pseudomycoides* | EEM16144.1 | F | 411 |
| s247 | seq_ID 56 | *Bacillus pumilus* | ABV62529.1 | F | 409 |
| s250 | seq_ID 57 | *Bacillus pumilus* | EDW21137.1 | F | 409 |
| s249 | seq_ID 58 | *Bacillus* sp. | EAR64404.1 | F | 425 |
| s218 | seq_ID 59 | *Bacillus* sp. | EDL66148.1 | F | 412 |
| s241 | seq_ID 60 | *Bacillus subtilis* | Q796C3.1 | F | 415 |
| s284 | seq_ID 61 | *Bacillus subtilis* | AAB84441.1 | F | 415 |
| s215 | seq_ID 62 | *Bacillus thuringiensis* | ABK86448.1 | F | 423 |
| s984 | seq_ID 63 | *Bacillus thuringiensis* | EEM21409.1 | F | 412 |
| s957 | seq_ID 64 | *Bacillus thuringiensis* | EEM82653.1 | F | 412 |
| s980 | seq_ID 65 | *Bacillus thuringiensis* | EEM52372.1 | F | 412 |
| s961 | seq_ID 66 | *Bacillus thuringiensis* | EEM27851.1 | F | 412 |
| s969 | seq_ID 67 | *Bacillus thuringiensis* | EEM40716.1 | F | 412 |
| s959 | seq_ID 68 | *Bacillus thuringiensis* | EEM46814.1 | F | 409 |
| s965 | seq_ID 69 | *Bacillus thuringiensis* | EEM94969.1 | F | 409 |
| s202 | seq_ID 70 | *Bacillus weihenstephanensis* | ABY44436.1 | F | 409 |
| s63 | seq_ID 71 | *Bacterium* Ellin514 | EEF57225.1 | F | 461 |
| s72 | seq_ID 72 | *Bacterium* Ellin514 | EEF59508.1 | Y | 435 |
| s87 | seq_ID 73 | *Beijerinckia indica* | ACB96717.1 | F | 441 |

-continued

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
|---|---|---|---|---|---|
| s69 | seq_ID 74 | *Blastopirellula marina* | EAQ81955.1 | F | 475 |
| s543 | seq_ID 75 | *Blastopirellula marina* | EAQ78122.1 | F | 389 |
| s156 | seq_ID 76 | *Bradyrhizobium japonicum* | CAA60250.1 | F | 439 |
| s938 | seq_ID 77 | *Acetobacter pasteurianus* | BAH98349.1 | F | 437 |
| s3 | seq_ID 78 | *Bradyrhizobium sp.* | CAL79893.1 | F | 447 |
| s201 | seq_ID 79 | *Brevibacillus brevis* | BAH44778.1 | F | 448 |
| s148 | seq_ID 80 | *Burkholderia ambifaria* | EDT05097.1 | F | 450 |
| s158 | seq_ID 81 | *Burkholderia ambifaria* | EDT37649.1 | F | 450 |
| s149 | seq_ID 82 | *Burkholderia ambifaria* | ACB68303.1 | F | 446 |
| s100 | seq_ID 83 | *Burkholderia ambifaria* | EDT42454.1 | F | 436 |
| s146 | seq_ID 84 | *Burkholderia cenocepacia* | EAY66961.1 | F | 451 |
| s139 | seq_ID 85 | *Burkholderia cenocepacia* | ACA95661.1 | F | 451 |
| s147 | seq_ID 86 | *Burkholderia cenocepacia* | CAR57099.1 | F | 451 |
| s95 | seq_ID 87 | *Burkholderia cenocepacia* | CAR56694.1 | F | 436 |
| s102 | seq_ID 88 | *Burkholderia dolosa* | EAY71311.1 | F | 437 |
| s941 | seq_ID 89 | *Burkholderia glumae* | ACR32572.1 | F | 555 |
| s945 | seq_ID 90 | *Burkholderia glumae* | ACR30752.1 | F | 449 |
| s132 | seq_ID 91 | *Burkholderia graminis* | EDT12320.1 | F | 462 |
| s104 | seq_ID 92 | *Burkholderia mallei* | ABM48844.1 | F | 436 |
| s140 | seq_ID 93 | *Burkholderia multivorans* | ABX19650.1 | F | 450 |
| s116 | seq_ID 94 | *Burkholderia multivorans* | ABX16859.1 | F | 436 |
| s91 | seq_ID 95 | *Burkholderia oklahomensis* | 167567074 | F | 447 |
| s111 | seq_ID 96 | *Burkholderia phymatum* | ACC73258.1 | F | 456 |
| s127 | seq_ID 97 | *Burkholderia phytofirmans* | ACD21317.1 | F | 455 |
| s120 | seq_ID 98 | *Burkholderia pseudomallei* | EEC32728.1 | F | 436 |
| s137 | seq_ID 99 | *Burkholderia sp.* | EEA03553.1 | F | 460 |
| s144 | seq_ID 100 | *Burkholderia sp.* | ABB06563.1 | F | 450 |
| s98 | seq_ID 101 | *Burkholderia sp.* | ABB10136.1 | F | 436 |
| s944 | seq_ID 102 | *Burkholderia sp.* CCGE1002 | EFA54357.1 | F | 473 |
| s89 | seq_ID 103 | *Burkholderia thailandensis* | 167840988 | F | 451 |
| s113 | seq_ID 104 | *Burkholderia thailandensis* | 167617352 | F | 442 |
| s154 | seq_ID 105 | *Burkholderia ubonensis* | 167589807 | F | 445 |
| s93 | seq_ID 106 | *Burkholderia ubonensis* | 167584986 | F | 436 |
| s96 | seq_ID 107 | *Burkholderia vietnamiensis* | ABO56791.1 | F | 436 |
| s150 | seq_ID 108 | *Burkholderia xenovorans* | ABE35912.1 | F | 457 |
| s54 | seq_ID 109 | *Candidatus Koribacter* | ABF40741.1 | F | 435 |
| s171 | seq_ID 110 | *Candidatus Kuenenia* | CAJ71215.1 | F | 273 |
| s79 | seq_ID 111 | *Candidatus Solibacter* | ABJ82180.1 | F | 439 |
| s99 | seq_ID 112 | *Candidatus Solibacter* | ABJ82254.1 | F | 429 |
| s917 | seq_ID 113 | *Catenulispora acidiphila* | ACU75510.1 | F | 418 |
| s65 | seq_ID 114 | *Chthoniobacter flavus* | EDY15838.1 | F | 433 |
| s637 | seq_ID 115 | *Chthoniobacter flavus* | EDY22035.1 | F | 384 |
| s38 | seq_ID 116 | *Crocosphaera Watsonii* | EAM53094.1 | F | 426 |
| s186 | seq_ID 117 | *Cupriavidus taiwanensis* | CAQ72562.1 | F | 454 |
| s32 | seq_ID 118 | *Cyanothece sp.* | ACB53858.1 | F | 441 |
| s40 | seq_ID 119 | *Cyanothece sp.* | ACK71719.1 | F | 430 |
| s30 | seq_ID 120 | *Cyanothece sp.* | EDY02410.1 | F | 429 |
| s29 | seq_ID 121 | *Cyanothece sp.* | ACK66841.1 | F | 429 |
| s47 | seq_ID 122 | *Cyanothece sp.* | EDX97382.1 | F | 428 |
| s35 | seq_ID 123 | *Cyanothece sp.* | EAZ91809.1 | F | 426 |
| s39 | seq_ID 124 | *Cyanothece sp.* | ACL45896.1 | F | 423 |
| s925 | seq_ID 125 | *Cyanothece sp.* PCC 8802 | ACV02092.1 | F | 429 |
| s64 | seq_ID 126 | *Desulfovibrio salexigens* | EEC62384.1 | F | 475 |
| s74 | seq_ID 127 | *Dryopteris crassirhizoma* | BAG68223.1 | F | 444 |
| s59 | seq_ID 128 | *Frankia alni* | CAJ61140.1 | Y | 533 |
| s48 | seq_ID 129 | *Frankia alni* | CAJ60090.1 | F | 493 |
| s56 | seq_ID 130 | *Frankia sp.* | ABD10207.1 | F | 530 |
| s60 | seq_ID 131 | *Frankia sp.* | ABW15063.1 | F | 512 |
| s31 | seq_ID 132 | *Frankia sp.* | ABW14125.1 | Y | 481 |
| s948 | seq_ID 133 | *Frankia sp.* Eu1lc | EFA59873.1 | F | 557 |
| s919 | seq_ID 134 | *Frankia sp.* Eu1lc | EFA59089.1 | F | 553 |
| s628 | seq_ID 135 | *Gemmata obscuriglobus* | 168700710 | F | 387 |
| s209 | seq_ID 136 | *Geobacillus sp.* | EED61885.1 | F | 404 |
| s206 | seq_ID 137 | *Geobacillus sp.* | EDY05760.1 | F | 403 |
| s964 | seq_ID 138 | *Geobacillus sp.* Y412MC52 | EEN95021.1 | F | 404 |
| s993 | seq_ID 139 | *Geobacillus sp.* Y412MC61 | ACX79399.1 | F | 404 |
| s205 | seq_ID 140 | *Geobacillus thermodenitrificans* | ABO67242.1 | F | 403 |
| s15 | seq_ID 141 | *Geobacter bemidjiensis* | ACH40355.1 | F | 468 |
| s8 | seq_ID 142 | *Geobacter lovleyi* | ACD95949.1 | F | 470 |

-continued

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
|---|---|---|---|---|---|
| s62 | seq_ID 143 | Geobacter metallireducens | ABB30662.1 | F | 493 |
| s12 | seq_ID 144 | Geobacter metallireducens | ABB33038.1 | F | 467 |
| s73 | seq_ID 145 | Geobacter sp. | ACM21577.1 | F | 487 |
| s10 | seq_ID 146 | Geobacter sp. | EDV72707.1 | F | 468 |
| s11 | seq_ID 147 | Geobacter sp. | ACM22003.1 | F | 467 |
| s913 | seq_ID 148 | Geobacter sp. M18 | EET34621.1 | F | 468 |
| s914 | seq_ID 149 | Geobacter sp. M21 | ACT16952.1 | F | 468 |
| s58 | seq_ID 150 | Geobacter sulfurreducens | AAR36453.1 | F | 493 |
| s7 | seq_ID 151 | Geobacter sulfurreducens | AAR34018.1 | F | 467 |
| s9 | seq_ID 152 | Geobacter uraniireducens | ABQ25226.1 | F | 467 |
| s46 | seq_ID 153 | Gloeobacter violaceus | BAC91998.1 | F | 425 |
| s67 | seq_ID 154 | Gluconacetobacter diazotrophicus | ACI51585.1 | F | 444 |
| s165 | seq_ID 155 | Gluconacetobacter diazotrophicus | CAP55563.1 | F | 444 |
| s68 | seq_ID 156 | Gluconobacter oxydans | AAW61994.1 | F | 445 |
| s80 | seq_ID 157 | Granulibacter bethesdensis | ABI63005.1 | F | 429 |
| s937 | seq_ID 158 | Hyphomicrobium denitrificans | EET65847.1 | F | 444 |
| s932 | seq_ID 159 | Leptospirillum ferrodiazotrophum | EES53667.1 | F | 460 |
| s24 | seq_ID 160 | Leptospirillum rubarum | EAY57382.1 | F | 448 |
| s25 | seq_ID 161 | Leptospirillum sp. | EDZ38599.1 | F | 448 |
| s174 | seq_ID 162 | Magnaporthe grisea | EDK02551.1 | F | 445 |
| s153 | seq_ID 163 | Magnetospirillum magnetotacticum | 46203107 | F | 447 |
| s49 | seq_ID 164 | Methylacidiphilum infernorum | ACD82457.1 | F | 456 |
| s169 | seq_ID 165 | Methylobacterium chloromethanicum | ACK83067.1 | F | 447 |
| s75 | seq_ID 166 | Methylobacterium chloromethanicum | ACK86232.1 | F | 426 |
| s946 | seq_ID 167 | Methylobacterium extorquens | CAX24364.1 | F | 447 |
| s141 | seq_ID 168 | Methylobacterium nodulans | ACL61886.1 | F | 442 |
| s152 | seq_ID 169 | Methylobacterium populi | ACB79998.1 | F | 447 |
| s162 | seq_ID 170 | Methylobacterium radiotolerans | ACB27373.1 | F | 445 |
| s180 | seq_ID 171 | Methylobacterium sp. | ACA20611.1 | F | 442 |
| s175 | seq_ID 172 | Methylocella silvestris | ACK52150.1 | F | 451 |
| s181 | seq_ID 173 | Methylococcus capsulatus | CAA71098.1 | F | 439 |
| s55 | seq_ID 174 | Microcystis aeruginosa | CAO86472.1 | F | 423 |
| s101 | seq_ID 175 | Neosartorya fischeri | EAW20752.1 | F | 448 |
| s129 | seq_ID 176 | Nitrobacter hamburgensis | ABE63461.1 | F | 433 |
| s161 | seq_ID 177 | Nitrobacter sp. | EAQ34404.1 | F | 430 |
| s160 | seq_ID 178 | Nitrobacter winogradskyi | ABA05523.1 | F | 433 |
| s157 | seq_ID 179 | Nitrococcus mobilis | EAR22397.1 | F | 436 |
| s164 | seq_ID 180 | Nitrosococcus oceani | ABA57818.1 | F | 446 |
| s170 | seq_ID 181 | Nitrosomonas europaea | CAD85079.1 | F | 452 |
| s173 | seq_ID 182 | Nitrosomonas eutropha | ABI59752.1 | F | 456 |
| s943 | seq_ID 183 | Nitrosomonas sp. AL212 | EET32702.1 | F | 452 |
| s142 | seq_ID 184 | Nitrosospira multiformis | ABB75845.1 | F | 439 |
| s52 | seq_ID 185 | Nostoc punctiforme | ACC84529.1 | F | 423 |
| s45 | seq_ID 186 | Nostoc sp. | BAB72732.1 | F | 423 |
| s122 | seq_ID 187 | Oligotropha carboxidovorans | ACI93782.1 | F | 433 |
| s233 | seq_ID 188 | Paenibacillus sp. | EDS49994.1 | F | 399 |
| s991 | seq_ID 189 | Paenibacillus sp. JDR-2 | ACS99948.1 | F | 399 |
| s950 | seq_ID 190 | Paenibacillus sp. oral taxon 786 | EES74793.1 | F | 428 |
| s1280 | seq_ID 191 | Paramecium tetraurelia | 145542269 | F | 400 |
| s71 | seq_ID 192 | Pelobacter carbinolicus | ABA87701.1 | F | 494 |
| s5 | seq_ID 193 | Pelobacter carbinolicus | ABA87615.1 | F | 435 |
| s66 | seq_ID 194 | Pelobacter propionicus | ABK98395.1 | F | 486 |
| s16 | seq_ID 195 | Pelobacter propionicus | ABK98811.1 | F | 467 |
| s136 | seq_ID 196 | Penicillium chrysogenum | CAP99707.1 | F | 440 |
| s936 | seq_ID 197 | Planctomyces limnophilus | EEO67214.1 | F | 490 |
| s1158 | seq_ID 198 | Planctomyces limnophilus | EEO68341.1 | F | 412 |
| s526 | seq_ID 199 | Planctomyces maris | EDL58855.1 | F | 392 |
| s992 | seq_ID 200 | Polypodiodes niponica | BAI48071.1 | Y | 521 |
| s942 | seq_ID 201 | Polypodiodes niponica | BAI48070.1 | F | 443 |
| s1202 | seq_ID 202 | Populus trichocarpa | EEF12098.1 | F | 162 |
| s168 | seq_ID 203 | Ralstonia eutropha | AAZ64302.1 | F | 452 |
| s190 | seq_ID 204 | Ralstonia eutropha | CAJ96989.1 | F | 451 |
| s81 | seq_ID 205 | Ralstonia metallidurans | ABF11015.1 | F | 448 |
| s110 | seq_ID 206 | Ralstonia metallidurans | ABF11268.1 | F | 430 |
| s123 | seq_ID 207 | Rhizobium sp. | P55348.1 | F | 433 |
| s657 | seq_ID 208 | Rhodopirellula baltica | CAD74517.1 | F | 428 |

-continued

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
|---|---|---|---|---|---|
| s4 | seq_ID 209 | Rhodopseudomonas palustris | ABJ08391.1 | F | 445 |
| s130 | seq_ID 210 | Rhodopseudomonas palustris | CAA71101.1 | F | 433 |
| s155 | seq_ID 211 | Rhodopseudomonas palustris | ABD06434.1 | F | 433 |
| s97 | seq_ID 212 | Rhodopseudomonas palustris | ABD87279.1 | F | 433 |
| s135 | seq_ID 213 | Rhodopseudomonas palustris | ACF02757.1 | F | 432 |
| s84 | seq_ID 214 | Rhodospirillum rubrum | ABC20867.1 | F | 437 |
| s1279 | seq_ID 215 | Rubrobacter xylanophilus | ABG05671.1 | F | 372 |
| s915 | seq_ID 216 | Saccharomonospora viridis | ACU97316.1 | F | 428 |
| s42 | seq_ID 217 | Saccharopolyspora erythraea | CAM03596.1 | F | 421 |
| s82 | seq_ID 218 | Schizosaccharomyces japonicus | EEB08219.1 | F | 437 |
| s923 | seq_ID 219 | Sphaerobacter thermophilus | ACZ39437.1 | F | 404 |
| s924 | seq_ID 220 | Streptomyces albus | 239983547 | F | 371 |
| s23 | seq_ID 221 | Streptomyces avermitilis | BAC69361.1 | F | 450 |
| s44 | seq_ID 222 | Acaryochloris marina | ABW29816.1 | F | 423 |
| s921 | seq_ID 223 | Streptomyces filamentosus | 239945642 | F | 447 |
| s934 | seq_ID 224 | Streptomyces flavogriseus | EEW70811.1 | F | 447 |
| s920 | seq_ID 225 | Streptomyces ghanaensis | 239927462 | F | 448 |
| s922 | seq_ID 226 | Streptomyces griseoflavus | 256812310 | F | 448 |
| s28 | seq_ID 227 | Streptomyces griseus | BAG17791.1 | F | 447 |
| s926 | seq_ID 228 | Streptomyces hygroscopicus | 256775136 | F | 414 |
| s916 | seq_ID 229 | Streptomyces lividans | 256783789 | F | 449 |
| s33 | seq_ID 230 | Streptomyces peucetius | ACA52082.1 | F | 455 |
| s27 | seq_ID 231 | Streptomyces pristinaespiralis | EDY61772.1 | F | 455 |
| s933 | seq_ID 232 | Streptomyces scabiei | CBG68454.1 | F | 447 |
| s37 | seq_ID 233 | Streptomyces sp. | EDX25760.1 | F | 453 |
| s34 | seq_ID 234 | Streptomyces sp. | EDY46371.1 | F | 453 |
| s931 | seq_ID 235 | Streptomyces sp. AA4 | 256668250 | F | 428 |
| s918 | seq_ID 236 | Streptomyces sp. C | 256770952 | F | 454 |
| s929 | seq_ID 237 | Streptomyces sp. Mg1 | 254385931 | F | 453 |
| s928 | seq_ID 238 | Streptomyces sp. SPB74 | 254379682 | F | 453 |
| s930 | seq_ID 239 | Streptomyces sp. SPB78 | 256680470 | F | 404 |
| s26 | seq_ID 240 | Streptomyces sviceus | EDY55942.1 | F | 453 |
| s927 | seq_ID 241 | Streptomyces viridochromogenes | 256805984 | F | 447 |
| s61 | seq_ID 242 | Synechococcus sp. | EDX84551.1 | F | 426 |
| s935 | seq_ID 243 | Synechococcus sp. PCC 7335 | 254422098 | F | 426 |
| s53 | seq_ID 244 | Synechocystis sp. | BAA17978.1 | F | 428 |
| s22 | seq_ID 245 | Syntrophobacter fumaroxidans | ABK18414.1 | F | 478 |
| s6 | seq_ID 246 | Syntrophobacter fumaroxidans | ABK17672.1 | F | 457 |
| s912 | seq_ID 247 | Teredinibacter turnerae | ACR13362.1 | F | 438 |
| s57 | seq_ID 248 | Thermosynechococcus elongatus | BAC09861.1 | F | 425 |
| s43 | seq_ID 249 | Trichodesmium erythraeum | ABG50159.1 | F | 418 |
| s1178 | seq_ID 250 | Uncultured organism | ACA58560.1 | F | 118 |
| s1176 | seq_ID 251 | Uncultured organism | ABL07557.1 | F | 118 |
| s1165 | seq_ID 252 | Uncultured organism | ACA58559.1 | F | 116 |
| s1166 | seq_ID 253 | Uncultured organism | ACA58558.1 | F | 116 |
| s1168 | seq_ID 254 | Uncultured organism | ABL07560.1 | F | 116 |
| s1169 | seq_ID 255 | Uncultured organism | ABL07565.1 | F | 116 |
| s1170 | seq_ID 256 | Uncultured organism | ABL07566.1 | F | 116 |
| s1167 | seq_ID 257 | Uncultured organism | ACA58545.1 | F | 116 |
| s1171 | seq_ID 258 | Uncultured organism | ACA58535.1 | F | 116 |
| s1180 | seq_ID 259 | Uncultured organism | ACA58549.1 | F | 116 |
| s1179 | seq_ID 260 | Uncultured organism | ACA58554.1 | F | 116 |
| s1181 | seq_ID 261 | Uncultured organism | ACA58555.1 | F | 116 |
| s1182 | seq_ID 262 | Uncultured organism | ACA58556.1 | F | 116 |
| s1235 | seq_ID 263 | Uncultured organism | ACA58530.1 | F | 116 |
| s1188 | seq_ID 264 | Uncultured organism | ACA58534.1 | F | 115 |
| s1237 | seq_ID 265 | Uncultured organism | ACA58552.1 | F | 115 |
| s1223 | seq_ID 266 | Uncultured organism | ABL07558.1 | F | 115 |
| s1200 | seq_ID 267 | Uncultured organism | ABL07542.1 | F | 115 |
| s1236 | seq_ID 268 | Uncultured organism | ACA58539.1 | F | 114 |
| s1238 | seq_ID 269 | Uncultured organism | ACA58537.1 | F | 114 |
| s1233 | seq_ID 270 | Uncultured organism | ACA58543.1 | F | 114 |
| s1173 | seq_ID 271 | Uncultured organism | ABL07553.1 | F | 114 |
| s1241 | seq_ID 272 | Uncultured organism | ABL07540.1 | F | 114 |
| s1242 | seq_ID 273 | Uncultured organism | ABL07544.1 | F | 114 |
| s1225 | seq_ID 274 | Uncultured organism | ACA58557.1 | F | 114 |
| s1183 | seq_ID 275 | Uncultured organism | ACA58520.1 | F | 113 |
| s1197 | seq_ID 276 | Uncultured organism | ACA58524.1 | F | 113 |
| s1185 | seq_ID 277 | Uncultured organism | ACA58522.1 | F | 113 |

-continued

Program: CLUSTALW,
Default parameters:
Protein Gap Open Penalty 10.0
Protein Gap Extension Penalty 0.2
Protein weight matrix: Gonnet series

| S_ID DB | SEQ ID NO | Organism | GI No. of the reference sequences | Aa | Position |
|---|---|---|---|---|---|
| s1190 | seq_ID 278 | Uncultured organism | ACA58525.1 | F | 113 |
| s1187 | seq_ID 279 | Uncultured organism | ACA58523.1 | F | 113 |
| s1184 | seq_ID 280 | Uncultured organism | ACA58521.1 | F | 113 |
| s1204 | seq_ID 281 | Uncultured organism | ACA58547.1 | F | 113 |
| s1221 | seq_ID 282 | Uncultured organism | ACA58544.1 | F | 113 |
| s1198 | seq_ID 283 | Uncultured organism | ACA58546.1 | F | 112 |
| s1226 | seq_ID 284 | Uncultured organism | ACA58527.1 | F | 112 |
| s1227 | seq_ID 285 | Uncultured organism | ABL07537.1 | F | 112 |
| s1232 | seq_ID 286 | Uncultured organism | ACA58510.1 | F | 112 |
| s1230 | seq_ID 287 | Uncultured organism | ACA58538.1 | F | 112 |
| s1229 | seq_ID 288 | Uncultured organism | ACA58542.1 | F | 112 |
| s1231 | seq_ID 289 | Uncultured organism | ACA58540.1 | F | 112 |
| s1207 | seq_ID 290 | Uncultured organism | ABL07564.1 | F | 112 |
| s1212 | seq_ID 291 | Uncultured organism | ABL07563.1 | F | 112 |
| s1208 | seq_ID 292 | Uncultured organism | ABL07562.1 | F | 112 |
| s1209 | seq_ID 293 | Uncultured organism | ABL07559.1 | F | 112 |
| s1214 | seq_ID 294 | Uncultured organism | ABL07556.1 | F | 112 |
| s1216 | seq_ID 295 | Uncultured organism | ACA58528.1 | F | 112 |
| s1219 | seq_ID 296 | Uncultured organism | ACA58536.1 | F | 112 |
| s1192 | seq_ID 297 | Uncultured organism | ABL07533.1 | F | 112 |
| s1195 | seq_ID 298 | Uncultured organism | ABL07536.1 | F | 112 |
| s1174 | seq_ID 299 | Uncultured organism | ABL07545.1 | F | 112 |
| s1186 | seq_ID 300 | Uncultured organism | ABL07548.1 | F | 112 |
| s1196 | seq_ID 301 | Uncultured organism | ACA58561.1 | F | 112 |
| s1172 | seq_ID 302 | Uncultured organism | ABL07555.1 | F | 112 |
| s1194 | seq_ID 303 | Uncultured organism | ABL07541.1 | F | 112 |
| s1211 | seq_ID 304 | Uncultured organism | ABL07554.1 | F | 112 |
| s1220 | seq_ID 305 | Uncultured organism | ABL07547.1 | F | 112 |
| s1203 | seq_ID 306 | Uncultured organism | ABL07550.1 | F | 112 |
| s1199 | seq_ID 307 | Uncultured organism | ABL07551.1 | F | 112 |
| s1228 | seq_ID 308 | Uncultured organism | ACA58509.1 | F | 111 |
| s1201 | seq_ID 309 | Uncultured organism | ACA58514.1 | F | 111 |
| s1205 | seq_ID 310 | Uncultured organism | ABL07543.1 | F | 111 |
| s1206 | seq_ID 311 | Uncultured organism | ABL07534.1 | F | 111 |
| s1177 | seq_ID 312 | Uncultured organism | ABL07546.1 | F | 111 |
| s1210 | seq_ID 313 | Uncultured organism | ABL07535.1 | F | 111 |
| s1175 | seq_ID 314 | Uncultured organism | ABL07552.1 | F | 111 |
| s1191 | seq_ID 315 | Uncultured organism | ABL07549.1 | F | 111 |
| s1222 | seq_ID 316 | Uncultured organism | ACA58553.1 | F | 111 |
| s1244 | seq_ID 317 | Uncultured organism | ABL07539.1 | F | 111 |
| s1213 | seq_ID 318 | Uncultured organism | ACA58532.1 | F | 110 |
| s1239 | seq_ID 319 | Uncultured organism | ACA58548.1 | F | 110 |
| s1215 | seq_ID 320 | Uncultured organism | ABL07561.1 | F | 110 |
| s1240 | seq_ID 321 | Uncultured organism | ACA58533.1 | F | 110 |
| s1234 | seq_ID 322 | Uncultured organism | ABL07538.1 | F | 109 |
| s1224 | seq_ID 323 | Uncultured organism | ACA58541.1 | F | 109 |
| s1217 | seq_ID 324 | Uncultured organism | ACA58529.1 | F | 109 |
| s596 | seq_ID 325 | *Verrucomicrobium spinosum* | 171910093 | F | 395 |
| s70 | seq_ID 326 | *Acidiphilium cryptum* | ABQ30890.1 | F | 430 |

Further potential cyclase mutants with the desired substrate properties can be produced starting from these, on the basis of the findings for mutants of Zm-SHC-1.

2. Further Proteins/Enzyme Mutants According to the Invention

The present invention is not limited to the mutants with cyclase activity concretely disclosed herein, but rather also extends to functional equivalents thereof.

"Functional equivalents" or analogs of the concretely disclosed enzymes and enzyme mutants (F486 and "F486-analog" mutants, derived from SEQ ID NO: 2 to 326, in particular SEQ ID NO: 2 to 6) are, within the scope of the present invention, various polypeptides thereof, which furthermore possess the desired biological activity, for example cyclase activity.

For example "functional equivalents" are understood to include enzymes and mutants that have, in a test applied for "cyclase activity" in the sense of the invention (i.e. with a reference substrate under standard conditions), an at least 1%, in particular at least about 5 to 10%, for example at least 10% or at least 20%, for example at least 50% or 75% or 90% higher or lower activity of an enzyme, comprising an amino acid sequence concretely defined herein (e.g. an F486 and "F486-analog" mutant, derived from SEQ ID NO: 2 to 326; in particular SEQ ID NO: 2 to 6).

The activity information for functional equivalents refers herein, unless stated otherwise, to activity determinations, performed by means of a reference substrate under standard conditions, as defined herein.

The "cyclase activity" in the sense of the invention can be detected by means of various known tests. Without being limited to this, we may mention a test using a reference substrate, for example citronellal racemate or R(+) form, under standard conditions, as described above and explained in the experimental section.

Functional equivalents are moreover stable e.g. between pH 4 to 11 and advantageously possess a pH optimum in a range from pH 5 to 10, such as in particular 6.5 to 9.5 or 7 to 8 or at about 7.5, and a temperature optimum in the range from 15° C. to 80° C. or 20° C. to 70° C., for example about 30 to 60° C. or about 35 to 45° C., such as at 40° C.

"Functional equivalents" are to be understood according to the invention to include in particular also "mutants", which, as well as the concretely stated mutation(s) (e.g. an F486 and "F486-analog" mutant, derived from SEQ ID NO: 2 to 326, in particular SEQ ID NO: 2 to 6), have in at least one sequence position of the aforementioned amino acid sequences, an amino acid other than that concretely stated, but nevertheless possess one of the aforementioned biological activities.

"Functional equivalents" comprise the mutants obtainable by one or more, for example 1 to 50, 2 to 30, 2 to 15, 4 to 12 or 5 to 10 "additional mutations", such as amino acid additions, substitutions, deletions and/or inversions, wherein the stated changes can occur in any sequence position, provided they lead to a mutant with the property profile according to the invention. Functional equivalence is in particular also present when the reactivity profiles between mutant and unaltered polypeptide coincide qualitatively, i.e. for example the same substrates are converted at a different rate.

"Additional mutations" of this kind occur at a position of the respective amino acid sequence different from position F486 according to SEQ ID NO: 2 or from the F486-analog position according to one of SEQ ID NOs: 3 to 326, in particular SEQ ID NO: 3 to 6.

Nonlimiting examples of suitable amino acid substitutions are given in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described as well as "functional derivatives" and "salts" of the polypeptides.

"Precursors" are natural or synthetic precursors of the polypeptides with or without the desired biological activity.

The term "salts" means both salts of carboxyl groups and salts of acid addition of amino groups of the protein molecules according to the invention. Salts of carboxyl groups can be produced in a manner known per se and comprise inorganic salts, for example sodium, calcium, ammonium, iron and zinc salts, and salts with organic bases, for example amines, such as triethanolamine, arginine, lysine, piperidine and the like. Salts of acid addition, for example salts with mineral acids, such as hydrochloric acid or sulfuric acid and salts with organic acids, such as acetic acid and oxalic acid, are also objects of the invention.

"Functional derivatives" of polypeptides according to the invention can also be produced on functional amino acid side groups or at their N- or C-terminal end by known techniques. Derivatives of this kind comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that are accessible from other organisms, and naturally occurring variants. For example areas of homologous sequence regions can be established by sequence comparison and equivalent enzymes can be determined based on the concrete information of the invention.

"Functional equivalents" also comprise fragments, preferably individual domains or sequence motifs, of the polypeptides according to the invention, which for example have the desired biological function.

"Functional equivalents" are moreover fusion proteins, which have one of the aforementioned polypeptide sequences or functional equivalents derived therefrom and at least one further, functionally different therefrom, heterologous sequence in functional N- or C-terminal linkage (i.e. without mutual substantial functional impairment of the fusion protein parts). Nonlimiting examples of heterologous sequences of this kind are e.g. signal peptides, histidine anchors or enzymes.

"Functional equivalents" that are also included according to the invention are homologs to the concretely disclosed proteins. These possess at least 60%, preferably at least 75%, especially at least 85%, for example 90, 91, 92, 93, 94, 95, 96, 97, 98 or 99%, homology (or identity) to one of the concretely disclosed amino acid sequences, calculated using the algorithm of Pearson and Lipman, Proc. Natl. Acad. Sci. (USA) 85(8), 1988, 2444-2448. A percentage homology or identity of a homologous polypeptide according to the invention means in particular percentage identity of the amino acid residues relative to the total length of one of the amino acid sequences concretely described herein. In particular, however, these homologs also have the F486 or "F486-analog" mutation, derived from SEQ ID NO:2 to 326, in particular SEQ ID NO: 2 to 6.

The percentage identity values can also be determined on the basis of BLAST alignments, blastp algorithms (protein-protein BLAST), or using the Clustal settings given below.

In the case of a possible protein glycosylation, "functional equivalents" according to the invention comprise proteins of the type designated above in deglycosylated or glycosylated form as well as modified forms obtainable by changing the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial databases of mutants, for example shortened mutants. For example a variegated database of protein variants can be produced by combinatorial mutagenesis at nucleic acid level, for example by enzymatic ligation of a mixture of synthetic oligonucleotides. There are a great many methods that can be used for producing databases of potential homologs from a degenerated oligonucleotide sequence. The chemical synthesis of a degenerated gene sequence can be carried out in an automatic DNA synthesizer, and the synthetic gene can then be ligated into a suitable expression vector. The use of a degenerated set of genes makes it possible to provide all sequences, in one mixture, which code for the desired set of potential protein sequences. Methods for the synthesis of degenerated oligonucleotides are known by a person skilled in the art (e.g. Narang, S. A. (1983) Tetrahedron 39:3; Itakura et al. (1984) Annu. Rev. Biochem. 53:323; Itakura et al., (1984) Science 198:1056; Ike et al. (1983) Nucleic Acids Res. 11:477).

Several techniques for screening gene products of combinatorial databases, which were produced by point mutations or shortening, and for screening cDNA databases for gene products with a chosen property, are known in the prior art. These techniques can be adapted for rapid screening of gene banks that have been produced by combinatorial mutagenesis of homologs according to the invention. The techniques used most often for screening large gene banks, as the basis for high-throughput analysis, comprise cloning the gene bank into replicatable expression vectors, transforming suitable cells with the resultant vector bank and expressing the combinatorial genes in conditions in which detection of the desired activity facilitates the isolation of the vector that codes for the gene whose product was detected. Recursive ensemble mutagenesis (REM), a technique that increases the frequency of functional mutants in the databases, can be used in combination with the screening tests, to identify homologs (Arkin and Yourvan (1992) PNAS 89:7811-7815; Delgrave et al. (1993) Protein Engineering 6(3):327-331).

3. Nucleic Acids and Constructs 3.1 Nucleic Acids

The invention also relates to nucleic acid sequences that code for an enzyme as described above or a mutant thereof described above with cyclase activity.

The present invention also relates to nucleic acids with a specified degree of identity to the concrete sequences described herein.

"Identity" between two nucleic acids means identity of the nucleotides in each case over the whole length of nucleic acid, in particular the identity that is calculated by comparison by means of the Vector NTI Suite 7.1 software from the company Informax (USA) using the Clustal method (Higgins D G, Sharp P M. Fast and sensitive multiple sequence alignments on a microcomputer. Comput Appl. Biosci. 1989 April; 5(2):151-1), setting the following parameters:

| Multiple alignment parameters: | |
| --- | --- |
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |

| Pairwise alignment parameter: | |
| --- | --- |
| FAST algorithm | on |
| K-tuple size | 1 |
| Gap penalty | 3 |
| Window size | 5 |
| Number of best diagonals | 5 |

As an alternative, the identity can also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, according to Internet address: ebi-.ac.uk/Tools/clustalw/index.html# and with the following parameters:

| | |
| --- | --- |
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All nucleic acid sequences mentioned herein (single-stranded and double-stranded DNA and RNA sequences, for example cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can for example be carried out in a known manner, by the phosphoroamidite technique (Voet, Voet, 2nd edition, Wiley Press New York, pages 896-897). The adding-on of synthetic oligonucleotides and filling of gaps using the Klenow fragment of DNA polymerase and ligation reactions as well as general cloning techniques are described in Sambrook et al. (1989), Molecular Cloning: A Laboratory Manual, Cold Spring Harbor Laboratory Press.

The invention also relates to nucleic acid sequences (single-stranded and double-stranded DNA and RNA sequences, for example cDNA and mRNA), coding for one of the above polypeptides and functional equivalents thereof, which are accessible e.g. using artificial nucleotide analogs.

The invention relates both to isolated nucleic acid molecules, which code for polypeptides or proteins according to the invention or biologically active segments thereof, and to nucleic acid fragments, which can be used for example as hybridization probes or primers for the identification or amplification of coding nucleic acids according to the invention.

The nucleic acid molecules according to the invention can in addition contain untranslated sequences of the 3'- and/or 5'-end of the coding gene region.

The invention further comprises the nucleic acid molecules complementary to the concretely described nucleotide sequences, or a segment thereof.

The nucleotide sequences according to the invention make it possible to produce probes and primers that can be used for the identification and/or cloning of homologous sequences in other cell types and organisms. Said probes or primers usually comprise a nucleotide sequence region which hybridizes under "stringent" conditions (see below) to at least about 12, preferably at least about 25, for example about 40, 50 or 75 successive nucleotides of a sense strand of a nucleic acid sequence according to the invention or of a corresponding antisense strand.

An "isolated" nucleic acid molecule is separate from other nucleic acid molecules that are present in the natural source of the nucleic acid, and moreover can be essentially free of other cellular material or culture medium, when it is produced by recombinant techniques, or free of chemical precursors or other chemicals, when it is chemically synthesized.

A nucleic acid molecule according to the invention can be isolated by standard techniques of molecular biology and the sequence information provided according to the invention. For example, cDNA can be isolated from a suitable cDNA-bank, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd edition, Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by polymerase chain reaction, using the oligonucleotide primers that were constructed on the basis of this sequence. The nucleic acid thus amplified can be cloned into a suitable vector and can be characterized by DNA sequence analysis.

The oligonucleotides according to the invention can moreover be produced by standard methods of synthesis, e.g. with an automatic DNA synthesizer.

Nucleic acid sequences according to the invention or derivatives thereof, homologs or parts of these sequences, can be isolated for example with usual hybridization methods or PCR techniques from other bacteria, e.g. via genomic or cDNA databases. These DNA sequences hybridize under standard conditions to the sequences according to the invention.

"Hybridization" means the capacity of a poly- or oligo-nucleotide to bind to an almost complementary sequence under standard conditions, whereas under these conditions nonspecific binding between noncomplementary partners does not occur. For this, the sequences can be up to 90-100% complementary. The property of complementary sequences of being able to bind specifically to one another is utilized for example in Northern or Southern blotting or in primer binding in PCR or RT-PCR.

Short oligonucleotides of the conserved regions are used advantageously for hybridization. However, longer fragments of the nucleic acids according to the invention or the complete sequences can also be used for hybridization. These standard conditions vary depending on the nucleic acid used (oligonucleotide, longer fragment or complete sequence) or depending on which type of nucleic acid, DNA or RNA, is used for hybridization. Thus, for example, the melting temperatures for DNA:DNA hybrids are approx. 10° C. lower than those of DNA:RNA hybrids of the same length.

Standard conditions mean for example, depending on the nucleic acid, temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° to 55° C. These stated temperatures for hybridization are for example calculated melting temperature values for a nucleic acid with a length of approx. 100 nucleotides and a G+C content of 50% in the absence of formamide. The experimental conditions for DNA hybridization are described in relevant textbooks on genetics, for example Sambrook et al., "Molecular Cloning", Cold Spring Harbor Laboratory, 1989, and can be calculated using formulas known by a person skilled in the art, for example depending on the length of the nucleic acids, the type of hybrids or the G+C content. Further information on hybridization can be obtained by a person skilled in the art from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular take place under stringent conditions. Said hybridization conditions are described for example by Sambrook, J., Fritsch, E. F., Maniatis, T. in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions mean in particular: Incubation at 42° C. overnight in a solution consisting of 50% formamide, 5×SSC (750 mM NaCl, 75 mM trisodium citrate), 50 mM sodium phosphate (pH 7.6), 5×Denhardt solution, 10% dextran sulfate and 20 g/ml denatured, sheared salmon sperm DNA, followed by a step of washing the filters with 0.1×SSC at 65° C.

The invention also relates to derivatives of the concretely disclosed or derivable nucleic acid sequences.

Thus, further nucleic acid sequences according to the invention coding for cyclase mutants can be derived e.g. from SEQ ID NO: 1 or from the coding sequences for SEQ ID NO: 2 to 326, in particular SEQ ID NO: 2 to 6, by an F486 or F486-analog mutation and differ from them by addition, substitution, insertion or deletion of single or several nucleotides, but furthermore code for polypeptides with the desired property profile.

The invention also includes nucleic acid sequences that comprise so-called silent mutations or are altered corresponding to the codon-usage of a special original or host organism, compared with a concretely stated sequence, as well as naturally occurring variants, for example splice variants or allele variants, thereof.

It also relates to sequences obtainable by conservative nucleotide substitutions (i.e. the amino acid in question is replaced with an amino acid of the same charge, size, polarity and/or solubility).

The invention also relates to the molecules derived by sequence polymorphisms from the concretely disclosed nucleic acids. These genetic polymorphisms can exist between individuals within a population owing to natural variation. These natural variations usually bring about a variance of 1 to 5% in the nucleotide sequence of a gene.

Derivatives of the nucleic acid sequences according to the invention coding for cyclase mutants derived from sequence SEQ ID NO: 1 or from one of the coding sequences for SEQ ID NO: 2 to 326, in particular SEQ ID NO: 2 to 6, include for example allele variants that have at least 60% homology at the derived amino acid level, preferably at least 80% homology, quite especially preferably at least 90% homology over the whole sequence region (regarding homology at the amino acid level, reference should be made to the above account relating to polypeptides). The homologies can advantageously be higher over partial regions of the sequences.

Furthermore, derivatives also mean homologs of the nucleic acid sequences according to the invention, for example fungal or bacterial homologs, shortened sequences, single-strand DNA or RNA of the coding and noncoding DNA sequence.

Moreover, derivatives mean for example fusions with promoters. The promoters, which are added to the given nucleotide sequences, can be altered by at least one nucleotide exchange, at least one insertion, inversion and/or deletion, without the functionality or efficacy of the promoters being impaired. Moreover, the efficacy of the promoters can be increased by altering their sequence or they can be exchanged completely for more effective promoters even of organisms of a different species.

3.2 Generation of Functional Mutants

Furthermore, methods for producing functional mutants of enzymes according to the invention are known by a person skilled in the art.

Depending on the technology used, a person skilled in the art can introduce completely random or even more-directed mutations in genes or also noncoding nucleic acid regions (which for example are important for the regulation of expression) and then prepare gene libraries. The necessary methods of molecular biology are known by a person skilled in the art and for example are described in Sambrook and Russell, Molecular Cloning. 3rd edition, Cold Spring Harbor Laboratory Press 2001.

Methods for altering genes and therefore for altering the proteins that they encode have long been familiar to a person skilled in the art, for example site-directed mutagenesis, in which single or several nucleotides of a gene are deliberately exchanged (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1), the error-prone polymerase chain reaction (error-prone PCR), in which nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an $E.$ $coli$ mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction, in which, by repeated strand separation and bringing together again, finally mosaic genes of full length are produced (Stemmer W P C (1994) Nature 370:389; Stemmer W P C (1994) Proc Natl Acad Sci USA 91:10747).

Using so-called directed evolution (described for instance in Reetz M T and Jaeger K-E (1999), Topics Curr Chem 200:31; Zhao H, Moore J C, Volkov A A, Arnold F H (1999), Methods for optimizing industrial enzymes by directed evolution, in: Demain A L, Davies J E (Ed.) Manual of industrial microbiology and biotechnology. American Society for Microbiology), a person skilled in the art can produce functional mutants in a directed manner and on a large scale. For this, in a first step, gene libraries of the respective proteins are first produced, for example using the methods given above. The gene libraries are expressed in a suitable way, for example by bacteria or by phage display systems.

The relevant genes of host organisms that express functional mutants with properties that largely correspond to the desired properties can be submitted to another round of mutation. The steps of mutation and selection or screening can be repeated iteratively until the present functional mutants have the desired properties to a sufficient extent. Using this iterative procedure, a limited number of mutations, for example 1, 2, 3, 4 or 5 mutations, can be effected in stages and can be assessed and selected for their influence on the enzyme property in question. The selected mutant can then be submitted to a further mutation step in the same way. In this way the number of individual mutants to be investigated can be reduced significantly.

The results according to the invention also provide important information relating to structure and sequence of the relevant enzymes, which is required for deliberately generating further enzymes with desired modified properties. In particular so-called "hot spots" can be defined, i.e. sequence segments that are potentially suitable for modifying an enzyme property by introducing targeted mutations.

Information can also be deduced regarding amino acid sequence positions, in the region of which mutations can be carried out that should probably have little effect on enzyme activity, and can be designated as potential "silent mutations".

3.3 Constructs

The invention further relates to, in particular recombinant, expression constructs, containing, under the genetic control of regulatory nucleic acid sequences, a nucleic acid sequence coding for a polypeptide according to the invention; and, in particular recombinant, vectors, comprising at least one of these expression constructs.

An "expression unit" means, according to the invention, a nucleic acid with expression activity, which comprises a promoter, as defined herein, and after functional linkage with a nucleic acid to be expressed or a gene, regulates the expression, i.e. the transcription and the translation of said nucleic acid or said gene. Therefore in this connection it is also called a "regulatory nucleic acid sequence". In addition to the promoter, other regulatory elements, for example enhancers, can also be present.

An "expression cassette" or "expression construct" means, according to the invention, an expression unit that is functionally linked to the nucleic acid to be expressed or the gene to be expressed. In contrast to an expression unit, an expression cassette therefore comprises not only nucleic acid sequences that regulate transcription and translation, but also the nucleic acid sequences that are to be expressed as protein as a result of the transcription and translation.

The terms "expression" or "overexpression" describe, in the context of the invention, the production or increase in intracellular activity of one or more enzymes in a microorganism, which are encoded by the corresponding DNA. For this, it is possible for example to introduce a gene into an organism, replace an existing gene with another gene, increase the copy number of the gene or genes, use a strong promoter or use a gene that codes for a corresponding enzyme with a high activity; optionally, these measures can be combined.

Preferably said constructs according to the invention comprise a promoter 5'-upstream of the respective coding sequence and a terminator sequence 3'-downstream and optionally other usual regulatory elements, in each case operatively linked with the coding sequence.

A "promoter", of a "nucleic acid with promoter activity" or of a "promoter sequence" means, according to the invention, a nucleic acid which, functionally linked to a nucleic acid to be transcribed, regulates the transcription of said nucleic acid.

A "functional" or "operative" linkage means, in this connection, for example the sequential arrangement of one of the nucleic acids with promoter activity and of a nucleic acid sequence to be transcribed and optionally further regulatory elements, for example nucleic acid sequences that ensure the transcription of nucleic acids, and for example a terminator, in such a way that each of the regulatory elements can perform its function during transcription of the nucleic acid sequence. This does not necessarily require a direct linkage in the chemical sense. Genetic control sequences, for example enhancer sequences, can even exert their function on the target sequence from more remote positions or even from other DNA molecules. Arrangements are preferred in which the nucleic acid sequence to be transcribed is positioned behind (i.e. at the 3'-end of) the promoter sequence, so that the two sequences are joined together covalently. The distance between the promoter sequence and the nucleic acid sequence to be expressed transgenically can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise in particular a sequence coding for a cyclase mutant, e.g. derived from SEQ ID NO: 1 or coding for a mutant of SEQ ID NO: 2 to 326 or derivatives and homologs thereof, and the nucleic acid sequences derivable therefrom, which have been linked operatively or functionally with one or more regulatory signals advantageously for controlling, e.g. increasing, gene expression.

In addition to these regulatory sequences, the natural regulation of these sequences can still be present before the actual structural genes and optionally can have been genetically altered, so that the natural regulation has been switched off and expression of the genes has been increased. The nucleic acid construct can, however, also be of simpler construction, i.e. no additional regulatory signals have been inserted before the coding sequence and the natural promoter, with its regulation, has not been removed. Instead, the natural regulatory sequence is mutated so that regulation no longer takes place and gene expression is increased.

A preferred nucleic acid construct advantageously also contains one or more of the "enhancer" sequences already mentioned, functionally linked to the promoter, which make increased expression of the nucleic acid sequence possible. Additional advantageous sequences can also be inserted at the 3'-end of the DNA sequences, such as further regulatory elements or terminators. One or more copies of the nucleic acids according to the invention can be contained in the construct. The construct can also contain other markers, such as antibiotic resistances or auxotrophy complementing genes, optionally for selection on the construct.

Examples of suitable regulatory sequences are contained in promoters such as cos-, tac-, trp-, tet-, trp-tet-, lpp-, lac-, lpp-lac-, lacI$^q$, T7-, T5-, T3-, gal-, trc-, ara-, rhaP (rhaP$_{BAD}$) SP6-, lambda-P$_R$- or in the lambda-P$_L$-promoter, which advantageously find application in gram-negative bacteria. Further advantageous regulatory sequences are contained for example in the gram-positive promoters any and SPO2, in the yeast or fungal promoters ADC1, MFalpha, AC, P-60, CYC1, GAPDH, TEF, rp28, ADH. Artificial promoters can also be used for regulation.

For expression in a host organism, the nucleic acid construct is advantageously inserted into a vector, for example a plasmid or a phage, which makes optimal expression of the genes in the host possible.

Apart from plasmids and phage, vectors are also to be understood as all other vectors known by a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent a further embodiment of the invention.

Suitable plasmids are for example in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCl, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The stated plasmids represent a small selection of the possible plasmids. Further plasmids are well known by a person skilled in the art and can for example be found in the book Cloning Vectors (Eds. Pouwels P. H. et al. Elsevier, Amsterdam-New York-Oxford, 1985, ISBN 0 444 904018).

In another embodiment of the vector, the vector containing the nucleic acid construct according to the invention or the nucleic acid according to the invention can also advantageously be introduced in the form of a linear DNA into the microorganisms and integrated via heterologous or homologous recombination into the genome of the host organism. This linear DNA can consist of a linearized vector such as a plasmid or only of the nucleic acid construct or the nucleic acid according to the invention.

For optimal expression of heterologous genes in organisms, it is advantageous to alter the nucleic acid sequences corresponding to the specific "codon usage" used in the organism. The "codon usage" can easily be determined on the basis of computer evaluations of other known genes of the organism in question.

An expression cassette according to the invention is produced by fusion of a suitable promoter with a suitable coding nucleotide sequence and a terminator signal or polyadenylation signal. Common recombination and cloning techniques are used, as described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y.

(1984) and in Ausubel, F. M. et al., Current Protocols in Molecular Biology, Greene Publishing Assoc. and Wiley Interscience (1987).

For expression in a suitable host organism, advantageously the recombinant nucleic acid construct or gene construct is inserted into a host-specific vector, which makes optimal expression of the genes in the host possible. Vectors are well known by a person skilled in the art and are given for example in "Cloning vectors" (Pouwels P. H. et al., Ed., Elsevier, Amsterdam-New York-Oxford, 1985).

4. Microorganisms

Depending on the context, the term "microorganism" can mean the wild-type microorganism or a genetically altered, recombinant microorganism or both.

Using the vectors according to the invention, recombinant microorganisms can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example coprecipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

In principle, all prokaryotic or eukaryotic organisms may be considered as recombinant host organisms for the nucleic acid according to the invention or the nucleic acid construct. Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria.

The host organism or the host organisms according to the invention preferably contain at least one of the nucleic acid sequences, nucleic acid constructs or vectors described in the present invention, which code for an enzyme with phenylethanol dehydrogenase activity according to the above definition.

Depending on the host organism, the organisms used in the method according to the invention are grown or cultured in a manner known by a person skilled in the art. Microorganisms are as a rule grown in a liquid medium, which contains a carbon source generally in the form of sugars, a nitrogen source generally in the form of organic nitrogen sources such as yeast extract or salts such as ammonium sulfate, trace elements such as iron, manganese and magnesium salts and optionally vitamins, at temperatures between 0° C. and 100° C., preferably between 10° C. to 60° C. with oxygen aeration. The pH of the liquid nutrient can be kept at a fixed value, i.e. regulated or not during culture. Culture can be batchwise, semi-batchwise or continuous. Nutrients can be present at the beginning of fermentation or can be supplied later, semicontinuously or continuously.

5. Recombinant Production of Enzymes According to the Invention

The invention further relates to methods for recombinant production of polypeptides according to the invention or functional, biologically active fragments thereof, wherein a polypeptide-producing microorganism is cultured, optionally the expression of the polypeptides is induced and these are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like.

Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 150 and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

For the expression of mutants according to the invention, reference may be made to the description of expression of the wild-type enzyme EbN1 and the expression systems usable for this in WO2005/108590 and WO2006/094945, to which reference is hereby expressly made.

6. Enzyme Immobilization

The enzymes according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

7. Enzymatic Cyclization of Terpenes 7.1 General Description

In particular, the method of cyclization according to the invention is carried out in the presence of an enzyme, wherein the enzyme is encoded by a nucleic acid sequence according to SEQ ID NO: 1 or a functional equivalent thereof, wherein the nucleic acid sequence is a constituent of a gene construct or vector. Said gene constructs or vectors are described in detail in international application PCT/EP2010/057696 on pages 16 to 20, to which reference is expressly made here. Said functional equivalents, in particular those with citronellal-isopulegol cyclase activity, comprise in particular an F486 or F486-analog mutation, as defined herein.

The host cell, which contains a gene construct or a vector, in which the nucleic acid sequence is contained that codes for the enzyme with the desired activity, is also designated as transgenic organism. The production of said transgenic organisms is known in principle and is discussed for example in international application PCT/EP2010/057696 on page 20, to which reference is expressly made here.

Cells from the group comprising bacteria, cyanobacteria, fungi and yeasts are preferably selected as transgenic organisms. The cell is preferably selected from fungi of the genus *Pichia* or bacteria of the genera *Escherichia, Corynebacterium, Ralstonia, Clostridium, Pseudomonas, Bacillus, Zymomonas, Rhodobacter, Streptomyces, Burkholderia, Lactobacillus* or *Lactococcus*. Especially preferably, the cell is selected from bacteria of the species *Escherichia coli, Pseudomonas putida, Burkholderia glumae, Streptomyces lividans, Streptomyces coelicolor* or *Zymomonas mobilis*.

A method according to the invention is preferred, characterized in that the enzyme with the activity of a citronellal-isopulegol cyclase is encoded by a gene that was isolated from a microorganism, selected from *Zymomonas mobilis, Methylococcus capsulatus, Rhodopseudomonas palustris, Bradyrhizobium japonicum, Frankia spec, Streptomyces coelicolor* and *Acetobacter pasteurianus*. The relevant genes isolated from *Zymomonas mobilis, Streptomyces coelicolor, Bradyrhizobium japonicum* and *Acetobacter pasteurianus* should be mentioned in particular.

A method according to the invention is further preferred, characterized in that the enzyme with cyclase activity was generated by a microorganism that overproduces the enzyme and that was selected from the group of microorganisms comprising the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.

In particular, a method according to the invention should be mentioned that is characterized in that the enzyme with cyclase activity was produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis*, which overproduce the enzyme with cyclase activity.

Further embodiments for carrying out the biocatalytic cyclization method according to the invention, such as, for example, the method for production of isopulegol: The method according to the invention is characterized in that the enzyme is in at least one of the following forms:
  a) free, optionally purified or partially purified polypeptide;
  b) immobilized polypeptide;
  c) polypeptide isolated from cells according to a) or b);
  d) whole cell, optionally dormant or growing cells, comprising at least one such polypeptide;
  e) lysate or homogenizate of the cells according to d).

Another embodiment of the method according to the invention is characterized in that the cells are microorganisms, preferably transgenic microorganisms expressing at least one heterologous nucleic acid molecule coding for a polypeptide with the cyclase activity.

A preferred embodiment of the method according to the invention comprises at least the following steps a), b) and d):
  a) isolating or recombinantly producing a microorganism producing an enzyme with cyclase activity from a natural source or,
  b) multiplying this microorganism,
  c) optionally isolating the enzyme with cyclase activity from the microorganism or preparing a protein fraction comprising said enzyme, and
  d) transferring the microorganism according to stage b) or the enzyme according to stage c) to a medium that contains substrate, e.g. citronellal of general formula (I).

In the method according to the invention, substrate, such as, for example, citronellal is contacted with the enzyme, that has the activity of a citronellal-isopulegol cyclase, in a medium and/or is incubated so that conversion of the substrate, such as, for example, of citronellal, to isopulegol, takes place in the presence of the enzyme. Preferably the medium is an aqueous reaction medium.

The pH of the aqueous reaction medium in which the method according to the invention is preferably carried out is advantageously maintained between pH 4 and 12, preferably between pH 4.5 and 9, especially preferably between pH 5 and 8.

The aqueous reaction media are preferably buffered solutions, which as a rule have a pH of preferably from 5 to 8. The buffer used can be a citrate, phosphate, TRIS (Tris (hydroxymethyl)-aminomethane) or MES buffer (2-(N-morpholino)ethanesulfonic acid). Moreover, the reaction medium can contain other additives, for example detergents (for example taurodeoxycholate).

The substrate, such as, for example, citronellal, is used preferably in a concentration of 2-200 mM, especially preferably 5-25 mM in the enzymatic reaction and can be supplied continuously or discontinuously.

As a rule the enzymatic cyclization takes place at a reaction temperature below the deactivation temperature of the enzyme used and above −10° C. Preferably the method according to the invention is carried out at a temperature between 0° C. and 95° C., especially preferably at a temperature between 150 and 6000, in particular between 20 and 400, e.g. at about 25 to 30° C.

A method according to the invention in which the reaction of citronellal to isopulegol takes place at a temperature in the range from 20 to 40° C. and/or a pH in the range from 4 to 8 is especially preferred.

As well as these single-phase aqueous systems, in another variant of the invention, two-phase systems are also used. Then, as well as an aqueous phase, organic, non-water-miscible reaction media are used as the second phase. As a result, the reaction products accumulate in the organic phase. After the reaction, the product, such as, for example, isopulegol, in the organic phase can easily be separated from the aqueous phase that comprises the biocatalyst.

A method according to the invention is preferred wherein the production of isopulegol takes place in single-phase aqueous systems or in two-phase systems.

The reaction product isopulegol can be extracted with organic solvents and optionally can be distilled for purification.

Suitable organic solvents are for example aliphatic hydrocarbons, preferably with 5 to 8 carbon atoms, such as pentane, cyclopentane, hexane, cyclohexane, heptane, octane or cyclooctane, halogenated aliphatic hydrocarbons, preferably with one or two carbon atoms, such as dichloromethane, chloroform, carbon tetrachloride, dichloroethane or tetrachloroethane, aromatic hydrocarbons, such as benzene, toluene, the xylenes, chlorobenzene or dichlorobenzene, aliphatic acyclic and cyclic ethers or alcohols, preferably with 4 to 8 carbon atoms, such as ethanol, isopropanol, diethyl ether, methyl-tert-butyl ether, ethyl-tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof. Especially preferably, the aforementioned heptane, methyl-tert-butyl ether, diisopropyl ether, tetrahydrofuran, and ethyl acetate are used.

The cyclases used according to the invention can be used in the method according to the invention as free or immobilized enzyme, as already described above.

For the method according to the invention it is possible to use dormant or growing, free or immobilized cells, which contain nucleic acids, nucleic acid constructs or vectors coding for the cyclase. Lysed cells, such as cell lysates or cell homogenates can also be used. Lysed cells are for example cells that have been permeabilized by a treatment for example with solvents, or cells that have been disrupted by an enzyme treatment, by a mechanical treatment (e.g. French press or ultrasound) or by some other method. The resultant raw extracts are advantageously suitable for the method according to the invention. Purified or partially purified enzymes can also be used for the method.

Where free organisms or enzymes are used for the method according to the invention, they are usefully isolated, via a filtration or centrifugation, for example, prior to the extraction.

The method according to the invention can be operated batchwise, semibatchwise or continuously.

7.2. Enzymatic Cyclization of Citronellal

The citronellal of formula (II) used in accordance with the invention, and converted by means of an enzyme having citronellal-isopulegol cyclase activity, is available commercially both as (+)-R-citronellal of the formula (R-II) and as (−)-S-citronellal of the formula (S-II), and as a racemate of the formula (II).

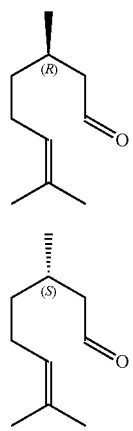

(R-II)

(S-II)

The isopulegol formed in accordance with the invention, of formula (I)

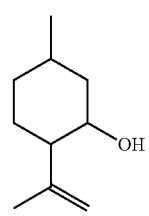

(I)

has a stereocenter in each of positions 1, 3 and 6, and so in principle there are 4 different diastereomers each with 2 enantiomers conceivable, in other words a total of 8 stereomers, if the starting point is the racemate of the citronellal of formula (I).

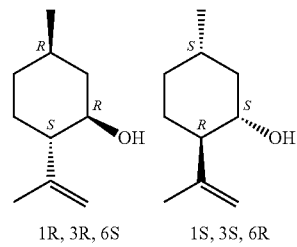

1R, 3R, 6S     1S, 3S, 6R

Isopulegol

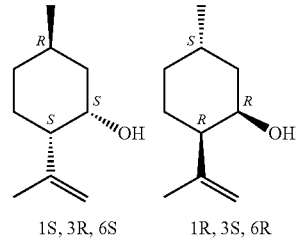

1S, 3R, 6S     1R, 3S, 6R

Non-Isopulegol

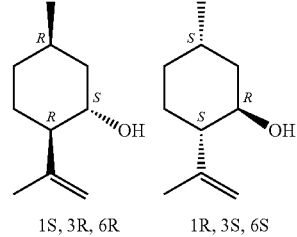

1S, 3R, 6R     1R, 3S, 6S

Iso-Isopulegol

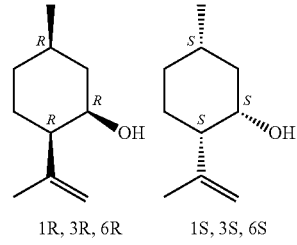

1R, 3R, 6R     1S, 3S, 6S

Epi-Isopulegol

Suitable enzymes having the activity of a citronellal-isopulegol cyclase are intramolecular transferases from the subclass of the isomerases; that is, proteins having the enzyme code EC 5.4 (enzyme code in accordance with Eur. J. Biochem. 1999, 264, 610-650). Preferably they are representatives having the enzyme code 5.4.99.17. Also suitable in particular as enzymes having the activity of citronellal-isopulegol cyclase are those cyclases which also bring about the cyclization of homofarnesol to ambroxan or of squalene to hopene, which are described exhaustively in international application PCT/EP2010/057696, hereby incorporated by reference; the enzymes and mutants described here are also suitable.

One particularly suitable embodiment of the method according to the invention is that wherein the enzyme used in the method according to the invention and having the activity of a citronellal-isopulegol cyclase possesses a polypeptide sequence which either a) is SEQ ID NO: 2, or
b) in which up to 25% of the amino acid residues are altered relative to SEQ ID NO: 2 by deletion, insertion, substitution or a combination thereof, and which still has at least 50% of the enzymatic activity of SEQ ID NO: 2.

Suitable enzymes with citronellal-isopulegol cyclase activity and comprising an amino sequence according to SEQ ID NO: 2, and also "functional equivalents" or analogs of the specifically disclosed enzymes (E) having citronellal-isopulegol cyclase activity, are described, as already indicated above, exhaustively in the international application PCT/EP2010/057696, hereby incorporated by reference.

In one particularly preferred embodiment of the method, the enzyme having citronellal-isopulegol cyclase activity is selected from enzymes which comprise an amino acid sequence according to SEQ ID NO: 2 or a sequence derived therefrom in which up to 25%, preferably up to 20%, more preferably up to 15%, in particular up to 10, 9, 8, 7, 6, 5, 4, 3, 2, 1% of the amino acid residues have been altered by a deletion, a substitution, an insertion or a combination of deletion, substitution and insertion, the polypeptide sequences altered relative to SEQ ID NO: 2 still possessing at least 50%, preferably 65%, more preferably 80%, more particularly more than 90% of the enzymatic activity of SEQ ID NO: 2. In this context, enzymatic activity of SEQ ID NO: 2 refers to the capacity to effect biocatalytic cyclization of citronellal of general formula (II) to the corresponding isopulegol of formula (I).

The method according to the invention is carried out preferably in the presence of an enzyme, the enzyme being encoded by a nucleic acid sequence according to SEQ ID NO: 1 or a functional equivalent thereof.

Functional equivalents here describe in principle nucleic acid sequences which under standard conditions undergo hybridization with a nucleic acid sequence or parts of a nucleic acid sequence and are capable of bringing about the expression of a protein having the same properties as those of the enzyme having citronellal-isopulegol cyclase activity in a cell or in an organism.

A functional equivalent is additionally understood to refer to nucleic acid sequences which are homologous or identical to a defined percentage with a particular nucleic acid sequence ("original nucleic acid sequence") and have the same activity as the original nucleic acid sequences, and also, in particular, natural or artificial mutations of these nucleic acid sequences.

The nucleic acid sequences which can be used for encoding the enzymes having citronellal-isopulegol cyclase activity that can be used in the method according to the invention are likewise described exhaustively in international application PCT/EP2010/057696, hereby incorporated by reference.

With particular preference the method according to the invention is carried out in the presence of an enzyme, the enzyme being encoded by a nucleic acid sequence according to SEQ ID NO: 1 or a functional equivalent thereof, the nucleic acid sequence being part of a gene construct or vector. Such gene constructs or vectors are described exhaustively in international application PCT/EP2010/057696 on pages 16 to 20, hereby incorporated by reference.

With very particular preference the method according to the invention is carried out in the presence of an enzyme, where the enzyme is encoded by a nucleic acid sequence according to SEQ ID NO: 1 or a functional equivalent thereof, the nucleic acid sequence being part of a gene construct or vector which are present in a host cell.

The host cell which comprises a gene construct or a vector in which the nucleic acid sequence is present that encodes the enzyme having the citronellal-isopulegol cyclase activity is also referred to as a transgenic organism. The production of such transgenic organisms is known in principle and is discussed, for example, in international application PCT/EP2010/057696 on page 20, hereby incorporated by reference.

Transgenic organisms selected are preferably cells from the group consisting of bacteria, cyanobacteria, fungi and yeasts. The cell is preferably selected from fungi of the genus *Pichia* or bacteria of the genera *Escherichia, Corynebacterium, Ralstonia, Clostridium, Pseudomonas, Bacillus, Zymomonas, Rhodobacter, Streptomyces, Burkholderia, Lactobacillus* or *Lactococcus*. With particular preference the cell is selected from bacteria of the species *Escherichia coli, Pseudomonas putida, Burkholderia glumae, Streptomyces lividans, Streptomyces coelicolor* or *Zymomonas mobilis*.

A preferred method according to the invention is that wherein the enzyme having the activity of a citronellal-isopulegol cyclase is encoded by a gene which has been isolated from a microorganism selected from the group of microorganisms consisting of *Zymomonas mobilis, Methylococcus capsulatus, Rhodopseudomonas palustris, Bradyrhizobium japonicum, Frankia* spec. and *Streptomyces coelicolor*. With particular preference the gene in question has been isolated from *Zymomonas mobilis*.

Preferred furthermore is a method according to the invention wherein the enzyme having the activity of a citronellal-isopulegol cyclase has been produced by a microorganism which overproduces the enzyme having the activity of a citronellal-isopulegol cyclase and which has been selected from the group of microorganisms consisting of the genera *Escherichia, Corynebacterium, Ralstonia, Clostridium, Pseudomonas, Bacillus, Zymomonas, Rhodobacter, Streptomyces, Burkholderia, Lactobacillus* and *Lactococcus*.

A particularly preferred method according to the invention is that wherein the enzyme having the activity of a citronellal-isopulegol cyclase has been produced by transgenic microorganisms of the species *Escherichia coli, Pseudomonas putida, Burkholderia glumae, Corynebacterium glutamicum, Saccharomyces cerevisiae, Pichia pastoris, Streptomyces lividans, Streptomyces coelicolor, Bacillus subtilis* or *Zymomonas mobilis* which overproduce the enzyme having the activity of a citronellal-isopulegol cyclase.

The above-described further embodiments for carrying out the biocatalytic method according to the invention for cyclizing terpenes apply correspondingly in respect of the production of isopulegol.

9A further subject of the present invention is also the use of an enzyme having the activity of a citronellal-isopulegol cyclase for the biocatalytic conversion of citronellal to isopulegol.

Preference is given to the use of an enzyme having the activity of a citronellal-isopulegol cyclase for the biocatalytic conversion of citronellal to isopulegol, wherein the enzyme possesses a polypeptide sequence which either a) is SEQ ID NO: 2, or
b) in which up to 25% of the amino acid residues are altered relative to SEQ ID NO: 2 by deletion, insertion, substitution or a combination thereof, and which still has at least 50% of the enzymatic activity of SEQ ID NO: 2.

Also preferred is the use of an enzyme having the activity of a citronellal-isopulegol cyclase for the biocatalytic conversion of citronellal to isopulegol, wherein the enzyme is encoded by a nucleic acid sequence according to SEQ ID NO: 1 or a functional equivalent thereof.

A further subject of the present invention is also the use of a gene construct or vector comprising a nucleic acid sequence according to SEQ ID NO: 1 or a functional equivalent thereof which encode a polypeptide having the activity of a citronellal-isopulegol cyclase which serves the biocatalytic conversion of citronellal to isopulegol in a method of production of isopulegol by cyclization of citronellal.

Likewise a further subject of the present invention is the use, as well, of a host cell which comprises a gene construct or a vector comprising a nucleic acid sequence according to SEQ ID NO: 1 or a functional equivalent thereof for producing an enzyme having the activity of a citronellal-isopulegol cyclase for the biocatalytic conversion of citronellal to isopulegol.

The method described above opens up for the first time the possibility of cyclizing citronellal to isopulegol by means of an enzyme.

8. Methods of Production of Menthol

The isopulegol prepared inventively can be converted into menthol by catalytic hydrogenation in a conventional way. Suitable for this purpose, as well as conventional hydrogenation processes, is, in particular, a catalytic method, as described in WO 2009/013192.

The method according to the invention is implemented in particular using catalysts comprising
   45% to 55% by weight of oxygen-containing compounds of nickel, calculated as NiO,
   25% to 35% by weight of oxygen-containing compounds of zirconium, calculated as $ZrO_2$,
   5% to 20% by weight of oxygen-containing compounds of copper, calculated as CuO,
   1% to 3% by weight of oxygen-containing compounds of molybdenum, calculated as $MoO_3$, and
   0% to 5% by weight of further components,
the figures in % by weight adding up to 100% by weight and relating to the dry, unreduced catalyst.

One particularly preferred catalyst is composed of 49% to 53% by weight of NiO, 15% to 19% by weight of CuO, 28% to 32% by weight of $ZrO_2$ and 1% to 2% by weight of $MoO_3$ and also, optionally, 0% to 3% by weight of further components such as graphite, for example, the respectively selected weight fractions of the individual components being based on the dry, unreduced catalyst and adding up to 100% by weight. Catalysts of this kind are known and can be produced for example as described in EP 0 696 572 or in WO 2009/013192.

In general the catalysts are used preferably in the form of unsupported catalyst. The term "unsupported catalyst" refers to a catalyst which in contrast to a supported catalyst is composed only of catalytically active material. Unsupported catalysts can be used by introducing the catalytically active material, ground to a powder, into the reaction vessel, or by disposing the catalytically active material in the reactor after grinding, mixing with shaping aids, shaping and heat-treating in the form of shaped catalyst bodies—for example, as spheres, cylinders, tablets, rings, coils, strands and the like.

In the context of one preferred embodiment of the hydrogenation method according to the invention, the selected heterogeneous catalyst is employed in the form of a fixed-bed catalyst.

To implement the method according to the invention, the isopulegol starting material as described above is contacted with hydrogen and with the selected catalyst. The hydrogen here may be used in undiluted form, typically in a purity of about 99.9% by volume, or in diluted form, i.e. in the form of mixtures with inert gases such as nitrogen or argon, for example. It is preferred to use hydrogen in undiluted form. The reaction can be carried out successfully without adding solvent or in the presence of organic solvents which are inert under the reaction conditions, such as, for example, methanol, ethanol, isopropanol, hexane, heptane, cyclohexane and the like. It is preferred to carry out the reaction without adding solvent.

The hydrogenation of isopulegol in accordance with the invention can be carried out under a hydrogen pressure (absolute) in the range from 1 to 200 bar, such as from 2 or 3 to 200 bar, in particular from 4 or 5 to 150 bar, such as from 5 to 100 bar, or in the range from 5 to 50 bar. As a reaction temperature for implementing the hydrogenation according to the invention, a temperature is selected, advantageously, that is in the range from 20 to 150° C., such as from 40 to 130° C., or from 60 to 110° C. and more particularly from 70 to 100° C.

The practical approach to the implementation is generally to supply the isopulegol for conversion to the catalyst, which is typically located in a fixed bed reactor heated, in particular, from the outside, such as a tube reactor, autoclave or tube-bundle reactor, for example, at the desired reaction temperature and under the desired pressure. The velocity over the catalyst in this case is generally 0.1 to 1.0, such as 0.1 to 0.6 or 0.2 to 0.4, kg of isopulegol per kg of catalyst per hour. In this context it may be useful to heat the isopulegol that is to be used, even before it is supplied to the reaction vessel or to the reactor, this heating being preferably to reaction temperature.

The reactor can be operated either in liquid phase mode or in trickle mode—that is, the starting materials may be passed through the reactor either from bottom to top or from top to bottom. The hydrogenation method of the invention can be carried out either batchwise or continuously. In both cases, unreacted starting material can be circulated together with the hydrogen.

The hydrogenation according to the invention may also be carried out in stages in a cascade of two or more reactors, i.e. 2 to in general 4, such as 2 or 3, for example, reactors connected in series, preferably fixed bed reactors. In this case, in the first reactor, typically referred to as the main reactor, the main conversion of the reaction is achieved under the reaction conditions described above, and the crude product obtained is passed to a second reactor, typically referred to as secondary reactor, in which the as yet unreacted starting material is at least largely converted inventively into L-menthol. The reaction conditions here may be selected, independently of one another, preferably in the ranges stated above.

The method of the invention can be carried out batchwise, semibatchwise or continuously. It is preferred to carry out the method continuously, more particularly entirely continuously, in which case the starting materials are introduced continuously into the reactor and the resulting reaction mixture or reaction product is discharged continuously from the reactor. It has further proven advantageous, in view of the position of the melting point of the reaction product according to the invention, namely menthol, especially L-menthol, to provide for heating of the transport lines used.

The method of the invention allows menthol to be produced by catalytic hydrogenation of isopulegol, with typically only a minor degree of formation of unwanted diastereomers of menthol. Accordingly, when using isopulegol with a corresponding purity, the method of the invention yields menthol of the formula (III) in a chemical purity of 97% by weight or more, preferably of 98% to 100% by weight, more preferably of 98.5% to 99.9% by weight, very preferably at least 99% to 99.9% by weight. The term "chemical purity" here also encompasses the diastereomeric purity of the resulting menthol in relation to the diastereomers neoisomenthol of formula (IIIa), neomenthol of formula (IIIb) and isomenthol of formula (IIIc). Accordingly, in the context, the method according to the invention preferably yields menthol having a diastereomeric purity of 97% by weight or more, preferably of 98% to 100% by weight, more preferably of 98.5% to 99.9% by weight and very preferably of at least 99% to 99.9% by weight.

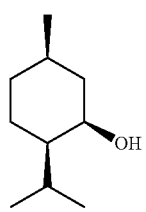

(IIIa)

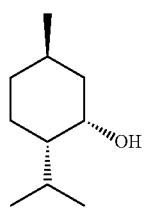

(IIIb)

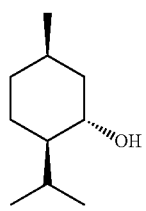

(IIIc)

Where isopulegol is used in optically active form—preferably, in accordance with the invention, mixtures comprising predominantly the L-isopulegol enantiomer—the method product according to the invention that is obtained is generally menthol in optically active form, preferably in the form of (−)- or L-menthol. The hydrogenation according to the invention proceeds generally largely without notable racemization of the material used. Accordingly, according to the enantiomeric excess of the optically active isopulegol used, optically active menthol, preferably L-menthol when using L-isopulegol, is obtained as the product, with an enatiomeric excess (ee) of 80% ee or more, preferably of 85% or 90% ee or more, more preferably of 95% to 100% ee, more preferably of 96% to 99.9% ee, very preferably of 97% to 99.8% ee, even more preferably of 98% to 99.7% ee, and with more particular preference of 98.5% to 99.6% ee.

The menthol obtained according to the invention is notable, furthermore, for a particularly low level of the unwanted by-products menthone of formula (IIId) and isomenthone of formula (IIIe) and neoisomenthol of formula (IIIa).

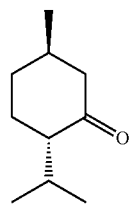

(IIId)

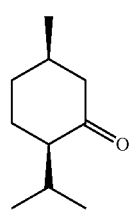

(IIIe)

These by-products are obtained generally, in the context of the method according to the invention, only in a proportion, relative to the amount of menthol obtained, of up to 0.5% by weight, preferably 0.4% by weight, more preferably 0.3% by weight, more particularly 0.2% by weight, and very preferably 0.1% to 0% by weight.

9. Examples of Substrates which can be Used for Enzymatic or Biocatalytic Conversions According to the Invention:

The enzymes and microorganisms described herein are especially suitable for converting compounds of the general formula IV above. Non-limiting examples thereof are summarized in table A below, which gives the structural formula and the chemical name.

TABLE A
Further substrates
Formula (IV)
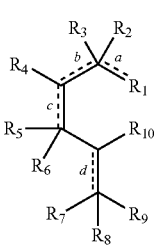
| Name |
|---|
| Citral 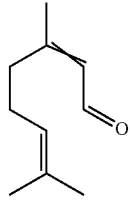 |
| Neral 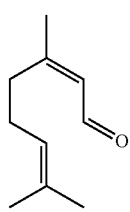 |
| Nerol 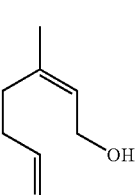 |
| Nerylacetone 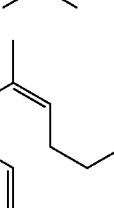 |
| Geranial 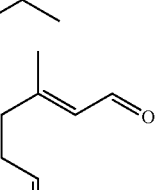 |
| Geraniol 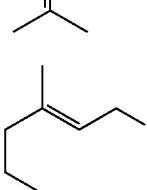 |
TABLE A-continued
Further substrates
Formula (IV)
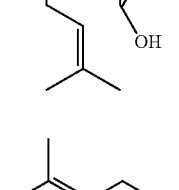
| Name |
|---|
| Geranylic acid 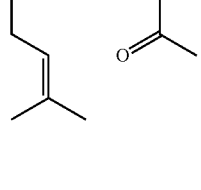 |
| cis-Geranylic acid 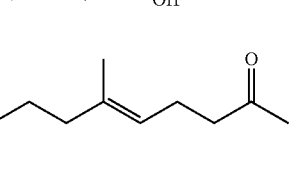 |
| Geranylacetone 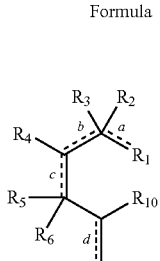 |
| Farnesol 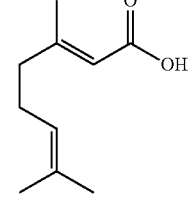 |
| Farnesylacetone 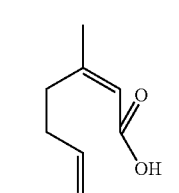 |

TABLE A-continued
Further substrates
Formula
(IV)
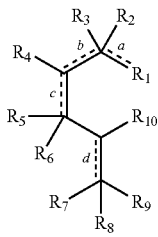
| Name |
|---|
| Homofarnesylic acid |
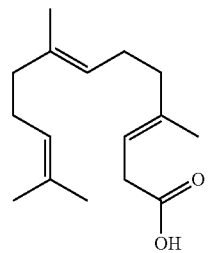 [SMILES: CC(C)=CCC/C(C)=C/CC/C(C)=C/CC(=O)O]
Homofarnesol
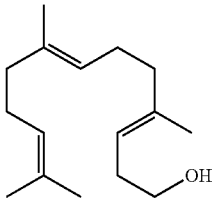 [SMILES: CC(C)=CCC/C(C)=C/CC/C(C)=C/CCO]
Trimethyl-tridecatetraene
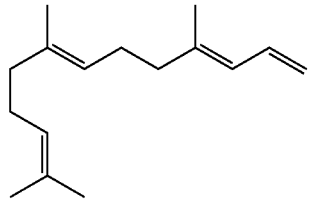 [SMILES: C=C/C=C(\C)CC/C=C(\C)CCC=C(C)C]
Melonal
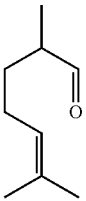
Nonadienal
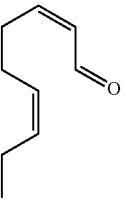
TABLE A-continued
Further substrates
Formula
(IV)
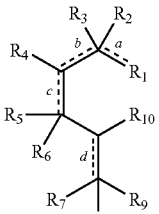
| Name |
|---|
| Citronellol |
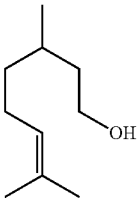
β-Citronellene
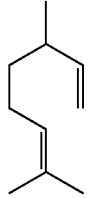
Citronellic acid
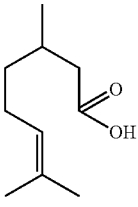
Hydroxycitronellal
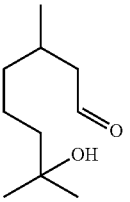
Heptanal
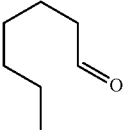
Linalool
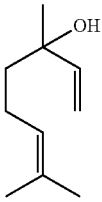

TABLE A-continued

Further substrates

Formula (IV)

[Structure of Formula IV with R1-R10 substituents]

| Name |
|---|
| Farnesene (β) |
| Myrcene |
| Myrcenol |
| Dihydromyrcenol |
| Lavandulol |
| Nerolidol |
| (E)-β-Ocimene (4 isomers present) |
| Tagetone |
| Solanone |
| 2,6,10-Trimethyl-9-undecanal |

The reaction products produced in the conversion of these substrates can be detected and quantified in a conventional way using standard analytical methods, such as chromatography, HPLC, gas chromatography, mass spectrometry, GC/MS or MALDI-TOF, and combinations thereof.

If nonimmobilized organisms or enzymes are used for the method according to the invention, preferably these are separated prior to extraction, for example by filtration or centrifugation.

The method according to the invention can be operated batchwise, semi-batchwise or continuously.

EXPERIMENTAL SECTION

In the absence of special information in the examples below, the general information below is taken to apply.

A. General Information

All materials and microorganisms used are commercially available products.

Unless stated otherwise, the cloning and expression of recombinant proteins is carried out by standard methods, as described for example in Sambrook, J., Fritsch, E. F. and Maniatis, T., Molecular Cloning: A Laboratory Manual, 2nd edition, Cold Spring Harbor Laboratory, Cold Spring Harbor Laboratory Press, Cold Spring Harbor, N.Y., 1989.

a) Bacterial Strains, Plasmids and Growing Conditions

All experiments were carried out with *E. coli*. The SHC proteins were expressed in *E. coli* BL21 (DE3) pLysS or *E. coli* Rosetta pLysRAR62, comprising pET16b constructs with the respective shc gene, by growing in Luria-Bertani medium, supplemented with ampicillin (100 μg/ml), chloramphenicol (34 μg/ml), and 0.5 mM isopropylthio-β-D-galactoside at $OD_{600}$ of 0.4 and additional growth for 4 hours at 30° C.

b) Vector Constructs

The respective squalene-hopene cyclase gene (e.g. *Zymomonas mobilis* ZMO1548 [NC_006526.2, region: 1578816 . . . 1580993]) was PCR-amplified from chromosomal DNA, using corresponding primer pairs (e.g. ZMO1548-fwd (5'-gcgctgtttcatatgggtattgaca-3') (SEQ. ID. NO: 327) and ZMO1548-rev (5'-gcgcttaccctggatcctcgaaaat-3') (SEQ. ID. NO: 328)). The restriction enzyme digested (e.g. with NdeI/BamHI) PCR product was cloned into pET16b, (obtaining e.g.) pET1584. The constructs were verified by DNA sequencing and transformed into *E. coli* XL1-blue.

The shc-gene from other microorganisms (e.g. from *A. acidocaldarius*) was cloned similarly.

All plasmids were transformed individually into *E. coli* BL21 (DE3) pLysS or *E. coli* Rosetta pLys-RAR62.

c) Cyclization Assay with Various Substrates (Standard Conditions)

Recombinant *E. coli* cells were suspended in 20 mM Tris-HCl pH 8.0 (3 ml per g moist cells). The cyclization mixture contained 250 μl of cell suspension, 50 μl of 1 M citrate buffer (pH 4.5), 20 mM (final concentration) of substrate and water to 500 μl. In the cyclization of squalene, 1% (v/v) Triton-X100 was added. For the homofarnesol cyclization, *E. coli* cells (6 g moist cells) were suspended in solubilization buffer (50 mM phosphate, 10 mM $MgCl_2$ (pH 6.5; total volume: 25 ml). The cells were lysed at 1500 bar using a Manton-Gaulin homogenizer. Insoluble cellular debris was centrifuged off (15 min at 4° C. and 7150*g). The cyclization mixture contained 1 ml raw cell extract and 20 mM homofarnesol in 1.25 ml buffer (50 mM potassium phosphate, 45 mM $MgCl_2$ (pH 6.5). The reaction mixture was stirred at 30° C. with a magnetic stirrer. The reaction was stopped by extraction with heptane. The organic phase was analyzed by gas chromatography. Controls were carried out with *E. coli* cells bearing an empty vector and with heat-inactivated SHC-expressing cells. Formation of cyclization products was never observed with the controls (data not shown).

d) Gas Chromatography

Terpenoids were analyzed qualitatively and quantitatively by gas chromatography using an Agilent 7890A gas chromatograph, equipped with a DB-5 column (20 m×0.1 mm×0.1 μm) and an ionization detector. 3 μl of the solvent extract was applied on the column (split ratio 1:5, helium flow rate 0.25 or 0.5 ml/min, injector temperature 250° C.). To separate linear and cyclic monoterpenoids, the initial furnace temperature (6000) was raised to 130° C. at 40° C./min, at 2° C./min to 150° C. and then at 40° C./min to 200° C. The retention times of the terpenoids were as follows: (R, S)-citronellal (7.55 min), isopulegol (7.70 min), neo-isopulegol (7.90 min), iso-isopulegol (8.10 min), neoiso-isopulegol (8.25 min), 1-decanol (9.91 min).

For the detection of triterpenes, the injector temperature was set at 300° C. The furnace temperature was initially 60° C., and was increased at 40° C./min to 220° C. and then at 6° C./min to 310° C. and held constant there for 10 min. Squalene and hopene eluted after 19.2 min and 26.9 min respectively.

Homofarnesol and ambroxan were analyzed on a 10 m Optima 1 column (Macherey&Nagel, Düren, Germany). The initial furnace temperature (100° C.) was increased at 5° C./min to 200° C. and held at this temperature for 5 min. Then it was increased at 30° C./min to 320°. An analysis took 40 min. The retention times were as follows: homofarnesol (10.8 min), ambroxan (9.9 min).

As an alternative, a Shimadzu GC-MS QP 2010 system with an FS Supreme 5 column (30 m×0.25 mm×0.25 μm) was used for coupled GC/MS analysis (split ratio 1:20; 3 min 120° C., increase to 135° C. at 2° C./min and further increase to 365° C. at 10° C./min, followed by cooling to 300° C. at 70° C./min). The GC-MS data were analyzed using LabSolutions GCsolutions Postrun software. It should be noted that the substrates citronellal racemate, (R)-citronellal and (S)-citronellal always contain small amounts of isopulegol and neo-isopulegol as impurities. The GC surface values for these linear terpenoids were established as 100%. The surface values for the isopulegol isomers in the product were corrected by the amount of isopulegol isomer that was already present in the substrate. The standard deviation was calculated on the basis of 24 individual tests using two separately grown *E. coli* cultures.

B. Examples

Example 1: Production of Mutants of the F486X Type of the Squalene-Hopene Cyclases by Rational Protein Design Using Quick-Change Mutagenesis The mutants of various squalene-hopene cyclases were incorporated by means of "quick-change" mutagenesis into the corresponding gene. The procedure based on the manufacturer's information (Agilent Technologies, Waldbronn) was largely followed. First, a PCR was carried out:

| | |
|---|---|
| PCR charge: | 1.8 μl DMSO |
| | 2 μl dNTPs (each 2.5 mM) |
| | 1.5 μl forward primer (10 pmol/μl) |
| | 1.5 μl reverse primer (10 pmol/μl) |
| | 1 μl templates (1 μg/μL; recombinant plasmid bearing SHC gene, for example pETZmSHC_1) |
| | 0.2 μl Prime-Star Polymerase (Takara, 2.5 Units/μl) |
| | 6 μl 5x buffer |
| | 16 μl $H_2O$ |
| PCR program: | (1) 95° C. 3 minutes |
| | (2) 95° C. 45 seconds |
| | (3) 53° C. 1 minute |
| | (4) 68° C. 17 minutes |
| | 5x repetition of steps (2), (3) and (4) |

After the PCR, 10 μl of the charge was digested with the restriction enzyme DpnI for at least 1 hour at 37° C. Then transformation into *E. coli* XL1-blue cells was carried out. After DNA sequencing, transformation into the expression strain e.g. *E. coli* Rosetta pLysRAR62 took place. The gene can also be modified similarly in other expression plasmids.

The following primers were used for the quick-change PCR. The respective exchange is shown printed in bold in the primer names. The genes that are modified by the respective primers are indicated with italics in the primer names; there is the following correspondence:

| Primer name | Sequence | SEQ ID NO |
|---|---|---|
| ZmSHC_1F486Ilefor | GTTATTATCCTTATCGATGGCTCCCCAACCG | 329 |
| ZmSHC_1F486Ilerev | GGTTGGGGAGCCATCGATAAGGATAATAACAG | 330 |
| ZmSHC_1F486Metfor | GTTATTATCCTTATCCATGGCTCCCCAACCG | 331 |
| ZmSHC_1F486Metrev | GGTTGGGGAGCCATGGATAAGGATAATAACAG | 332 |
| ZmSHC_1F486Thrfor | GTTATTATCCTTATCGGTGGCTCCCCAACCG | 333 |
| ZmSHC_1F486Thrrev | GGTTGGGGAGCCACCGATAAGGATAATAACAG | 334 |
| ZmSHC_1F486Glnfor | GTTATTATCCTTATCCTGGGCTCCCCAACCG | 335 |
| ZmSHC_1F486Glnrev | GGTTGGGGAGCCCAGGATAAGGATAATAACAG | 336 |
| ZmSHC_1F486Asnfor | GTTATTATCCTTATCGTTGGCTCCCCAACCG | 337 |
| ZmSHC_1F486Asnrev | GGTTGGGGAGCCAACGATAAGGATAATAACAG | 338 |
| ZmSHC_1F486Lysfor | GTTATTATCCTTATCTTTGGCTCCCCAACCG | 339 |
| ZmSHC_1F486Lysrev | GGTTGGGGAGCCAAAGATAAGGATAATAACAG | 340 |
| ZmSHC_1F486Aspfor | GTTATTATCCTTATCATCGGCTCCCCAACCG | 341 |
| ZmSHC_1F486Asprev | GGTTGGGGAGCCGATGATAAGGATAATAACAG | 342 |
| ZmSHC_1F486Glufor | GTTATTATCCTTATCTTCGGCTCCCCAACCG | 343 |
| ZmSHC_1F486Glurev | GGTTGGGGAGCCGAAGATAAGGATAATAACAG | 344 |
| ZmSHC_1F486Trpfor | GTTATTATCCTTATCCCAGGCTCCCCAACCG | 345 |
| ZmSHC_1F486Trprev | GGTTGGGGAGCCTGGGATAAGGATAATAACAG | 346 |
| ZmSHC_1F486Argfor | GTTATTATCCTTATCACGGGCTCCCCAACCG | 347 |
| ZmSHC_1F486Argrev | GGTTGGGGAGCCCGTGATAAGGATAATAACAG | 348 |
| ZmSHC_1F486Cysfor | GTTATTATCCTTATCGCAGGCTCCCCAACCG | 349 |
| ZmSHC_1F486Cysrev | GGTTGGGGAGCCTGCGATAAGGATAATAACAG | 350 |
| ZmSHC_1F486Gfor | GTTATTATCCTTATCACCGGCTCCCCAACCG | 351 |
| ZmSHC_1F486Grev | GGTTGGGGAGCCGGTGATAAGGATAATAACAG | 352 |
| ZmSHC_1F486Sfor | GTTATTATCCTTATCGCTGGCTCCCCAACCG | 353 |
| ZmSHC_1F486Srev | GGTTGGGGAGCCAGCGATAAGGATAATAACAG | 354 |
| ZmSHC_1F486Pfor | GTTATTATCCTTATCCGGGGCTCCCCAACCG | 355 |
| ZmSHC_1F486Prev | GGTTGGGGAGCCCCGGATAAGGATAATAACAG | 356 |
| ZmSHC_1F486Hfor | GTTATTATCCTTATCATGGGCTCCCCAACCG | 357 |
| ZmSHC_1F486Hrev | GGTTGGGGAGCCCATGATAAGGATAATAACAG | 358 |
| ZmSHC_1F486Lfor | GTTATTATCCTTATCCAGGGCTCCCCAACCG | 359 |
| ZmSHC_1F486Lrev | GGTTGGGGAGCCCTGGATAAGGATAATAACAG | 360 |
| ZmSHC_1F486Vfor | GTTATTATCCTTATCAACGGCTCCCCAACCG | 361 |
| ZmSHC_1F486Vrev | GGTTGGGGAGCCGTTGATAAGGATAATAACAG | 362 |
| ZmSHC_1F486Afor | GTTATTATCCTTATCCGCGGCTCCCCAACCG | 363 |
| ZmSHC_1F486Arev | GGTTGGGGAGCCGCGGATAAGGATAATAACAG | 364 |
| ZmSHC_1F486Yfor | GTTATTATCCTTATCATAGGCTCCCCAACCG | 365 |
| ZmSHC_1F486Yrev | GGTTGGGGAGCCTATGATAAGGATAATAACAG | 366 |
| ZmSHC_1Y702Cfor | GCCGATAAAAATCGCAACGCAGCATAAACG | 367 |
| ZmSHC_1Y702Crev | CGTTTATGCTGCGTTGCGATTTTTATCGGC | 368 |
| ZmSHC_1Y702Ffor | GCCGATAAAAATCTTTACGCAGCATAAACG | 369 |
| ZmSHC_1Y702Frev | CGTTTATGCTGCGTAAAGATTTTTATCGGC | 370 |
| ZmSHC_1Y702Afor | GCCGATAAAAATCCGCACGCAGCATAAACG | 371 |
| ZmSHC_1Y702Arev | CGTTTATGCTGCGTGCGGATTTTTATCGGC | 372 |
| ZmSHC_1Y702Sfor | GCCGATAAAAATCGCTACGCAGCATAAACG | 373 |
| ZmSHC_1Y702Srev | CGTTTATGCTGCGTAGCGATTTTTATCGGC | 374 |
| ZmSHC_1Y561Afor | GAACCGCACCGGTGCCATAGATCGCATTAACG | 375 |
| ZmSHC_1Y561Arev | GGTTTGGTCGTTGGGCGTTAATGCGATCTATGG | 376 |
| ZmSHC_1Y705Afor | CCATAATCGGGAAGAATTGCCGCGCAAAATC | 377 |
| ZmSHC_1Y705Arev | CTGCGTTATGATTTTGCGCGGCAATTCTTC | 378 |
| ZmSHC_2F486Cfor | GGCGGTTGGGGCGCTTGCGATGCCAATAACAG | 379 |

-continued

| Primer name | Sequence | SEQ ID NO |
|---|---|---|
| ZmSHC_2F486Crev | CTGTTATTGGCATCGCAAGCGCCCCAACCG CC | 380 |
| ApF486Crev | CATTATCTTTATCGCATGCACCCCAACCAC C | 381 |
| ApF486Cfor | GGTGGTTGGGGTGCATGCGATAAAGATAAT G | 382 |
| BjF486Cfor | CGGCTGGGGCGCGTGCGATAAAGATAAC | 383 |
| BjF486Crev | GTTATCTTTATCGCACGCGCCCCAGCCG | 384 |
| ScF486Cfor | CGGCGCCTGGGGCGCCTGCGACGTCGACA AC | 385 |
| ScF486Crev | GTTGTCGACGTCGCAGGCGCCCCAGGCGC CG | 386 |

ZmSHC_1 SEQ ID NO: 2;
ZmSHC_2 SEQ ID NO: 6;
Ap SEQ ID NO: 4;
Bj SEQ ID NO: 5 and
Sc SEQ ID NO: 3.

Example 2: Activity Tests with Mutants of Squalene-Hopene Cyclase-1 (SHC-1) from *Zymomonas mobilis*

The influence of various single mutations, produced according to example 1, in the sequence position corresponding to F486, on the cyclase activity was determined for various substrates.

a) Citronellal

After the general detection of a slight cyclization activity of the squalene-hopene cyclase-1 from *Zymomonas mobilis* (SEQ ID NO:2) with respect to citronellal, the turnover rate was greatly improved by rational protein design. Exchange of the phenylalanine residue F486 for alanine led in preliminary tests (cf. FIG. 2) to a greatly increased production of isopulegol (2) starting from citronellal (1).

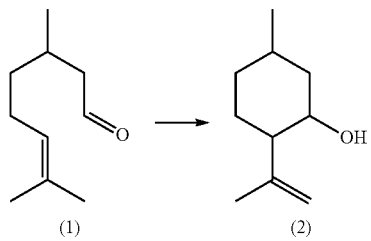

The increased activity of the SHC_1-F486A mutant was then investigated in more detail. In addition to a far better conversion of the citronellal substrate, it was also found that this prefers the R(+) isomer as substrate and compared with the WT it is also converted in a much shorter time (cf. FIG. 2). Whereas with the WT enzyme the reaction with R(+)-citronellal is not measurable until after quite long incubation, the F486A mutant shows high conversions, in particular at the start of the reaction. This effect is not observed with S(−)-citronellal as substrate. It is notable that the F486A mutant only forms isopulegol I and II, whatever the stereoconfiguration of the substrate. The WT, in contrast, is dependent on the stereoconfiguration of the substrate and forms, as well as isopulegol I, mainly isopulegol II from R(+)-citronellal and almost exclusively isopulegol III from S(−)-citronellal.

Figure 3:
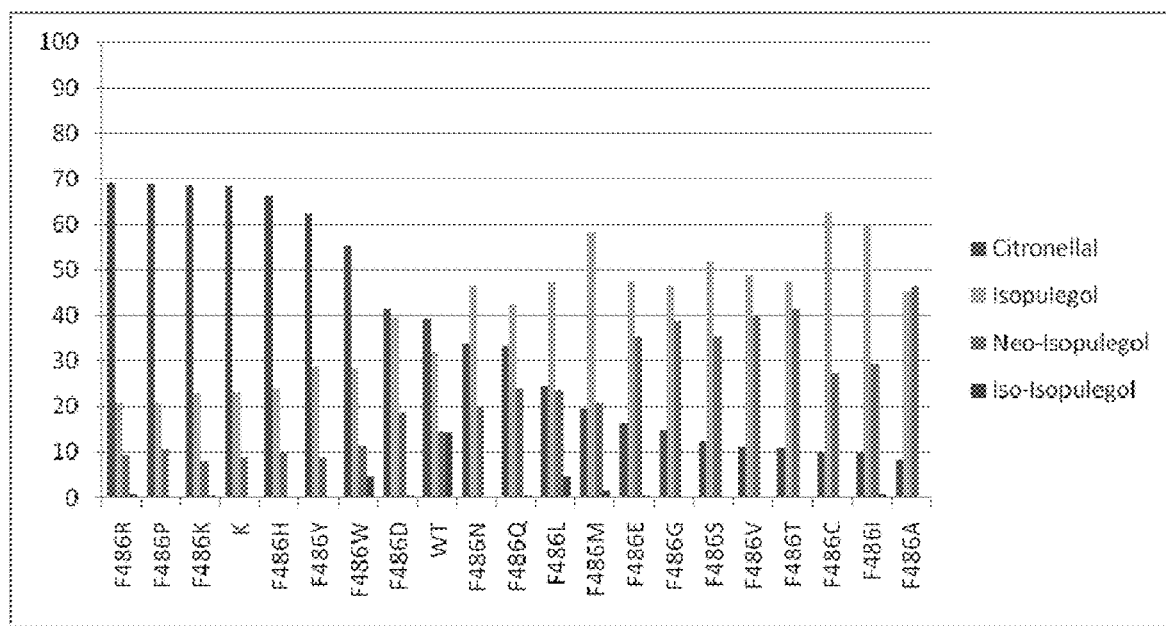
FIG. 3 shows the turnover of the various mutants of Zm-SHC-1 compared with the wild type (wt) and the control without enzyme (K) with 10 mM citronellal racemate as substrate. The percentage distribution of substrate and isopulegol product isomers after incubation overnight at 30° C. is shown in each case.

Based on these results, in further experiments the importance of the amino acid residues at position 486 was investigated more closely. For this, by means of mutagenesis, the phenylalanine residue was exchanged against each further amino acid and the activity of the various muteins was tested with citronellal as substrate (for sequences see FIGS. 1a and b). It was found that some amino acids at this position not only improve the conversion of citronellal by the enzyme, but additionally lead to higher product specificity in the reaction, so that fewer isomers of isopulegol are produced (see FIG. 3).

Exchange for arginine, proline and lysine leads to a loss in activity with respect to citronellal. The amounts of product determined also occur, in the same distribution, as contamination in the negative control ('K' see FIG. 3). The highest activity was observed after exchange for valine, threonine, cysteine, isoleucine and alanine. Overall, the altered product spectrum of some muteins is notable. Not all show the formation of three isopulegol peaks as the wild type as well as the quantitative distribution differs.

There are altogether $2^3$ isopulegol isomers:

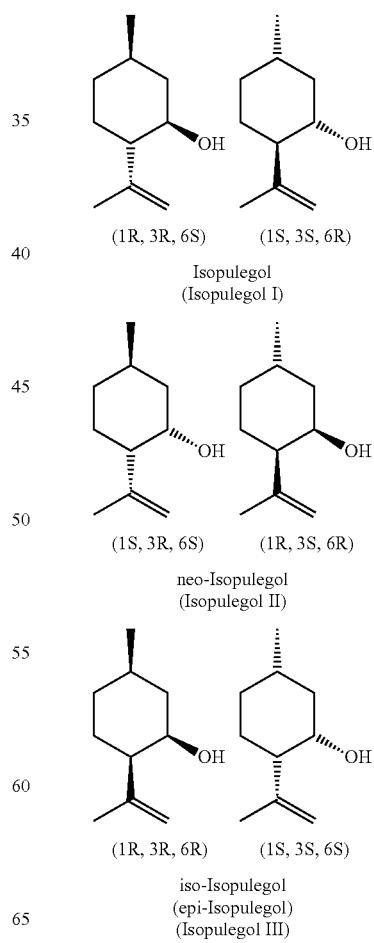

(1S, 3R, 6R)    (1R, 3S, 6S)

neo-iso-Isopulegol
(Isopulegol IV)

Until now, the main product (isopulegol I) has been assigned to the enantiomeric pair (1R,3R,6S)-isopulegol or (1S,3R,6R)-isopulegol.

The highest yield of isopulegol with the least by-products (consisting of further isomers) accompanied by high enzyme activity is displayed by the Zm-SHC-1 F486C mutant.

b) Squalene

Figure 4:
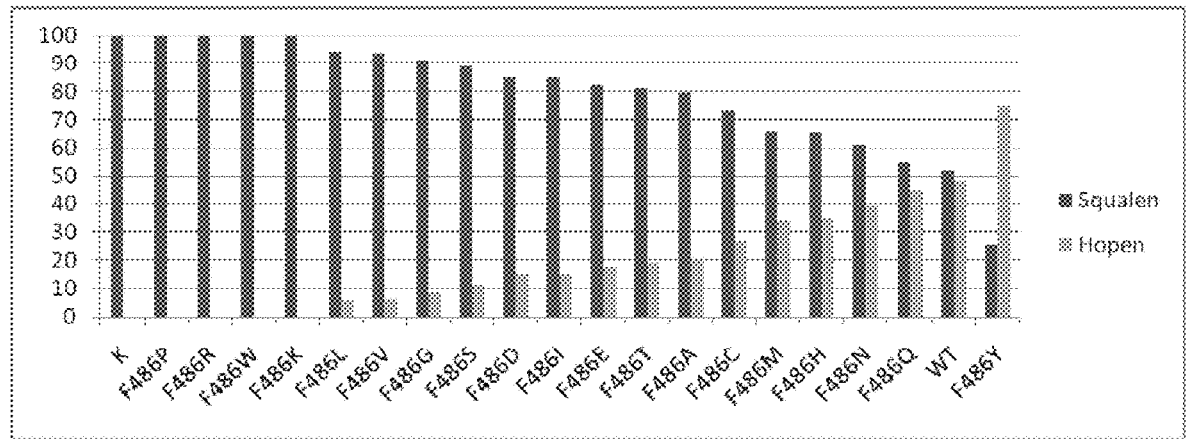
FIG. 4 shows the turnover of the various Zm-SHC-1 mutants compared with the wild type (wt) and the control without enzyme (K) with 25 mM squalene as substrate in the presence of 1% Triton. The percentage distribution of squalene and hopene after incubation for 70 h at 300 is shown in each case.

Clear changes in activity after mutation at position F486 are also seen with squalene as substrate. Interestingly, in this case the exchange of phenylalanine for tyrosine produces almost a doubling of the conversion (see FIG. 4).

Example 3: Activity Tests with Mutants of Other Squalene-Hopene Cyclases

The influence of various single mutations, produced according to example 1, in the sequence position corresponding to F486 on the cyclase activity of various other SHCs was determined for various citronellal substrates (in each case 20 mM overnight incubation):

The mutants are as follows:
Ap-SHC: F481C,
Bj-SHC: F447C,
Sc-SHC: F449C,
Zm SHC-2: F438C The phenylalanine residues are located in positions that are analogous to the F486 of Zm-SHC-1 (SEQ ID NO:2).

Figure 5:
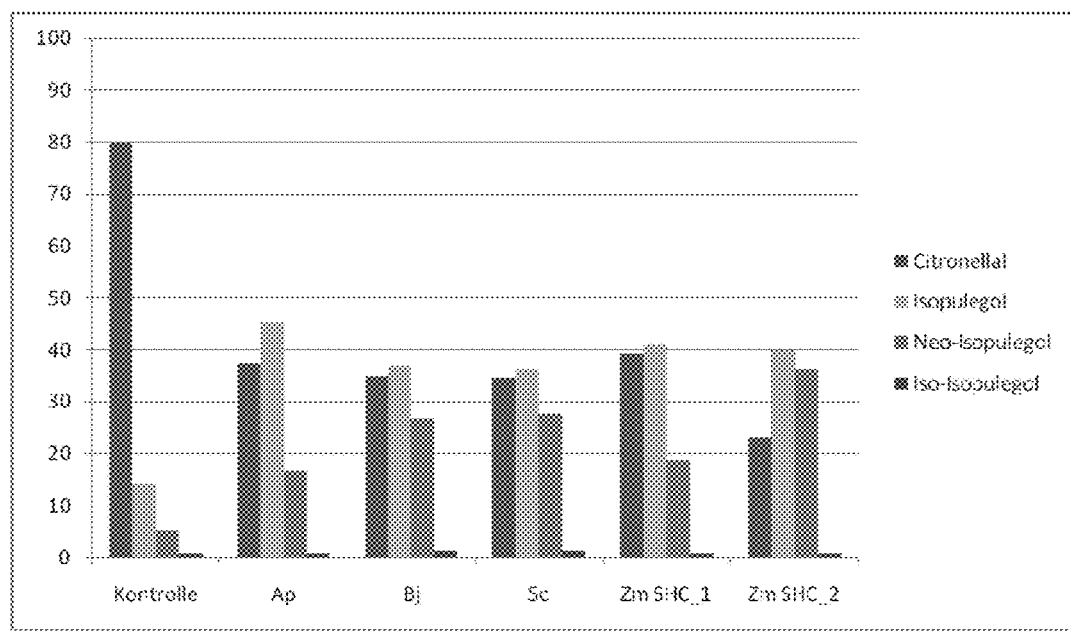
FIGS. 5 to 7 show the reaction of in each case 20 mM substrate after incubation overnight with the mutants Ap-SHC: F481C, Bj-SHC: F447C, Sc-SHC: F449C, Zm SHC-2: F438C and Zm SHC-1 compared with the control; the substrates were citronellal racemate in FIG. 5, R(+)-citronellal in FIG. 6 and S(−)-citronellal in FIG. 7.
Figure 6:
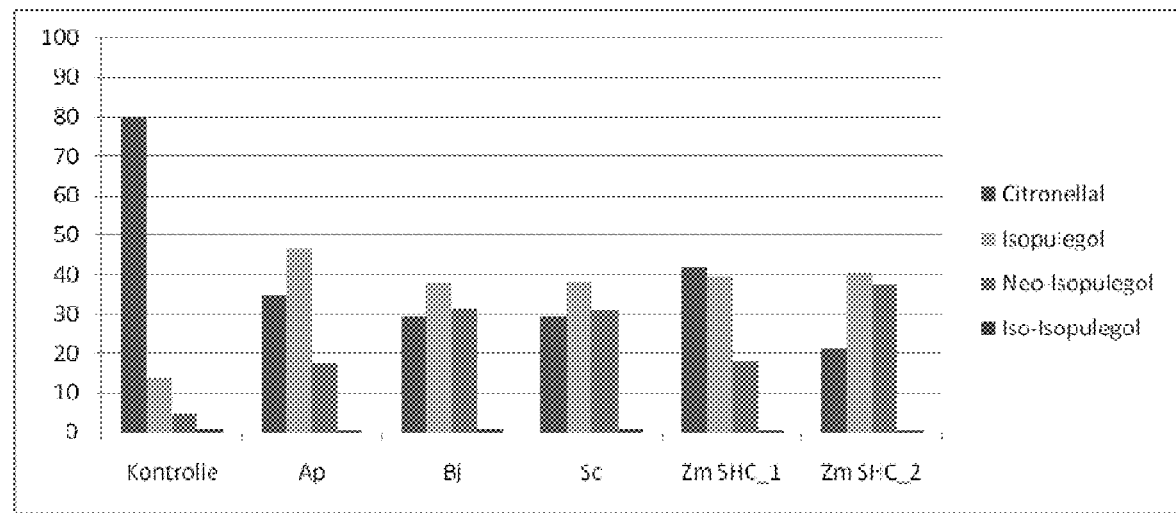
Figure 7:
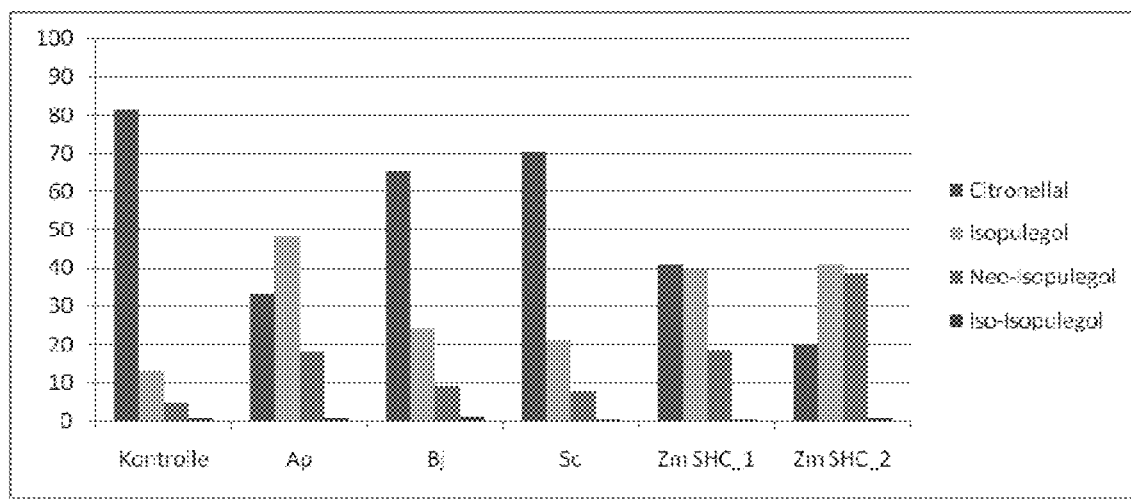

The results can be seen in FIG. 5 (citronellal racemate as substrate), FIG. 6 (R(+)-citronellal as substrate), and FIG. 7 (S(−)-citronellal as substrate). The control was a charge without active biocatalyst.

It can be seen that the wild-type enzymes, through mutation at the stated position corresponding to F486 (of Zm SHC-1), can now cyclize citronellal to isopulegol and moreover convert the R(+) form with increased selectivity compared with the S(−) form.

Example 4: Conversion of Compounds of Formula IV

These substances were converted under conditions corresponding to those employed for the conversion of citronellal as described above.

Example 5: Isolation and Characterization of the Squalene-Hopene Cyclase from *Zymomonas mobilis* (Zm-SHC)

International application PCT/EP2010/057696, hereby incorporated by reference, describes how, using specific oligonucleotides, the Zm-SHC gene from the genomic DNA of *Zymomonas mobilis* was amplified and expressed in *Escherichia coli*.

a) Material and Methods:

Addressed below are only materials and methods not mentioned in this form in international application PCT/EP2010/057696.

b) Strains, Plasmids and Culture Conditions:

The *E. coli* strain DH5α, the *E. coli* strain BL21 (DE3) pLysS (Novagen) and the *E. coli* Rosetta strain were used. The plasmid pET16b (Novagen) was used for cloning. For the overexpression of the SHC, moreover, the plasmid pLysRAR62 was additionally transformed for the adaptation of the codon usage to *E. coli*. Furthermore, the plasmid pDHE+ZmSHC-1 from *E. coli* Lu15568 was used (international application PCT/EP2010/057696). The strains were grown using LB medium at 30° C.

c) Chemicals:

Squalene, (+/−)-citronellal, (+)-R-citronellal and (−)-S-citronellal were purchased from Sigma (Sigma-Aldrich Chemie GmbH, Munich). Restriction enzymes, T4 ligase, and DNA polymerase came from New England Biolabs (New England Biolabs GmbH, Frankfurt).

d) Isolation of DNA and Transformation:

Plasmids were isolated from *E. coli* using the Qiaprep Spin Miniprep Kits from Qiagen (Qiagen, GmbH, Hilden). For gel extractions or PCR purifications, the Qiaquick Gel Extraction Kit from Qiagen was used. All of the *E. coli* strains used were transformed using the $CaCl_2$ method.

e) PCR and Sequencing:

The DNA from *Zymomonas mobilis* subspec. *mobilis* CP4 was provided by Prof. Sprenger (Institute of Microbiology, University of Stuttgart). The PCR was carried out using Prime Star Polymerase. The following primers were used for synthesizing the squalene-hopene cyclase gene from *Zymomonas mobilis*:

```
SHC_1:
SHC-for
TATGCATATGGGTATTGACAGAAT      (SEQ ID NO: 387)

SHC-rev
CCGGATCCTCAATTATTCAAATCAATC   (SEQ ID NO: 388)
```

The correctness of the cloned genes was verified by means of sequencing by the company GATC Biotech. Sequence analyses were carried out using the program Clone Manager 7.0. After restriction of the corresponding amplificates, they were cloned in-frame into the pET16b vector using N-terminally encoded His-tag. The plasmids were subsequently transformed first in *E. coli* DH5α and thereafter in *E. coli* BL21 (DE3)pLysS and *E. coli* Rosetta. For better expression, the plasmid pLysRAR62 was transformed into the *E. coli* Rosetta strains in addition to the pET16b constructs. Corresponding clonings with empty vectors were carried out in parallel. In addition, the plasmid pDHE+ZmSHC_1 (corresponding to SHC_1 with codon usage adapted to *E. coli*) was transformed in *E. coli* BL21 (DE3) pLysS.

f) Expression and Cell Digestion:

The corresponding *E. coli* Bl21 (DE3) pLySS and *E. coli* Rosetta transformants were cultured in LB medium with ampicillin and chloramphenicol (100 μg/ml and 32 μg/ml, respectively) at 3000. The synthesis of the squalene-hopene cyclases was induced by addition of 0.5-1 mM IPTG or 0.1% rhamnose (when using the pDHE derivatives) with an $OD_{600}$ of 0.4-0.6. The cells were allowed to grow further for 4-6 hours, and subsequently harvested. This was done by centrifuging off the cells and taking them up in 5 ml/g wet weight of 25 mM Tris/HCl with 40% glycerol. If the cells were not used further immediately, they were stored at −20° C. For digestion of the cells, they were each subjected 2× to a French Press and used, either directly or following removal of the cell debris by centrifugation, for the activity assays. Alternatively, cell digestion took place using ultrasound. Following centrifugation, the SHC proteins were subsequently dissolved with solubilization buffer (50 mM Tris/HCl pH 8, 10 mM $MgCl_2$, 1% Triton X-100) to remove the cell debris, and hence partially enriched.

g) Activity Assays:

Each batch for determining the activity of the squalene-hopene cyclases had a final volume of 1 ml. This was made up of 600 µl of cells digested by French Press (alternatively 800 µl after solubilization from the cell membrane), 100 mM Na citrate buffer with different pH levels (pH 4.0 to pH 8.0 were used for testing) and 10 mM substrate solution [(+/−)citronellal, (+)-R-citronellal and (−)-S-citronellal]. In addition to the substrate and $H_2O$, the substrate solution also comprised Triton X-100, which was present in each of the activity batches at a concentration of 0.2%.

The batches were incubated with shaking for 6 hours to 24 hours at temperatures of 22° C., 30° C. and 37° C. The substrate and possible products were extracted with one volume of chloroform or hexane/propanol in a ratio of 2:3. The extract was used directly for analysis by gas chromatography.

h) GC Measurements:

The gas-chromatographic measurements took place on an Agilent 7890A gas chromatograph with flame ionization detector. The column used was a DB-5 (Agilent Technologies) with a length of 20 m, a diameter of 0.1 mm and 0.25 µM coating. Substances were identified by comparison of the retention times with available standard solutions.

For verification, the samples were analyzed in parallel on a Shimadzu Gas chromatograph with mass spectrometer. Using the column FS Supreme with a length of 30 m, an internal diameter of 0.25 mm and a coating of 0.25 µm, the retention times were again compared with standard solutions, and the respective mass spectra of the substances present were analyzed.

With the aid of a standard, the diastereomer identified below as isopulegol I was assigned to (1R,3R,6S) or (1S,3S,6R) isopulegol, whereas no assignment was possible for the isomers identified as isopulegol II and isopulegol III.

i) Results of the Activity Assays:
1. Test 1a: (comparative) (controls i.e. results with boiled-off protein, with empty vector and without protein)

|  | pH 4.0 | pH 4.5 | pH 5.0 | pH 5.5 | pH 6.0 | pH 6.5 | pH 7.0 |
|---|---|---|---|---|---|---|---|
| Citronellal | 85.4 | 85.4 | 86.0 | 85.6 | 84.4 | 84.7 | 85.1 |
| Isopulegol I | 10.8 | 10.8 | 10.4 | 10.8 | 11.7 | 11.5 | 11.2 |
| Isopulegol II | 3.8 | 3.8 | 3.6 | 3.6 | 3.9 | 3.8 | 3.7 |
| Isopulegol III | 0 | 0 | 0 | 0 | 0 | 0 | 0 | information below concerning the substrate rac-citronellal, take place with the amounts of isopufegol found in the controls having already been deducted.

2. Test 1 b: Comparison of the two overexpressed SHC_1 proteins (from pDHE and pET16b vector and influence of the His-tag on activity at pH 4.5)

|  | pDHE | pET16b |
|---|---|---|
| Citronellal | 95.2 | 95.2 |
| Isopulegol I | 0.7 | 0.8 |
| Isopulegol II | 1.7 | 1.6 |
| Isopulegol III | 2.4 | 2.4 |

3. Test 1c: pH dependence

|  | pH 4.0 | pH 4.5 | pH 5.0 | pH 5.5 | pH 6.0 | pH 6.5 | pH 7.0 |
|---|---|---|---|---|---|---|---|
| Citronellal | 95.9 | 94.9 | 94.7 | 94.4 | 95.1 | 98.7 | 98.8 |
| Isopulegol I | 0.4 | 0.8 | 0.8 | 1.0 | 1.1 | 0.8 | 0.5 |
| Isopulegol II | 1.1 | 2.4 | 2.1 | 2.1 | 1.6 | 0.5 | 0.7 |
| Isopulegol III | 2.6 | 1.9 | 2.4 | 2.5 | 2.2 | 0 | 0 |

4. Test 1d: Influence of salts at pH 4.5

|  | none | $BaCl_2$ | $CaCl_2$ | $MgCl_2$ |
|---|---|---|---|---|
| Citronellal | 94.9 | 95.2 | 94.9 | 95.0 |
| Isopulegol I | 0.7 | 0.8 | 1.0 | 0.9 |
| Isopulegol II | 2.5 | 2.4 | 2.4 | 2.5 |
| Isopulegol III | 1.9 | 1.6 | 1.7 | 1.6 |

5. Test 1e: Influence of temperature at pH 4.5

|  | 22° C. | 30° C. | 37° C. |
|---|---|---|---|
| Citronellal | 95.3 | 94.9 | 95.4 |
| Isopulegol I | 0.8 | 1.0 | 0.8 |
| Isopulegol II | 1.8 | 2.2 | 1.6 |
| Isopulegol III | 2.1 | 1.9 | 2.2 |

6. Test 2: S(−)-Citronellal as substrate

|  | pH 4.0 | CTRL | pH 4.5 | CTRL | pH 5.0 | CTRL | pH 5.5 | CTRL |
|---|---|---|---|---|---|---|---|---|
| Citronellal | 90.8 | 95.5 | 90.8 | 95.7 | 91.7 | 96.2 | 92.4 | 96.2 |
| Isopulegol I | 4.9 | 4.5 | 4.7 | 4.3 | 4.4 | 3.8 | 4.1 | 3.8 |
| Isopulegol II | 0 | 0 | 0 | 0 | 0 | 0 | 0 | 0 |
| Isopulegol III | 4.3 | 0 | 4.5 | 0 | 3.9 | 0 | 3.5 | 0 |

|  | pH 6.0 | CTRL | pH 6.5 | CTRL | pH 7.0 | CTRL |
|---|---|---|---|---|---|---|
| Citronellal | 94.1 | 96.6 | 96.4 | 96.5 | 96.5 | 96.4 |
| Isopulegol I | 3.8 | 3.4 | 3.6 | 3.5 | 3.5 | 3.6 |
| Isopulegol II | 0 | 0 | 0 | 0 | 0 | 0 |
| Isopulegol III | 2.1 | 0 | 0 | 0 | 0 | 0 |

7. Test 3: R-(+)-Citronellal as substrate

|  | pH 4.0 | CTRL | pH 4.5 | CTRL | pH 5.0 | CTRL | pH 5.5 | CTRL |
|---|---|---|---|---|---|---|---|---|
| Citronellal | 80.0 | 84.2 | 78.4 | 83.8 | 81.1 | 85.6 | 81.7 | 86.8 |
| Isopulegol I | 15.9 | 15.8 | 16.0 | 16.2 | 14.1 | 14.4 | 13.5 | 13.2 |
| Isopulegol II | 4.1 | 0 | 5.6 | 0 | 4.8 | 0 | 4.8 | 0 |
| Isopulegol III | 4.3 | 0 | 4.5 | 0 | 3.9 | 0 | 3.5 | 0 |

|  | pH 6.0 | CTRL | pH 6.5 | CTRL | pH 7.0 | CTRL |
|---|---|---|---|---|---|---|
| Citronellal | 81 | 85.5 | 80.8 | 85.8 | 81.4 | 86.2 |
| Isopulegol I | 14.3 | 14.5 | 14.5 | 14.2 | 14.0 | 13.8 |
| Isopulegol II | 4.7 | 0 | 4.7 | 0 | 4.6 | 0 |
| Isopulegol III | 2.1 | 0 | 0 | 0 | 0 | 0 | j) Summary of the Results:

The squalene-hopene cyclase from *Zymomonas mobilis* was prepared recombinantly in *E. coli*. The enzyme is able to convert citronellal to isopulegol.

Here, the two overproduced Zm-SHC-1 proteins, once without and once with N-terminally appended His-tag, showed no differences in their activity under the conditions tested (cf. Test 1 b).

This reaction was verified after 12 hours with the techniques described. The dependence of the reaction on the pH level was low. In a pH range from pH 4 to pH 6, conversion rates totaling about 5% were measured for different isopulegol isomers after 20-hour incubation.

Here it was not critical whether the batches were incubated at RT, 3000 or 3700. The conversion was also not increased by addition of divalent ions, such as $MgCl_2$, for example (cf. Test 1d). What was critical, however, was that the cell extracts, in the case of measurements above a pH of 5, either were dialyzed before the substrate was added, or EDTA was added to the batches, in order to suppress reduction of the citronellal substrate to citronellol by enzymes of the host. No effect of this treatment on the activity of the Zm-SHC-1 was found. Where this treatment was not carried out, the substrate was reduced almost completely to citronellol within 20 hours, and there was no longer any measurable cyclization to isopulegol. Zm-SHC-1 is therefore able to cyclize citronellal, but not citronellol, to isopulegol. It is very likely that unspecific dehydrogenases are responsible for the reduction reaction.

In order to rule out a chemical reaction being responsible for the cyclization, boiled-off cell extracts were used. In these controls and in controls with cell extracts from cultivation with empty vectors, however, no corresponding conversion was found (cf. Test 1a).

With (+/−)-citronellal as the substrate it was possible, following the reaction, to detect various isomers of isopulegol, which have not yet been precisely identified (cf. Tests 2 and 3). In order to verify whether these isomers originated from the different isomers of the starting substrate or if only one isomer was accepted as the substrate and was differently converted, the same studies were carried out with (+)-R-citronellal and (−)-S-citronellal. Here it was found that, depending on the substrate, different isopulegol isomers are formed. Interestingly, the conversion of (+)-R-citronellal took place from a pH of 4 to a pH of 7 without substantial differences, at a rate of about 5%. The enantiomer, in contrast, was converted with conversion rates of approximately 4.5% only up to a pH level of pH 6. Here as well, the conversion rate showed virtually no fluctuation in terms of the individual pH levels between pH 4 and pH 6.

Sequences:
SEQ ID NO: 1-326 nucleic acid/amino acid sequences of various SHC genes
SEQ ID NO: 327-388 PCR primers
The disclosure of the publications cited herein is expressly referred to.
There follows a listing of SHC enzyme sequences which can be used in accordance with the invention:

```
Enzyme Sequences
                                                                    >seq_ID 4
MNMASRFSLKKILRSGSDTQGTNVNTLIQSGTSDIVRQKPAPQEPADLSALKAMGNSLTHTLSSAC

EWLMKQQKPDGHWVGSVGSNASMEAEWCLALWFLGLEDHPLRPRLGKALLEMQRPDGSWGTY

YGAGSGDINATVESYAALRSLGYAEDDPAVSKAAAWIISKGGLKNVRVFTRYWLALIGEWPWEKT

PNLPPEIIWFPDNFVFSIYNFAQWARATMMPLAILSARRPSRPLRPQDRLDALFPGGRANFDYELP

TKEGRDVIADFFRLADKGLHWLQSSFLKRAPSREAAIKYVLEWIIWHQDADGGWGGIQPPWVYGL

MALHGEGYQFHHPVMAKALDALNDPGWRHDKGDASWIQATNSPVWDTMLSLMALHDANAEERF

TPEMDKALDWLLSRQVRVKGDWSVKLPNTEPGGWAFEYANDRYPDTDDTAVALIAIASCRNRPE

WQAKGVEEAIGRGVRWLVAMQSSCGGWGAFDKDNNKSILAKIPFCDFGEALDPPSVDVTAHVLE

AFGLLGLPRDLPCIQRGLAYIRKEQDPTGPWFGRWGVNYLYGTGAVLPALAALGEDMTQPYISKA

CDWLINCQQENGGWGESCASYMEVSSIGHGATTPSQTAWALMGLIAANRPQDYEAIAKGCRYLID

LQEEDGSWNEEEFTGTGFPGYGVGQTIKLDDPAISKRLMQGAELSRAFMLRYDLYRQLFPIIALSR

ASRLIKLGN
                                                                    >seq_ID 2
MGIDRMNSLSRLLMKKIFGAEKTSYKPASDTIIGTDTLKRPNRRPEPTAKVDKTIFKTMGNSLNNTL

VSACDWLIGQQKPDGHWVGAVESNASMEAEWCLALWFLGLEDHPLRPRLGNALLEMQREDGS
```

```
WGVYFGAGNGDINATVEAYAALRSLGYSADNPVLKKAAAWIAEKGGLKNIRVFTRYWLALIGEWP

WEKTPNLPPEIIWFPDNFVFSIYNFAQWARATMVPIAILSARRPSRPLRPQDRLDELFPEGRARFDY

ELPKKEGIDLWSQFFRTTDRGLHWVQSNLLKRNSLREAAIRHVLEWIIRHQDADGGWGGIQPPWV

YGLMALHGEGYQLYHPVMAKALSALDDPGWRHDRGESSWIQATNSPVWDTMLALMALKDAKAE

DRFTPEMDKAADWLLARQVKVKGDWSIKLPDVEPGGWAFEYANDRYPDTDDTAVALIALSSYRD

KEEWQKKGVEDAITRGVNWLIAMQSECGGWGAFDKDNNRSILSKIPFCDFGESIDPPSVDVTAHV

LEAFGTLGLSRDMPVIQKAIDYVRSEQEAEGAWFGRWGVNYIYGTGAVLPALAAIGEDMTQPYITK

ACDWLVAHQQEDGGWGESCSSYMEIDSIGKGPTTPSQTAWALMGLIAANRPEDYEAIAKGCHYLI

DRQEQDGSWKEEEFTGTGFPGYGVGQTIKLDDPALSKRLLQGAELSRAFMLRYDFYRQFFPIMAL

SRAERLIDLNN

>seq_ID 5
MTVTSSASARATRDPGNYQTALQSTVRAAADWLIANQKPDGHWVGRAESNACMEAQWCLALWF

MGLEDHPLRKRLGQSLLDSQRPDGAWQVYFGAPNGDINATVEAYAALRSLGFRDDEPAVRRARE

WIEAKGGLRNIRVFTRYWLALIGEWPWEKTPNIPPEVIWFPLWFPFSIYNFAQWARATLMPIAVLSA

RRPSRPLPPENRLDALFPHGRKAFDYELPVKAGAGGWDRFFRGADKVLHKLQNLGNRLNLGLFR

PAATSRVLEWMIRHQDFDGAWGGIQPPWIYGLMALYAEGYPLNHPVLAKGLDALNDPGWRVDVG

DATYIQATNSPVWDTILTLLAFDDAGVLGDYPEAVDKAVDWVLQRQVRVPGDWSMKLPHVKPGG

WAFEYANNYYPDTDDTAVALIALAPLRHDPKWKAKGIDEAIQLGVDWLIGMQSQGGGWGAFDKD

NNQKILTKIPFCDYGEALDPPSVDVTAHIIEAFGKLGISRNHPSMVQALDYIRREQEPSGPWFGRW

GVNYVYGTGAVLPALAAIGEDMTQPYIGRACDWLVAHQQADGGWGESCASYMDVSAVGRGTTT

ASQTAWALMALLAANRPQDKDAIERGCMWLVERQSAGTWDEPEFTGTGFPGYGVGQTIKLNDPA

LSQRLMQGPELSRAFMLRYGMYRHYFPLMALGRALRPQSHS

>seq_ID 78
MTLTSSASARAPRDPGNYQTALQSTVRAAADWLIANQKPDGHWVGRAESNACMEAQWCLALWF

MGLEDHPLRKRLGQSLLDTQRPDGAWQVYFNAPNGDINATVEAYAALRSLGYPDSEPAVRRARE

WIEAKGGLRNIRVFTRYWLALIGEWPWEKTPNIPPEVIWFPLWFPFSIYNFAQWARATLMPIALLSA

RRPSRPLPPENRLDTLFPRGRDAFDYELPVKANAGGWDKFFRGADKVLHALQNFGNRLNLGLFR

PAATSRVLEWMIRHQDFDGAWGGIQPPWIYGLMALYAEGYPLNHPVLAKGLDALNDPGWRVDVG

EATYIQATNSPVWDTILTLLAFDDAGVLGDYPDAVDKAVNWVLARQVRVPGDWSMKLPHVKPGG

WAFEYANNHYPDTDDTAVALIALAPLRHDPKWKAKGIDEAIQLGVDWLIGMQSQGGGWGAFDKD

NNQQILTKIPFCDYGEALDPPSVDVTAHIVEAFGKLGISRNHPSMVQALDYIRKEQEPSGPWFGRW

GVNYVYGTGAVLPALAAIGEDMTQPYIGRACDWLVAHQQPDGGWGESCASYMDISAVGRGTTTA

SQTAWALMALLAANRPQDKDAIERGCMWLVERQSAGTWDEPEFTGTGFPGYGVGQTIKLTDPSL

QERLMQGPELSRAFMLRYGMYRHYFPLMALGRALRPQGHG

>seq_ID 209
MDSILAPRADAPRNIDGALRESVQQAADWLVANQKPDGHWVGRAETNATMEAQWCLALWFLGL

EDHPLRVRLGRALLDTQRPDGAWHVFYGAPNGDINATVEAYAALRSLGHRDDEEPLRKARDWILS

KGGLANIRVFTRYWLALIGEWPWEKTPNILPEVIWLPTWFPFSIYNFAQWARATLMPIAVLSAHRPS

RPLAPQDRLDALFPQGRDSFNYDLPARLGAGVWDVIFRKIDTILHRLQDWGARRGPHGIMRRGAI

DHVLQWIIRHQDYDGSWGGIQPPWIYGLMALHTEGYAMTHPVMAKALDALNEPGWRIDIGDATFI

QATNSPVWDTMLSLLAFDDAGLGERYPEQVERAVRWVLKRQVLVPGDWSVKLPDVKPGGWAFE

YANNFYPDTDDTSVALMALAPFRHDPKWQAEGIEDAIQRGIDWLVAMQCKEGGWGAFDKDNDKK
```

-continued

ILAKIPFCDFGEALDPPSADVTAHIIEAFAKVGLDRNHPSIVRALDYLKREQEPEGPWFGRWGVNYV

YGTGAVLPALAAIGEDMRQPYIARACDWLIARQQANGGWGESCVSYMDAKQAGEGTATASQTA

WALMALIAADRPQDRDAIERGCLYLTETQRDGTWQEVHYTGTGFPGYGVGQTIKLNDPLLSKRLM

QGPELSRSFMLRYDLYRHYFPMMAIGRVLRQRGDRSGH

>seq_ID 193
MNVIRQLNSGVNAAKSLDDGIESAIEWLAENQDKEGFWVGMLESNSCIEAEWILAMHLLGVKDDP

KYDKVVQAILNEQREDGSWAVYYDAPAGDINATVEAYAALRTAGFGAGDERLIKARNWIFSHGGL

KNVRVFTRYWLALIGEWPWDETPALAPEIIYLPAWCPLNIYDFACWARATLVPLSVLSVRRPVKPL

PAESRLDELFPEGRENADYSLPESEKGLAERFFLVVDWFLKKYNRLPMQFGREKAIRLCLEWIVRH

QDYDGGWGGIQPPLIYSLIALNTEGYGINHPVISKGLDAFNPPWAYEKNGGVYLQCSESPVWDTLF

TMLALFESGCSFDDTPMMRPALDWILSKQITSWGDWQVKVRGVRPGGWAFERANTAYPDVDDT

ALALVVLAEARRHVKDSAAVDAALERAEEWILGLQCRNGGWAAFDRDNNSAIVTKIPFCDFGEVLD

PPSVDVTAHVVEALAALGRDRHDPVVARALKYIRSEQEPGGSWFGRWGVNHIYGTCAVLPALAAI

GEDMRAPYVLRAADWLVRHQNDDGGWGESCASYMDDSQCGQGSSTASQTGWALMALVAMSS

HDYDEAIRRGLDYLLSHQKSGTWDEPQYTGTGFPGYGVGERTNLKEAGATLDQGCELARGFMIN

YNMYRHYFPLIAMARARRHLGLAANPRHQDSRSSVEVAPEALRGRACG

>seq_ID 246
MRRLDTFPPEIPTGSRDKPPSGEEHSCSTPAEPLRSRLDEGILRAVDWLVCDQHPDGFWAGMLQ

SNSCMEAEWVLAMHFLGIDDDPKYDGVIRAILGEQRADGSWGVFHKAPNGDINTTVECYAALRAS

GLAPESAPLSSAREWILAGGGLANIRNFTKYWLALIGEWPWEGTPTIPPELIFFPPRMPLNIYHFAS

WARSTIVPLSILSARRPVRPLPEDRRLDELFPQGRSAFDFRLPRKDGWLSWEGFFHVCDRILRLYA

RTRRAPFRETAIRVCLEWIIRRQETDGAWSGIQPPWIYALLALHAEGYGLDHPILRAGLRAFDSHW

SYERDGGIYLQASESPVWDTVLSLRALADCGEERKASVSIASALEWLLNRQISVPGDWAVRVPSV

PCGGWAFQRANSFYPDVDDTAVAIEVLARLRPFTANQSAVDRAIRSARDWVLAMQCSNGGWAAF

DRDNDFKLVTKIPFCDFGELLDPPSVDVTAHVIEALAALGWDMTSREIEAAVSFIRREQEAEGSWF

GRWGVNHIYGTATVLPALRAIGEDMSSAYVLRAADWLASRQNADGGWGETPASYMDDSLRGVG

ESTASQTAWAIMGLVAVGSGAHDDTVRRGIDFLLFAQHGGTWEEPQYTGTGFPGYSVGERIRLR

DMGASLKQGTELQRAFMINYNLYRHYFPLMALGRARYHLQLRRSAREGGNGETTPNGSAL

>seq_ID 151
MKISKNPISHALTSFNDAARETADNSAARKSGKIHHLPATIWKKKESTVSSPLDIAIERTQEFFFREQ

LPAGYWWAELESNATITAEYIMLFHFMGLVNREKERKMANYLLRQQTTEGYWTIWHGGPGDLSTT

IEAYFALKLAGYPADHPSMSKARAFILEHGGILKARVFTKIFLALFGEFSWLGVPSMPIEMMLLPAGF

TFNMYEFSSWSRATIIPLSIVMAERPVRKLPPWARVQELYVRPPRPTDYTFTKEDGILTWKNIFIGID

HVLKVYEASPIRPGRKKAMAIAEKWVLEHQEPTGDWGGIQPAMLNSVLALHVLGYANDHPAVAKG

LQALANFCIEGEDELVLQSCVSPVWDTALGLMAMVDSGVPTDHPSLSKAAQWLLDREVRRPGDW

KIKCPDLEPGGWAFEFMNDWYPDVDDSGIVMMAIKNVKVKDQRAKEDTITRGIAWCLGMQSKNG

GWGAFDKDNTKHILNKIPFADLEALIDPPTADLTGRMLELMGTYGYPKDHPAAVRALKFIRETQEP

DGPWWGRWGVNYIYGTWSVMSGLAAFGEDMSQPWIRKAVDWLVEHQNEDGGWGECCESYAD

PRLAGVGPSTASQTGWALLTLLAAGEVASSSVVRGVQYLLDTQKPDGTWDEDAFTGTGFPKFFMI

KYHIYRNCFPLMALGRYRTLAGKGL

>seq_ID 142
MKSRKYPISHALTSFNHTTVAPVEAPAPISVKSPAKVHRLPSSIWKKMEGSAGNPLDKAVELTRDF

FFREQLPDGYWWAELESNVTITAEYIMLFHFLGMVDKDKERKMANYLLRQQTEEGYWTVWHNGP

-continued

```
GDLSTTIEAYFALKLAGYHADHIALRKARDFILANGGILKSRVFTKTFLAMFGEFSWLGVPSMPIELM

LLPDWAYLNVYEFSSWARATIIPMSVLMANRPVYKLPPHARVQELYVRPPRPTDYTFTKEDGIFSL

KNFFIGVDHLLKIYESSPIRPFKKRATEKVEQWILEHQEKTGDWGGIQPAMLNAILALHCLGYANDH

PAVAKGLEALANFTIEDSDSLVLQSCISPVWDTALVQAMQEASVPLDHPSLIKASQWLLDREVRIK

GDWKIKSPDLEPGGWAFEFQNDWYPDVDDSTAVMIAIKDIKVKNTKARQDAIRRGIDWCLGMQSE

NGGWAAFDKDNTKHMLNKIPFADLEALIDPPTADLTGRMLELMGNFGYTKDHPQAVSALEFLKNE

QEPEGPWFGRWGVNYIYGTWYVLIGLEAIGEDMNSPYIKKSVNWIKSRQNLDGGWGEVCDSYW

DRTLMGCGPSTASQTSWALMALMAAGEVGCQAVERGIQYLLATQNSDGTWDEEAFTGTGFPKY

FMIKYHIYRNCFPLTALGRYRRLTAGTHAQ
```

>seq_ID 152
```
MNSCKHPISHALTSFNGETADAAKKQPVKPGAKIHHLPASIWKKKEGESKSPLDIAIENSRDFFFRE

QLPDGYWWAELESNCTITAEYLMLYHFMGIVDQERERKMATYLLSKQTAEGFWTIYFGGPGDLST

TVEAYFALKLAGYPADHPAMAKARAFILDNGGIIKCRVFTKIFLALFGEFAWFGVPSMPIELILLPNW

AYFNMYELSSWSRATIIPLSIVMTERPVRKLPPSSRVQELYVRPPRPIDYTFSKEDGIITWKNFFIGV

DHILKVYESNPIRPFKKRALATAENWVLDHQESTGDWGGIQPAMLNSVLALHCLGYANDHPAVAK

GLEALANFCIETEDSLVLQSCISPIWDTALALKALVDSDVPTDHPALVKAAQWLLDKEVRKPGDWKI

KCPELESGGWAFEFLNDWYPDVDDSGFVMMALKDVAVKDRKSMDGAIKRGINWCLGMQSKNGG

WGAFDKDNTKYLLNKIPFADLEALIDPPTADLTGRMLELMGTFGYSKDYPAAVRALEFIKKNQEPE

GSWWGRWGVNYIYGTWSVLGGLAAIGEDLNQPYIRKAVNWLKSRQNMDGGWGETCESYHDTS

LAGIGESTPSQTGWALLSLMSAGEANSSTVARGIQYLIANQKSDGTWDEEQYTGTGFPKFFMIKY

HIYRNCFPLTALGTYRKLTGGMA
```

>seq_ID 146
```
MTSPFKHPISNALTSFNGNFAEPEQCVEQQTGAKVHHLPASIWKRKMGKAKSPLDVAIEGSRDFF

FQEQLPKGYWWAELESNVTITAEYIMLFHFLGLVDRERQRKMSNYLLSKQTEEGFWPIYYGGPGD

LSTTIEAYFALKLSGYPADHPALAKARAFILEQGGVVKSRVFTKIFLALFGEFEWQGVPSMPVELNL

LPDWAYINIYEFSSWARATIVPLSVVMHSRPVRRVPPSARVQELFVRQPTAADYSFAKNDGIFTWE

NFFLGLDRVLKVYEKSPLRPFKNMALAKAEEWVLEHQEPTGDWGGIQPAMLNAVLALNVLGYQN

DHPAVEQGLRALANFCIETEDQLVLQSCVSPVWDTALALKALLDAGVPPDHPSLVKGAQWLLDKE

VTRPGDWRVKSPALEPGGWAFEFLNDWYPDVDDSGFVMIALKGIQVKDRKSMDAAIKRGINWCL

GMQSKNGGWGAFDKDNTRHVLNKIPFADLEALIDPPTADLTGRMLELMGTFNYPITLPAAQRAIEF

LKKNQEPEGPWWGRWGVNYLYGTWSVLCGLAAIGEDMDQPYIRKAVNWIKSRQNIDGGWGETC

QSYHDRTLAGVGESTPSQTGWALLGLLAAGEMHSATVVRGVQYLISTQNSDGTWDEQQYTGTG

FPKYFMIKYHIYRNCFPLMALGTYRTLTRTQP
```

>seq_ID 147
```
MSPCKHPISHALTSFNGETADSVPVQTPKTGAKIHHLPPSIWKKKEGELKSPLDIAIENSRDFFFRE

QLPDGYWWAELESNCTITAEYVMLYHFMDLVDRERERKMANYLLSKQTEEGFWTIYYGGPGDLS

TTVEAYFALKLAGYPADHPAMVKARAFILDNGGIIKTRVFTKIFLALFGEFAWFGVPSMPIELILLPN

WAYFNMYELSSWSRATIIPLSIVMTQRPVRKLPPASRVQELYVRPPSPIDYTFTKEDGIFTWKNFFI

GVDHILKVYESNPIRPFKKKAMLAAENWVLEHQEATGDWGGIQPAMLNSVLALHCLGYANNHPAV

AKGLEALENFCIESEDSLVLQSCISPVWDTALALKALVDSDVPNDHPALVKAAQWLLDKEIRKAGD

WKVKSPELEPGGWAFEFLNDWYPDVDDSGFVMMALKDVAVKDRKSMDTAIKRGISWCLGMQSK

NGGWGAFDKDNTKYLLNKIPFADLEALIDPPTVDLTGRMMELMGTFGYAKDYPPAVRALDFIKRN
```

```
QEPDGSWWGRWGVNYIYGTWSVLCGLSAMGEDLNQPYIRKAINWLKSRQNIDGGWGETCESYH

DSSLAGIGASTASQTGWALLALMAVGEENASAVARGVQYLLATQKSDGTWDEDLYTGTGFPKFF

MIKYHIYRNCFPLTALGTYRRKTGGRAEMQVSEHNK
```

>seq_ID 144
```
MKISKHPISHALTSFNETAKETKEEPQKKRGGKVHHLPASIWKKRDVETTSPLDQAIKRSQEFFLRE

QLPAGYWWAELESNVTITAEYVILFHFMGLVNRDKDRKMATYLLSKQTEEGCWCIWHGGPGDLS

TTIEAYFALKLAGYPADHPAMQKARTFILGKGGILKARVFTKIFLALFGEFSWLGVPSMPIEMMLLPN

GFTFNLYEFSSWSRATIIPLSIVMAERPVRKLPPWARVQELYVRPPRPMDYTFTKEDGILTWKNIFI

GIDHILKVYEASPIRPGMKKAMAIAEQWVLDHQEPTGDWGGIQPAMLNSVLALHCLGYANDHPAV

AKGLQALANFCIESDDEIVLQSCISPVWDTALALMAMVDSEVPTDHPALVKAAQWLLDREVRKVG

DWKIKAPNLEPGGWAFEFQNDWYPDVDDSGIVMMAIKDVKVKDSKAKAEAIQRGIAWCIGMQSK

NGGWGAFDKDNTKHILNKIPFADLEALIDPPTADLTGRMLELMGTFGYPKDHPAAVRALQFVKENQ

EPDGPWWGRWGVNYIYGTWSVLCGLKAYGEDMGQPYVRKAVEWLAAHQNPDGGWGECCESY

CDQKLAGTGPSTASQTGWALLSMLAAGDVDHPAVARGIRYLIETQQPDGTWDEDQFTGTGFPKY

FMIKYHIYRNCFPLMAMGRYRALKGHKG
```

>seq_ID 15
```
MAEQLVEAPAYARTLDRAVEYLLSCQKDEGYWWGPLLSNVTMEAEYVLLCHILDRVDRDRMEKIR

RYLLHEQREDGTWALYPGGPPDLDTTIEAYVALKYIGMSRDEEPMQKALRFIQSQGGIESSRVFTR

MWLALVGEYPWEKVPMVPPEIMFLGKRMPLNIYEFGSWARATVVAISIVMSRQPVFPLPERARVP

ELYDTDVPPRRRGAKGGGGRIFDALDRALHGYQKLSVHPFRRAAEIRALDWLLERQAGDGSWGG

IQPPWFYTLIALKILDMTQHPAFIKGWEGLELYGVDLDYGGWMFQASISPVWDTGLAVLALRAAGL

PADHDRLVKAGEWLLDRQITVPGDWAVKRPNLKPGGFAFQFDNVYYPDVDDTAVVVWALNSLRL

PDERRRRDVMTKGFRWIVGMQSSNGGWGAYDVDNTSDLPNHIPFCDFGEVTDPPSEDVTAHVL

ECFGSFGYDDAWKVIRRAVEYLKREQRPDGSWFGRWGVNYLYGTGAVVPALKAVGIDVREPFIQ

KALDWVEQHQNPDGGWGEDCRSYEDPAYAGKGASTPSQTAWALMALIAGGRAESDSVRRGVQ

YLVETQRPDGGWDEPYYTGTGFPGDFYLGYTMYRHVFPTLALGRYKQAIERR
```

>seq_ID 16
```
MAEQLVEAPAYARTLDRAVEYLLSCQKDEGYWWGPLLSNVTMEAEYVLLCHILDRVDRDRMEKIR

RYLLHEQREDGTWALYPGGPPDLDTTIEAYVALKYIGMSRDEEPMQKALRFIQSQGGIESSRVFTR

MWLALVGEYPWEKVPMVPPEIMFLGKRMPLNIYEFGSWARATVVALSIVMSRQPVFPLPERARVP

ELYETDVPPRRRGAKGGGGWIFDALDRALHGYQKLSVHPFRRAAEIRALDWLLERQAGDGSWG

GIQPPWFYALIALKILDMTQHPAFIKGWEGLELYGVELDYGGWMFQASISPVWDTGLAVLALRAAG

LPADHDRLVKAGEWLLDRQITVPGDWAVKRPNLKPGGFAFQFDNVYYPDVDDTAVVVWALNTLR

LPDERRRRDAMTKGFRWIVGMQSSNGGWGAYDVDNTSDLPNHIPFCDFGEVTDPPSEDVTAHVL

ECFGSFGYDDAWKVIRRAVEYLKREQKPDGSWFGRWGVNYLYGTGAVVSALKAVGIDTREPYIQ

KALDWVEQHQNPDGGWGEDCRSYEDPAYAGKGASTPSQTAWALMALIAGGRAESEAARRGVQ

YLVETQRPDGGWDEPYYTGTGFPGDFYLGYTMYRHVFPTLALGRYKQAIERR
```

>seq_ID 141
```
MTSPFKHPISNALTSFNGNVAEPEQSVEQQSGAKVHHLPASIWKRKMGRAKSPLDVAIEGSRDFF

FQEQLPKGYWWAELESNVTITAEYIMLFHFLGLVDPERQRKMSTYLLSKQTEEGFWTIYYGGPGD

LSTTIEAYFALKLSGYPEDHPALAKARAFILEQGGVKSRVFTKIFLALFGEFDWQGIPSMPVELNLL

PDWAYINIYEFSSWARATIVPLSVVMHSRPVRRVPPSARVQELFVRQPTAADYSFAKNDGLFTWE
```

```
                                                        -continued
KFFLGLDRVLKVYEKSPLRPFKKTALAKAEEWVLEHQEPTGDWGGIQPAMLNAILALNVLGYRND

HPAVEQGLRALANFCIETEDQLVLQSCVSPVWDTALALKALLDAGVPPDHPSLVKGAQWLLDKEV

TRAGDWRVKSPNLEAGGWAFEFLNDWYPDVDDSGFVMIALKGIQVKDHKAMDAAIKRGINWCLG

MQSKNGGWGAFDKDNTKHVLNKIPFADLEALIDPPTADLTGRMLELMGTFDYPVTFPAAQRAIEFL

KKNQEPEGPWWGRWGVNYLYGTWSVLCGLAAIGEDMDQPYIRKAVNWIKSRQNIDGGWGETC

QSYHDRTLAGVGESTPSQTGWALLSLLAAGEMHSATVVRGVQYLISTQNSDGTWDEQQYTGTGF

PKYFMIKYHIYRNCFPLMALGTYRTLTRTQP

>seq_ID 195
MNPAKYKISSSLTSLNAEPVEQAPLPAKRTGSKVHRLPPSIWKKMVAEAKSPLDKGIERTRDFFLR

EQLPDGYWWAELESNVTISAEYVMLFHFLGMVDRERERKLANYILAKQTSEGFWSLWHNGPGDL

STTIEAYFALKLAGYSADHPAMAKARAFVLANGGIIKARVFTKIFLALFGEFAWFGVPSMPIELMLLP

DWAYFNMYEFSSWSRATIIPLSVVMSERPVRKLPPRAQVQELFVRPPRPTDYTITREDGLFTWKN

FFIGADHLIKVYESSPIRPFKKRAVALAENWILEHQEQSGDWGGIQPAMLNSILALHCLGYANDHPA

VAKGLDALANFCIEDDDCIVLQSCVSPVWDTALALVALQEADVPADHPALVKAAQWLLNLEVRRK

GDWQVKCPELEPGGWAFEFLNDWYPDVDDSGFVMLSIKNIKVRDRKHREEAIKRGIAWCLGMQS

ENGGWGAFDRNNTKYLLNKIPFADLEALIDPPTADLTGRMLELMGNFDYPKSHPAAERALAFLKKE

QESEGPWWGRWGVNYLYGTWSVLCGLEAIGEDMNQPYIRKAVNWIKSRQNNDGGWGEVCESY

FDRSLMGSGPSTASQTGWALLALMAAGEANSRAAAQGVKYLLETQNEDGTWDEDAFTGTGFPK

FFMIKYHIYRNCFPLTALGRYRRLTAAKG

>seq_ID 3
MTATTDGSTGASLRPLAASASDTDITIPAAAAGVPEAAARATRRATDFLLAKQDAEGWWKGDLET

NVTMDAEDLLLRQFLGIQDEETTRAAALFIRGEQREDGTWATFYGGPGELSTTIEAYVALRLAGDS

PEAPHMARAAEWIRSRGGIASARVFTRIWLALFGWWKWDDLPELPPELIYFPTWVPLNIYDFGCW

ARQTIVPLTIVSAKRPVRPAPFPLDELHTDPARPNPPRPLAPVASWDGAFQRIDKALHAYRKVAPR

RLRRAAMNSAARWIIERQENDGCWGGIQPPAVYSVIALYLLGYDLEHPVMRAGLESLDRFAVWRE

DGARMIEACQSPVWDTCLATIALADAGVPEDHPQLVKASDWMLGEQIVRPGDWSVKRPGLPPGG

WAFEFHNDNYPDIDDTAEVVLALRRVRHHDPERVEKAIGRGVRWNLGMQSKNGAWGAFDVDNT

SAFPNRLPFCDFGEVIDPPSADVTAHVVEMLAVEGLAHDPRTRRGIQWLLDAQETDGSWFGRWG

VNYVYGTGSVIPALTAAGLPTSHPAIRRAVRWLESVQNEDGGWGEDLRSYRYVREWSGRGASTA

SQTGWALMALLAAGERDSKAVERGVAWLAATQREDGSWDEPYFTGTGFPWDFSINYNLYRQVF

PLTALGRYVHGEPFAKKPRAADAPAEAAPAEVKGS

>seq_ID 18
MTKQLLDTPMVQATLEAGVAHLLRRQAPDGYWWAPLLSNVCMEAEYVLLCHCLGKKNPEREAQI

RKYIISQRREDGTWSIYPGGPSDLNATVEAYVALKYLGEPASDPQMVQAKEFIQNEGGIESTRVFT

RLWLAMVGQYPWDKLPVIPPEIMHLPKSVPLNIYDFASWARATIVTLSYRHESPTCDATSGLCKGS

GIVRGEGPPKRRSAKGGDSGFFVALDKFLKAYNKWPIQPGRKSGEQKALEWILAHQEADGCWGG

IQPPWFYALLALKCLNMTDHPAFVKGFEGLEAYGVHTSDGGWMFQASISPIWDTGLTVLALRSAG

LPPDHPALIKAGEWLVSKQILKDGDWKVRRRKAKPGGWAFEFHCENYPDVDDTAMVVLALNGIQL

PDEGKRRDALTRGFRWLREMQSSNGGWGAYDVDNTRQLTKSDSIFATSGEVIDPPSEDVTAHVL

ECFGSFGYDEAWKVIRKAVEYLKAQQRPDGSWFGRWGVNYVYGIGAVVPGLKAVGVDMREPWV

QKSLDWLVEHQNEDGGWGEDCRSYDDPRLAGQGVSTPSQTAWALMALIAGGRVESDAVLRGVT

YLHDTQRADGGWDEEVYTGTGFPGDFYLAYTMYRDILPVWALGRYQEAMQRIRG
```

>seq_ID 245
MNPIRGKRGSAADFLEEEYQWENLADHGESGRTPGGGHPAALKEYEAGSATEHTGHHCVHHLG
VRNSWLRKIEKAIDNACGQLFKTQYEDGYWWSELESNVTITSEYIMLLYLLEVSRPEQQKSMVKYL
LNQQRPDGSWGLYYGDGGNLSTTIEAYFALKLAGEHCESEPMRRAREFILSKGGIESARVFTKIWL
ALFSQYDWDKVPSMPVELVLLPSSLYFNIYEFSSWARGTVVPLSIVMSIRPRCPLPAKCSIKELYVP
GSKHKNFASCTHKLFFLFDRIAKAFERRPVPSLRNKAVQAAETWVLDHQEDSGDWGGIQPPMVY
SVLALYYLGYPLDHEVIVKGIKALDAFCMEDEEGTRMQSCVSPVWDTALTVLSMLDAGVAAEHPG
LEKAGRWLLENQVLIGGDWQIKNDSLPGGWAFEFYNTRYPDVDDSAVVLSTLNRFNAERVEGLE
FAKCRGMEWCLSMQSSNGGWAAFDKDNTLEILNRIPFADQEAMVDYPTADVTGRVLEAMGYLGY
DGSHPRARKAIQFLKKRQERDGCWWGRWGVNYIYGTWSVLKGLISIGEDPRAAYIRAAVRWVKD
HQNSDGGWGETCESYENPELRGQGPSTPSQTAWALMSLIACGEMKSQEASRGIQYLLRTQKRD
GTWEELHFTGTGFPKHFYIRYHNYRNCFPLMALGQYLRALER >seq_ID 221
MTATTDGSTGALPPRAASASEPHDTIPQAAGSVGIQDAAARATQRATDFLLSRQDAEGWWKGDL
ETNVTMDAEDLLLRQFLGIQDEKTTRAAGLFIRGEQRADGTWATFYGGPGDLSATIEAYVALRLAG
DGPDEPHMAKASAWIRERGGIASARVFTRIWLALFGWWKWDDLPELPPELIYFPKWMPLNIYDFG
CWARQTIVPLTVVSAKRPVRPAPFPLDELHADANDPNPAKPLAPMVSWDGLFQRLDVALHTYRKV
APRRLRKAAMNTAARWIIERQENDGCWGGIQPPAVYSVIALYLLGYDLEHPVMREGLASLDRFAV
WRDDGARMIEACQSPVWDTCLATIALADAGVPADHPQLVRAADWMLGEEIVRPGDWAVKRPQLP
PGGWAFEFHNDNYPDIDDTAEVVLALRRVKHHDPERLDNAIRRGVRWNLGMQSKDGGWGAFDV
DNTSPFPNRLPFCDFGEVIDPPSADVTAHVVEMLAFEGLSHDPRTRRGIQWLLSAQEANGSWFG
RWGVNYVYGTGSVVPALVAAGLPASHPAIRRAVTWLETVQNDDGGWGEDLRSYPEAAEWSGKG
ASTASQTGWALLALLAAGERESKAVERGIEWLAQTQRPDGSWDEPYFTGTGFPWDFSINYHLYR
QVFPLTALGRYVNGEPLVEVKGG >seq_ID 160
MKGKEPTREELLSFSSGIQMDSSAENTTPVSTEELQEKVRLAAESLISRQVEEGYWVEPLEADVTI
TSEYILLQYLLGRERDEFFRRAAPFILESQGEDGGWPLYHGGPAEISATVKAYLALKLLGYDADHP
AMQRARALVLERGGAINVNVFTRITLALFGQYDWKGVPALPPEMILLPRWFPLSIYTVSYWSRTVIV
PLLFIYHYKPLLELPPEKGVQELFITPMSEVRVHYAWDKHWVSWKNLFFVLDRILQAWNRHPPSFL
RRKALKKAMEWMIPRLKGEGGLGAIYPAMANSVLALRLEGYAMDHPLVRRAIQSIDDLVFDLGEQ
QSVQPCHSPIWDTALALGALYEAGLDEGSPFVSRALDWFCRKEVRTVGDWSVRVPGVEAGGWA
FQFENDYYPDIDDTSVVLMDFAKWVPEMGAYRDVFRRAIEWTLSMQGTDGGWGAFDKDNDFLFL
NNIPFADHGALLDPSTSDVTGRVTELLGILGYDARTPVVRRALRFLRKEQEENGSWYGRWGVNYI
YGTWSVVSALKAVGEDMSAPYVQKAMQFLFSRQNPDGGWGESCYSYFRKDTAGEGVSTSSQTA
WALIALIHGGHVRHPAVSKGIDFLLSRQQADGKWLEQEYTGTGFPKVFYLRYNMYRDYFSLWALS
LYRNVLLDGQSRVERLARRWKGNPYPVRSRFLA >seq_ID 161
MEGKDPTREELLSFTSGIQMDSRVGNTNPVSTEELQEKVRLAAESLISRQGEEGYWVEPLEADITI
TSEYVLLQYLLGRERDEFFRRAAPFILESQGEDGGWPLYNGGPAEISATVKAYLALKLLGYDADHP
AMQRARALVLERGGAINVNVFTRITLALFGQYDWKGVPALPPEMILLPRWFPLSIYTVSYWSRTVIV
PLLFIYHYKPLLELPPEKGVQELFITPMSEVRVHYAWDKHWVSWKNLFFVLDRILQAWNRHPPSFL
RRKALKKAMEWMIPRLKGEGGLGAIYPAMANSVLALRLEGYEMDHPLVRRAIQSIDDLVFDLGEQ
QSVQPCHSPIWDTALALGALYEAGLDEGSPFVSRALDWFCRKEVRTVGDWSVRVPGVEAGGWA -continued

FQFENDYYPDIDDTSVVLMDFAKWVPEMGAYRDVFRRAIEWTLSMQGTDGGWGAFDKDNDFLFL

NNIPFADHGALLDPSTSDVTGRVTELLGILGYDARTPVVRRALRFLRKEQEENGSWYGRWGVNYI

YGTWSVVSALKAVGEDMSAPYVQRAMQFLFSRQNPDGGWGESCYSYFRKDTAGEGVSTASQT

AWALIALIHGGHVRHPAVSKGIDFLLSRQQADGKWLEQEYTGTGFPKVFYLRYNMYRDYFSLWAL

SLYRNVLLDGQSRVERLSRRWKGTPYPVRSRFLA

>seq_ID 240
MHEGEAMTATTDGSTGALPPRAAAASETHLDTPVAAGIQEAAVRAVQRATEHLLARQDAEGWWK

GDLETNVTMDAEDLLLRQFLGIRDESTTRAAAKFIRGEQREDGTWAGFYGGPGELSTTVEAYVAL

RLDGDAPDAPHMAKASAWIRAQGGIAAARVFTRIWLALFGWWKWEDLPELPPELIYFPKWAPLNI

YDFGCWARQTIVPLTIVSAKRPVRPAPFPLDELHADPADPNPAKPLAPVASWDGAFQRLDKAMHQ

LRKVAPRRLRRAAMNSAARWIIERQENDGCWGGIQPPAVYSVIALHLLGYDLQHPVMRAGLESLD

RFAIWREDGSRMIEACQSPVWDTCLATIALVDAGVPADHPQLVKAADWMLGEEIVRPGDWSVKR

PQLPPGGWAFEFHNDNYPDIDDTAEVVLALRRVRHHDPDRVENAIGRGVRWNLGMQSKNGAWG

AFDVDNTSPFPNRLPFCDFGEVIDPPSADVTAHVVEMLAVEGLSHDPRTRRGIEWLLAEQEPDGS

WFGRWGVNYIYGTGSVVPALTAAGLPASHPAIRRAVAWLEKVQNDDGGWGEDLRSYKYVKEWS

GRGASTASQTAWALMALLAAGERDSKAVERGVEWLASTQRADGSWDEPYFTGTGFPWDFSINY

HLYRQVFPLTALGRYVHGEPFSRTEAL

>seq_ID 231
MTATTDGSSGPVRAGAATAGDTTTTTAARTTAPGTDVREAAGRAAERAVEHLLARQDAQGWWK

GDLETNVTMDAEDLLLRQFLGIQDAATVEASARFIRGQQRDDGTWATFYGGPGELSTTIEAYVALR

LAGDRPDDPHMQRAASWVRSRGGIAAARVFTRIWLALFGWWKWDDLPELPPELILLPKWVPLNIY

DFGCWARQTIVPLTVVSAKRPVRPAPFALDELHTDPAMPNPQKRFAPAASWDGFFQRADKALHL

YHKVAPRRLRRAAMNAAARWIIERQENDGCWGGIQPPAVYSVIALHLLGYDLEHPVMRAGLESLD

RFAVHREEEGLPVRMIEACQSPVWDTCLATIALADAGLPADHPALVKAADWMLSEQIVRPGDWAV

RRPGLGPGGWAFEFHNDNYPDIDDTAEVILALRRVKHPDPERVEAAVARGTRWNLGMQSLNGA

WGAFDADNTSPFPNRLPFCDFGEVIDPPSADVTAHVVEMLAHEGMAEDPRTRRGVRWLLREQEA

NGAWFGRWGVNYVYGTGAVVPALIAAGLPASHPSVRRAVTWLESVQNEDGGWGEDLRSYREE

QSIGRGASTASQTGWALLALLSAGERDGRAVERGVAWLARTQRPDGSWDEPYFTGTGFPWDFSI

NYHLYRQVFPLTALGRFLHGEKPVGRAAAREGG

>seq_ID 227
MTATTDGSTGAANPSEATAHDPTDTTTAADDLTVAARRAAERSVEHLLGRQDEQGWWKGDLAT

NVTMDAEDLLLRQFLSIQDPETTRAAALFIRGEQLGDGTWNTFYGGPGDLSATIEAYVALRLAGDR

PDEPHMARAAGWIRDQGGIAAARVFTRIWLALFGWWKWDDLPELPPELMFFPKWVPLNIYDFGC

WARQTIVPLTIVSAKRPVRPAPFALDELHTDPDHPNPPRKLAPPTSWDGLFQRLDKGLHLYHKVAP

RPLRRVAMNLAARWIIERQENDGCWGGIQPPAVYSVIALHLLGYDLDHPVMKAGLASLDRFAVRR

EDGARMIEACQSPVWDTCLATIALADAGLRPDHPALVKAADWMLAEEITRPGDWSVRKPELAPGG

WAFEFHNDNYPDIDDTAEVVLALRRVRHPDPARLQAAIDRGVRWNLGMQSRNGAWGAFDADNT

SPFPNRLPFCDFGEVIDPPSADVTGHVVEMLAVEGLASHPRTREGIEWLLAEQEACGAWFGRWG

VNYVYGTGSVVPALITAGLPAGHPAIRRAVAWLESVQNDDGGWGEDLRSYQEEKWIGHGESTAS

QTAWALLALLAAGRRDTRPVARGVTWLTEAQQADGSWDEPYFTGTGFPWDFSINYHLYRQVFPL

TALGRYVHGDPFADRAMAAEGA

-continued

>seq_ID 121
MQTQNRVTSTQKVELSNLTKAIIASQNYIMSRQYPEGYWWGELESNITLTAETILLHKIWKTDKTRP
FHKVETYLRRQQNEQGGWELFYGDGGELSTSVEAYMALRLLGVTPEDPALIRAKDFILSQGGISKT
RIFTKFHLALIGCYDWKGIPSIPPWIMLFPDNFPFTIYEMSSWARESTVPLLIVFDKKPIFEIEPAFNLD
ELYAEGVENVKYALPRNHNWSDIFLGLDKLFKWTEKNNLVPFHKKSLQAAERWMLNHQQESGDW
GGIMPPMVNSLIAFKVLNYDVADPSVQRGFEAIDRFSIEEEDTYRVQACVSPVWDTAWVIRALVDS
GLKPDHPSLVKAGEWLLDKQILEYGDWAIKNKQGKPGGWAFEFINRFYPDLDDSAVVVMALNGIK
LPDENCKKAAINRCLEWMATMQCKPGGWAAFDVDNDQAWINEIPYGDLKAMIDPNTADVTARVL
EMVGSCGLKMDENRVQKALFYLEKEQESDGSWFGRWGVNYIYGTSGVLSALAVIAPNTHKPQME
KAVNWLISCQNEDGGWGETCWSYNDPSLKGTGVSTASQTAWALIGLLDAGEALETLATDAIKRGI
NYLLDTQTPDGTWEEAEFTGTGFPCHFYIRYHLYRHYFPLIALGRYWKIGLKNLKG >seq_ID 120
MQTQNRVTSTQKVELSNLTQAIIASQNYILSRQYPEGYWWGELESNITLTAETVLLHKIWKTDKTRP
FHKVETYLRRQQNEQGGWELFYGDGGELSTSVEAYMALRLLGVTPEDPALIRAKDFILSKGGISKT
RIFTKFHLALIGCYDWKGIPSIPPWIMLFPDNFPFTIYEMSSWARESTVPLLIVFDKKPIFEIEPAFNLD
ELYAEGVENVKYALPRNHNWSDIFLGLDKLFKWTEKNNLVPFHKKSLQAAEKWMLNHQQESGDW
GGIMPPMVNSLIAFKVLNYDVADPSVQRGFEAIDRFSIEEEDTYRVQACVSPVWDTAWVIRALVDS
GLKPDHPSLVKAGEWLLDKQILEYGDWAIKNKQGKPGGWAFEFINRFYPDLDDSAVVVMALNGIK
LPDENRKKAAINRCLEWMATMQCKPGGWAAFDVDNDQAWINEIPYGDLKAMIDPNTADVTARVL
EMVGSCGLKMDENRVQKALFYLEKEQESDGSWFGRWGVNYIYGTSGVLSALAVIAPNTHKPQME
KAVNWLISCQNEDGGWGETCWSYNDSSLKGTGISTASQTAWAIIGLLDAGEALETLATDAIKRGID
YLLATQTPDGTWEEAEFTGTGFPCHFYIRYHLYRHYFPLIALGRYWKIGLKTPSVIPLN >seq_ID 132
MFQGSDRPPVTLVMNDMRGPDMNVSDTVSVTRESIPTQTSAGDATARDLTAAVGSELTRALRLA
TDHLLALQDGTGWWKFDLETNTSMDAEDLLLREYLGIRTTEVTAASARFIRSRQSDDGSWPQYFG
GPGELSTTVESYIALRLAGDDASAPHMLSAATWVRDHGGVPATRVFTRIWLALFGWWRWEDLPA
LPPEIMLLPRRAPLNIYSFGSWARQTLVSLTVVSALRPVRPAPFDLDELYPDGPASAWSGAGPSNV
LERISTRFTAKEIFLGIDRLLHVYHRRPVRSMRNHALRAAERWIIARQEADGCFGGIQPPAVYSIIAL
RLLGYELDHPVLKAALRALDDYSVTLPDGSRMVEASQSPVWDTALAVNALADAGATAAIAPDHPA
LVRAAGWLLGQEVRHRRGDWAVNHPDVPASGWAFEFENDTYPDTDDTAEVLLALRRVRHPARD
ELDAAERRAVAWLFGLQSSDGGWGAYDADNTSTIPYQIPFADFGALTDPPSADVTAHVVELLAEA
GLGGDDRTRRGVDWLLDHQEADGSWFGRWGVNYVYGTGSVMPALRAAGLEPSHPAMRAGAD
WLLTHQNADGGWGEDLRSYTDPEWSGRGESTASQTAWAMLALLTVGDQPEVSGALARGARWL
ADHQRPDGSWDEDQFTGTGFPGDFYINYHGYRLLWPIMALGRYLRG >seq_ID 118
MLTYKEYRRSVTEIAMQTRDRQTQKPALSLNDAITASQNYLLSLQYPQGYWWAELESNITLTAETV
LLHKIWGTDKTRPLHKVEAYLRQQQREQGGWELFYGDGGEISTSVEAYMALRLLGVPQDDPALIR
AKDFILSKGGISKTRIFTKFHLALIGCYSWKGIPSIPPWIMLFPNSFPFTIYEMASWARESTVPLIIVFN
DKPVFAVDPIFNLDELYAEGIENVKYELPKNNNWGDIFLGLDKVFKFAEQVDLVPFRKKGLQAAER
WMLNHQQETGDWGGIMPPMVNSLLAFRVLNYDVNDPSVQRGFEAIDRFSIEENETYRVQACVSP
VWDTAWCVRALTNSGLPKDHFSLVKAGKWLLEKQCLEYGDWAVKNKTGKPGGWAFEFTNRFYP
DIDDSAVVVMALNGIKLPDEARKQAAINRCVKWIETMQCKEGGWAAFDVDNDQAWLNEVPYGDL -continued

KAMIDPNTADVTARVVEMVGSCDLEISSKRLNKALNYLYKEQEKDGSWFGRWGVNYIYGTSGVLS

ALAVINPEKHQPQIEQGINWLLSCQNKDGGWGETCWSYNDSNLKGKGISTASQTAWALIGLLDAG

EALNHFETDSIQRGISYLLNTQTEEGTWEESEFTGTGFPCHFYIRYHFYRHYFPLIALGRYQNLSSE

FGIRNSEL

>seq_ID 230

MTATTDGSSGPLRGGAATAGETTSTSAARTTEPGTDLREAAARAAERAVEHLLARQDAEGWWK

GDLETNVTMDAEDLLLRQFLGIQDPATVGASARFIRGQQRDDGTWATFYGGPGELSTTVEAYVAL

RLAGDRPDDPHMQRAASWVRSRGGIAASRVFTRIWLALFGWWKWEDLPELPPELIFLPKWFPLNI

YDFGCWARQTIVPLTVVSAKRPVRPAPFALDELHTDPALPNPGKRLAPAASWDGFFQRADKALHA

YHKVAPRRLRRAAMNAAARWIIERQENDGCWGGIQPPAVYSVIALHLLGYDLEHPVMRAGLESLD

RFAVHHEEEGLPVRMIEACQSPVWDTCLATIALADAGLPADHPALVKAADWMLSEQIVRPGDWSV

RRPGLGPGGWAFEFHNDNYPDIDDTAEVVLALRRVKHPDPERVDAAVARGTRWNLGMQSRDGA

WGAFDADNTSPFPNRLPFCDFGEVIDPPSADVTAHVVEILAHEGMAHDPRTRRGVRWLLAHQEA

NGAWFGRWGVNYVYGTGAVVPALTAAGLPGSHPAIRRAVAWLESVQNEDGGWGEDLRSYREE

KSIGRGVSTASQTGWALLALLAAGERESKAVERGVAHLAQTQAPDGSWDEPYFTGTGFPWDFSI

NYHLYRQVFPLTALGRYVHGEKLPGRAGAREGR

>seq_ID 234

MHEGEAMTATTDGSTGAATPPATTASAPLHLSPEARETHEATARATRRAVDFLLARQSDEGWWK

GDLATNVTMDAEDLLLRQFLGIRDEATTRAAALFIRGEQQEDGTWNTFYGGPGDLSATIEGYVALR

LAGDSPEAPHMRKASAFVRAQGGVARARVFTRIWLALFGWWKWEDLPEMPPELMFFPKWAPLNI

YDFGCWARQTIVPLTVVCAQRPVRPAPFALEELHTDPADPDPAQPAPPVVSWDNVFHKLDKLLHG

YRRIAPRRVREAAMRAAATWIVERQENDGCWGGIQPPAVYSIMALNLLGYDLDHPVLRAGLASLD

RFAVWREDGARMIEACQSPVWDTCLATVALADAGVPADHPQMIKAADWMLAEQIVRPGDWVVR

RPDLPPGGWAFEFHNDNYPDIDDTAEVVLALRRVAHPDATRVDKAVRRAVDWNVGMQSKNGAW

GAFDADNTSPFPNRLPFSDFGEVIDPPSADVTAHVVEMLAEEGLAHHPRTRRGIEWLLKNQEGNG

SWFGRWGVNYVYGTGAVVPALVAAGLPASHPAIRRSVSWLGQVQNEDGGWGEDLRSYQDSAW

HGRGHSTASQTAWALLALLAAGERETEQVRRGIAYLVETQTEDGTWDEPWFTGTGFPWDFTINY

HLYRQVFPVTALGRYLNGTGPGEN

>seq_ID 123
MQTRDRQTHKPALSLNDAITASQNYLLSLQYPQGYWWAELESNITLTAETVLLHKIWGTDKTRPLH

KVEAYLRQQQREHGGWELFYGDGGEISTSVEAYMALRLLGVPSNDPALIRAKNFIISQGGISKTRIF

TKFHLALIGCYSWKGIPSIPPWIMLFPNSFPFTIYEMASWARESTVPLIIVFNDKPVFAIDPIFNLDELY

AEGIENVKYELPKNNNWGDLFLGLDKVFKLAEQVDLVPFRKQGLQAAERWMLDHQQETGDWGGI

MPPMVNSLLAFRVLNYDVADPSVQRGFEAIDRFSIEENDTYRVQACVSPVWDTAWCIRALTDSGL

PKDHFSLVKAGKWLLEKQVLEYGDWAVKNKTGKPGGWAFEFTNRFYPDIDDSATVVMALNGIKLP

DEALKQAAINRCLKWIETMQCKAGGWAAFDVDNDQAWLNEIPYGDLKAMIDPNTADVTARVVEM

VGSCDLEMSSDRLNKALDYLYEEQEKDGSWFGRWGVNYIYGTSGVLSALAVINPKQHKSQIEQG

MNWLLSCQNEDGGWGETCWSYNDSLKGKGVSTPSQTAWALIGLLDAGEVLNHFETDSIERGIN

YLLNTQTEEGTWEESEFTGTGFPCHFYIRYHFYRHYFPLIALGRYQQMLGS

>seq_ID 10
MTQASVREDAKAALDRAVDYLLSLQDEKGFWKGELETNVTIEAEDLLLREFLGIRTPDITAETARWI

RAKQRSDGTWATFYDGPPDLSTSVEAYVALKLAGDDPAAPHMEKAAAYIRGAGGVERTRVFTRL

WLALFGLWPDDLPTLPPEMIFLPSWFPPLNIYDWGCWARQTVVPLTIVSALRPVRPIPLSIDEIRTG

-continued

```
APPPPRDPAWTIRGFFQRLDDLLRGYRRVADHGPARLFRRLAMRRAAEWIIARQEADGSWGGIQ

PPWVYSLIALHLLGYPLDHPVLRRGLDGLNGFTIREETADGAVRRLEACQSPVWDTALAVTALRDA

GLPADHPRVQAAARWLVGEEVRVAGDWAVRRPGLPPGGWAFEFANDNYPDTDDTAEVVLALRR

VRLEDADQQALEAAVRRATTWVIGMQSTDGGWGAFDADNTRELVLRLPFCDFGAVIDPPSADVT

AHIVEMLAALGMRDHPATVAGVRWLLAHQEPDGSWFGRWGANHIYGTGAVVPALIAAGVSPDTP

PIRRAIRWLEEHQNPDGGWGEDLRSYTDPALWVGRGVSTASQTAWALLALLAAGEEASPAVDRG

VRWLVTTQQPDGGWDEPHYTGTGFPGDFYINYHLYRLVFPISALGRYVNR
```

>seq_ID 233
```
MRRRRSPRGPGAGPEADYGPARASAPDRLRGDAARGDAARRVQDATARAIRNLLGRQDPAGW

WKGDLETNVTMDAEDLLLRQFLGIRDEAVTQAAALFIRREQREDGTWATFHGGPPELSATIEAYVA

LRLAGDAPDAPHMATASAWIRAHGGLAAARVFTRIWLALFGWWDWENLPELPPELVLLPPWVPL

NIYDFGCWARQTIVPLTVVSAMRPVRPAPFALDELHTDARVPVPPRRMAPPTTWNGAFQWMDRA

LHVYRRFAPRRLREAAMASAGRWIIERQENDGCWGGIQPPAVYSVIALHLLGYDLGHPVMRAGLE

SLDRFAVWREDGSRMIEACQSPVWDTCLAAIALADAGVRPDHPALVKAADWMLGEEIVRTGDWA

VRRPGLAPGGWAFEFHNDTYPDIDDTAEVVLALRRIRHPDPARVEAAIARGVSWNLGMQSRGGA

WGAFDADNTSPFPNRLPFCDFGEVIDPPSADVTAHVVEMLAAEGRAADPRTRRGIAWLLAEQEPE

GPWFGRWGTNYVYGTGSVVPALTAAGLSPGHPAIRRAVLWLESVQNPDGGWGEDQRSYQDRA

WAGKGESTPSQTAWALMALLSAGERDAKTVERGIAYLVETQLADGGWDEPHFTGTGFPWDFSIN

YHLYRHVFPLTALGRYLYGEPFGHDGRHIGAHLGDRTGVPAEGV
```

>seq_ID 116
```
MQTQDRLTQKQPLSLKDAITASQNYLLSLQYPQGYWWAELESNITLTAETVLLHKIWGTDKTRPLH

KVEAYLRQQQREHGGWELFYGDGGEISTSVEAYMALRLLGVPQDDPALIRAKDFIISKGGISKTRIF

TKFHLALIGCYDWKGIPSIPPWIMLFPDSFPFTIYEMASWARESTVPLIIVFNDKPVFSVDPVFNLDE

LYAEGVENVKYELPKNNNWGDIFLGIDQVFKFAEQVDLVPFRKEGLKAAEKWILNHQQETGDWGG

IMPPMLNSLLAFRTLNYDVNDPSVKLGFEAIDRFSIEEDDTYRLQACVSPIWDTAWCVRALTDSGL

EKDHFSLVKAGKWLLDKQVMEYGDWAVKNKAGKPGGWAFEFTNRFYPDLDDSATVVMALNGIKL

PDEARKQAAINRCLQWIETMQCKEGGWAAFDLNNDQAWLNEVPYGDLKAMIDPNTADVTARVVE

MLGSCDLEIESDRLNKSLNYLYKEQEKDGSWFGRWGVNYIYGTSGVLSALAVINPEKHKTQMEQG

INWLLSCQNKDGGWGETCRSYNDPSLKGKGVSTPSQTAWSLIGLLDAGEALNKFETDAIERGVNY

LLDTQTEEGTWEESEFTGTGFPCHFYIRYHFYRHYFPLIALGRYQNLSSEFGVRS
```

>seq_ID 124
```
MQIRATVDTAKLEKAIAASQEHLLSTQYPEGYWWAELESNVTMTAEVVLLHKIWKTDGTRPMHKA

EKYLRSEQREHGGWELFYGDGGDLSTSVETYTALRLLGVPASDPALLKAKDFILRRGGISKTRIFT

KLHLALIGCYDWRGLPSLPPWVMLLPENFPFTIYELSSWARGSTVPLLIVMDRKPVFSVNPQINVD

ELYAEGRDRVKFELPRKGDWTDLFIELDGLFKFTEQNNLVPFREEGLRAAERWVLERQEATGDW

GGIIPAMLNSLLALRALGYHPADPYVRRGMAAVDRFAIETADTYRVQPCVSPVWDTALVMRGLIDS

GLPADHPAIVKAGEWLLEKQILAYGDWAVKNKTGQPGAWAFEFENRFYPDVDDSAVVVMALQAA

QLPDEDLKQQAIERCVKWIATMQCKPGGWAAFDVDNDQDWLNQIPYGDLKAMIDPNTADVTARV

LEMIGRSGVTTGEASVERALAYLRREQEVEGCWFGRWGVNYIYGTSGVLAALALIAPKSDHAMIQ

RGADWLVRCQNADGGWGETCRSYNDPHLKGQGPSTASQTAWALIGLLAAGEATGEFAWGAIDR

GINYLLATQQQDGRWDEDWFTGTGFPGHFYLKYHLYQQHFPLTALGRYSSLTGLKQELKIPLQLK

SKPEVVMIEDSDLLSDEDAT
```

```
                                                          >seq_ID 119
MQIQDRNSSPQVTEVLNQVKDAIAASQDYLMSIQYPEGYWWAELESNVTITAEVVLLHKIWGTDKT

RPLHKVETYLRRQQREHGGWELFYGDGGDLSTSVEAYMALRLLGVSIDDPALIRGREFILKRGGIS

KSRIFTKLHLALIGCYDWRGIPSIPPWIMLLPENFPFTIYEMSSWARSSTVPLLIVFDKKPVYCCDPTI

NLDELYSEGIENVKYDLPKTGDWTDIFVWLDGVFKFAQDYNLVPLRQESLQAAERWVLERQEDSG

DWGGIIPAMLNSLLALRALNYEAVDPIVHRGLQSVDNFAIETEDTYHVQPCISPVWDTAWAIRALVE

SGLKADDPRLVKGAQWLLDKQILDYGDWAVKNKQGTPGGWAFEFDNRWYPDLDDSAVVVMALD

QVKMPNEDLKNGAIRRCVRWMATMQCKDGGWGAFDLDNDQNWLNFLPYADLKAMIDPNTSDVT

ARVLEMLGTCGLIMDSNRVQKAIAYLEKEQEPDGSWFGRWGVNYIYGTSGVLSALAVIAPETHQK

ELKKGAAWLVGCQNADGGWGETCFSYNDSSLKGKGDSTASQTAWGLIGLLAAGEATGEFFKTAI

ERGVNYLLKTQREDGTWDENYFTGTGFPCHFYLKYHLYLQYFPLIALSRYQRLLT

>seq_ID 9
MSVSERAQPGGNPIPGSTSQSAVKFGRIDAALEDVKRAIAGAKDRVFAQQSKDGWWCGELEADS

MLEADYIFAHTLLGTGDAGKMKRALTEMLRYQNEDGSWSIYPGGPGNISLTVKCYFSAKLMGMTA

DNPILVKAREWILAHGGVVECNTFTKIYLCFLGQYEYDAVPAIPPEIVLFPNWFYFNIYEISSWSRAIL

VPLSIAYAKKPFKKIPPEQGIDELFVGGREKANLHLRWDSKNLLSWRNFFLALDRVTHWFERVHIR

PLRSIALKKAEKWMLARFEMSDGLGAIYPAMLNAIIALRCLGYSLDDPQVLRAMDEFEKLGIDEPEG

TAEYAEPTFRMQPCVSPVWDTAQAVFALGEAGVPRNDPRMQKAADWLLSKEVRHKGDWAMKV

RNAQPGGWYFEFNNEFYPDVDDSAQVLLALNKVDNPRERYQDVCQRAIDWIFAMQCRNGGWA

SFDKDNTKMIFQYVPFADHNAMLDPPTVDITGRILEMLATYGYTRKDRRVEKAIKFIYDEQEPDGS

WFGRWGVNYLYGTFLVLRGLEAIGVWNHEPQIQQAAEWIRSVQNADGGWGETCGSYDDPNTRG

VGPSTPSQTAWAILGLLSAGDDRSDSVAKGIKWLLAHQKPDGGWDESTGSGSKHQALYTGTGFP

RVFYLAYHQYRDYFPLLALTNYEKAMERGE

>seq_ID 217
MTEEVLQRTAAPAEVLAAAREHLLSLQHERGWWKGELETNVTMDVEDLLLRRFLGILTTAETEQA

ARWIRSRQRADGTWAQFHGGPGDLSTTVEAYVGLKLAGDDVDSEHMAAARAWILERGGIEETRV

FTRIWLALFGEWSWDDLPAMPPELVLLPPWVPLNLADWGCWARQTIVPLTVVCTLRPRRDLGVG

LAELRSGRRRRKVPSPSWAGAFQVLDGALHGYQRHPLRGLREHAMRRAAEWIVARQEADGSWG

GIQPPWVYSLLALHLLGYPLDHPVLRQGLAGLERFLIREETPEGTVRRLEACQSPVWDTVLSMQAL

RDAGLAADHPALRRAADFVLAEEIRVKGDWSVRRPDLAPGGWAFEFDNDGYPDIDDTAEVVLALN

RVDHERPGAVNAAIDRGVRWMSGMQSADGGWGAFDADNTRELVNELPFCDFGAVIDPPSADVT

AHVVEALCVLGRGDGEAVRRGVRWLLDHQELDGSWFGRWGANHVYGTGAAVPALVRAGLRRD

HLALRRAVRWLEVHQNDDGGWGEDLRSYDDPVWVGRGRSTASQTAWALLALLAVDLHDTDAVR

RGVGFLAETQRPDGTWDEPQFTGTGFPGDFYINYHLYRLVFPVTALGRYEQARREQSGGSG

>seq_ID 249
MIEKNKVKQSILASQKHLLSLQETEGYWWGQLESNVTITAEIILLHKIWQTDKKIPLNKAKNYLISQQ

REHGGWELFYGDGGDLSTSIEAYMALRLLGVSRTDPIMIEAQNFIIKKGGISCSRIFTKLHLALIGCY

SWQGIPSIPSSIMLLPEDFPFTIYEMSSWARSSTVPLLIVFDKKPIFSVNPTINLDELYAEGINNASFE

LPRKYDLTDLFLGLDKAFKFAENLNLMPLQQEGLKAAEKWILERQEVTGDWGGIIPAMLNSMLALK

CLEYDVADPVVVRGLEAIDRFAIENEDSYRVQACVSPVWDTAWVIRSLVDSGISPSHPAMVKAGQ

WLLQQQILDYGDWVFKNKFGKPGGWAFEFMNRFYPDIDDTAVVVMALDVVELPDEDLKGKAIAR

GMEWIASMQCEAGGWAAFDVDNNQDWLNATPYGDLKAMIDPNTADVTGRVLEMVGCCGLAMD
```

```
SWRVKRGIDFLVREQEEEGCWFGRWGVNYIYGTSGVILALAVMARESHRGYIERGASWLVGCQN
SDGGWGESCWSYNDPSLKGKGKSTASQTAWALIGLLAAGEGTGNFARDAIDGGVGFLVSTQND
DGSWLEDEFTGTGFPGHFYIKYHFYSQYFPLMALGRYESLLSG
>seq_ID 222
MAVRDRVNPKTLEAAIAASQSYLLTQQDETGYWWAELESNVSITSEVVLLHKIWGTDRSRPLEKVE
TYLRSQQRDHGGWELYFDDGGEISVSVEAYMALKLLGVPMEDPAMVRARQFILEHGGISRTRVFT
KLHLALIGCYEWRGIPSLPPWVMLLPEQFPFTIYEMSSWARGSTVPLLIVMDREPVYAVEAGFNLD
ELYVEGRHRAQFDLPLSNEWTDAFIYLDGLFKFAESTNLVPFREEGIRAAERWILERQEATGDWG
GIIPAMLNSLLGLKALDYDVHDPIIERGMAALDAFALETEDQYWIQPCISPVWDTALVVRGLAESGL
APDHPALVKAGEWLLNKQILDYGDWSVKNPGGLPGGWAFEFDNRFYPDVDDTAVVVMALNEVQL
PDEQAKDAAIARAVNWIATMQCRPGGWAAFDINNDQDWLNALPYGDLKAMIDPNTADVTARVLE
MIGRCHQTTGKNSVDRALRYLRTEQEPEGCWFGRWGVNYIYGTSGVLAALALIDPQGWQSQIQQ
AAAWLVSCQNTDGGWGETCASYDNPKLKGQGPSTASQTAWAIMGLLSAGEATSVYAEAAIERGV
NYLTTTQKMDGTWDEDYFTGTGFPGHFYLKYHLYQQHFPLTALGRYQAMLQQKS
>seq_ID 186
MRTQDRVQVNSIAEAIAASQKYLLSLQNPAGYWWAELESNVTITAEVVLLHKIWGTDKTRPLHKVE
AYLRSQQKQHGGWELFYGDGGELSTSVEAYMALKLLGVPATDPAMIQARDFILQRGGISKTRIFTK
FHLALIGCYNWRGLPSLPAWVMLLPNQFPVNIYEMSSWARSSTVPLLIVFDQKPVYQVNPTITLDE
LYAEGVENVRYELPRSGDWTDLFLTLDEGFKLAESFNFIPFREEGIKAAEKWIIERQEATGDWGGII
PAMLNSMLALRSLGYDTNDPIVERGLQALDNFAIETVDCYRVQPCVSPVWDTAWVIRALIDSGIAP
DHPAIVKAGEWLLQKQILDYGDWNVKNRQGKPGAWAFEFENRFYPDVDDTAVVVMALHAAKLPN
EQLKQKACDRALQWVASMQCKPGGWAAFDLDNDQDWLNSVPYGDLKAMIDPNTADVTARVIEM
LGACNLSIDSHNLERALTYLLNEQEAEGCWFGRWGVNYIYGTSGVLSALALINPQKYQRHIQQGAT
WLVGCQNPDGGWGETCFSYNDPSLKGQGDSTPSQTAWALIGLIAAGEATGNFAHDAIERGINHLV
STQQPDGSWFEAYFTGTGFPCHFYLKYHYYQQYFPLIALGRYQAIKSL
>seq_ID 153
MQVQPRIEKKHLDSAIEASQAYLLARQYSPGYWWAELESNVSMTAEVVLLHKIWRTDTGRPLAKA
TAHLLAEQRAHGGWELFYGDGGDLNTSIEAYMALKLLGLTADHPALARARAFILAKGGISRARIFTK
IHLALIGCYDWRGVPSIPPWVMLLPEAFPVNIYEMSSWARGSTVPLLIVFDRKPVFAVEPAITLDELF
VEGRAQARFDLPRSSSDWWANLFVDLDWGFKLAESLGAVPLREEGLKAAERWVLERQEATGDW
GGIIPAMLNSLLALRCLDYDPHDPVVERGMAAVDRFAIETESTYRLQPCVSPVWDTALTMRALVDS
GLPPDHPALAAAGTWLLKKQILDYGDWAVKNRTGPPGGWAFEFDNRFYPDVDDTAVVVMALDAV
RLADETAKGQAIARAVCWVASMQCRGGGWAAFDIDNDAHWLNSLPYADLKAMIDPNTADVTARV
LEMYGRCRLIPAAAGAQRALDYLRRTQEPEGCWFGRWGVNYLYGTSGVLSALAAFAPAERTAIER
AAAWLRGCQNTDGGWGETCGSYVDRTLMGQGPSTASQTAWALLGLIDASRVARFSDSSALERG
LAYLVETQKADGSWDEPYFTGTGFPGHFYLKYHLYQQHFPLSALGRYRRLLS
>seq_ID 122
MQIQARNISTKVIEVFSKVKEAIAASQQYLLSIQYPEGYWWAELESNVTITAEAVLLHKIWGTDTTR
PLHKVETYLRRQQREHGGWELFYGDGGDLSTSVEAYMALRLLGVSASDPALVRAKAFILSRGGIS
KSRIFTKMHLALIGCYDWRGVPSIPPWIMLLPENFPFTIYEMSSWARGSTVPLLIVFDKKPVYQCGIT
LDELYSEGINHVRYDLPRNGDWTDVFVWLDGVFKFAETNNLIPFRNESLKAAERWVLERQEDTGD
WGGIIPAMLNSLLALRALDYEVNDPIVHRGFKSVDNFAIETEETYHVQPCISPVWDTAWVLRALVES
GLKPDEPVLVKGAQWLLDKQILDYGDWAVKNKEGTPGGWAFEFDNRWYPDLDDSAVVVMALEQ
```

-continued

```
VKMPDEQLKYGAMRRCVRWMATMQCKAGGWGAFDVNNDQNWLNYLPYADLKAMIDPNTADVT

ARVLEMLGTCELSMDHDRVKRAIAYLEQEQEADGSWFGRWGVNYIYGTSGALSALAAIAPVTHQA

QIEKGAAWLVGCQNPDGGWGETCFSYNNPALRGKGDSTASQTAWGLIGLLAAGEATGKFAKTAL

ERGVNYLLATQRPDGTWDESYFTGTGFPCHFYLKYHLYLQYFPLIALSRYQRLLGFN

>seq_ID 129
MSLTSDPSPAAPTAEKSPKRPTIPVPATADAYGISRSSPPLPAATGRPQAAGPASAGVATARARDH

LLALQSEEGWWKGDLETNVTMDAEDLFMKQFLGIRGDDETEQTARWIRSQQLADGGWPTFYGG

PADLSTTIEAYIALRLAGDAVDAPHMARAAELVRAQGGVAASRVFTRIWLAALGQWSWDDVPVIPP

ELIFLPSWIPLNVYDFACWARQTIVALTIVGSLRPSHDLGFSIDELKVPAAARKPAALRSWEGAFER

LDKLLHRYEKRPIKLLRTLALRRATEWVVARQEADGCWGGIQPPWVYSVMALHLMGYPLNHPVIA

TAFRGMERYVIRRDTPQGPIRQIEACQSPVWDTALAVVALADAGVPGDHPAMVKAGRWLVDEEV

RVAGDWAVRRPELAPGGWAFEFDNDFYPDVDDTAEVVLALRRLLGAGHVAPPASRQGRAEAPP

VNTVEDADPRLAAAMRAAAARGVDWSVGMRSSNGAWGAFDADNVRTLTTKIPFCDFGEVVDPP

SADVTAHIVEMLADLGRSDHPITQRAVQWLLDNQEPGGSWFGRWGVNHLYGTGAVVPALIGAGV

PTDHPAITAAVRWLLEHQSPEGGWGEDLRSYTDPAWIGRGELTASQTAWALLALLAVDPHSLAVK

RGVRWLCETQRPDGTWDEPYFTGTGFPGDFSLNYHLYRLVFPLTALGRYVSLTGVATP

>seq_ID 164
MHSGRVFLEKENREENRATFHSSPLILVEESLNLPKKVEETIKKAQRYLLSIQKEDGHWVGELFVD

VTLACDCIHLMHWRGKIDYKKQLRLVKHIVDRQLPDGGWNIYPGGPSEVNATVKAYFALKLAGFSP

DDPLMAKARSTILRLGGIPKCMTYTKLGLALLGVYPWDRLPVIPPEIILFPNWFPFNIYEISAWSRAM

LVPLSVIHHFKPTRNLPEKYQLHELFPYGTEHGKFSWLKKGARYLSKQGLFLACDKFLQYWDKTSL

KPFRKMALKKAEKWLLERISAGSDGLGAIFPAMHYAIMALIAMGYTEDNPILKKAIADFEGLEVDDK

KNDDLRIQPCLSPVWDTAVGLVALAESGVARNAKELKRAAYWLLDREIKIKGDWHVRNPHPEPSG

WAFEYNNVYYPDVDDTLMVLLALRLIDIEDKIRKEEVMQRALRWVISFQCKNGGWAAFDKDVYKK

WLEDIPFADHNAILDPPCSDITARALELFGKMGIKKTERFVQKAIAYLKETQENDGSWMGRWGVNY

IYGTWQALRGLQAIGENMNQEWILRARDWLESCQNEDGGWGETPASYDNPQLKGKGPSTASQT

AWAVSGIMACGDIFRPSVSRGIKYLCDRQLSDGSWAEEFLTGTGFPGVFYLKYDMYRNAWPLLVI

GEYHRQYLKAKEQVSYWVDGTIGRKVKKERLPEI

>seq_ID 20
MRTQDRVQVNSIAEAIAASQKYLLSLQNPTGYWWAELESNVTITAEVVLLHKIWGTDKTRPLHKIEA

YLRSQQKQHGGWELFYGDGGELSTSVEAYMALKLLGVPATDPAMIQARDFILQRGGISKTRIFTKF

HLALIGCYNWRGLPSLPAWVMLLPNQFPVNIYEMSSWARSSTVPLLIVFDQKPVYQVNPAITLDEL

YAEGVENVRYELPRSGDWTDLFLTLDEGFKLAESFNFIPFREEGIKAAEKWIIERQEATGDWGGIIP

AMLNSMLALRVLGYATNDPIVERGLQAIDNFAIETADCYRVQPCVSPVWDTAWVIRALIDSGMAPD

HPAIVKAGEWLLQKQIFDYGDWNVKNRQGQPGAWAFEFDNRFYPDVDDTAVVVMALHAAKLPHE

QLKQKACDRALQWVASMQCKPGGWAAFDIDNDQDWLNAVPYGDLKAMIDPNTADVTARVIEML

GACNLSIDSHDLERALTYLLNEQEAEGCWFGRWGVNYIYGTSGVLCALALINPQKYQRHIQQGAT

WLVGCQNPDGGWGETCFSYNDPSLKGQGDSTPSQTAWALIGLIAAGEATGNFAHDVIERGINHLV

STQQPDGSWFEAYFTGTGFPCHFYLKYHYYQQYFPLIALGRYQAINPL

>seq_ID 185
MQTQDRVKVNQVAEAIAASQQYLLSIQNPAGYWWAELESNVTITAETVLLHKIWGTDQTRPLHKV

EAYLRQEQRQHGGWELFYGDGGELSTSVEAYMALRLLGVPATDPAMIRAQAFILQRGGISKTRIFT
```

-continued

```
KLHLALIGCYNWRGIPSLPPWIMLLPKAFPVNIYEMSSWARSSTVPLLVVCDRKPVFITDPTINLDEL

YAEGIDRVRWELPQSGDWTDLFLTLDQGFKWAESLNLVPFREEGIKAAEKWILERQEATGDWGGI

IPAMLNSMLALRCLDYDRSDPIVERGLQAIDNFAIETDNSYRVQPCVSPVWDTAWVMRALVESGF

VPDHPAVVKAGEWLLQKQILDYGDWAVKNRQGKPGAWAFEFENRFYPDVDDSAVVVMALHLAKL

PNEKIKQAAIARAVNWIASMQCKPGGWAAFDLDNDQDWLNSIPYGDLKAMIDPNTADVTARVVEM

LGACDLSIDSDNLERSLTYLLREQETEGCWFGRWGVNYIYGTSGVLSALALIDPQRHKLSIERGAA

WLLGCQNLDGGWGETCRSYDDPSLKGKGDSTASQTAWALIGLLAAGEATGKLAVKAIEQGIGYL

MATQQPDGTWFEANFTGTGFPCYFYLKYHLYQQYFPLIALGRYQAAIKES
```

>seq_ID 244

```
MVIAASPSVPCPSTEQVRQAIAASRDFLLSEQYADGYWWSELESNVTITAEVVILHKIWGTAAQRP

LEKAKNYLLQQQRDHGGWELYYGDGGELSTSVEAYTALRILGVPATDPALVKAKNFIVGRGGISKS

RIFTKMHLALIGCYDWRGTPSIPPWVMLLPNNFFFNIYEMSSWARSSTVPLMIVCDQKPVYDIAQG

LRVDELYAEGMENVQYKLPESGTIWDIFIGLDSLFKLQEQAKVVPFREQGLALAEKWILERQEVSG

DWGGIIPAMLNSLLALKVLGYDVNDLYVQRGLAAIDNFAVETEDSYAIQACVSPVWDTAWVVRALA

EADLGKDHPALVKAGQWLLDKQILTYGDWQIKNPHGEPGAWAFEFDNNFYPDIDDTCVVMMALQ

GITLPDEERKQGAINKALQWIATMQCKTGGWAAFDIDNDQDWLNQLPYGDLKAMIDPSTADITARV

VEMLGACGLTMDSPRVERGLTYLLQEQEQDGSWFGRWGVNYLYGTSGALSALAIYDAQRFAPQI

KTAIAWLLSCQNADGGWGETCESYKNKQLKGQGNSTASQTAWALIGLLDALKYLPSLGQDAKLTT

AIEGGVAFLVQGQTPKGTWEEAEYTGTGFPCHFYIRYHYYRQYFPLIALARYSHLQAS
```

>seq_ID 109

```
MDDRHIQSEITFGKIDGIRERIQQAMDAAKRYLFSKQDPEGFWCGELEADTTLQSDYIVMHTLLGT

GDPVKMQKAGKQILQHQNPDGGWNIYPDGPSNISAAVKAYFSLKLIGHKPDEPEMTKAREWILAH

GGVTACNTFSKMYLCFFGQYDYDTVPAIPPEIVLFPNWFWFNLYEISSWSRGILVPLAICYAKKPFK

KIPDEANIDELFVEGRHANLHLTWDKKPFSWRNFFLVLNNMVHFFERVHVRPLRKLAMKRAEKWM

LERLEMSDGLGGIYPAILNSIIALRALGYSTDDPQVIRAMDEFEKLGIEEDDTFRMQPCMSPVWDTA

YALYALGEAGVPGSDPRMQKAAEWMLKKQVTHKGDWAVKVRNVQPGGWYFEFNNEFYPDVDD

TAQVILSLNHVRTSNERYQDDTVKRALDWQLAMQCKNGGWASFDKDNNKMVFQYIPFADHNAML

DPATVDITGRVLEALSHHGYSLKDKVVQRAVKFIQSEQEPDGSWFGRWGVNYIYGTMLCLRGLAA

VGVDHHEPMVQQAAEWLRMVQNPDGGWGESVGSYDDPKLRGQGPSTASQTAWAVMGLLAAN

DLRSDSVTRGIAWLLENQKPNGSWWEKWITGTGFPRVFYLKYTMYAEYFPLIAFAEYLRRLNTPLD

EKVKLGPQA
```

>seq_ID 174

```
MQIQDKITEIAAKTAKAIELSQNYLLSTQYSEGYWWAELESNVTITSEAILLHKIWKTDKKRPLDKAA

TYLRQQQCPNGAWELFYGDGGDLSTTVEAYMGLRLLGIPANDPALEKAREFILAKGGISKTRIFTK

MHLALIGCYDWQGVPSIPAWIMLLPENFPFTIYEMSSWARGSTVPLLIVFDKKPVYKMGFNLDELY

TEGVNNVKYELPKNNNWSDVFLWLDGLFKWAEKTDLVPFRQESLKAAEKWVIERQEDTGDWGGI

IPAMLNSLLALKALDYDVYDPIVARGLKAVDNFAIETDNTYCVQPCVSPVWDTAWVIRSLIESGLNP

AHPAMIKAGQWLIDQQILDYGDWAIKNKIGTPGGWAFEFDNRWYPDLDDSAVVVMALELIKMPDE

NIKTSVMKRAVNWMATMQCKAGGWGAFDIDNDQNWLNSLPYADLKAMIDPNTADVTARVLEMLG

TCDVKMGENRVKKALDYLEKEQEADGSWFGRWGVNYIYGTSGALSALAFLEPNQYRQQLQKGA

NWLSSCQNVDGGWGETCFSYNNPKFKGQGNSTASQTAWALIGLLAVGKVTGNYQREVIEKGVN

YLLVTQKENGTWDEDYFTGTGFPCHFYLKYHFYQQYFPLLALGRYRALI
```

>seq_ID 130
MSLTSDPSPAAPKAAKSSKRVNIPAPATPDAYGISRSSPPLSGGGVSGGGVSGGGAATADGTPPT
TQTSVDPDLAAAMTAANQARDHLLGLQSEEGWWKGDLETNVTIDAEHLFMKQFLGIRTEEETEPI
ARWVRSQQLADGGWATYYGGPAELSTTVEAYIALRLAGDEPDAPHMAAAAALIRSQGGVAAARV
FTRIWLATFGEWSWDDVPVLPPELIFLPSWFPLNVYDFGCWARQTIVALTIVGSLRPVRDLGFSIDE
IKVAAPVTPPKPAPLHSWEGAFERLDAILHRYERRPIKVLRTLALRRATEWVVARQEADGCWGGIQ
PPWIYSVMALHLMGYPLNHPVIATAFRGMERYIIRRETPEGPTAQIEACQSPVWDTALAVVALSDA
GVPADHPAMVRAGRWLVDEEVRVAGDWAVRRPALAPGGWAFEFDNDFYPDTDDTAEVVLALRR
LLGGSHVTPGGTVTPSGSVTPGGTAELSPAARDRASRGLAAVDPQLAGAMRAAAARGVDWSVG
MRSSDGAWGAFDADNVRTLTAKIPFCDFGEVVDPPSADVTAHIVEMLADLGRSDHPITRRAVQWL
LDNQEPGGSWFGRWGINHVYGTGAVVPALIAAGVPADHPAITAAVRWLLEHQSPDGGWGEDPR
SYDDPAWIGRGELTASQTAWALLALLAVDPHSKAVKRGVRWLCETQRPDGTWDEPQFTGTGFP
GDFYLNYHLYRLVFPLTALGRYVTLTGVATP >seq_ID 248
MPTSLATAIDPKQLQQAIRASQDFLFSQQYAEGYWWAELESNVTMTAEVILLHKIWGTEQRLPLAK
AEQYLRNHQRDHGGWELFYGDGGDLSTSVEAYMGLRLLGVPETDPALVKARQFILARGGISKTRI
FTKLHLALIGCYDWRGIPSLPPWIMLLPEGSPFTIYEMSSWARSSTVPLLIVMDRKPVYGMDPPITL
DELYSEGRANVVWELPRQGDWRDVFIGLDRVFKLFETLNIHPLREQGLKAAEEWVLERQEASGD
WGGIIPAMLNSLLALRALDYAVDDPIVQRGMAAVDRFAIETETEYRVQPCVSPVWDTALVMRAMV
DSGVAPDHPALVKAGEWLLSKQILDYGDWHIKNKKGRPGGWAFEFENRFYPDVDDTAVVVMALH
AVTLPNENLKRRAIERAVAWIASMQCRPGGWAAFDVDNDQDWLNGIPYGDLKAMIDPNTADVTA
RVLEMVGRCQLAFDRVALDRALAYLRNEQEPEGCWFGRWGVNYLYGTSGVLTALSLVAPRYDR
WRIRRAAEWLMQCQNADGGWGETCWSYHDPSLKGKGDSTASQTAWAIIGLLAAGDATGDYATE
AIERGIAYLLETQRPDGTWHEDYFTGTGFPCHFYLKYHYYQQHFPLTALGRYARWRNLLAT >seq_ID 150
MAKGILNKFAVIAGTKKAGPPAGEERTVIAPIKEISGKAVHCSQAVKKAEEYLLALQNPEGYWVFEL
EADVTIPSEYIMLQRFLGREISPELGKRLENYLLDRQLPDGGWPLYAEDGFANISATVKAYLALKVL
GHSPQAPHMIRARLMVLSLGGAARCNVFTRILLALFGQIPWHTPPAMPVEIVLLPQWFFFHLSKVS
YWSRTVIVPLLLLYAKQPVCRLRPEEGIPELFSTPPDKLRHLDGFQPGYWRKNAFIIFDRLLKRFNR
FIPSALHRKAIAEAEQWTRSHMQGSGGIGAIFPAMAYAVMALRVLGCGEGDPDYIRGLQAIDDLLQ
HRTPQEADPPRTDGTCIDSGMSAAFALTPSAHAAADGTGSSSICQPCNSPIWDTCLSLSALMEAG
MPASHPAATQAVEWLLSQQILSPGDWSLKVPDLEGGGWAFQFENTLYPDLDDTSKVIMSLLRAGA
LENERYRDRIARGVNWVLGMQSSDGGWAAFDIDNNYHYLNDIPFADHGALLDPSTSDLTGRCIEL
LSMVGFDRTFPPIARGIGFLRSEQEENGAWFGRWGVNYIYGTWSVLSGLRQAGEDMQQPYIRKA
VGWLASCQNHDGGWGETCYSYDDPSLAGKGASTPSQTAWSLLGLMAAGEVNSLAVRRGVRYLL
DHQNQWGTWEEKHFTGTGFPRVFYLRYHGYRHFFPLWALGVYSRLSSGQKACQDERRHASPG
DLHLPWLERIKKR >seq_ID 128
MPDLELRDVDRADGRHHAPNLGRTDTLSPSAPTGEPAPASTPAAVATPTPTPTTAPAPAPAPENA
LRETVQRAAEHLLRLQDPRGWWKFDLETNPTMDAEDLLLREYLGIRTVEQTEATAKHIRSRRLDD
GSWPTYFGGPGELSTTVECYIALRLAGDSPDDEPLRRSAAWIRERGGIPATRVFTRIWLALFGWW
RWEDLPVLPPEIMFLPPRAPLSIYSFASWARQTIVPLTIVSAARPQCPAPFDLAELDPDEVPAAQSH
GAAQSPDTRSPAGGRTLRGAMRRLGGDRPNTAKVFFRGLDAALHRYHRHPIGPLRRHALRTAER -continued

```
WIIARQEADGCFGGIQPPAVYSIIALRLLGYDLDHPVLAAALRSLDAYTLHREDGSRMIEASQSPIW

DTALAVLALADAGIDAPADVDVAPALPTQRVATGAPAPSAPVPTALERAADWLLGQEIQHRRGDW

AITHPGVAPGGWAFEFDNDTYPDTDDTAEVVLALHRLNRLRRLRHPTNTRIDAALERSTAWLFALQ

SRDGGWGAYDSDNASTLVYQIPFADFGALTDPSSADVTAHVVELLCETGRIRDPRTLRGVDWLLR

NQEADGSWYGRWGVNYVYGTGSVLPALQAAGLPPTHPAMVAGARWLLSRQNSDGGWGEDIRS

YGDPAWSGRGLSTPSQTAWAMLGLLATDHGGVHADALAAAARWLTEQQRPDGGWDEEMFTGT

GFPGFFYLNYHGYRLVWPVMALGRYLHSRQHPSD
```

>seq_ID 131
```
MSLTSDQSSAAPTAAAQSPKIPNPSVARPSADAGSFETAGAVRTDSVSIDSVSTGTPVDPVVGAM

RRGRDHLLSLQAEEGWWKGELETNVTMDAEDLMLRQFLGILTPSTATETGRWIRSQQLSDGGWA

TFYGGPSDLSTTIEAYVALRLAGDDPDAPHMRSAAEWVRSAGGIAASRVFTRIWLALFGEWSWDD

VPVLPAEMTFLPPWFPLNIYDFACWARQTVVALTIVGSLRPVRSFGFTLDELRVQAPKATKAPLRS

WAGAFERLDSVLHRYEKRPFQPLRRLALRRAAEWVIARQEADGCWGGIQPPMVYSIMALHLMGY

PLNHPVISMAFRALDRFTIREETPEGTVRRIEACQSPVWDTALAVVALADAGLGGDHPAMVRAGR

WLADEEVRVAGDWAVRRPTLAPGGWAFEFDNDFYPDVDDTAEVVIAIRRLLGDGHGPVDHSDGS

GPGSAAATAASAAAEAAVAAAGTIAAADPELAARLRAAAERGVDWSVGMRSSNGAWAAFDADNV

RTLVRKIPFCDFGEVVDPPSADVTAHMVEMLALLGRSDHPITQRGVRWLLDNQEAGGSWFGRWG

VNHVYGTGAVVPALISAGVDAEHPAIVSSMHWLVEHQTPEGGWGEDLRSYRDDEWIGRGEPTAS

QTAWALLALLAAEPASGTAEWEAVERGVRWLCDTQRPDGTWDEPQFTGTGFPWDFSINYHLYRL

VFPVTALGRYVTLTGRSTS
```

>seq_ID 242
```
MSISALQTDRLSQTLTQSVVAAQQHLLSIQNPEGYWWANLESNASITAEVVLLHKIWGTLDSQPLA

KLENYLRAQQKTHGGWELYWNDGGELSTSVEAYMGLRLLGVPASDPALVKAKQFILHRGGVSKT

RIFTKFHLALIGCYRWQGLPSLPAWVMQLESPFPFSIYELSSWARGSTVPLLIVFDKKPVYPLQPSP

TLDELFTESAENVRWELEEKGDWSDAFLWLDKAFKLAESVDLVPFREESIRKAEKWVLERQEPSG

DWGGIIPAMLNSMLALRALGYSVSDPVVRRGFQAIDNFMVESETECWAQPCISPVWDTGLAVRSL

TDSGLSPNHPALVKAGEWLLDKQILSYGDWSVKNPQGQPGGWAFEFENSFYPDVDDTAVVAMAL

QDITLPNEPLKRRAIARAVRWIATMQCKTGGWAAFDINNDQDWLNDIPYGDLRAMIDPSTADITGR

VLEMHGRFAADLDLANSYAADLSPYRLSRGLNYLIKEQELDGSWFGRWGVNYIYGTGQALSALALI

APERCRIQIERGIAWFVSVQNADGGWGETCESYKDKSLKGKGISTASQTAWALLGLLDVSFCLDP

AAKIAVDRGIQYLVSTQSEGTWQEESFTGTGFPQHFYLRYRLCHYFPLMALGRYQRVINSSAGI
```

>seq_ID 143
```
MAKGILNKFAVIAGNKNAGLTAEEECTVVAPIKEVSGKAVHCRQAVKMAEEYLLALQNPEGYWVFE

LEADVTIPSEYIMLQRFLGREISPELRMRLENYLLDRQLPDGGWPLYAVDGFANISATVKAYLALKV

LGHSPQAPHMIRARIMVLSLGGAARCNVFTRILLALFGQLPWHTPPAMPVEIVLLPQRFFFHLSKVS

YWSRTVIVPMLLLYAKQPVCRLRPEEGIPELFNTPPDKLRNLDGFQSGRWRKNAFIIIDRLLKRFNR

FIPSAIHRKAMAEAEHWTRSRMQGSGGIGAIFPAMAYAVMALRVLGCREDDPDYVRGMQAIDDLL

QHRTPQEADSPRTGGPCIDSGTSAAFAFDPSPHAAADGRGNSSICQPCNSPIWDTCLSLSALMEA

GMPASHPAAKQAVEWLLSQQIFSPGDWSLKAPDLEGGGWAFQFENTLYPDLDDTSKVIMSLLRA

GALENGLYRDRVARGVNWVLGMQSSDGGWAAFDIDNNYHYLNDIPFADHGALLDPSTSDLTGRC

IELLSMVGFDRTFPPIAQGIGFLRSKQEGSGAWFGRWGVNYIYGTWSVLSGLRQAGEDMQQPYIR

RAVGWLTSCQNHDGGWGETCYSYDDPSLAGQGESTPSQTAWSLLGLMAAGDVHSLAVRRGVR
```

-continued

YLLDHQNQWGTWEEKHFTGTGFPRVFYLRYHGYRHYFPLWALGVYSRLSSGQKTRQEERRHSS
PGDLHLPWLERIGRR

>seq_ID 71
MIKNFTALWPIRRVKGVSVTSQDGHSANGASKPDFEVRPHVDLETAIHRSQSFLLKEQKPEGYWV
GELIVDSTLVSDTIAYHHWNGKVDMEWQRKAVNHIFSMQLPDGGWNIYYGGPAEINATVKAYLAL
KLAGVPVMDPRMLRARSVALSMGGVPRMNTFSKLYLALLGLFPWNYVPTIPCEVILIGKWFHVNFY
EMSSWSRSMLVPLAIINHFKPTRKLQNQVKLDELYPEGYHERDLALPPDPEFLTFRNFFLWLDKLH
KFAELWVQAGIHPFRRRALKKCEHWMLERFEGSNGLAAIFPAMLNSLIALKALGYPGDHPEVKRA
EKELKNLEHETADTVRIEPCFSPVWDTAIVAICLHESGIPSDHPALKKSAEWLIDKEIRFRGDWYFK
NPVDVEPSGWVFEFENKWNPDVDDTAMVLLALRKIPTSDVKRRDECFQRGLKWMMAFQCKDGG
WAAFDKDCTKGILEKVPFADHNAMLDPECADITARILELLGYEGVGVDHPQIKKALQFIQEEQEDD
GSWYGRWGVNYIYGTWQVLRGLRALNINMNQPWLLKARDWLESVQHEDGGWGERCNTYDDPV
FKGQGPSTASQTAWAVMGLCTFDDPQRPSLMRGIDYLIKTQNSDGSWTEHEITGTGFPRVFYLKY
DMYRNSWPLLALATYRNLYASSEKTANGHTNGHSVQLPEALKTPPAFK >seq_ID 126
MNKKSAMKLKKKAKNHVVSLLQPTDALNRVMKRFRSLQSPEGYWVFALEADVTIPSEYIMFNRFL
GRKMDKGLAERLGNYIRAKQMADGGWPLHDNDGPVNISASVKAYMALKMLGDNKDAEHMVRAR
QIILAKGGAETANVFTRICLATFGQIPWHCPPAMPIEIVLLPKWFFFHLDKVSYWSRSVIYPLLIIYAK
QPVCRLRPEEAVPELFCKPAEEHIHIDKYRDKGWRKNLFILLDRVLKRTIHLVPKSINKKALNYAEK
WTREHMAGRGGIGAIFPAMANAVMALSLLGYDESDPDFARGMQSVDDLMVDKFHVPEKSPWEH
TVITGGAELSAAPELDISPDHGTAENLEQAMCQPCNSPIWDTCLTLSAMMEAGENQDSKSTQQAL
NWLWDQQIFFRGDWISKAPKLEGGGWAFQFENTFYPDLDDTAMVLMAMCRAGVLDQPEHRENFI
KGVNWLIGMQSSNGGWAAFDIDNCAEYLNDIPFADHGALLDPPTSDLTARVIELLGVLGYDKSFRP
IKDGIEFLKKEQEDDGSWFGRWGVNYIYGTWSVLCGLRQAGEDMNSSYVCKAVEWFENHQNKD
GGWGESCLSYNDKNYAGLGDSTASQTAWALLGLMAAGRVHSKAVSRGVRYLLDTQKDDGSWD
ESLFTGTGFPRVFYLRYHGYSQYFPMWALGVYQRFSADEDTKQIMMRRKSPLDLGRKW >seq_ID 114
MIFTDTPTGSTQNRLDVAIRRAQQNLLRLQHNEGYWCGELFVDSTLCSDYVLFMHWADEIDPVME
EKCVAHIRRRQLEDGGWNIYEGGPSDVNATVKAYFALKLAGHAPTQPWMQEARACILRLGGIPKM
NTYAKLYLALLGQFPWRYLPTVPVEIMFMPRWFFFDIYEVSSWSRAMLMPLAILNHYKPTKHLPAD
KQLHELYPIGSEESDLGLGMQKPRFSWPNFFLFCDRLIKIMHSLPWKPWKRAALARAEAWMTQR
MGEGSDGLAAIFPAMLNSMIALRTLRYSREHPLYVKAKNDFAGLFVDDPQDFRIQPCLSPVWDTAI
NLVALLESGLDPHDPKIEAAVNWLKEKEVRINGDWYVKNHHVPPSGWAFEFNNVYYPDTDDTMM
VLAALARAGAHEESAPVETKAMFERALKWLLSFQCRDGGWAAFDKDVTQGWLEDVPFADHNAIL
DPTCSDLTGRVLELLGLIDYDRNCTPVRRALKFLRDTQEDDGSWYGRWGVNYIYGTWQVLRGLR
SIGEDMRQQWIVRARDWLESCQNEDGGWGETCASYDDPILKGKGPSTASQTAWALMGLIAAAD
PTEPGAFDRKSIRQGVDYLLSTQVADGSWVEPEVTGTGFPRVFYLRYDMYRNNFPLMALATYRK
AREGKLPVRQRE >seq_ID 194
MKKATRSVFSLLDGGKISDSGSRGDSRHAGSRLDSVTKSAAALLASRQNPDGHWVFDLEADVTIP
AEYVMMRCFIGEPLDSDMASRLSAYLLERQLPDGGWPLYAVDGNANISATVKAYFALKLLGHDKY
APHMVSARRMILAQGGAERSNVFTRITLALFGQVPWHTTPAMPIEIMLLPKWFFFHLSKVAYWSRT -continued

VIVPLLILYNKQPVCRLGYSEGIAELFSTSPDMLVHLDHFRYRAWRKNAFIVLDRLLKRTMHLVPGRI

KRRALEEAERWTRERMKGDGSIGAIYPAMANAVMALKTLGCGDSDPDYLRGLRAIDRLLIHGKPE

AGALPADGAGTLFPVLDGASSAAVDLYPASLSDTAKSHAFSFCQPCNSPVWDTALSLTALSEAGG

GGYSPERAMEWLFNRQIATQGDWTERCPGLECGGWAFQYENALYPDVDDTAKVLMSLFRAGAL

ERGEYPEKIAKAVRWVLGMQGADGGWGAFDVDNNHFYLNDIPFADHGALLDPSTADLTGRCIEM

LGMLGHGPDYPPITRGIEFLREEQEPFGGWFGRWGVNYIYGTWSVLSGLSQAGEDMGRPYVRKA

VEWLVSCQNDDGGWGETCASYDDPSLAGSGASTASQTAWALLGLMAAGEADHAAVRAGIAYLA

DSFADGWDERHFTGTGFPRVFYLRYHGYSLFFPVWALGVYARHREGGKTVQEQVRERGVNGVF

DFVMGGSA

>seq_ID 154
MMANATDTIELPPSRAADRIVPMTDIDQAVDAAHAALGRRQQDDGHWVFELEADATIPAEYVLLEH

YLDRIDPALEERIGVYLRRIQGDHGGWPLYHGGKFDVSATVKAYFALKAIGDDIDAPHMARARAAIL

DHGGAERSNVFTRFQLALFGEVPWHATPVMPVELMLLPRKALFSVWNMSYWSRTVIAPLLVLAAL

RPRAINPRDVHVPELFVTPPDQVRDWIRGPYRSQLGRLFKYVDIALRPAERLIPDATRQRAIKAAVD

FIEPRLNGEDGLGAIYPAMANTVMMYRALGVPDSDPRAATAWEAVRRLLVELDGEAYCQPCVSPI

WDTGLAGHAMIEAASGPEGIRPEDTKKKLAAAAEWLRERQILNVKGDWAINCPDVPPGGWAFQY

NNDYYPDVDDTAVVGMLLHREGDPANDEALERARQWIIGMQSSNGGWGAFDIDNNLDFLNHIPF

ADHGALLDPPTADVTARCISFLAQLGHPEDRPVIERGIAYLRTDQEREGCWFGRWGTNYIYGTWS

VLCAYNAAGVAHDDPSVVRAVDWLRSVQREDGGWGEDCASYEGATPGIYTESLPSQTAWAVLG

LMAVGLRDDPAVMRGMAYLTRTQKDDGEWDEEPYNAVGFPKVFYLRYHGYRQFFPLLALSRYR

NLASSNSRHVAFGF

>seq_ID 156
MLIYSDILEKEDRVSETLSRQSVEPDEINHAIEGAQAALGGKQKSDGHWVYELEADATIPAEYVLLE

HYLDRIDPEKQAKIGVYLRRIQGHHGGWPLYHDGGFDLSATVKAYFALKAIGDDINAPHMRIAREAI

LDHGGAARTNVFTRIQLALFGEVPWDATPVMPVELMLLPRKAFFSVWNMSYWSRAVIAPLLVLNA

LRPKAINPRGIHVQELFVKPPSEVKDWIRGPYRSVWGRFFKHLDSALRPVLPLIPRSVHKKALKAAS

DFIEPRLSRGGLGAIYPAMANVVMMYRAQGVPDSDPRAKTAWDAIQDLLVDHGDEIYCQPCVSPV

WDTGLSGLAMIEAASGPAGTKTKETLAALKKSAEWLREHQILDVKGDWAINAPDLRPGGWAFQYE

NDYYPDVDDTAVVAMLLHRVDPENSREAISRAREWIIGMQSTNGGWGAFDIDNDHELLNHIPFSD

HGALLDPPTADVSARCISFLAQLGDPDDRPVILKAIEYLRSEQEPEGCWFGRWGTNYIYGTWSVLC

ALNIAGVPHDDPMVLRAVNWLESVQRPDGGWGEDCATYEGGTAGTYKKSLPSQTAWAVLALMA

VGRRESEAVKRGVAYLVSQQNEKGEWQEEAYNAVGFPKVFYLRYHGYKQFFPLTALARYRNLGV

SNSGKVEYGF

>seq_ID 74
MEGASPTASNRISQYAVDLRAKARAAVASTCDWLLSHQHADGHWCAELEGDSILQSEYILLLAWL

GKERTEIARRCAAHLLKQQEPNGAWTQFPGAPIDVGSSVKAYFALKLTGHDAAADYMVRARNAIL

EAGGADKVNSFTRFYLALLGQIPFELCPAVPPEMVLLPNWSPINIYRISSWSRTIFVPLSIVWAHRAA

RDIVEDVSIHELFIRKPEDWPELRCPGLEKPAGLFSWDRFFRTADSGLKLLEKYGLRPLRKRALRQ

AQQWMLDRFQQSDGPGAIFPPIVWSAIALRTLGYAEDSPEIQYCLDHLERLVLEDGETTKLQPCKS

PVWDTSITLRALAAAGLGLAQEPTCRGVEWLLSKEVRVPGDWTNNVDCEPGGWFFEYENAFYPD

NDDTSMGIMALADQLAAANITLEVHPGETLANTSVVGGRGIAEQLAGSSAAMMEQAAAATRRAV

AWMVAMQNKDGGWGAFDKNNDAEFLCHVPFADHNAMIDPSTPDLSARVIESFGRLGVTIESPGK

-continued

LGDTVRRAVAYIRANQLSDGSWFGRWGVNYIYGTWQCLVGLRAVGVPANDPAIEQGKLWLLAHQ

QACGGWGESCETYEDPSLRGQGSPTASQTAWALLGIIAAGGANLAEVVHGVQYLMDTQREDGA

WDEIEFTGTGFPRVFYLKYHYYPIYFPLLALAEWNRATARS

>seq_ID 326
MFDTISFDFDALDQAISRAHARLSAEQRADGHYVYELEADATIPAEYVLLEHFLDRIDPELEARIGVF

LRGIQGNSPQNPGGWPLFHDGAMDISASVKAYFALKAIGDDPDAPHMRRAREAILARGGAARTNV

FTRIQLALFGAVPWRACPVMPVEIMLLPDWFPITIWKISYWSRTVIAPLLVLLTERPIARNPRNVRID

ELFVTPPDQVTDYIRGPYRSNWGYLFKAIDSALRPLERHFPARSRKRAIQAAIDFITPRLNGEDGLG

AIYPAMANTVMMYHTLGYSPDHPDYATAWASVRKLVTDASYRFEGASYVQPCLSPVWDTSLAAH

ALAEAGSPGDAQLAAACDWLIPRQILDVKGDWAYRKPDAPPGGWAFQYNNAHYPDVDDTAVVG

MILDRNGDPAHREAVERARQWILGMQSRSGGWGAFDSDNEFHYLNHIPFADHGALLDPPTADVT

ARCISFLAQLGHAEDRPAIERGVAYLRREQEQDGSWFGRWGTNYIYGTWSSLCALNAAGVAQDD

PMMVRAVEWLLARQRPDGGWGEDCETYAHAKPGEYHESLPSQTAWALLGLMAAGQAEHEAVA

RGIAWLQSVQEDDGSWTEQPYNAVGFPRVFYLRYHGYPRFFPLLAMARYRNLARGNSRQVQFG

F

>seq_ID 192
MDKIKMKNINQPKFRVFRGGQKAATPCPGTTNERRGALDRGRLSASLKHSREWLLSLQADAGNW

VFALEADTTIASEYVMLQRFLGRPLAPELQQRLANYLLSRQLPDGGWPLYAEDGFANISTTVKAYL

ALKLLGYPTHCDPLVRARQIVLALGGAEKCNVFTRIALALFGQIPWRTTPAMPVEIMLLPRWFYFHL

SKISYWARTVVVPLLILYAKRPVCRLEPWEGIPELFVTPPDKLGYLDVCKPGQWRKNVFIWVDRLT

RKMVRCVPRRLHNLALRAAETWTREHMQGAGGIGAIFPAMANAVMALRTLGCSPDDADYQRGLK

ALDDLLIDRCDVPPREDTPVSPCWCTGTSAAPMLDPSPAGSHAQGGDQGICQPCASPIWDTGLAL

TALLEGGLDARHPAVDRAVRWLLDQQVDVKGDWAQRVPNLEAGGWAFQFENALYPDLDDTSKV

LMSLIRAGAMDNPGYRQELSRAINWVIGMQNSDGGWGAFDVDNNYLYLNDIPFADHGALLDPSTA

DVTGRCIEMLAMAGFGRDFLPIARGVDFLRREQEDFGGWYGRWGVNYIYGTWSALSGLIHAGED

LQAPYIRQAVGWLESVQNPDGGWGETCYSYDDPALAGRGVSTASQTAWALLGLMAAGEVDNLA

VRRGIQYLVEEQNRAGGWDERHFTGTGFPRVFYLRYHGYSQYFPLWALGLYERLSSGNPSRQQ

MVRRAGPAGLHLPVLDRRKKLRRKRKA

>seq_ID 72
MKSEEVTIKPAVGLEKDELNAAITRSQSFLLCEQKPEGYWVGELMVDSTIVSDTIAYHHWNGKVDP

EWQRKAVNHILSMQLPEGGWNIYQNGPPEVNATIKAYLALKLAGIPITDPRMLKARQVALTLGGVP

RMNTFSKLYLALLGLWPWKYVPTIPCEVLLLGKWFHVNIWDMSNWSRAMIVPLAIINHYKPTRPVK

VDLSELFLEGFHERDLALPKDPQSFTWRNFFLGLDQLHKFAELWVNAGIHPFRRLALKKCEQWML

ERFEGSDGLAAIFPAMLNSLIALKSLGYPDDHPEVLRAERELKKLEHETKDTVRIEPCLSPGWDTAI

AAMCLRESGVPAEHPRLKKAGDWLVNREVRFKADWHHKNPVDVEPSGWVFQFNNKWNPDLDD

TAMVLLALRLIPTDHPRRRDEAFQRGLKWLLAFQCRDGGWAAYDKDCTKNILEKVPFADHNAMLD

PECADITARVLELLGFEGYALDHPQVQEAVEYLREHQETDGSWYGRWGVNYIYGTWQTLRGLWA

LKMDMNQPWLLKARDWLESVQLPDGGWGERCNTYDDPVFKGQGPSTASQTAWAVMALCTFGD

PKRPSLVRGIQYLIENQNEDGSWTELETTGTGFPRVYYLKYDIYRNTWPLLAMATYRKMLDPKEVR

VK

>seq_ID 145
MNKHKGTFSVIEGGKTTQARGSETCAIMDAADLEKVTSVAASQLAGQQQDDGHWVFDLEADVTIP

AEYVMLQRFIGREIDPEISERLAAYMQERQLPDGGWPLYAVDGNVNISASVKAYFALKLLGHDKNA

-continued

PHMVRARQLILSLGGAAKCNVFTRITLATFGQIPWHTAPAMPIEIMLLPRWFFFHLNKVAYWSRTVI

VPLLILYATQPICRLQYNEGITELFTTPPDMLVHLDKFRHHAWRKNVFIALDRVLKRTMHLVPGRIKQ

HALAEAERWTRARMQGDGGIGAIYPAMANAVMALKTLGCSDDDADYLRGLEAVDNLMVHRNLKT

GTIPMDDDSGGIAIDNSSAAPELSPTYLTDTAGNTEFSFCQPCNSPIWDTCMSLSALCESGYAENN

SGVTDRAIKWLFSQQIATPGDWSEKCPGLESGGWAFQYENSRYPDVDDTAKVLMSLFRAGALEK

PEYREKIERAIRWVQGMQSTDGGWGAFDVDNDYFYLNDIPFADHGALLDPSTADLTGRCIEMMG

MLGHGPDYPPIARGIAYLKKEQEPFGGWFGRWGVNYIYGTWSVLSGLHQAGENMDAPYVRKAVE

WLISCQNSDGGWGETCASYDDPSLAGSGASTASQTSWALMALMAAGEWRHSAVRNGVRYLTES

YCNGWNEKQFTGTGFPRVFYLRYHGYSLFFPVWALAVYSRYINGTATVQEKVREKQFRQCLMV

>seq_ID 127
MLPYNQDFYNEDEALKDDHCEGAGNVSNPPTLDEAIKRSQDFLLSQQYPEGYWWAELEGNPTIT

SHTVILYKILGIEDEYPMDKMEKYLRRMQCIHGGWELFYGDGGQLSVTIESYVALRLLNVPPTDPAL

KKALKFIIDKGGVXKSRMFTKICLALLGCFDWRGIPSLPPWVMLLPGWFLSSIYETACWARGCVVP

LIVVFDKKPVFKVSPEVSFDELYAEGREHACKTLPFCGDWTSHFFIAVDRVFKMMERLGVVPFQQ

WGIREAEKWLLERQEDTGDFLGVYPPMFYSVVCMKTLGYEVTDPVVRRALLSFKKFSIERADECS

VQSSLSPVWDTALVVRSLVESGLPPDHPALQRAGEWLLQKQITKHGDWSFKNQSGVAGGWAFQ

FFNRWYPDLDDSAVVVMALDCLKLPNEDVKNGAITRCLKWISSMQCKGGGWAAFDKDNHQHWIN

STPFSDLKAMVDPSTTDISARVLEMVGRLKLHGTSFDEAHFLPPESIARGLVYLRREQENEGCWF

GRWGVNYIYGTCGALVALSLVAPMTHEEEIARGARWLVQVQNMHGKKINGPQDGGWGETCFSY

NDPALKGQGDVSTASQTAWALQGLLAAGDALGKYEVESIGHGVQYLLSTQRKDGSWHESQFTG

GGFPIHFYLRYHFYAQHFTLSSLARYRTRLQASKIKPPIP

>seq_ID 166
MNTEPRFSAPETLRAIAGAGRALGRHQRRDGHWVFELEADATIPAEYVLLEHYMDRITPERQARIG

AYLRRIQGEHGGWPMFHAGEFNISASVKAYCALKAIGDDPQAPHMVRARQAILGHGGAERANVFT

RIQLALFGAIPWRGVPVMPVEIMHLPKWFFFNIWAMSYWARTCVVPLLVLQARKPRARNPRQVSF

DEIFRTEPDEVRDWIRGPYRSRWGVVFKHIDTVLRWTEPLFSKVARESAIFKAVDFVEERLNGEDG

LGAIYPAMAYALMMYDVLGYPEDDPRCVTIWKAIDKLLIETDEEVYCQPCVSPVWDTSLSGHAMIE

AARTGGIEAQAELDAACDWLVARQVKDVRGDWAETRPDAEPGGWAFQYRNDHYPDVDDTAVVA

MLLHRNGRPEHAEAIEKARRWVVGVQSRNGGWGAFDADNDREFLNHIPFSDHGALLDPPTADVT

GRCISFLSQLGHEEDRPVIERALAYLRAEQERDGSWYGRWGTNYVYGTWTVLCGLNAAGIPHDD

PMVRRAVDWLVSIQRADGGWGEDERSYDVGHYVENAESLPSQTAWAMLGLMSVGQADHPAVL

RGAAYLQRTQGPDGEWQERAYNAVGFPRVFYLKYHGYRLFFPLFALSRLHNLQRGNSREVSFGF

>seq_ID 21
MSGEVRVAGDALAEDAGRAAAAASQYLYRTQQRDHWRAELESNVTVTAEYVLLRQALGLDLEER

RDALVRYLCSRQKADGSFGIASTLPGDVSTTAEAYLALRLLGLDREDERLRAAERFIRGAGGLARV

RVFTRINLALFGLFPWEAVPTVPAELIFLPRWAPVNVYRLASWARSTMVPLFVLFHHRPVFALPGG

AGSDWLDHLWLGPGDKRVPYRTSVMETVRRHGPGWKAFFNAADAWLRVHDRLRHLPPLGRLRT

EALRACEEWILARQEASGDWAGIFPPMLNGVLALHVAGHGLDAAPVRRGLEAIERFAVSDREGFRI

EACQSPVWDTILALIGLLDSGESPTDPRLVAARRWIEGMQLTNDWGDWKVYDPRGEPGGWAFEY

ANSWYPDVDDTAAVIVGLLKHDPASRAGETVRRAAAWVASMQNRDGGWAAFDVNNDRLFLNEIP

FSDMDSLCDPSSPDVTGRVLEAFGMLDAPHLRAACRRGVAYLRRAQEPEGSWYGRWGVNYVY

GTSNVLNGLARQRVPASDPMVARALGWLDSVQNADGGFGEGLESYADRAAMGRGPSTASQTA

```
WGVMGLLAYRAADDAAVRRGIAWLVERQLADGEAQGSWEEEAFTGTGFPRHFYLRYHLYRHYF

PLMALGRFCAQGRG
```

>seq_ID 111
```
MSYEWTEPVRPGRRHAVSPVQNFCQSLAPAIQRACDALFSQQAADGFWCGELTADTTLESDYILL

QLWLNQPDDHGWNPPTRPRIDRAGRSILERQLPDGGFNIYAGGPSEVSATIKAYCALKLAGLDPH

SPPLRRARERILALGGLQAANSYVKINLSLFGLYPRKHVPSVPPEIVMLPGNVLYEMSSWTRSILVP

LSIVQARGSNRRAPNGFNLDELLLPGVKLALPKRKGLAVLFHHLDRMFKVWEKRGSERIRGAAIRE

AERWLIARTHYTEGLGAIYPAMMYFIMALDALGYAEDHPDRSEAIRHFESLLIETDDRFLFQPCVSP

VWDTAICAFALGEAGNTDDPRMTLAADWLISKEVRRKGDWSIKRPDTEPSGWAFEFANEFYPDID

DTAMVLLALMHANGSNPEAQAAAERRAVNWLLAMQSSDGGWAAFDVDNNWAMLNQVPFADHN

AMLDPTCPDITGRVLECLCRRGMAGHDAARRGVAYLLQAQEKDGSWYGRWGVNYIYGSFLAMR

GLTTSGAPGSQDAVDRAARWLRAIQNPDGGWGESCASYARDGYVAAPSSASQTAWALLGLCAA

GDRDSAQFRRGVEYLLTLQAPDGKWPEGATTGTGFPNVFYLTYAMRDYFPLLALSQV
```

>seq_ID 157
```
MPKDIPADLASEAISGDMLEQAVLRASMALHRKQQTDGHWVFELEADATIPAEYVLLEHFLDRIDD

DLERKIGVYLRRIQGDHGGWPLFHEGAFNLSASVKAYYALKAIGDDPDAPHMRRAREAILAAGGA

ERSNVFTRIQLALFGQIPWRGVPVMPAELMIAPKWFPINMWKVSYWSRTVIAPLLVLMDRKPKARN

PRNVHVRELFLHDPDRIRDWIRGPFRSGWGHFFKYLDSVLRVVEPVALKPMRPRSIRLAVDFVRE

RLNGEDGLGAIYPAMANSVMMYDVLGYSPDHPEAAIAWESVRKLLVIKEDEAYCQPCLSPIWDTG

LSGHAMAEAEGAVSPGVAAACDWLRNRQITDVVGDWAEIRPGVQPGGWAFQYNNAHYPDVDDT

AVVAMLLHRQGDPAHEESIRKAREWIIGLQCRDGGWGAFDADNDKDYLNHIPFADHGALLDPPTA

DVTARCISFLAQLGNPEDKPVIDRAMAWLRKEQEADGSWFGRWGTNYIYGTWSVLCAMNVAGM

PHDDPAIRRAVNFLVATQREDGGWGEDEETYDPASGAQPGRYKESTPSQTAWALIGLMAAGEAE

HEATRRGIAYLQATQKPDGEWDEAAYTAVGFPRVFYLKYHGYRQFFPLMALSRYKNLRSSNMKK

VSFGF
```

>seq_ID 205
```
MNQAATITRPQDETLTTSARRPAQPALPDPLDAGIAHVVESLLAQQQSDGHWVYELEADATIPAEY

ILMVHYLGETPDLVLEGKIANYLRRIQNADGGWPLFHAGASDISASVKGYFALKMAGDNPEAEHMR

RARAAIHAMGGAEASNVFTRTLLALYGVMPWQAVPMMPVEIMLLPEWFPFHLSKVSYWARTVIVP

LLVLNSLRPQARNPRKIGIDELFVRPCQATRLPRRAPHQSPLWVGVFRTLDAVVRMAEPLFPRGLR

QRAIERAREFTVERLNGEDGLGAIFPAMVNSVLMFDVLGVPESDPNRAIARRSIDKLLVIKDDEAYC

QPCLSPVWDTSLAAHALLEVGEPRTIAAAARGLDWLLPLQELELRGDWTVRRPNVRPGGWAFQY

ANPHYPDVDDTAVVAAAMDRVDKGDRSNRYDEAVSRACEWIVGMQSSNGGWGAFEPENTHLYL

NNIPFADHGALLDPPTADVSARCLAMLCQLGQMPANSEPAARALRYLLDEQEADGSWFGRWGTN

YIYGTWSALCGLNAAGIGTDAPEMKRAAQWLLSIQNEDGGWGESGDSYKLEYRGYEKAPSTASQ

TAWAMLGLMAAGAGDHPALVRGVEYLLRTQASHGFWDEPYFTAVGFPRVFYLRYHGYSRFFPL

WALARFRNLLRDGNRAISWGL
```

>seq_ID 218
```
MKTDGNTTLDTTISMEELERTVKSAYEALAKDQQDDGHWIYELEADVTIPAQFILLEHTLDKIDEELE

QKIANYLRRCQSREHWGWPVYYGGEFNISASVQAYFALKMTGEDINAPHMVRAREAILAHGGPEY

ANVFTRIQLSLFGEASWLATPFMPVEIMLLPRWMYFSIWNMSYWSRTTVAPLLIVADLKPKAINPRN

VHIPELFPTPPDKVKTWIHGPFRSKWGHVFKFIDTAIRPFTRFVPSFLHKKAYKAALDFIEPRLNGVD
```

-continued

GLGAIYPPMSYSAVMYRALGIPDDDPRAATNWEALKGLLVIKEREAYCQACVSPVWDTALSGHAL

MEASFGPDGINADRTEKLIDRAAHWLRAHQVLNVVGDWAINNPNLQPGGWAFQYGNDYYPDVD

DTAVAAMLLHRQNLPENEEALDRARKWIIGMQSSNGGWGAFDIDNDKQILNDIPFADHGALLDPPT

ADVSARCISLLAELGHPEDRPVIERGIKYLRKEQEEDGSWFGRWGTNYIYGAWSVLCAFNASGVP

HDDPSVLKCVNFLKSVQREDGGWGESCETYEGSAHGVYTESLPSQTAWAVLGLMASGRRTDPA

VKRGIVWLIQHQQDNGEWAEEPFNAVGFPRMFYLHYLGYKQFFPLLALARYRHMEKSGTNNVSF

AF

>seq_ID 11
MLPYNQDHHFGKVAENATMPPTLDEAIERSQDFLLSLQYPEGYWWAELEANVTLTAQTIMLYKILG

IDHKYPIHKMKTYILRTQRAHGGWEIFYGDGGCLSTTIGAYMALRILGVPKTDPVLQKALKLIHSKG

GVTKSRMFTKICLALLGCYDWKGIPSLPPWLVLLPSWFPFSLYDTASWVRGCVVPLTIIFDKKPVYK

LNPLLCLDELYSEGKGKARVHLSFIPGDWTSNFFVGLDHVFKYMENLGVVPFRQWGIKEAERWTL

ERHEDSGDFHGIYPPMFYSIVSYSLLGYEITDPVVHRALESMRGFTVEREDECVVQSCISPMWDTA

FVIRSLAESGLQPDHPALQKAGEWLLQKQATQHGNWFYKKRTGRAGGWAFQFFNRWYPDVDDS

AAVSMALNAIKLQDDDVKKGAIKRCAEWISVMQCKDGGWAAYDCDNDREWLNCTPFGDLKAMID

PNTVDVTARVLEMVGRVKEAGDASAILPPRAIARGLAYLRREQETEGCWYGRWGVNYIYGTSGAL

MALALVAPSTHKEEIERGARWLVEVQNKRGTKGANGYSHTNGAREGGVAMNGNCKNMGAPEDG

GWGETCFSYNDITLKGRNEVSTVSQTAWALQGLLAAGDALGKYEVESIEHGVQYLLSTQRKDGS

WCEKHFTGGGFPRFFYIRYHLYAGHFPLSALARYRDRVRAGKMAK

>seq_ID 214
MDATAPLRDPGAPSAENCSVDRRELDDVIGESCRWLGERQNQDGHWVFELEADATIPAEYILLNH

FLDEIDDAREARIASYLRAIQGKHGGWPLFHDGDFDMSATVKAYYALKLTGDGVDEPHMVRARQA

ILEHGGAERTNVFTRFTLAMFDQVPWRACPVTPVEALLLPRFAPFHWSKVSYWSRTVMTPLMILY

SRRARAVNPRGIGVRELFRRDPEVIRDWLKNPTGHWIGDALIQIDKVLRVIEPAIHWAFRDRAEKW

ALDFIEERLNGRDGLGGIYPAIANTLMAYHTLGYAKDHPGYRIAREAVDGLCTPHAKGEYVQPCLS

PVWDTCLASHAIQEAGQSAGDRAVDQSNAWLRERQVLDVVGDWKSNRGHLRPGGWAFQYNNP

HYPDVDDTAVVVMALARSKEDEANREAIARAEEWIIGMQSSNGGWGAFDAENEHDFLNHVPFAD

HGALLDPPTVDVSARCLGMLAQLGRPKTDPVVARGLDYLWREQEADGSWFGRWGTNYIYGTWS

ALNAFNAVEWDMTDPRICKAVDWLKSRQRDDGGWGEDCATYWKERRSVSKASTPSQTAWAVL

GLMAAGEVDSPEVERGIRYLLEAPRDGGKWEEELYNAVGFPRIFYLRYHGYSAYFPLWALARYRN

LTSGNCKRTIHGM

>seq_ID 73
MPEEAILTETHPLDATTIETAITRARKALLGEQRADGHFVFELEADVSIPCEYILFYHFIGRPAPAELE

AKIGHYLRARQSAEHDGWPLFQDGAFNISSSVKAYFALKAIGDTPDMPHMQRARTAILAHGGAAA

ANVFTRSLLALFGLIPWHGIPVMPIEIMHLPEWFPFHIAKISYWGRTVLVPMMVVHALKPKPANTCTI

RIDELFVIPPDQVRHWPGSPGKRFPWTAIFAGIDKVLQIAEPYFPRRSRQSAIDKAVAFVTKRLNGE

DGLGAIYPAMAYSALMYLSIGRSLSDPHIQLVLKAIDKLVVVKDHEAYVQPCVSPVWDTALASHAL

MEAGDGDKPILDSLKKGLAWLKPLQVTDIAGDWAWKKPDVKPGGWAFQYGNAYYPDLDDTAVVV

MAMDRARDRWPEIDEDNFRPSIARAREWIVGLQSENGGFGAFDADNDRDYLNAIPFADHGALLDP

PTADVTARCISMLTQLGEKPENSETLRRAIAYLFAEQEKDGSWFGRWGLNYIYGTWSVLCSLNAA

```
GIAHDAPEVRRAVAWLRTIQNEDGGWGEDAESYALDYAGYQQAPSTSSQTAWAVLGLMAAGEK

DDPAVARGIAYLTRTQGEDGFWTEKRFTATGFPRVFYLRYHGYSKFFPLWAMARYRNLHNGNHA

SVLTGM
```

>seq_ID 103
```
MNDMTEMHTLDATAVPAAPAAADAPAPSAATTGLDAAVARATDALLAAQNADGHWVYELEADSTI

PAEYVLLVHYLGEEPNAELEQKIARYLRRIQQPDGGWPLFTDGAPNISASVKAYFALKVIGDDENA

EHMQRARRAIHAMGGAEMSNVFTRIQLALYGVVPWYAVPMMPVEIILLPQWFPFHLSKVSYWART

VIVPLLVLNAKRPVAKNPRGVRIDELFKSAPVNTGLLPKQPHQHAGWFAFFRAVDGVLRLADGLFP

RYTRERAIRQAAAFVDERLNGEDGLGAIYPAMANAVMMYAALGYPEDHPNRAIARQSIEKLLVVGE

EEAYCQPCLSPVWDTSLAAHALLETGDERAREAAVRGLDWLVPRQILDVRGDWISRRPHVRPGG

WAFQYANAHYPDVDDTAVVVMAMDRVAKHDQTDAYRESIARAREWVVGMQSSDGGWGAFEPE

NTQYYLNNIPFSDHGALLDPPTADVSGRCLSMLAQLGETSASSEPARRALDYMLKEQEPDGSWY

GRWGMNYIYGTWTALCSLNAAGLGHDDPRVKRAAQWLLSIQNPDGGWGEDGDSYKLDYRGYE

RAPSTSSQTAWALLGLMAAGEVDNPAVARGIGHLLGTQREHGLWDETRFTATGFPRVFYLRYHG

YRKFFPLWALARYRNLKRAGAARVTVGM
```

>seq_ID 95
```
MNDMTEMHTLDAAAAPAADAPAVTAVTAGLDAAVARATDALLAAQNADGHWVYELEADSTIPAEY

VLLVHYLGEEPNAELEQKIARYLRRIQQPDGGWPLFTDGAPNVSASVKAYFALKVIGDDENAEHM

QRARRAIHAMGGAETSNVFTRIQLALYGVVPWYAVPMMPVEVMLLPQWFPFHLSKVSYWARTVIV

PLLVLNAKRPVAKNPRGVRIDELFKSAPVNTGLLPKQPHQSTGWFAFFRAVDGVLRLVDGLFPRY

TRERAIRQAVAFVDERLNGEDGLGAIYPAMANAVMMYAALGYPEDHPNRAIARQSIEKLLVVGEEE

AYCQPCLSPVWDTSLAAHALLETGDERARDAAVRGLDWLIPRQILDVRGDWISRRPHVRPGGWA

FQYANPHYPDVDDTAVVVMAMDRVAKLDQSDAYREQIARAREWVVGMQSSDGGWGAFEPENT

QYYLNNIPFSDHGALLDPPTADVSGRCLSMLAQLGETNASSEPARRAFDYMLKEQEPDGSWYGR

WGMNYIYGTWTALCALNAAGLGHDDPRVKRAAQWLLSIQNQDGGWGEDGESYKLDYRGYERAP

SSSSQTAWALLGLMAAGEVDNPVVARGIDYLLGAQCEHGLWDETRFTATGFPRVFYLRYHGYRK

FFPLWALARYRNLKRANTTRVTVGM
```

>seq_ID 106
```
MNDLTDMPTLAADSAAADLDAAVARATDALLAAQQADGHWVYELEADSTIPAEYILLVHYLGETPN

LELEQKIGRYLRRIQQPDGGWPLFTDGAPNISASVKAYFALKVIGDDENAEHMQRARRAIHAMGG

AEMSNVFTRIQLALYGAIPWRAVPMMPVEIMLLPQWFPFHLSKVSYWARTVIVPLLVLNAKRPIAKN

PRGVRIDELFIDPPVNAGLLPRQHQSAGWFAFFRVVDHALRAVDGLFPSYTRERAIRQAVAFVD

ERLNGEDGLGAIYPAMANAVMMYDALGYPEDHPNRAIARRSVEKLLVVHDDEAYCQPCLSPVWD

TSLAAHALLETGDPRAEDAVVRGLEWLRPLQILDVRGDWISRRPNVRPGGWAFQYANPHYPDVD

DTAVVVMAMDRVEKLRHSDAYREAISRAREWVVGMQSSDGGWGAFEPENTQYYLNNIPFSDHG

ALLDPPTADVSGRCLSMLSQLGETAANSEAARRSLDYMLKEQEPDGSWYGRWGMNYVYGTWTA

LCSLNAAGLGPDDPRVKRGAQWLLSVQNKDGGWGEDGDSYKLDYRGYEQAPSTSSQTAWALL

GLMAAGEVNHPAVARGIDYLIAEQKEHGLWDETRFTATGFPRVFYLRYHGYRKFFPLWALARYRN

LKRANATRVTVGM
```

>seq_ID 87
```
MNDLTEMATLSAGAVPAGVDAAVARATDALLAAQQADGHWVYELEADSTIPAEYVLLVHYLGETP

NLELEQKIGKYLRRIQQADGGWPLFTDGAPNISASVKAYFALKVIGDDENAEHMQRARRAIHAMG
```

-continued

GAEMSNVFTRIQLALYGAIPWRAVPMMPVEIMLLPQWFPFHLSKVSYWARTVIVPLLVLNAKRPLA

KNPRGVRIDELFIDPPVNAGLLPRQGHQSPGWFAFFRVVDHALRAVDGLFPSYTRERAIRQAVSF

VDERLNGEDGLGAIYPAMANSVMMYAALGYAEDHPNRAIARKSVEKLLVVHDDEAYCQPCLSPV

WDTSLAAHALLETGDARAQEAVLRGLEWLRPLQILDVRGDWISRRPNVRPGGWAFQYANAHYPD

VDDTAVVVMAMDRAQKLTQSDTYRESMARAREWVVGMQSSDGGWGAFEPENTQYYLNNIPFSD

HGALLDPPTADVSGRCLSMLSQLGETPLNSEPARRALDYMLKEQEPDGSWYGRWGMNYVYGT

WTALCSLNAAGLTPDDPRMKRGAQWLLSIQNKDGGWGEDGDSYKLNYRGYEQAPSTASQTAWA

LLGLMAAGEVNNPAVARGVDYLVAQQNEEGLWDETRFTATGFPRVFYLRYHGYRKFFPLWALAR

YRNLKRANATRVTVGM

>seq_ID 107
MNDLTDMANLSAGTVPAGLDASVARATDALLAAQNADGHWVYELEADSTIPAEYVLLVHFLGETP

NLELEQKIGRYLRRIQQADGGWPLFTDGAPNVSASVKAYFALKVIGDDENAEHMQRARRAIHAMG

GAEMSNVFTRIQLALFGAIPWRAVPMMPVEIMLLPQWFPFHLSKVSYWARTVIVPLLVLNAKRPLA

KNPRGVRIGELFIDPPVNAGLLPRQGHQSPGWFAFFRVVDHALRAADGLFPSYTRERAIRQAVSF

VDERLNGEDGLGAIYPAMANAVMMYDVLGYPEDHPNRAIARKSIEKLLVVHDDEAYCQPCLSPVW

DTSLVAHALLETGDARAEQAVLRGLDWLRPLQILDVRGDWISRRPNVRPGGWAFQYANAHYPDV

DDTAVVVMAMDRAQKLQNTDTYRESIARAREWVVGMQSSDGGWGAFEPENTQYYLNNIPFSDH

GALLDPPTADVSGRCLSMLAQLGESALSSEPARRALDYMLKEQEPDGSWYGRWGMNYVYGTWT

ALCSLNAAGLGPEDPRVKRAAQWLLSIQNKDGGWGEDGDSYKLNYRGFEPAPSTASQTAWALLG

LMAAGEVNHPAVERGIGYLIAQQNDEGLWDETRFTATGFPRVFYLRYHGYRKFFPLWALARYRNL

KRANATRVTVGI

>seq_ID 212
MESGNNKQPAAAIGALDASIESATNALLGYRQPDGHWVFELEADCTIPAEYVLLRHYLGEPVDAAL

EAKIANYLRRVQGAHGGWPLVHDGGFDMSASVKGYFALKMIGDDIDAPHMAKAREAIRSRGGAIH

SNVFTRFLLSMFGITTWRSVPVLPVEIMLLPMWSPFHLNKISYWARTTIVPLMVLAALKPRAVNRLD

IGLDELFLQDPKSIKMPAKAPHQSWALFKLFAGIDAVLRTIEPLFPKRLRDHAIKLAVDFVEERLNGE

DGLGAIYPPMANTVMMYKVLGFPEDHPPRAITRRGIDKLLVIGEDEAYCQPCVSPVWDTALTCHAL

LEVGGEAAVPPAKRGMDWLLPKQVLDLKGDWAVKRPNLRPGGWAFQYNNAHYPDLDDTAVVVM

AMDRSRRATGSREYDEAIARAREWIEGMQSDDGGWAAFDVNNLEYYLNNIPFSDHGAMLDPPTE

DVTARCVSMLSQLGETAASSKAVADGVEYLRRTQLPDGSWYGRWGLNYIYGTWSVLCALNAAGV

DHQDPVIRKAVTWLASVQNPDGGWGEGAESYRLNYTRYEQAPTTASQTSWALLGLMAAGEVDS

PVVARGVEYLKSTQTGKGLWDEQRYTATGFPRVFYLRYHGYAKFFPLWALARYRNLRSTNSKVV

GVGM

>seq_ID 101
MNDLTEMATLSAGAVPAGVDTAVARATDALLAAQNADGHWVYELEADSTIPAEYVLLVHYLGETP

NLELEQKIGKYLRRIQQADGGWPLFTDGAPNISASVKAYFALKVIGDDENAEHMQRARRAIHAMG

GAEMSNVFTRIQLALYGAIPWRAVPMMPVEIMLLPQWFPFHLSKVSYWARTVIVPLLVLNAKRPLA

KNPRGVRIDELFIDPPVNAGLLPRQGHQSAGWFAFFRVVDHALRAVDGLFPNYTRERAIRQAVSF

VDERLNGEDGLGAIYPAMANSVMMYDVLGYAEDHPNRAIARKSIEKLLVVQEDEAYCQPCLSPVW

DTSLAANALLETRDARAEDAAIRGLEWLRPLQILDVRGDWISRRPHVRPGGWAFQYANAHYPDVD

DTAVVAVAMERAQQLKQNDAYRDSIARAREWVVGMQSSDGGWGAFEPENTQYYLNNIPFSDHG

ALLDPPTADVSGRCLSMLSQLGETPLNSEPARRALDYMLKEQEPDGSWYGRWGMNYVYGTWTA

```
LCSLNAAGLTPDDPRVKRGAQWLLSIQNKDGGWGEDGDSYKLNYRGFEQAPSTASQTAWALLGL

MAAGEVNNPAVARGIDYLIAEQNAEGLWDETRFTATGFPRVFYLRYHGYRKFFPLWALARYRNLK

RDNTTRVTVGL
```

>seq_ID 112
```
MSAPSHVGNTLEHAAELATRKAMAYLTCLQERDGHWCAELTADTTLESDYILFQLWLYPPQDGK

WEPETRPLIRKAVNSILERQLPDGGFNICVGGPSEVSASVKAYVAMKLAGLPPEDDRMARLRERIL

ALGGIQAANSYVKVNLSLFDLYPREFSPSIPPEVALLPFDLLYQMSAWTRAIVISLGIVHAANPRRPA

PAGFNLQELWLPGVSPEFRRDPSFFTWHNTFLTVDKALKLWERYGSKAVRRRAVEKAKTWMIER

LHHSDGLGAIYPPMMYSVMALDVLGYAKDDPLRVEALRHFNNLMVDDGDRFFFQPCFSPVWDTAI

GAYALVQADPSHEAIAPAADWLIAKEVRRKGDWSVKRPNTEPSGWAFEYSNEYYPDIDDTAMVM

LALGETRASNTEAQAAACKRGLAWLLAMQSSDGGWAAFDADNNWEFLSQVPFADHNAMLDPTC

ADITGRVLEALASQGLDRNHKAVRRGAEWLIRHQENDGSWYGRWGVAYIYGTCFALRGLAASGE

NDREAHILRAGEWLRSIQNADGGWGESCKSYDNRIFTGGPSTPSQTAWAILGLIAGGDANSLSVQ

HGIEYLLETQRSDGSWDEQFATGTGFPPRVFYLNYHMYKDYFPLLALASFVKARAGSNG
```

>seq_ID 83
```
MNDLTEMATLSAGTVPAGLDAAVASATDALLAAQNADGHWVYELEADSTIPAEYVLLVHYLGETP

NLELEQKIGRYLRRVQQADGGWPLFTDGAPNISASVKAYFALKVIGDDENAEHMQRARRAIHAMG

GAEMSNVFTRIQLALYGAIPWRAVPMMPVEIMLLPQWFPFHLSKVSYWARTVIVPLLVLNAKRPIAK

NPRGVRIDELFVDPPVNAGLLPRQGHQSPGWFAFFRVVDHVLRAADGLFPSYTRERAIRQAVSFV

DERLNGEDGLGAIYPAMANAVMMYDVLGYAEDHPNRAIARKSIEKLLVVHEDEAYCQPCLSPVWD

TSLAAHALLETGDARAEEAVIRGLEWLRPLQILDVRGDWISRRPHVRPGGWAFQYANAHYPDVDD

TAVVAVAMDRVQKLKHNDTFRDSIALAREWVVGMQSSDGGWGAFEPENTQYYLNNIPFSDHGAL

LDPPTADVSGRCLSMLAQLGETPLNSEPARRALDYMLKEQEPDGSWYGRWGMNYVYGTWTALC

ALNAAGLTPDDPRVKRGAQWLLSIQNKDGGWGEDGDSYKLNYRGFEQAPSTASQTAWALLGLM

AAGEVNNPAVARGVEYLIAEQKEHGLWDETRFTATGFPRVFYLRYHGYRKFFPLWALARYRNLKR

DNATHVTFGL
```

>seq_ID 175
```
MLQTEAITTEGLRFRSLAPDDPLLPRVKQALKLSGQHSREEMHSDGHWCGEVKTNATTSAEHVLL

CQALDINLDADREAFISWFRCTQGADGGWSTAPDQAGDISVTVEAYLALKILGLSEDDAAMRSAR

DFAIAAGGVARVRIFTRIYLAMFGLFPWAAVPELPPELILLPSRVPVSIYHWSAWARATVVPLLIISHH

RPIYALPGGKATCSDYLDELWCDPRNKMVPYNHDKPTAWRSDPFALIFTLADSILHRLDGLRSFNP

LRRFALRKCVDWILEHQEDMGDIGDIMPPLHGAMLALRLEGYPLHSDPIHRGLEAIERFAYRDQQG

KRIQTTVSAFWDTSLMLVALGDAGMASSPWLTRSLGWLQQHQRLGNYGDWKVNNPGLKAGGFS

FGYFNTWYPDVDDTASAVLAIIRQDERLVCSASVLDALNWLLGMQNTDGGWGAFDRDNNKLFLN

KIPFSDMEAFCDPSTPDVTGHVLEAFGIFLAVSARQQSPTKADVLTDRIVSASRRAICYLSDTHVSS

GGWYGRWGCNYIYGTSAVLCALAYFGSKSDTLSGVRSVKDAVNQAIRWLETVQNQDGGWGETV

NSYKDPSRAGSGPSTASQTAWAIMALLPYLPPSTEVIQRGVEYLLRTQTKTASQGATWHEKAYTG

TGFPKYFYMGYSFYCHYFPMMALGRYAYPCPEWHENWRPKKE
```

>seq_ID 88
```
MNDLTDMATLSAGAAPAADLDAAVARATDALLAAQNADGHWVYELEADSTIPAEYVLLVHYLGET

PNLELERKIGRYLRRIQQADGGWPLFTDGAPNVSASVKAYFALKVIGDDENAEHMQRARRAIHAM

GGAEMSNVFTRIQLALYGAIPWRAVPMMPVEIMLLPQWFPFHLSKVSYWARTVIVPLLVLNAKRPL

AKNPRGVRIDELFIDPPVNAGLLPRQGHQSAGWFAFFRVVDHVLRAVDGLFPKYTRERAIRQAVS
```

-continued

FVDERLNGEDGLGAIYPAMANAVMMYDVLGYAEDHPNRAIARKSIEKLLVVHDDEAYCQPCLSPV
WDTSLAAHALLETGDPRAEDAALRGLEWLRPLQILDVRGDWISRRPNVRPGGWAFQYANAHYPD
VDDTAVVAMAMDRAQKLRQSDTYRESIARAREWVVGMQSSDGGWGAFEPENTQYYLNNIPFSD
HGALLDPPTADVSGRCLSMLSQLGESALTSEPARRALDYMLKEQEPDGSWYGRWGMNYVYGTW
TALCALNAAGLGPDDPRVKRAAQWLLSIQNKDGGWGEDGDSYKLNYRGYEQAPSTASQTAWAL
LGLMAAGEVNNPAVARGIDYLLAEQKEHGLWDEVRFTATGFPRVFYLRYHGYRKFFPLWALARYR
NLKRANATRVTVGM

>seq_ID 92
MNDMTEMHTLDATAAPAGLDAAVARATDALLAAQQADGHWVYELEADSTIPAEYVLLVHYLGEAP
NVELEQKIARYLRRIQQPDGGWPLFTDGAPNISASVKAYFALKVIGDDENAEHMQRARRAIHAMG
GAEMSNVFTRIQLALYGVVPWYAVPMMPVEIMLLPQWFPFHLSKVSYWARTVIVPLLVLNAKRPV
AKNPRGVRIDELFKGAPVSTGLLPKQPHQSAGWFAFFRAVDGVLRLVDGLFPRYTRERAIRQAVA
FVDERLNGEDGLGAIYPAMANAVMMYAALGYPEDHPNRAIARRSIEKLLVVGEQEAYCQPCLSPV
WDTSLAAHALLETGDARAREAAVRGLDWLVPRQILDVRGDWISRRPHVRPGGWAFQYANAHYP
DVDDTAVVAMAMDRVAKLDRTDAYRESIARAREWVVGMQSSDGGWGAFEPENTQYYLNNIPFS
DHGALLDPPTADVSGRCLSMLAQFGETSASSEPARRALDYMLKEQEPDGSWYGRWGMNYIYGT
WTALCSLNAAGLGHDDPRVKRAAQWLLSIQNADGGWGEDGDSYKLDYRGYERAPSTSSQTAWA
LLGLMAAGEVDNPAVARGVDYLLGTQREHGLWDETRFTATGFPRVFYLRYHGYRKFFPLWALAR
YRNLKRANAMRVTVGM >seq_ID 206
MTRKTIPASELDAAIVRARDALLDRQHPDGHWCFELECDATITAEYILMMHFVDEIDTALQARMAKY
LRAVQRLDGHGAWDLYFGGDLDISCSVKAYFALKAAGDPPDAPHMVRAREAILARGGAAKSNVFT
RILLATFGEIPWRGTPFMPVEFVLFPRWAPIHMDKVAYWARTTMVPLLVLCSIRAAAKNPLGVHVQ
ELFVTPPELEREYFPRKRGLQQAFLVADRVVRHLEPLIPRALRRRAIQRAVEWSEARMNGEDGFG
GIFPPMVYSYEMMVLLDYPEDHPLRVECKAALKKLVVHRDDGSSYCQPCLSPVWDTAWSVMALE
QAPSDARTETAIARAYDWLTDRQVLDLRGDWENNAAPSTPPGGWAFQYENPYYPDIDDSAVVLA
MLHARGKRTGQPGRYEMPVARCLDWIIGLQSRNGGFGAFDANCDRDFLNAIPFADHGALLDPPT
EDVSGRVLLALGITERPQDATARERCIQYLRDTQQPDGSWWGRWGTNYIYGTWSVLAGLGLAGV
DRKLPMVRNGLQWLRGKQNADGGWGETNDSYARPELAGKHEDGSMAEQTAWAMLGQMAVGE
GDADSVHRGAAYLLDAQNEDGFWMHPYHNAPGFPRIFHLKYHGYTAYFPLWALGRYRRLAAARA
SAMQTAKAESAESMTAH >seq_ID 96
MNDLSMTQTLGEVLPQTLIDDHAPVAAALATGAAPVDALDAAVTRATEAILAVQKDDGHWVYELEA
DATIPAEYVLLVHFLGETPNLELEQKIARYLRRIQLPNGGWPLFTDGAMDVSASVKAYFALKMIGDP
EDAAHMVRARECILANGGAEAANVFTRILLALFGVVTWYAVPMMPVEIMLLPKWFPFHLSKVSYW
ARTVIVPLLVLNAKRPVARNPRGVRIDELFRGAPVTTGLLPRSGHQSKSWFAFFRAVDGVLRVTDG
LFPKASRERAIKAAVSFVDERLNGVDGLGAIFPAMANSVMMYDVLGYPADHPNRAIARESIEKLLV
VHEDEAYCQPCLSPVWDTSLAAHALLETGDARAEEAAERGLAWLRPLQILDVRGDWISRRPDVRP
GGWAFQYNNAHYPDVDDTAVVAMAMHRSAAVTNSNVDANAIARAREWVVGMQSSDGGWGAFE
PENTQYYLNNIPFSDHGALLDPPTADVSGRCLSMLAQLGEMPATSEPARRAYDYLLKEQEDDGS

```
WYGRWGMNYIYGTWTALCALNAAGISLEDARIKRAAQWLVSIQNADGGWGEDGTSYKLDYRGYE

KAPSIPSQTAWALLGLMAAGYVDHPAVARGIDYLQREQRDHGLWDEERFSATGFPRVFYLRYHG

YRKYFPLWALARYRNLKRTGEKRVTVGM
```

```
                                                                  >seq_ID 104
MNDMTEMHTLDATAAPAAPTVATGLDAAVARATDALLAAQNADGHWVYELEADSTIPAEYVLLVH

YLGEAPNVELERKIARYLRRIQLPDGGWPLFTDGAPNISASVKAYFALKVIGDDENAEHMQRARRA

IHAMGGAEMSNVFTRIQLALYGVVPWYAVPMMPVEIMLLPQWFPFHLSKVSYWARTVIVPLLVLNA

KRPVAKNPRGVRIDELFKSAPVNTGLLPKQPHQSAGWFAFFRAVDGVLRLTDGLFPRYTRERAIR

QAVAFVDERLNGEDGLGAIYPAMANAVMMYAALGYPEDHPNRAIARQSIEKLLVVGEDEAYCQPC

LSPVWDTSLAAHALLETGDERAREAAVRGLDWLVPRQILDVRGDWISRRPHVRPGGWAFQYANA

HYPDVDDTAVVAMAMDRVAKLDRTDAYRESIARAREWVVGMQSSDGGWGAFEPENTQYYLNNI

PFSDHGALLDPPTADVSGRCLSMLAQFGETSASSEPARRALDYMLKEQEPDGSWYGRWGMNYI

YGTWTALCSLNAAGLGHDDPRVKRAAQWLLSIQNPDGGWGEDGDSYKLDYRGYERAPSTSSQT

AWALLGLMAAGEVDHPAVARGIDHLLGTQREHGLWDETRFTATGFPRVFYLRYHGYRKFFPLWA

LARYRNLKRANATRVTVGM
```

```
                                                                  >seq_ID 27
MAHQETMASETSISLHTLACDATKLAGTYALRQVREDGHWYGEMKSNATITAEYVFLAQALGFSIE

EDRDDLIKYFLSEQNTDGSWSLAYDFPGDVSVTAEAYFALCLLGLDRSHPAMASAREFTLSKGGIA

KVRVFTRMFFACFGLFPWSAVPELPAELILLPAAAPMSIYQLASWARATVVPMLVIRHHRPIYALPN

GRSSSNEYLDELWVDPTDKMVPYSPSLWSLWNDDLTAFGFTLADNILKALGGLRWFPSRKIALRH

CVAWILERQEPEGDIGGIFPPLHAALFALALEGYGLESSPVRRGIDALQNTYAWRDSTGLRIQGCIS

PILDTILMTIGLIDSSLPAESPLVARSSRYLKAHQQLGNEGDWRVYNGNVPSGGFNFEYFNSWYPD

IDDTAAAILAMVKQDPNLLDLGPILSAVQWILGLQNDDGGWAAFDRENNYLFLNKIPFSDMDSFCD

PSTADVTGRVIECFGLNGKNPIPRFFIDDMSSATERAIDFLSTEQEADGSWYGRWGSNYIYGTSAV

LCGLVYHLEGWDDTYPVMEKRHKVDTHAALDWLKRHQNPDGGWGERLESYYEPRLAGNGPSTA

SQTAWALMGLLAYLAPTDESITRGIQYLSRTQIKEGELAGSWKEDHYTGTGFPNHFYLCYTLYSQY

FPMMALGRYTSLSGYRPLENLESTVEDHKGNSSDC
```

```
                                                                  >seq_ID 28
MMTLREEGHKEGITPGKEQLTSDIEHSLKLATEYALSSIRSDGHWCGELRSNVTITAEYIFLRHALG

LDLRTDNAAYCRYILSQQNCDGSWGLAPEYPGDVSTTTEAYLALKLLGTSPDMPAMQQARAFVR

KAGGAEKVRVFTRIFLATFGLFPWDAVPQLPVELILLPSSCPINMYTLASWARGTIAPLLIICHHQPV

YALPEDYLDELWLDPTDKNVPYGSSLRDLLSRGDITGLAFSVVDNLLYYLNGLRSVPLLRSYARRK

CIQWILERQEPTGDWAGIFPPMHASIYAFVLEGYELNDPPVRLGIQALENFAWEDEKGKRIQACVS

PVWDTALMSIGLCDAMSPDKQILQQAITWIRNRQLLKPCGDWRIYRSKLAPGGFSFEYENSHYPD

VDDTAAIILAQLKQDPQSVASDSVIAAATWILGMQNPDGGWAAFDVENDKLFLNKIPFSDMDSLCD

TSCADITGRILEAFGLMMKRELKRPVLSPMLRHACIRGITYLASTQESNGAWFGRWGCNYIYGTCH

ALGLVAPALQWLKSKQNDDGGWGEPLLSYRTPGTQLQQQSTPSQTAWALMGLLAHLPLTDPAIE

RGIRWLVCSQQPEKGNGASWPEAVYTGTGFPNHFYLGYDYYRHYFPMMALGRYLQASQAQA
```

```
                                                                  >seq_ID 94
MNDLTDMATLSAGTVPAELDAAVARATDALLAAQNADGHWVYELEADSTIPAEYVLLVHYLGETP

NLELEQKIGRYLRRIQQADGGWPLFTDGAPNISASVKAYFALKVIGDDENAEHMQRARRAIHAMG

GAEMSNVFTRIQLALYGAIPWRAVPMMPVEIMLLPQWFPFHLSKVSYWARTVIVPLLVLNAKRPLA
```

-continued

```
KNPRGVRIDELFIDPPVNAGLLPRQGHQSAGWFAFFRAVDHVLRAVDGLFPAYTRERAIRQAVAF

VDERLNGEDGLGAIYPAMANAVMMYDVLGYAEDHPNRAIARKSIEKLLVVHEDEAYCQPCLSPVW

DTSLAAHALLETRDPRAEQAAVRGLDWLRPLQILDVRGDWISRRPHVRPGGWAFQYANPHYPDV

DDTAVVAMAMDRAQKLNQSDTYRESIARAREWVVGMQSSDGGWGAFEPENTQYYLNNIPFSDH

GALLDPPTADVSGRCLSMLSQLGETALNSDAARRALDYMLKEQEPDGSWYGRWGMNYVYGTWT

ALCALNAAGLGPDDARVKRAAQWLLSIQNKDGGWGEDGDSYKLNYRGYEPAPSTASQTAWALL

GLMAAGEVNNPAVKRGIDYLIAEQKEHGLWDEARFTATGFPRVFYLRYHGYRKFFPLWALARYRN

LKRDNITRVTVGI
```

>seq_ID 30
```
MERSSLLVPASIDSHSRESETTGLDQAIVRARAALLGRQGADGHWCFELESDCTITAEYILMMHFT

DEIDEDLQERMARYLRATQVQETHGGWPQYVGGAIDLSCTVKAYYALKAAGDSPEAPHMRRARE

AVLALGGAAKSNVFTRILLAMFEQVPWRAVPYLPVEIMLLPRWAPIHIEKMSYWARTTLVPLTILCSL

KARAANPKRVDIRELFVTAPEQERHYFLRGGLLNRIFLGLDKFARTLDRWMPKSLRQHAIRKAEAW

FLPRMNGEDGLGAIFPPMVNCYEAMILLGYPKDHPARKTCLRSIQKLIVHRDDGSAYCQPCVSPV

WDTAWSAMALIHSGDDTATQTAIARAGDWLVQRQELDCRGDWEAQAPQAAPGGWAFQYANGY

YPDIDDTALVAALLHISDRRRGQPGQHAFNIDRAVDWMLALQSRNGGFAAFDADNTHYYLNAIPFA

DHGALLDPPTEDVSGRVAACLGILKRDQDRDGLRRCIDYLRTTQQPDGSWWGRWGSNYIYGTW

SALSGLALAGEDLRQPYLRKSVDWLRTRQHPDGGWGETNDSYIDPHLAGTNAGISTPHSTAWAV

LAQLAMGEVESDSVRRGIAFLLACQQTDGLWSHPSHNAPGFPRVYYLKYHGYAAYFPLYALARYR

HLLNRSREQR
```

>seq_ID 98
```
MNDMTEMHTLDATAAPAGLDAAVARATDALLAAQQADGHWVYELEADSTIPAEYVLLVHYLGEAP

NVELELQKIARYLRRIQQPDGGWPLFTDGAPNISASVKAYFALKVIGDDENAEHMQRARRAIHAMG

GAEMSNVFTRIQLALYGVVPWYAVPMMPVEIMLLPQWFPFHLSKVSYWARTVIVPLLVLNAKRPV

AKNPRGVRIDELFKGAPVSTGLLPKQPHQSAGWFAFFRAVDGVLRLVDGLFPRYTRERAIRQAVA

FVDERLNGEDGLGAIYPAMANAVMMYAALGYPEDHPNRAIARRSIEKLLVVGEQEAYCQPCLSPV

WDTSLAAHALLETGDARAREAAVRGLDWLVPRQILDVRGDWISRRPHVRPGGWAFQYANAHYP

DVDDTAVVAMAMDRVAKLDRTDAYRESIARAREWVVGMQSSDGGWGAFEPENTQYYLNNIPFS

DHGALLDPPTADVSGRCLSMLAQFGETSASSEPARRALDYMLKEQEPDGSWYGRWGMNYIYGT

WTALCSLNAAGLGHDDPRVKRAAQWLLSIQNADGGWGEDGDSYKLDYRGYERAPSTSSQTAWA

LLGLMAAGAVDNPAVARGVDYLLGTQREHSLWDETRFTATGFPRVFYLRYHGYRKFFPLWALAR

YRNLKRANATRVTVGM
```

>seq_ID 187
```
MTSDTASAAALDPRRLATSITRASRALHDVQQPDSHWVFELEADVTIPAEYVMMRHYFAEPVDAEI

EAKIAKYLRRMQNDNGGWSLFYGHEFDMSASVKAYYALKMIGDSPDAPHMKKAREAMLARGGAS

RANVFTRIMLALFGQVSWKAVPMMPVEIMLLPRWFPFHLTKVSYWARTVIVPLLVLMTLKPRAKNP

RGIGVRELFLEDPQTVGPTPKAAHQSQLWFTSFDIIDRVLRITDPFFPKGMRKRAIAKAEAFVTERL

NGVDGLGAIFPAMVNSIMMYDVLGYPPNDPNRALARESVERLLVIKDDEAYCQPCVSPVWDTALA

AHSMLESGEAADIEAAKAGLDWLLPRQVLDLKGDWADKRPDVRPGGWAFQYNNAHYPDLDDTA

VVVMAMDRVRRLDGTTKYDEAIARATEWILGLQSENGGWAAFDADNLEYYLNNIPFADHGALLDP

PTEDVTARCLSMLAQLGDTLETSEPMRRGVEYLRKTQLPDGSWFGRWGINYVYGTWSVLCALNA

VGVPHDDPMIAKAADWLESIQNEDGGWGEDGNSYKLNYKGYERAATTASQTAWATLALMAAGR
```

-continued

VDRDATQRGIDNLVQSQEADGFWGEPYYTGGGFPRVFYLRYHGYSKFFPLWAMARYRNLRSSN

SRFVGAGM

>seq_ID 207
MNKHSGNRTAIDPAALEMSIASATEALLAYRHADGHWAFELEADSTIPSEYILLRHYLAEPIDVVLEA

KIGNYLRRTQGAHGGWPLVHDGPFDMSASVKSYFALKMIGDSVDAAHMVKAREAIRARGGAANS

NVLTRFLLALYGVVSWRAVPVLPIEIVLLPIWSPFHLYKISYWARTTIVPLMVLAVLKPRAKNPKGVGI

EELFLQDTKSVGMNPKAPHQSWGWFLLFRGIDGILRVIEPHLPKKLRERAIASALAFTEERLNGED

GMGAIYPSMANIVMMYDALGKDDHFPPRAIARRAIDKLLVIGEEEAYCQPCLSPVWDTALTCHALQ

EVGGANAVAKAKQGLDWLKPRQVLDVKGDWAVKAPNIRPGGWPFQYNNAHYPDLDDTAVVVMA

MDRAQRHAGSKEYATAIARGREWIEGMQSRDGGWAAFDVNNLEYYLNNLPFADHGALLDPPTED

VTARCVSMLAQVGEFTQRSKAVAEGIAYLRRTQHAEGSWYGRWGLNYIYGTWSVLCALNAAGID

HQDPMIRKAVEWLVSIQSWDGGWGEDAISYRLDYSGYEQAPSTSSQTAWALLGLMAAGEVEHPA

VARGVNYLKNAQTENGLWDEQRYTATGFPRVFYLRYHGYSKFFPLWALARYRNLRSTNV

>seq_ID 29
MTTGHRQFDDGLSERERLIHEAGLTLQRSMDYAYNVVRSDGHWCGEMSSNVTITAEYIFLRQALG

LDLKTDGAAYCRHILSQQNSDGSWGLAPEYPGDVSTTTEAYLALKMLGLSTDAPAMQQAKAFVLN

AGGVAKVRVFTRIFLATFGLFPWKAVPQLPVELILLPSACPINIYKFASWARGTIAPLLIICHHQPVYA

LPNGVFAENEYLDELWQDSTNKSEPYSPSIWELLSQGDITGLTFSLLDKLLYQLNGLRSIPLLRSYA

LKQCMKWILERQEPTGDWAGIFPPMHASVYAFVLEGYKLEDPPVRLGIEALENFAWEDAKGKRVQ

PCVSPVWDTTLMSIALSDAATPNHQIVDRAIQWIRDRQLLEPRGDWRVYRPRLAPGGFSFEYTNS

HYPDIDDSAAIILAQVKHDPISANSSSVIAAATWILGMQNPDGGWAAFDVENDKLFLNKIPFSDMDS

LCDTSCADITGRILEAFGLLIRRVPDKDSSQLFQLLPAIRAACRRGIRYLASTQEANGAWFGRWGC

NYIYGTSHALCGLAYFLQEDQQVPAMVQPALQWLKSQQNDDGGWGESLLSYQSPERKEQRSTA

SQTAWALMGLLAHLPHTDIVIERGIRWLVSSQRPVETLGSTWPEPVYTGTGFPNHFYLGYDYYRH

YFPMMALGRYLRGVQG

>seq_ID 25
MLQTEAITTEGLRVRSLSPDDPLLPRIKQAIKLSGQHSRGEMHSDGHWCGEVKTNATTSAEHVLLC

QALGINLDADREAFISWFRCTQGADGGWSTAPDQAGDISVTVEAYLALKILGLSEDDAAMRRARD

FAIAAGGVAKVRIFTRIYLALFGLFPWAAVPELPPELILLPSRVPVSIYHWSAWARATVVPLLIISHHR

PIYALPGGGKGTSSDYLDELWCDPQNKMIPYNHDEPTAWRSDPFASIFTLADSILHRLDGLRSFNP

FRRFALQKCVDWILEHQEDMGDIGDIMPPLHGAMLALRLEGYPLHSGPIHRGLEAIERFAYRDKQG

KRIQTTVSAFWDTSLMLIALGDAGMASKPWLTRSLGWLQQHQRLGNYGDWKVNNHGLKAGGFS

FGYFNTWYPDVDDTASAVLAMIRQDERLVHSASVLDALNWLLGMQNTDGGWGAFDRDNDKHFL

NKIPFSDMDALCDPSTPDVTGHVLEAFGLFLALSKADALADRVVAASRRAIRYLSDTHVLSRGWYG

RWGCNYIYGTSAVLCALAYFGSENDALSGVRVMKDAINQAIRWLETVQNPDGGWGETVDSYKDP

SRAGSGPSTASQTAWAIMALLPYLPPSTEVIQRGMEYLLRTQTKTASQGATWHEKAYTATGFPKY

FYMGYSLYAHYFPMMALGRYAYPCPAWHENWRLKRD

>seq_ID 97
MNDLSQAQPLDAILPDFADAAPSAPAPAVTGEAPTASLDAAITRATEAILAAQKPDGHWVYELEAD

ATIPAEYVLLVHYLGETPNLELEQKIARYLRRIQLPDGGWPLFTDGALDISASVKAYFALKMIGDPAD

AEHMVRAREAILAHGGAETVNVFTRILLALFGVVSWRAVPMMPVEIMLLPMWFPFHLSKVSYWAR

TVIVPLLVLNAKRPVARNPRRVRIDELFRGAPVNTGPRDRAPHQHAGWFRFFSGVDVLLRAVDGL

FPKSTRERAVRQAVAFVDERLNGEDGLGAIFPAMANSVMMYDVLGYPADHPNRAIARQSIDKLLVI

-continued

KDDEAYCQPCLSPVWDTSLAAHALLETGEAHAEQAAERGLAWLRPLQILDVRGDWISRRPNVRP

GGWAFQYNNAHYPDVDDTAVVAMAMQRSATVTQSDVDRDAIARAREWVVGMQSSDGGWGAFE

PENTQYYLNNIPFSDHGALLDPPTADVSGRCLSMLAQLGELPQNSEPAQRAFDYMLKEQESDGS

WYGRWGLNYIYGTWTALCSLNAAGLPHDDPRMKRAAQWLLSIQNEDGGWGEGGESYKLDYHG

YERAPSTASQTAWALMGLMAAGEVNHEAVARGVAYLEREQREHGLWDETRFTATGFPRVFYLR

YHGYRKFFPLWALARFRHLKRNGLTRVAVGM

>seq_ID 176
MNSVNATVAPIDDAALGGSIGAATRGLLDLKQPDGHFVFELEADATIPSEYVLLRHYLGEPVDAALE

AKIAVYLRRIQGAHGGWPLVHDGPFDMSASVKAYFALKMIGDSIDAPHMARAREAILSRGGAANV

NVFTRFLLSLFEVLTWRSAPVLPIEIMLLPMWSPFHINKISYWARTTMVPLMVLAALKPRARNPRGI

GIRELFLQDPATVGTPKRAPHQSPAWFTLFNSLDWILRKIEPLFPKRLRARAIEKAIAFVEERLNGED

GLGAIFPPMVNTVMMYDALGFPPEHPPRAVARRGIDKLLVIGKDEAYCQPCVSPIWDTALTCHALL

EAGGPEALSGAGKSLDWLLPKQELVLKGDWAVKRPDVRPGGWAFQYANAHYPDLDDTAVVVMA

MDRVRRNDRSDKYNEAIARGREWIEGMQSRDGGFAAFDADNLEYYLNNIPFSDHAALLDPPTEDV

TARCVSMLAQLGETVRSSPSMAAGVDYLRRTQLKEGSWYGRWGLNYIYGTWSVVCALNAAGVD

HQDPAMRKAVDWLVSIQNADGGWGEDAVSYRLDYKGFEGAPTTASQTAWALLALMAAGEVENP

AVARGMKYLIDTQTKKGLWDEQRFTATGFPRVFYLRYHGYSRFFPLWALARYRNLRSTNSKVVG

VGM

>seq_ID 210
MDSGTFNPGGERGNTLDASIDAARAALLGYRRDDGHWVFELEADCTIPAEYVLLRHYLGEPIDAAL

EAKIAVYLRRTQGAHGGWPLVYDGEFDMSATVKGYFALKMIGDSIDAPHMAKAREAILSRGGAVH

ANVFTRFLLAMFGILTWRAVPVLPVEIMLLPMWSPFHLNKISYWARTTIVPLMVLAALKPRAVNRLG

VGLDELFLQDPKSIGMPARGPHQNRGLFALFGAIDAVLRVIEPLIPKKLRKHAIDRAVAFVEERLNG

EDGLGAIYPPMANTVMMYKVLGYPEDHPPRAITRRGIDLLLVIGEEEAYCQPCVSPIWDTSLTCHAL

LEAGGAEAAQPVREGLDWLLPKQVLDLKGDWAVKAPNVRPGGWAFQYNNAHYPDLDDTAVVVM

ALDRARRDQPSAAYDNAIARGREWIEGMQSDDGGWAAFDVNNTEYYLNNIPFSDHGAMLDPPTE

DVTARCVSMLAQLGETEQTSKAVARGVAYLRKTQLPDGSWYGRWGMNYIYGTWAVLCALNAAG

VDHQDPAIRKAVAWLASIQNADGGWGEDGVSYRLDYRGYETAPSTASQTAWALLSIMAAGEVDH

PAVARGIEYLKGTQTEKGLWDEQRHTATGFPRVFYLRYHGYSKFFPLWGLARYRNLRATNSKVV

GVGM

>seq_ID 23
MTTGHRQFDDGLSERERLIHEAGLTLQRSMDYAYNVVRSDGHWCGEMSSNVTITAEYIFLRQALG

LDLKTDGAAYCRHILSQQNSDGSWGLAPEYPGDVSTTTEAYLALKMLGLSTDAPAMQQAKAFVLN

AGGVAKVRVFTRIFLATFGLFPWKAVPQLPVELILLPSACPINIYKFASWARGTIAPLLIICHHQPVYA

LPNGVFAENEYLDELWQDPTNKSEPYSPSIWELLSQGDITGLTFSLLDKLLYQLNGLRSIPLLRSYA

LKQCMKWILERQEPTGDWAGIFPPMHASVYAFVLEGYKLEDPPVRLGIEALENFAWEDAKGKRVQ

PCVSPVWDTTLMSIALSDAATPNHQIVDRAIQWIRDRQLLEPRGDWRVYRPRLAPGGFSFEYTNS

HYPDIDDSAAIILAQVKHDPISANSSSVIAAATWILGMQNPDGGWAAFDVENDKLFLNKIPFSDMDS

LCDTSCADITGRILEAFGLLIRRVPDKDSSQLFQLLPAIRAACRRGIRYLASTQEANGAWFGRWGC

NYIYGTSHALCGLAYFLQEDQQVPAMVQPALQWLKSQQNDDGGWGESLLSYQSPERKEQRSTA

SQTAWALMGLLAHLPHTDIVIERGIRWLVSSQRPVETLGSTWPEPVYTGTGFPNHFYLGYDYYRH

YFPMMALGRYLRGVQG

```
>seq_ID 91
MNDLSQAHVLGAAMPETAGEAQNAQAAANSAAAAAEASAVLAPSLDAAITRATDAILAAQKPDGH
WVYELEADATIPAEYVLLVHYLGETPNVELEQKIARYLRRIQLPNGGWPLFTDGAIDISASVKAYFAL
KMIGDPVDAEHMVRAREAILAHGGAETVNVFTRILLALFGVVSWRAVPMMPVEITLLPMWFPFHLS
KVSYWARTVIVPLLVLNAKRPLARNPRRVRIDELFRGAPVNTGMPARAPHQHVGWFGFFRVVDTV
LRAVDGLFPKATRERAVREAVAFVDQRLNGEDGLGAIFPAMANSVMMYDVLGYPADHPNRAIARR
SIEKLLVIKDDEAYCQPCLSPVWDTSLAAHALLETGDARAEQAAERGLAWLRPLQILDVRGDWISR
RPNVRPGGWAFQYNNAYYPDVDDTAVVAMAMHRSEALTHSGADREAIARAREWVVGMQSSDG
GWGAFEPENTQYYLNNIPFSDHGALLDPPTADVSGRCLSMLAQLGEFPQNSEPAQRALDYMLKE
QEADGSWYGRWGLNYIYGTWTALCSLNAAGLPHDDPRIRRAAQWLLSIQNEDGGWGEGGESYK
LDYRGYERAPSTASQTAWALMGLMAAGEVDHEAVARGIEYLQREQREHGLWDETRFTATGFPRV
FYLRYHGYRKFFPLWALARYRHLKRNGLTRVAVGM >seq_ID 213
MDSGSYTTGVERNALEASIDAARSALLNYRRDDGHWVFELEADCTIPAEYVLLRHYLGEPVDAELE
AKIAVYLRRIQGAHGGWPLVHDGDFDMSASVKGYFALKMIGDSIDAPHMVRAREAIRSRGGAIHSN
VFTRFLLTLYGVTTWRAVPVLPVEIMLLPSWSPFTLTKISYWARTTMVPLLVLCALKPQAKNPKGV
GIDELFLQDPKTIGMPVKAPHQNWALFKLFGSIDAVLRVIEPVMPKGIRKRAIDKALAFIEERLNGED
GMGAIFPPMANAVMMYEALGYPEDYPPRASQRRGIDLLLVDRGDEAYCQPCVSPVWDTALASHA
VLEADGHEGAKSVRPALDWLLPRQVLDVKGDWAVKAPNVRPGGWAFQYNNAHYPDLDDTAVVV
MALDRARKDQPNPAYDAAIARAREWIEGMQSDDGGWGAFDINNTEYYLNNIPFSDHGAMLDPPT
EDVTARCVSMLAQLGETMDSSPALARAVGYLRDTQLAEGSWYGRWGMNYIYGTWSVLCALNAA
GVPHADPMIRKAVAWLESVQNRDGGWGEDAVSYRLDYRGYESAPSTASQTAWALLALMAAGEV
DHPAVARGIEYLKSTQTEKGLWDEQRYTATGFPRVFYLRYHGYSKFFPLWALARYRNLQATNSKV
VGVGM >seq_ID 196
MSMTSREDHDASSLISQVEHALKLSNDYALGLVHPDGHWYGEMNTNVTVTAEYVFLRQALRLDLK
TDIAAYCHYLLSQQNSDGSWGLAPEYPGDVSTSTEAYLALKILGTSPHTPAMRNARAFVLKAGGIA
RVRIFTRIFLATFGLFPWSAVPELPVELMLLPSICPINIYKFASWARGTIAPLLIICHHQPVYSLPNGKS
TDNDYLDELWVDCINKSVPYGLPLWDLMSQGEFAGLAFGVLDKVLYQLNGLRSIPLIRAYARKQCI
QWILERQEKTGDWAGIFPPMHANMYAFTLEGYKLDDDPVRLGFQALERFAWEDEKGKRIQACVS
PVWDTALMTIGLCDAMSPNKQTIDHALAWIRARQLLEPRGDWRVYRPQLAPGGFSFEYENSWYP
DVDDTAAIILAQVKHDNGSIGSNSVIAAATWILGMQNPDGGWAAFDVENDKLFLNKIPFSDMDSLC
DTSCADITGRILEAYGLMMMKYFSAKSDADPLLHTLRAACMRGMHYLASTQEPNGSWYGRWGC
NYIYGTSHVLCGLAYFVEKRLVCVMVKSALQWLKSRQNDDGGWGESLLSYQSPDREQQASTPSQ
TAWALMGLLSHLPVTDDAIERGIRYLVSSQRPEKGIGSSWPQAEYTGTGFPNHFYLGYDYYRHYF
PMMALGRYLQGSRGLN >seq_ID 99
MNDLSQTQPLAAVLPEAADAPAVADASATAAPEPVQAASPSALDASITRATDTILAAQKPDGHWVY
ELEADATIPAEYVLLVHYLGETPNLELEQKIARYLRRIQLPNGGWPLFTDGALDISASVKAYFALKMI
GDPVDAEHMVRARDAILAHGGAERANVFTRILLALFGVVSWRAVPMMPVEIMLLPVWFPFHLSKV
SYWARTVIVPLLVLNAKRPLARNPRKVRIDELFRAAPVNTGMNERAPHQHAGWFGFFRCVDTVLR
AVDGLLPKATRERAIRAAVAFVDERLNGEDGLGAIFPAMANSVMMYDVLGYPADHPHRAIARKSL
```

-continued

DKLLVIKDDEAYCQPCLSPVWDTSLAAHALLETGEARAEQAAERGLAWLRPLQILDVRGDWISRR

PNVRPGGWAFQYNNAHYPDVDDTAVVAMAMHRSAALTQSDVDREAIARAREWVVGMQSSDGG

WGAFEPENTQYYLNNIPFSDHGALLDPPTADVSGRCLSMFAQIGELPQSSEPARRAFDYMLQEQE

PDGSWYGRWGLNYIYGTWTALSSLNAAGMPHDDPRMRRAAQWLVSIQNEDGGWGEGGESYKL

DYHGYERAPSTASQTAWALLGLMAAGEVNHEAVARGIDYLQREQREHGLWDETRFSATGFPRVF

YLRYHGYRKFFPLWALARFRHLKRHGLTRVTVGM

>seq_ID 85
MIRRMNKSAPSPWSALDAAIARGRDALVRLQQPDGSWCFELESDATITAEYILMMHFMDRIDDVR

QERMARYLRANQRLDTHGAWDLYVDGAPDVSCSVKAYFALKAAGDSEHAPHMIRARDAILKLGG

AARSNVFTRILLATFGQVPWRAAPFMPIEFVLFPKWVPISMYKVAYWARTTMVPLLVLCSLKARAR

NPRNVSIRELFVTPPEQERHYFLPARGMRRLFLALDRTVRPIEPLLPKRLRQRAIRHAEAWCAERM

NGEDGLGGIFPPIVYSYQMMQVLGYPDDHPLRRDCENALEKLLVTRPDGSMYCQPCLSPVWDTA

WSTMALEQARGVAAPETGDTASGALRELDERIARAYDWLATRQVNDLRGDWIENAPADVEPGG

WAFQYANPYYPDIDDTALVTAMLDRRGRTHRGADGTHPYASRVARALDWMRGLQSRNGGFAAF

DADCDRMYLNAIPFADHGALLDPPTEDVSGRVLLCFGVTKRAADRASLAHAIDYVKRTQQPDGSW

WGRWGTNYLYGTWSVLAGLALAGEDKSQPYITRALDWLRARQHADGGWGETNDSYIDPKLAGT

NDGESTSNCTAWALLAQMAFGDCESDSVKRGIAYLQSVQQEDGFWWHRSHNAPGFPRIFYLKY

HGYTAYFPLWALARYRRLAGAKDADATRSPASATPATDNALA

>seq_ID 93
MIRAMNKSALSPWSALDTAIARGRDALARLQQPDGSWCFELESDATITAEYILMMHFMDRIDDALQ

ERMARYLRAIQRLDTHGAWDLYVDGAPDVSCSVKAYFALKAAGDSEHAPHMIRAREAILKLGGAA

RSNVFTRILLATFGQVPWRATPFMPIEFVLFPKWVPISMYKVAYWARTTMVPLLVLCSLKARARNP

RNVAIPELFVTPPDQERHYFPPTRGMRRAFLILDRVVRHVEPLLPKRLRRRAIRHAEAWCAQRMN

GEDGLGGIFPPIVYSYQMMDVLGYPEDHPLRRDCENALAKLLVTRPDGSVYCQPCLSPVWDTAW

STMALEQARSVAVPESDESARALDELDARIARAYDWLATRQVNDLRGDWIENAPADTQPGGWAF

QYANPYYPDIDDSAVVTAMLDRRGRTHRNADGSHPYAARVARALDWMRALQSRNGGFAAFDAD

CDRLYLNAIPFADHGALLDPPTEDVSGRVLLCFGVTRRAEDRASLARAIDYVKRTQQPDGSWWGR

WGTNYLYGTWSVLAGLTLAGEDPSQPYIARALEWLRAHQHADGGWGETNDSYLDPALAGTNGG

ESTSNCTAWALLAQMAFGDCASDSVKRGIAYLQSVQQDDGFWWHRSHNAPGFPRIFYLKYHGYT

AYFPLWALARYRRLAGAAEARARASSGRAPHAADTALA

>seq_ID 168
MGKVETLHRMSTQDITLDDVERRVSLASKALMRLAGPDGHWCFELEADATIPSEYILYHHFRGSIP

SAELEGKIANYLRRTQSAQHDGWSLVHDGPFDMSATVKAYFALKMIGDSIEAPHMRRAREAILRR

GGAAHANVFTRTLLALYGEVPWSAVPVMPVEVMLLPRWFPFHLDKVSYWARTVMVPLFVLQAKK

PRARNPRGIGIQELFVEPPERVKRWPAGPQESSPWRPVFAAIDKVLQKVEGSFPAGSRARAIDKA

VAFVSERLNGEDGLGAIFPAMVNAVLMYEALGYPEDHPLVATARSSVEKLVTVKEHEAYVQPCLS

PVWDTALSAHALMEAGGVEAERHAKRALDWLKPLQVLDIKGDWAASKPNVRPGGWAFQYANPH

YPDLDDTAVVVMAMDRAQVRRSPGPDAADYGQSIARAREWVEGLQSRDGGWAAFDADNTYHYL

NYIPFSDHGALLDPPTADVTARCVSMLAQLGETRESCPPLDRGVAYLLADQEADGSWYGRWGMN

YIYGTWSVLCALNAAGVDPASEPVRRAVNWLTTIQNPDGGWGEDAASYKLEYRGYERAPSTASQ

TAWALLGLMAAGEADSPAVARGINYLTRSQGADGLWTEDRYTATGFPRVFYLRYHGYAKFFPLW

ALARYRNLQQSNSRRVAVGM

>seq_ID 184
MKKFGGMARTSLQAQSPGSNNTPSMDEKMLKAGLEAARGALLAQQREDGHWCFPLEADCTIPA
EYILMMHFMDEVDLDLEVRIARFIREKQDVAHGGWPLYYGGEFDLSCSVKAYYALKIVGDSPDAPH
MVRARAAILKHGGAARANVFTRLLLAMYDQLPWRGVPFVPVEIILFPKWFPFHTSKVAYWSRTVM
VPLSILCSLKARAANPRKVAIRELFTVPPGEERNYFPVRTALNRVFLLIERTLSLLEPFIPQGVRRLAL
RRAESWIVERLNGDSGLGAIFPAMVNAGEALALLGYPYDHPAREQCRKALRLLLVEEGERTWCQP
CVSPVWDTVLTCLAFQEDTEVDQKPIRKALDWLVPCQVLDAPADWQEDHPGLPGGGWAFQYAN
PHYPDLDDTAAVAWALYQADPKAYQESISRAADWLAGMQSSNGGFAAFDSDNTYYYLNEIPFAD
HGALLDPPTSDVSARCAGFLALYGQSRHKQALERSLAYLFNEQEASGAWFGRWGSNYIYGTWSV
LEAFRLAGIDAGHPAIRRAVHWLKSVQREDGGWGESNDSYLSPQQAGQFHTSTSFHTAWALLAL
MGAGEWRSHEVHRGIAYLLREQDSDGLWHEPWFTAPGFPRVFYLKYYGYTKYFPVWALTRFHAL
NRKFPG >seq_ID 12
MMYNNQWYFNQFNDIFCFPEQQKEYFPPTGTNISLNLKKRPDRQLLAHGASDLNGPFHLSQHNA
FSAMLLAEVQKVLRLAVGHSLDLQRTDGAWCGEVHSNATFTAQYVFLQQQLGLPLDPTEIEGLSR
WLFSQQNEDGSWGLGPGLGGDVSTTTETYLALKILGVSPEDPRMAAARSSIIKAGSLPATRMFTR
VFLASFGLIPWSAVPPLPAELILLPTLFPVNIYNLSSWARATCVPLLLIRHHEPLHSLPNGRHAENDF
LDELWTKDIPRDFCYTTPLSRMWRLGDYAGIFFTSADHGLRFLGQYFNSPLRNLSRRKIINWILDH
QEQSGEWAGYWPPQHNNIWALSLEGYSLDHPVLRRGIAAVKSFVLHDVTGMRAQVTVSQVWDT
ALMSIALSDSAPSTGIISPTQAIDWLMHHEVASHRGDWRVLRPKLATGGFCFEEFNTLYPDVDDTA
AVIMALIKSNPAHLISGCVRRAAQWILGMQNRDGGWGAFDWNNDKFFLNKIPFSDMDSLCDPSTP
DVTGRIIECFGMMMAGRHGYSLDGPLESRLRASSQLAIAYLLGCQENNGSWWGRWGVNYLYGT
SNVLCGLAYYYDRSGLSKGDGKSNSHIVSAVDRASEWLKARQHSNGGWGEGPESYDSAQLAGC
GQPTASQSAWVTMALLNYLSPTDEVIQRGISYLVRSQVKYGDESRATWPLERYTATGFPGHLYME
YDYYRHYFPIMALGRYVNKLSESHKLL >seq_ID 100
MIRRMTTPTPSPWSALDTAIARGRDALVRLQQPDGSWCFELESDATITAEYILMMHFMDKIDDLRQ
EKMARYLRANQRLDTHGGWALYVDGDPDVSCSVKAYFALKAAGDSEHAPHMVRARDAILKLGGA
ARANVFTRILLATFGQVPWRAAPFMPIEFVLFPKWVPISMYKVAYWARTTMVPLLVLCSLKARARN
PRNISIRELFVTPPDEERQYFPPARGMRKLFLALDRTVRHVEPLMPKGLRQRAIRHAEAWCAERM
NGEDGLGGIFPPIVYCYQMMEVLGYPDDHPLRRDCENALEKLLVTRPDGSMYCQPCLSPVWDTA
WSTMALEQARGVAVAEDGEPGDARRALDERITRAYDWLAERQVNDLRGDWIENAPADVQPGGW
AFQYANPYYPDIDDTAVVTAMLDRRGRTHANADGTNPYATRVARALDWMRGLQSRNGGFGAFD
ADCDRLYLNAIPFADHGALLDPPTEDVSGRVLLCFGVTKRADEHASLARCIDYVKRTQQPDGSWW
GRWGTNYIYGTWSVLAGLALAGEDKSQPYIARAIEWLRARQHADGGWGETNDSYIDPKLGGTNG
GESTSNFTAWALLAQMAFGDCESDSVKRGIAYLQSVQQEDGFWWHRSHNAPGFPRIFYLKYHGY
TAYFPLWALARYRRLAGVANKRVSTADKTADAMA >seq_ID 84
MIRRMNQSAPSSWSALDAAIARGRDALVRLQQPDGSWCFELESDATITAEYILMMHFMDRIDDVR
QEKMARYLRANQRLDTHGAWDLYVDGAPDVSCSVKAYFALKAAGDSEHAPHMIRARDAILKLGGG
AARSNVFTRILLATFGQVPWRAAPFMAVEFVLFPKWVPISMYKVAYWARTTMVPLLVLCSLKARA
RNPRNVSIRELFVTPPEQERHYFPPARGMRRLFLALDRTVRPIEPLLPKRLRQRAIRHAEAWCAER
MNGEDGLGGIFPPIVYSYQMMQVLGYPDDHPLRRDCENALEKLLVTRPDGSMYCQPCLSPVWDT AWSTMALEQARGVAAPETGDTATGAPRDLDGRIARAYDWLATRQVNDLRGDWIENAPADVEPG
GWAFQYANPYYPDIDDTALVTAMLDRRGRTHRAADGTHPYASCVSRALDWMRGLQSRNGGFAA
FDADCDRMYLNAIPFADHGALLDPPTEDVSGRVLLCFGVTKRAADRASLARAIDYVKRTQQPDGS
WWGRWGTNYLYGTWSVLAGLALAGEDKSQPYIARALDWLRARQHADGGWGETNDSYLDPKLA
GTNGGESTSNCTAWALLAQMAFGDCESDSVKRGIAYLQSVQQEDGFWWHRSHNAPGFPRIFYL
KYHGYTAYFPLWALARYRRLAGAKDAGATRSGASGASATSVTDDALA >seq_ID 86
MIRRMNKSAPSPWSTLDTAIARGRDALVRLQQPDGSWCFELESDATITAEYILMMHFMDRIDDVR
QEKMARYLRANQRLDTHGAWDLYVDGAPDVSCSVKAYFALKAAGDSEQAPHMIRARDAILKLGG
AARSNVFTRILLATFGQVPWRAAPFMPIEFVLFPKWVPISMYKVAYWARTTMVPLLVLCSLKARAR
NPRNVSIRELFVTPPEQERRYFPPARGMRRLFLALDRAVRHIEPLMPKRLRQRAIRHAQAWCAER
MNGEDGLGGIFPPIVYSYQMMQVLGYPDDHPLRRDCENALEKLLVTRPDGSVYCQPCLSPVWDT
AWSTMALEQARGVAAPETGETAAGTLRELDERIARAYDWLAARQVNDLRGDWIENVPADVEPGG
WAFQYANPYYPDIDDSALVTAMLDRRGRTHRHADGTNPYAPRVARALDWMRGLQSRNGGFAAF
DADCDRMYLNAIPFADHGALLDPPTEDVSGRVLLCFGVTKRAEDRASLARCIDYVKRTQQPDGSW
WGRWGTNYLYGTWSVLAGLALAGEDKSQPYIARALDWLRARQHADGGWGETNDSYLDPTLAGT
NGGESTSNCTAWALLAQMAFGDCESDSVKRGIAYLQSVQQEDGFWWHRSHNAPGFPRIFYLKY
HGYTAYFPLWALARYRRLAGAAAAPPAALVAADTALA >seq_ID 80
MIRRMNKPAPSPWSALDTAIARGRDALMRLQQPDGSWCFELESDATITAEYILMMHFMDKIDDAR
QEKMARYLRAIQRLDTHGGWDLYLDGDPDLSCSVKAYFALKAAGDSEHAPHMVRARDAILKLGG
AARSNVFTRILLATFGQVPWRATPFMPIEFVLFPKWVPISMYKVAYWARTTMVPLLVLCSLKARAR
NPRNIAIPELFVTPPDQERQYFPPARGMRRAFLALDRVVRHVEPLLPKRLRQRAIRHAQAWCAER
MNGEDGLGGIFPPIVYSYQMMDVLGYPDDHPLRRDCENALEKLLVTRPDGSMYCQPCLSPVWDT
AWSTMALEQARGVAVPEAGAPAGALDELDARIARAYDWLAERQVNDLRGDWIENAPADTQPGG
WAFQYANPYYPDIDDSAVITAMLDRRGRTHRNADGSHPYAARVARALDWMRGLQSRNGGFAAF
DADCDRMYLNAIPFADHGALLDPPTEDVSGRVLLCFGVTKRADDRASLARAIDYVKRTQQPDGSW
WGRWGTNYLYGTWSVLAGLALAGEDPSQPYIARALAWLRARQHADGGWGETNDSYIDPALGT
NAGESTSNCTAWALLAQMAFGDGESESVKRGIAYLQSVQQDDGFWWHRSHNAPGFPRIFYLKY
HGYTAYFPLWALARYRRLAGGASSAGAHTVPASTGADAALA >seq_ID 82
MNKPAPSPWSALDTAIARGRDALMRLQQPDGSWCFELESDATITAEYILMMHFMDKIDDVRQEKM
ARYLRAIQRLDTHGGWDLYVDGDPDVSCSVKAYFALKAAGDSEHAPHMVRARDAILALGGAARS
NVFTRILLATFGQVPWRATPFMPIEFVLFPKWVPISMYKVAYWARTTMVPLLVLCSLKARARNPRNI
AIPELFVTPPDEERHYFPPARGMRRAFLALDRVVRHVEPLLPKRLRQRAIRHAQAWCAERMNGED
GLGGIFPPIVYSYQMMDVLGYPDDHPRRDCENALEKLLVTRTDGSMYCQPCLSPVWDTAWSTM
ALEQARAVAVPEAGARASALDELDARIARAYDWLAERQVNDLRGDWIENAPADTQPGGWAFQYA
NPYYPDIDDTAVVTAMLDRRGRTHRNADGSHPYAARVARALDWMRGLQSRNGGFAAFDADCDR
MYLNAIPFADHGALLDPPTEDVSGRVLLCFGVTKRAADRASLARAIDYVKRTQQPDGSWWGRWG
TNYLYGTWSVLAGLALAGEDPSQPYIARALAWLRARQHADGGWGETNDSYIDPTLAGTNAGEST
SNCTAWALLAQMAFGDCESESVRRGIAYLQSVQQDDGFWWHRSHNAPGFPRIFYLKYHGYTAYF
PLWALARYRRLASGVSSAGVHAVPASTGADAALA

```
>seq_ID 108
MNDLSQTQPRDAVLPEAAGAVPPASAPAPAAASEAPAASLDTAITRATDAILAAQKPDGHWVYEL
EADATIPAEYVLLVHYLGETPNVELEQKIARYLRRIQLPDGGWPLFTDGAPDVSASVKAYFALKMIG
DPADAEHMVRAREAILANGGAEAVNVFTRILLALFGVVSWRAVPMMPVEIMLLPMWFPFHLSKVS
YWARTVIVPLLVLNAKRPLARNPRRVRIDELFRGAPVNTGPRDRAPHQHAGWFRFFSGVDMLLRA
VDGLFPKATRERAVRAAVAFVDERLNGEDGLGAIFPAMANSVMMYDVLGYPADHPNRAIARQSIE
KLLVIKDDEAYCQPCLSPVWDTSLVAHALLETGEARAEQAAERGLAWLRPLQILDVRGDWISRRP
NVRPGGWAFQYNNDYYPDVDDTAVVVMAMHRSAALTHSEVDREAIARAREWVVGMQSSDGGW
GAFEPENTQYYLNNIPFSDHGALLDPPTADVSGRCLSMLAQLGELPQGSEPAQRAFAYMLKEQEP
DGSWYGRWGLNYIYGTWTALCSLNAAGMPHDDPRMKRAAKWLLSIQNEDGGWGEGGESYKLD
YHGYERAPSTASQTAWALMGLMAAGEVNHEAVARGVAYLQREQREHGLWDETRFTATGFPRVF
YLRYHGYRKFFPLWALARFRHLKRHGLTRVAVGM >seq_ID 169
MREAAVSKVETLQRPKTRDVSLDDVERGVQNAARALTEMTQTDGHICFELEADATIPSEYILFHQF
RGTVPRDGLEAKIGNYLRRTQSKVHGGWALVHDGPFDMSATVKAYFALKMIGDDIEAPHMRAAR
KAILQRGGAANANVFTRILLALYGEVPWAAVPVMPVEVMHLPKWFPFHLDKVSYWARCTMVPLFV
IQAKKPRAKNPRGIGVAELFVTPPDSVRTWPGSPHATWPWTPIFGAIDRVLQKTQDHFPKVPRQR
AIDKAVAWVSERLNGEDGLGAIFPSMVNSVLMYEVLGYPPDHPQVKIALEAIEKLVAEKDDEAYVQ
PCLSPVWDTALTSHAMLETGGAAAEANARAGLDWLKPLQILDIKGDWAETKPNVRPGGWAFQYA
NPHYPDLDDTAVVVMAMDRAQRQHGLVSGMPDYSASIARAREWVEGLQSADGGWAAFDADNN
HHYLNHIPFSDHGALLDPPTADVTARVVSMLSQLGETRETSRALDRGVTYLLNDQEKDGSWYGR
WGMNFIYGTWSVLCALNAAGVDPQSPEIRKAVAWLIRIQNPDGGWGEDASSYKLNPEFEPGYST
ASQTAWALLALMAVGEVDDPAVARGVNYLMRTQGQDGLWNEERYTATGFPRVFYLRYHGYPKF
FPLWAMARFRNLKKGNSRQVQFGM >seq_ID 163
MREAAVSKVETLQRPKTRDVSLDDVERGVQSAARALTDMTQADGHICFELEADATIPSEYILFHHF
RGTEPRAGLEAKIGNYLRRTQSKVHGGWALVHDGPFDMSASVKAYFALKMIGDDIEAPHMRAVR
KAILQRGGAANANVFTRILLALYGEVPWTAVPVMPVEVMHLPKWFPFHLDKVSYWARCTMVPLFV
IQAKKPRAKNPRGVGVAELFVTPPDSVRTWPGSPHATWPWTPIFGAIDRVLQKTQDHFPKVPRQR
AIDKAVAWVSERLNGEDGLGAIFPSMVNSVLMYEVLGYPPDHPQVKIALEAIEKLVAEKDDEAYVQ
PCLSPVWDTALTSHAMLEVGGTQAEANARAGLDWLKPLQILDIKGDWAETKPNVRPGGWAFQYA
NPHYPDLDDTAVVVMAMDRAQRQHGLVSGMPDYSTSIARAREWVEGLQSADGGWAAFDADNN
HHYLNHIPFSDHGALLDPPTADVTARVVSMLAQLGETRETSRALDRGVTYLLNDQEKDGSWYGR
WGMNFIYGTWSVLCALNAAGVDPQSPEIRKAVAWLIRIQNPDGGWGEDASSYKLNPEFEPGYST
ASQTAWALLALMAVGEVDDPAVARGVNYLMRTQGADGLWNEERYTATGFPRVFYLRYHGYPKF
FPLWAMARFRNLKRGNSRQVQFGM >seq_ID 105
MKPNHTFSPAALDAAILRGRDTLSGLQQPDGSWCFELESDATITAEYILMMHFMDKIDEVRQAQM
ARYLRAIQRVETHGAWDLYVDGAPDISCSVKAYFALKAAGDSEHAPHMIRAREAILKLGGAARSNV
FTRILLATFGQVPWRAAPFMPVEFVLFPKWVPISMYKVAYWARTTMVPLLVLCSLRARARNPRNV
SIAELFVTPPDEERHYFPPAKGMRKLFLALDRTVRHLEPLLPRRLRQRAIRHAEAWCAERMNGED
GLGGIFPPIVYSYQMMEVLGYPEDHPLRRDCEDALEKLLVTRADGSVYCQPCLSPVWDTAWSTM
```

```
ALEQARGATPAAPDTQVSERELDARIARAYDWLATRQVNDLEGDWRENARPGTLPGGWAFQYA

NPYYPDIDDSAVVTAMLDRRGRAQARASGENPYAERVTRALDWMRGLQSRNGGFGAFDADCDR

LYLNAIPFADHGALLDPPTEDVSGRVLLCFGVTKRPADRAAAARAIEYVKRTQQPDGSWWGRWG

TNYLYGTWSVLAGLALSGEDKSQPYIARALDWLRAHQHADGGWGETNDSYADPRLRATNYGEST

SNCTAWALLAQMAFGDWQSDSVRRGIAYLLSVQQDDGFWWHRSHNAPGFPRIFYLKYHGYTAY

FPLWALARYRRLAGAQAAPSSPGPGTAATIADPAVA
                                                     >seq_ID 211
MTSGTTILGAERGRTLDASIDAARAALLGYRRDDGHWVFELEADCTIPAEYVLLRHYLGEPVDAAL

EAKIAVYLRRTQGAHGGWPLVHDGEFDVSATVKAYFALKMIGDSIDAPHMAKAREAILARGGAIHV

NVFTRFLLSMFGILTWRSVPVLPVEIMLLPMWAPFHLNKISYWARTTIVPLMVLAALKPRAVNKLDI

GLDELFLQDPQSIGMPAKAPHQSWGLFTLFGSIDAVLRVIEPLIPKKLRSYAIGRAVAFIEERLNGED

GLGAIYPPMANTVMMYKVLGYGEDHPPRAITRRGIDLLLVVGEEEAYCQPCVSPIWDTSLTCHALL

EAGGAEAALPVRKGLDWLIPKQVLDLKGDWAVKAPNVRPGGWAFQYNNAHYPDLDDTAVVVMA

LDRARRDQPSAAYDNAIARGREWIEGMQSDDGGWAAFDVNNTEYYLNNIPFSDHGALLDPPTED

VTARCVSMLAQLGETAETSSALARGVAYLRKTQLAEGSWYGRWGLNYIYGTWSVLCALNAAGVA

HQDPAMRKAVAWLASIQNADGGWGEDAVSYRLDYRGYESAPSTASQTAWALLALMAAGEVDHP

AVARGVEYLKGTQTEKGVWDEQRYTATGFPRVFYLRHGYSKFFPLWALARYRNLRATNSKVVG

VGM

>seq_ID 76
MDSVNATAREAKESKISESEILESSIASATQGVLGFQQSDGHWVFELEADCTIPAEYVLLRHYLAEP

VDTVLEAKIGNYLRRVQGAHGGWPLVHDGEFDMSASVKAYFALKMIGDSIDAPHMVRAREAIHAR

GGAIHSNVFTRFMLAMFGIVTWRAVPVLPIEIMLLPFWSPFHINKISYWARTTMVPLMVIAALKPRAK

NPKGVGIDELFLQDPRSIGMTAKAPHQSMAWFLLFRSLDAILRVIEPLFPKSLRKRAIDTALAFSEER

LNGEDGMGAIYPPMANLVMMYDALGKDENYPPRAVTRRGIDKLLVIGDDEAYCQPCVSPVWDTTL

TAHALLEAGGDKAGPAAKHGLDWLIPKQELEVKGDWAVKRPDVRPGGWAFQYNNAYYPDLDDT

AVVVMSMDRMRREHGVTGYDSAIDRGREWIEGMQSDDGGWAAFDVNNLEYYLNNIPFSDHGAL

LDPPTEDVTARCVSMLAQLGETAKTSKHVADGVAYLRKTQHPEGSWYGRWGMNFIYGTWSVLC

ALNMAGVRHDDPMIRKAADWLASIQNKDGGWGEDTVSYRLDYKGWEAAPSTASQTAWALLALM

AAGEVDHPAVARGVEYLIATQNEKGLWDEQRYTATGFPRVFYLRYHGYSKFFPLWGLARYRNLR

NTNSRVVGVGM
                                                     >seq_ID 179
MEQQPELISGGVGGVAYPWDLGSQAIEEAILAARAALLAHLHPDGYWCFELEADCTIPAEYIMMMH

YTGELEAALELKLARYIRECQLQEGGWPLYYGGAMDISCSVKAYFALKLAGDDPEAAHMRRARKA

VLERGGAVNANVFTHIALALFGEIPWRGVPFMPPEILLLPRWFPFHLSKVSYWSRTVMVPLFILAAH

KPRARNPRAIHISELFVTDPQLETGYFKARSRLNRLFITLDALGRRIEPFIPRAVRAKALRRAAEWFI

TRLNGEHGLGAIFPAMVNSYEALELLLGYAADHPLRQQVRKGLRDLVVEQADRAYCQPCLSPIWDT

ALACLALQEADRGSSSAQVRHALDWLQARQLLDTPGDWSEQHPSLPGGGWPFQFRNDHYPDLD

DTAIVAWAMQRASDPERYGAAIRRATVWLLGMQSANGGFAAFDSDNTRYYLNEIPFADHGALLDP

PTSDVTARVVALLGSLDGEVHDRSALNRAVAFLHREQEAEGCWYGRWGTNYIYGTWSVLTALEQ

LGYDFNAPWVRKAVIWLKSVQRDDGGWGESNDTYLDHRPQDRQADESTPFQTAWAVLALIAAG

ECRSPEVWRGVEYLLRHQRPDGLWYCPWFTAPGFPRVFYLKYHGYDAYFPLMALARYRNCVLD

NDA
```

-continued

>seq_ID 81
MIRRMNKPAPSPWSALDAAIARGRDALMRLQQPDGSWCFELESDATITAEYILMMHFMDKIDDAR

QEKMARYLRAIQRLDTHGGWDLYVDGDPDVSCSVKAYFALKAAGDSEHAPHMVRARDAILALGG

AARSNVFTRILLATFGQVPWRAAPFMPIEFVLFPKWVPISMYKVAYWTRTTMVPLLVLCSLKAHAR

NPRNIAIPELFVTPPDQERHYFPPARGMRRAFLALDRVVRHAEPLLPKRLRQRAIRHAQAWCAER

MNGEDGLGGIFPPIVYSYQMMDVLGYPADHPLRRDCENALEKLLVTRPDGSMYCQPCLSPVWDT

AWSTMALEQARGVAVHEAGAPASALDELDARIARAYDWLAERQVNDLRGDWIENAPADTQPGG

WAFQYANPYYPDIDDSAVVTAMLDRRGRTHRNADGTHPYAARVARALDWMRGLQSRNGGFAAF

DADCDRMYLNAIPFADHGALLDPPTEDVSGRVLLCFGVTKRADDRASLARAIDYVKRTQQPDGSW

WGRWGTNYLYGTWSVLAGLALAGEDPSQPYIARALAWLRARQHADGGWGETNDSYIDPALAGT

NAGESTSNCTAWALLAQMAFGDGESESVKRGIAYLQSVQQDDGFWWHRSHNAPGFTRIFYLKYH

GYTAYFPLWALARYRRLAGGASSAGAHAVPASTAADAALA

>seq_ID 22
MATLTTMATTATMATTEASQPLEAQARTALTKATSYAWEIISNRHWCGELESNVTVTCEHIFFLYVL

YQHIDPDEGSQYRQWLLSQQNADGSWGIAPNYPGDVSTSAEAYLALRIIGMSPDSPELFQARTFIR

AAGGLSKMRMFTRIFFAEFGLVPWTAIPQLPAEFILVPAHFPISIYRLASWARSNVVPLLIIAHHRPLY

PLPNGLHKQNPFLDELWLDPATKPLPYGSLDPTDPLSFVFTILDKALSYLGGLRRCPTRGYARRRC

IQWILQHQEKAGDWAGIIPPMHAGIKALWLEGYKLHDEPIQLGLAAIERFTWTDNRGKRLQCCISPV

WDTVLMIRALQDTPASLGIKSDPRIADALAWTAENQHRGPEGDWRVYQPNIPVGGWAFEYSNTW

YPDIDDTAAAVLAFLTHDPATARSRLVRDAVLWIVGMQNADGGWAAFDHENNRLFLNKIPFSDME

SLCDPSTPDVTGRTIECLGMLRDLLMLPAEKAGKKGEKYGYPDGERDAAADSHLLKIINTACARAIP

YLIRTQEATGAWYGRWAVNYVYGTCLVLCGLQYFKHDPTFAPEIDTMATRAVKWLRQIQNSDGG

WGESVLSYREPWRAGCGPSTPSQTAWALMGLLTVCGGEDRSVQRGVRHLVDTQDDILSKGEGG

AAAWTEREFTSTGFPNHFYISYTLYRVYFPITALGRYLSLVEGGKKENGGGA

>seq_ID 178
MNSINATAAPIDDNVLGDRIGAATRGLLSLKQSDGHFVFELEADATIPSEYILMRHYLGEPVDTVLE

AKIAAYLRRIQGAHGGWPLVHDGPFDMSASVKAYFALKMAGDSIDAPHMARAREAILSRGGAANV

NVFTRFLLSFFGELTWRSVPVLPVEIMLLPMWSPFHLNKVSYWARTTMVPLMVLAALKPRARNPR

GIGIRELFLEDPATVGTPKRAPHQSPGWFALFTGFDRVLRLIEPLSPKWLRARAMKKAIAFVEERLN

GEDGLGAIFPPMVNTVMMYDALGFPPEHPPRAVTRRGIDKLLVVGENEAYCQPCVSPIWDTALSC

HALLEAGGPEAVNSAGKCLDWLLLKQELVLKGDWAVKRPDVRPGGWAFQYANGHYPDLDDTAV

VVMAMDRVRRNGPNGRYDEAIARGREWIEGMQSRDGGFAAFDADNLEYYLNNIPFSDHAALLDP

PTEDVTARCVSMLAQLGETVDSSSSMAAGVEYLRRTQLAEGSWYGRWGLNYIYGTWSVLCALNV

AGVDHQDPVIRRAVNWLVSIQNADGGWGEDAVSYRLDYKGFEGAPTTASQTAWALLALMAAGEV

ENPAVARGIKYLIDTQTKKGLWDEQRYTATGFPRVFYLRYHGYSKFFPLWALARYRNLRSTNSKA

VGVGM

>seq_ID 177
MNATVAQIGDAVLEDRIGSATRGLLNLKQSDGHFVFELEADATIPSEYILLRHYLGEPVDTVLEAKIA

AYLRRIQGAHGGWPLVHDGPFDMSASVKAYFALKMIGDSVDAPHMARAREAILSRGGAANVNVF

TRFLLSFFEVLTWRSVPVLPVEIMLLPMWSPFHLNKISYWARTTMVPLMVLAVLKPRARNPRDVGI

RELFLQDPATVRTPKRAPHQSPAWFALFSSLDWILRRIEPLFPKRLRARAMEKAIAFVEERLNGED

GLGAIFPPMVNTVMMYDALGFPPEHPPRAVTRRGIDKLLVIGEDEAYCQPCVSPIWDTALSCHALL

EAGAPEALNSAGKCLDWLLPKQELVLKGDWAAKRPDVRPGGWAFQYANGHYPDLDDTAVVVMA

-continued

MDRVRRNGRGDKYDEAIERGREWIEGMQSRDGGFAAFDADNLEYYLNNIPFSDHAALLDPPTED
VTARCVSMLAQLGATVDGSSSMAAGVEYLRRTQLAEGSWYGRWGLNYIYGTWSVLCALNAAGV
DHQDPAIRKAVDWLLSIQNEDGGWGEDAVSYRLDYKGFEGAPTTASQTAWALLALMAAGEVENP
AVTRGIKYLIDTQTKKGLWDEQRYTATGFPRVFYLRYHGYSKFFPLWALARYRNLRSTNSKVVGV
GM

>seq_ID 170
MREAVSKVEALQRSKTQGISLEDVERGVAQATRALTALAHDDGHICFELEADATIPSEYILFHHFRG
TQVPGDLEAKIGNYLRRTQGRHGGWALVHEGPFDMSCTVKAYFALKMIGDDIEAPHMRRAREGIL
SRGGAANANVFTRFMLALYGEVPWRAVPVMPVEVMFLPKWFPFHLDKISYWARTTVVPLFVLQA
TKPRARNPRGISVQELFVTPPESVRSWPGSPHATWPWTPIFGFIDRVLQRVENHLPRKSRQRAME
MARAWVSERLNGEDGLGAIFPAMVNSVLMYEVMGYRPDHPQVRVACDAIEKLVVEKADEAYVQP
CVSPVWDTALASHALLEAGGPEAEAQARAGLDWLKPRQVLDIVGDWAARKPKVRPGGWAFQYA
NAHYPDLDDTAVVVMAMDRAMHQHGLVAGMPDYKASIARAREWVEGLQSEDGGWAAFDADNN
HMYLNHIPFSDHGALLDPPTADVTARVVGMLSQLGETRETSRALDRGVNYLLNDQEEDGSWYGR
WGMNFIYGTWSVLCALNAAGVDPADPRIQKAVSWLIRIQNPDGGWGEDASSYKIDPAFEPGSSTA
SQTAWALLALMAAGAVDDPAVTRGINFLTRTQGADGFWKEERYTATGFPRVFYLRYHGYPKFFPL
WAMARFRNLKRGNSRRVQFGM >seq_ID 14
MLLAEVQKALRLAVGHSLDLQRADGAWCGEVHSNATFTSQYVFLQQQIGLPLDPTEIEGLSRWLF
SQQNEDGSWGLGPGLGGDVSTTTETYLALKILGVSPEDPRMAAARTSIIKAGSLPATRMFTRVFLA
SFGLIPWSAVPPLPAELILLPTLFPVNIYNLSSWARATCVPLLLIRHHEPLHSLPNGRHAENDFLDEL
WTKDIPRDFCYTTPLSRMWRLGDYAGIFFTSADHGLRFLGQYFHSPLRNLSRRKIINWILDHQEQS
GEWAGYWPPQHNNIWALSLEGYSLDHPVLRRGIAAVKSFVLHDATGMRAQVTVSQVWDTALMSI
ALSDSAPSTGIISPTQAIDWLMHHEVASHRGDWRVLRPKLATGGFCFEEFNTLYPDVDDTAAVIMA
LIKSNPAHLISGCVRRAAQWILGMQNRDGGWGAFDWNNDKFFLNKIPFSDMDSLCDPSTPDVTG
RIIECFGMMMAGRHGYSLDCQLENRLRASSQLAIAYLLGCQENNGSWWGRWGVNYLYGTSNVL
CGLAYYYDRSSLSKGDVKSNSNIVSAVDRASEWLKARQHSNGGWGEGPESYDNAQLAGCGQPT
ASQSAWVTMALLNYLSPTDEVIQRGVSYLVRNQVKYGDESRATWLLERYTATGFPGHLYMEYDY
YRHYFPIMALGRYVNKLSGSHKLL >seq_ID 180
MTRALRQAPESAGAIGIAAASPATETSGQDTHPREISGAITAARDALLKLQQADGHWCFMLEADCT
IPAEYILWTHFTGELEPEIERKLAARLRAKQASHGGWPLYEGGDLDISCSVKVYYALKLVGDDPNA
PHMRRAREAILAQGGGARANVFIRLALAMFSQIPWRGVPFIPVEIMLLPRWFPFHLSKVSYWSRT
VMVPLAILYSLKAQAQNPRNVHIQELFTVPPEQERHYFPVRSRLNKILLSVERTARLLEPLIPSMLRR
RALKKAETWFTERLNGEDGLGGIFPAMVNAHESLILLGYSPDHPWRVQAKKALQNLVIEEKNSASC
QPCLSPIWDTGLAALALQETEGGHTTAPVIRALDWLKERQILEQSGDWQVQHPNLKGGGWAFQY
NNSYYPDLDDTALVAWSMDQAATPERYGEAIGRACDWLCGMQSRNGGFAAFESDNTHYYLNEIP
FADHGALLDPPTADVTARCIVLLGRLNKPQYAETLQRALDYLRREQEPNGSWFGRWGTNYIYGT
WSALTALEQANIDPQEGFIRKAVEWLKQVQRLDGGWGEDNYSYFDSSLAGRYQESTPVHTAWAL
LALMAVGEANSEAVKKGIAYLLQIQQEDGLWDHPAFNAPGFPRVFYLKYHGYDKFFPLWALARYR
NHLNRQC

```
>seq_ID 155
MMANATDTIELPPSRAADRIVPMTDIDQAVDAAHAALGRRQQDDGHWVFELEADATIPAEYVLLEH
YLDRIDPALEERIGVYLRRIQGDHGGWPLYHGGKFDVSATVKAYFALKAIGDDIDAPHMARARAAIL
DHGGAERSNVFTRFQLALFGEVPWHATPVMPVELMLLPRKALFSVWNMSYWSRTVIAPLLVLAAL
RPRAINPRDVHVPELFVTPPDQVRDWIRGPYRSQLGRLFKYVDIALRPAERLIPDATRQRAIKAAVD
FIEPRLNGEDGLGAIYPAMANTVMMYRALGVPDSDPRAATAWEAVRRLLVELDGEAYCQPCVSPI
WDTGLAGHAMIEAASGPKGIRPEDTKKKLAAAAEWLRERQILNGEGRLGDQLPRRAPRRLGLPVQ
QRLLPRRGRHGSGRHVLHREGDPANDEALERARQWIIGMQSSNGGWGAFDIDNNLDFLNHIPFA
DHGALLDPPTADVTARCISFLAQLGHPEDRPVIERGIAYLRTDQEREGCWFGRWGTNYIYGTWSV
LCAYNAAGVAHDDPSVVRAVDWLRSVQREDGGWGEDCASYEGATPGIYTESLPSQTAWAVLGL
MAVGLRDDPAVMRGMAYLTRTQKDDGEWDEEPYNAVGFPKVFYLRYHGYRQFFPLLALSRYRN
LASSNSRHVAFGF >seq_ID 8
MNRMLQPLHSGAGIFRSSLDRVIAQARQALGGRQAEDGHWCFEFEADCTIPAEYILMQHYMDER
DEALEARIAVYLRGKQADHGGWPLYYGGHFDLSASVKVYYALKLAGDDPELPHMRRAREAILAHG
GAERSNVFTRITLALFAQVPWRAVPFIPVEIMLLPRWFPFHIYKVASWSRTVMVPLFILCSLKARAK
NPLQVHIRELFRRPPDQITDYFSHARRGIVAYIFLSLDRFWRLMEGWIPHGIRRRALKKAEAWFTAR
INGEDGLNGIFPAMVNAHEALELLGYPPDHDYRRQTGAALRKLVVERANDAYCQPCVSPVWDTCL
ALHALLEEDGEVSPAVQNGIRWLKNRQIGAEPGDWRESRPHLAGGGWAFQYANPYYPDLDDTAA
VGWALARAGRAEDRDSIEKAANWLAGMQSRNGGFGAYDVDNTHYYLNEIPFADHKALLDPPTAD
VTGRVVAFLAHLARPRDRDVLRRAVAYLLREQESSGAWFGRWGTNYIYGTWSVLMALAELNDPS
LKPTMERAAYWLRAVQQGDGGWGESNDSYSDPGLAGMGQTSTAAQTAWACLGLMAAGDRDSV
ALHRGIAWLQAHQEGDGCWQAPFFNAPGFPKVFYLIYHGYAFYFPLWALARYRNLGCMAHE >seq_ID 203
MSMNEAVLAAPRAAVATAAPALQAPIEALSPLDAGIGHAVDALLAQQNADGHWVYELEADATIPAE
YVLMVHYLGETPDLSLEARIARYLRRIQNADGGWPLFHEGRSDISASVKAYFALKMAGDDPQAAH
MARAREVILAMGGAETSNVFTRTLLALYGVMPWQAVPMMPVEIMLLPQWFPFHLSKVSYWARTVI
VPLLVLNSLRPQARNPRKVGIDELFLGSRDAVRLPPRAPHQHKGWHALFHGADVLLRTAEHVMPR
GLRRRAIDAAKAFVRERLNGEDGLGAIFPAMANSVMMFDVLGVPPDDPDRAIARRSIDKLLVVHGD
EAYCQPCLSPVWDTALAAHALLEASEPRATAAVTRALDWLRPLQVLDVRGDWTVRRPDVRPGG
WAFQYANPHYPDVDDTAVVVAAMHRAARTDHSGRADPNAEATARAIEWIVGMQSANGGWGAFE
PENTHLYLNNIPFADHGALLDPPTADVSARCLSMLCQTGATPDKSEPAARALQYLLAEQLPDGSW
FGRWGTNYIYGTWSALCALNAAGLGPDAPPLRRAAEWLVAIQNPDGGWGEDGDSYKLEYRGYE
TAPSVASQTAWALLALMAAGQAAHPAVTRGIDYLLRTQQADGLWHEPRFTAVGFPRVFYLRYHG
YARYFPLWALARYRNLERSGNRQVAWGL >seq_ID 165
MREAAVSKVETLQRPKTRDVSLDDVERGVQSATRALTEMTQADGHICFELEADATIPSEYILFHQF
RGTEPRPGLEAKIGNYLRRTQSKVHGGWALVHDGPFDMSASVKAYFALKMIGDDIEAPHMRAVR
KAILQRGGAANANVFTRILLALYGEVPWAAVPVMPVEVMHLPKWFPFHLDKVSYWARCTMVPLFV
IQAKKPRAKNPRGVGVAELFVTPPDSVRTWPGSPHATWPWTPIFGGIDRVLQKTQDHFPKVPRQ
RAIDKAVAWVSERLNGEDGLGAIFPAMVNSVLMYEVGYPPEHPQVKIALEAIEKLVAEKEDEAYV
QPCLSPVWDTALNSHAMLEAGGHQAEANARAGLDWLKPLQILDIKGDWAETKPNVRPGGWAFQ
```

-continued

```
YANPHYPDLDDTAVVVMAMDRAQRQHGLVSGMPDYSESIARAREWVEGLQSADGGWAAFDAD

NNHHYLNHIPFSDHGALLDPPTADVTARVVSMLSQLGETRATSRALDRGVTYLLNDQEKDGSWY

GRWGMNFIYGTWSVLCALNTAGVDPQSPEIRKAVAWLIRIQNPDGGWGEDASSYKLNPEFEPGY

STASQTAWALLALMAAGEVDDPAVARGVNYLVRTQGQDGLWSEERYTATGFPRVFYLRYHGYPK

FFPLWAMARFRNLKRGNSRQVQFGM
```

>seq_ID 181
```
MSISPTFSGSSLQKSSLSDHSTISEPFTVVDRVNGISAVALDDAITRARSALLAQQREDGHWCFSLE

ADCTIPAEYILMMHFMDEIDTALERRIANFLRNRQVTDGHGGWPLYYGGDFDMSCSVKVYYALKL

AGDSPEAAHMVRARNAILERGGAARSNVFTRLLLAMYRQIPWRGVPFVPAEIMLLPRWFPFHLSK

VAYWSRTVMVPLSILCTLKAKAANPRNIHVRELFTVDPEMEKNYFPVRTPLNHLLLYLERLGSKLEP

LIPSFIRRRALKKAEQWTIERLNGRDGLGAIFPAMVNAYEALTLLGYDHDHPLLQQCRLALRELLVN

EGEDITWCQPCVSPVWDTVLASLALQEDERADNGPVRHALDWLVPLQALDQPGDWRNSRPDLP

GGGWAFQYANPHYPDLDDTAAAAWALCQADTEDYRTSITRAADWLAGMQSSNGGFAAFDIDNV

HYYLNEIPFADHGALLDPPSSDVTARCIGLLALNGEARHQETVKRGLTFLFNEQEPSGAWFGRWG

TNYVYGTWSVLEALKLARVDHDHQAVKRAVQWLKSVQRADGGWGETNDSYLDSELAGQLETST

SFQTAWAVLGLMAAGEVGSTAVRNGIDYLIRTQSAAGLWEEPWFTAPGFPKVFYLKYHGYSKYFP

LWALNRYRAMNSRSVV
```

>seq_ID 110
```
MILFPAGFYFSIYEISYWSRCIVVPLSIAIARKPHVTVGDDLLKELYLVPREDVVYRIERDQDGFCWY

NFFIDADSIFRRYEQHPIKFIRRIAKKMAEKWLLEHMEKSGGLGAIWPAMINSIFAMKCLDYPDDHP

ALTAQMKEVEALVIYEGDMLYLQPCVSPVWDTAWSIIAMNDSGIPGSHPVLQKAGKWLLSKEVRD

FGDWKLKCKVEEPSGWYFQYANEFYPDTDDTGAVLMALQRVSLPEDMHKEKTLLRALRWLQAM

QCDDGGWGAFDRNNNKTILNNIPFADFNALLDPSTSDVTGRCIEFFGRIGFNKTYLNIKKAVEFLKK

EQDEDGSWFGRWGSNYIYGTWSVISGLIAVGEDINKAYIKKAIAWLKSVQNSDGGWGETIKSYED

SALKGIGKSTPSQTAWALLTLITAGEIKSSSTERGIDFLLSTQKEDGSWDEREFTATGFPKVFYLKY

HMYRNYFPLMALGRYRHFTHKLATSQ
```

>seq_ID 182
```
MSISQAFFRTLIQKSSLSDSSLVSENFPADDVAGNEANEISAVTLDEAITRAYTALLAQQREDGHWC

FPLEADCTIPAEYILMMHFMDEVDTVLERKIANFLRTRQVTDGHGGWPLYYGGDFDMSCSVKTYY

ALKLAGDSPEAAHMVHARNAILERGGAARSNVFTRLLLAMYRQIPWRGVPFVPAEIMLLPRWFPF

HLSKVAYWSRTVMVPLSILCTLKAKAINPRNVHVQELFVVDPVKEKNYFPVRTSLNRLLLYVERLAS

KLEPFIPSFIRRRAVKKAEQWVIERLNGNDGLGAIFPAMVNAYEALTLLGHDRDHPLLQQCRQSLR

ELLVDEGEEITWCQPCVSPVWDTVLATLALQEDKQADSEPIRRALDWIVPLQILDEPGDWRDSRP

NLLGGGWAFQYANPHYPDLDDTAAVAWALIQTGAEDYRVSITRAADWLAGMQSSNGGFAAFDID

NAYYYLNEIPFADHGALLDPPTSDVSARCVGLLALNGEVRHQEAVKRGLDFLFNEQESSGAWFGR

WGSNYIYGTWSVLEAFRLARVDKGHQAVQRAIQWLESVQRADGGWGETNDSYLDPQLAGQLEA

STSFQTAWAVLGLMAAGEVENTAVRKGIDYLLRTQIATGLWEEPWFTAPGFPRVFYLKYHGYSKY

FPLWALNRYRTLSSKSAV
```

>seq_ID 162
```
MSPFLQASDDNNPLFKESCQALDHATEFARDTLVNKEHWCGWVLSNVTVTAEWIFLQYILGLEMS

NEDRRGFLKHFTSSQRPDGSWSLATQTTTGGELSCTIEAYLALKILGVSPEEDYMVRARDYVRSH

GGAEKMRMLSRFHLAMFGLIPWAAVPQMPPELIFMPSWSLVNIYKFSSWARCNIVGLCMLRVHEP

LYALPNGKQLDNDYLDELWLDPYHKAIPYTVPYLQLMQTSPLGVLFQLGDLFLWLLSFLGFWFLRR
```

```
WAVSSSIQWTLDHQEPSGDWGGIYPPMHHNILALMLEGWSQDDPVIQRGIGACQRFLAEDPAHG

KWMQPSVSPVWDTFLMIRAVADAKTTDDADKLLVKPVDWVLAQQIDDDHIGDWRIYRPDIPAGGF

AFEYFNKWYPDVDDTAVGVVALMRHDPSLVNDDRILKAAAWTLGMQNRDFGWAAFDADNNAFY

LHATPFSDMDSLTDSSTPDVTGHVLEMLGLMYRLERQGRVKSPEMLAFLSQSHGACDRGLGYLL

GSQEAFGGWYGRWGVNYIFGTSAALCALAYFADRKGVRGKMAAGADWLRSRQNPDGGWGELL

ESYDNKALAGRGRSTPSQTAWALQGLLELEDPRGEVVEAGVNWLLRHQVTSPSRNSGRVSATW

PEDDYTATGFPGHFYLKYELYCHYFPMMALARYRSCIQDGA
```

>seq_ID 172
```
MDDRVGAATFEAQPRAGFGSVEAAISRAREALLAVQKPDGHFVFELEADVSIPAEYILFRHFLGDP

AKTEIERKIGVYLRRRQTAAGGWPLFAEGVFNVSSSVKAYFALKIIGDDPNAPHMAKARNAILAHG

GAAQSNVFTRSLLALYGEVPWRAVPAMPVEIMHLPRWFPFHLSKVSYWGRTVIAPLIVVHALKPRA

KNPRKISVSELFVAPAETVSRWPGAPHKSFPWTTIFGAIDRVLHKTEPLLPARSHQTAIDKAVAFVT

ARLNGEDGLGAIYPAMAYSAMMFFALGAPLSDPRIVQIRKAIDRLLVIKDGEAYCQPCVSPVWDTA

LASHALMESAGQRPEARTAPAAAAVFEALDWLKPLQVLDVKGDWATQNPDVRPGGWAFQYANP

HYPDLDDTAVVVLAMDRAVKTSPLIAGEEETAYVEAISRAREWILGLQSANGGFGAFDADNDRDYL

NYIPFADHGALLDPPTADVTARCVSMLGQLGERPETSPALARAIDYLLSEQEEEGSWFGRWGMN

YIYGTWSVLSAFNAVERPADCAATRKAAAWLKRIQNPDGGWGEDGESYALGYKGYNPAPSTASQ

TAWALLALMAAGEVDAPEVALGLDYLVSTQADDGFWDEARFTATGFPRVFYLRYHGYAKFFPLW

AMARYRNLKSGNRLKTQFGM
```

>seq_ID 24
```
MLGAIREPPIDVQIALHSRDDNQTGLVLRGTRRTVDRVLKGLCSSPCFFCSVSLTMATLTTTMATT

ATMATTEASKPLEAQARTALTKATNYAWEIFSNRHWCGELESNVTVTCEHIFFLYVLYQHIDPGEG

SQYRQWLLSQQNSDGSWGIAPNYPGDISTSAEAYLALRIIGMSTDSPELYRARTFIRAAGGLSKMR

MFTRIFFAEFGLVPWTAIPQLPAEFILVPAHFPISIYRLASWARSNVVPLLIIAHHRPLYPLPNGLHKQ

NPFLDELWLDPATKPLPYGSSDPTDPVAFVFTILDKALSYLGGLRRSPTRGYARRRCVQWILQHQ

EKAGDWAGIIPPMHAGIKALLLEGYKLHDEPIQLGLAAIERFTWADNRGKRLQCCISPVWDTVLMIR

ALQDTPASLGIKLDPRIADALAWTAENQHRGPEGDWRVYKPNIPVGGWAFEYHNTWYPDIDDTAA

AVLAFLTHDPATARSRLVRDAVLWIVGMQNADGGWAAFDHENNQLFLNKIPFSDMESLCDPSTPD

VTGRTIECLGMLRDLLMRPAENAENGEKYGYPDGEGDAAADAHLLQIINTACARAIPYLIRSQEATG

TWYGRWAVNYVYGTCLVLCGLQYFKHDPKFAPEIQAMAARAVKWLKQVQNSDGGWGESLLSYR

EPWRAGCGPSTPSQTAWALMGILTVCGGEDRSVQRGVRHLVDTQDDTLSQGDGGAAAWTERE

FTIREPLHEASQRIGSD
```

>seq_ID 26
```
MATLTTTMATTATMATTEASKPLEAQARTALTKATNYAWEIFSNRHWCGELESNVTVTCEHIFFLY

VLYQHIDPGEGSQYRQWLLLQQNSDGSWGIAPNYPGDISTSAEAYLALRIIGMSTDSPELYRARTFI

RAAGGLSKMRMFTRIFFAEFGLVPWTAIPQLPAEFILVPAHFPISIYRLASWARSNVVPLLIIAHHRPL

YPLPNGLHKQNPFLDELWLDPATKPLPYGSSDPTDPVAFVFTILDKALSYLGGLRRSPTRGYARRR

CVQWILQHQEKAGDWAGIIPPMHAGIKALLLEGYKLHDEPIQLGLAAIERFTWADNRGKRLQCCISP

VWDTRVYKPNIPVGGWAFEYHNTWYPDIDDTAAAVLAFLTHDPATARSRLVRDAVLWIVGMQNA

DGGWAAFDHENNQLFLNKIPFSDMESLCDPSTPDVTGRTIECLGMLRDLLMRPAENAENGEKYG

YPDGEGDAAADAHLLQIINTACARAIPYLIRSQEATGTWYGRWAVNYVYGTCLVLCGLQYFKHDPK

FAPEIQAMAARAVKWLKQVQNSDGGWGESLLSYREPWRAGCGPSTPSQTAWALMGILTVCGGE
```

```
DRSVQRGVRHLVDTQDDTLSQGDGGAAAWTEREFTSTGFPNHFYISYTLYRVYFPITALGRYLSLI
EGGQEKKKKGGGT
```

```
                                                              >seq_ID 171
MGKVETLHRTSTQDITLDDVERRVTLASKALMRLANADGHWCFELEADATIPSEYILYHHFRGSIPT
AELEGKIAAYLRRTQSAQHDGWALIHDGPFDMSATVKAYFALKMVGDPIDAPHMRRARDAILRRG
GAAHANVFTRIMLALYGEVPWTAVPVMPVEVMLLPRWFPFHLDKVSYWARTVMVPLFVLQAKKP
RARNPRGIGIRELFVEAPERVKRWPAGPQESSPWRPVFAAIDKVLQKVEGFFPAGSRARAIDKAV
AFVSERLNGEDGLGAIFPAMVNTVLMFEALGYPDDHPFAVTARSSVEKLVTVKEHEAYVQPCLSP
VWDTALAAHALMEAGGTEAERHAKRAMDWLKPLQVLDIKGDWAASKPDVRPGGWAFQYANPHY
PDLDDTAVVVMAMDRVQSRRSPGPDAADYGLSIARAREWVEGLQSRDGGWAAFDADNTYHYLN
YIPFSDHGALLDPPTADVTARCVSMLSQLGETRETCPPLDRGVAYLLADQEADGSWYGRWGMNY
IYGTWSVLCALNAAGIDPACEPVRRAVTWLTAIQNPDGGWGEDASSYKLEYRGYERAPSTASQTA
WALLALMAAGEADNPAVARGINYLTRTQGADGLWAEDRYTATGFPRVFYLRYHGYAKFFPLWAL
ARYRNLQRGNSLKVAVGM
```

```
                                                              >seq_ID 173
MLREATAISNLEPPLTASYVESPLDAAIRQAKDRLLSLQHLEGYWVFELEADCTIPAEYILMMHFMD
EIDAALQAKIANYLRHHQSADGSYPLFRGGAGDISCTVKVYYALKLAGDSIDAPHMKKAREWILAQ
GGAARSNVFTRIMLAMFEQIPWRGIPFTPVEIMLLPKWFPFHLDKVSYWSRTVMVPLFILCSHKVT
ARNPSRIHVRELFTVEPQKERHYFDHVKTPLGKAILALERFGRMLEPLIPKAVRKKATQKAFDWFT
ARLNGVDGLGAIFPAMVNAYEALDFLGVPPDDERRRLARESIDRLLVFQGDSVYCQPCVSPIWDT
ALTSLTLQEVARHTADLRLDAALSKGLKWLASKQIDKDAPGDWRVNRAGLEGGGWAFQFGNDYY
PDVDDSAVVAHALLGSEDPSFDDNLRRAANWIAGMQSRNGGFGAFDADNTYYYLNSIPFADHGA
LLDPPTADVSARCAMFLARWVNRQPELRPVLERTIDYLRREQEADGSWFGRWGTNYIYGPGAVL
LAYEGRRVPNDDPSVRRAVAWLKSIQREDGGWGEDNFSYHDPSYRGRFHTSTAFQTGFALIALM
AAGEXGSPEVQAGVDYLLRQQRPDGFWNDECFTAPGFPRVFYLKYHGYDKFFPLWALARYRNE
RYALA
```

```
                                                              >seq_ID 117
MNETAFANPAPQVGPAQRQPAAPQEAPAARLPAPALDRGIDRALDALLHQQRPDGHWVYELEAD
ATIPAEYVLMVHYLGEDPDRDLEARIARYLRRIQNPDGGWPLFHQGRSDISASVKAYFALKMAGDD
PQSAPMQRARQAIHAMGGAEATNVFTRTLLALYGVLPWKAVPMMPVEIMLLPRWFPFHLSKVSY
WARTVIVPLLVLNSLRPQARNPRGVGINELFVGNCHTVGLPPRAAHQHAGWYTVFRGLDALLRLA
EPLFPRTLRRRAIAAAQRFVRERLNGEDGLGAIFPAMANSVMMFDVLGVPPEDPARAVARRSIERL
LVEHGDEAYCQPCLSPVWDTALATHALLETGEARAAQAAGRALDWLRPLQVLDLRGDWAVRRPL
VRPGGWAFQYANAYYPDVDDTAVVAAAMDRFMRAHHAPGRYGEAVARATEWIVGMQSGNGGW
GAFEPENTHLYLNNIPFADHGALLDPPTADVSARCLSMLCQTGATPANSEPAARALRYLLAEQMP
DGSWFGRWGTNYIYGTWSALCALNAAGLPPEAPELCRAVAWLARIQNADGGWGEDGSSYRLDY
SGYEPAPSVASQTAWALLALMAAGAAQHPAVARGIDYLLRTQQPGGLWHEPRFTAVGFPRVFYL
RYHGYARYFPLWALARYRNLQRGLGDHGGNSGQVAWGL
```

```
                                                              >seq_ID 204
MSMNETAFATAVPRIAPASAGDSPAPRDAAQALDQGIGRAIDALLHQQRPDGHWVYELEADATIP
AEYVLMVHYLGEAPDLELEARLARYLRRIQNPDGGWPLFHEGRSDVSASVKAYFALKMAGDDPQ
AAHMQRARRAVHALGGAEASNVFTRTLLALYGVMPWLAVPMMPVEIMLLPQWFPFHLSKVSYWA
```

```
RTVIVPLLVLNSLRPQARNPRGVGINELFVGNCHTVGLPPRAAHQHAGWYTVFRGLDALLRVAEPL

VPRTLRRRAIAAAQAFVRERLNGEDGLGAIFPAMANSVMMFDVLGVPPDDPARALARQSVERLLV

EHGDEAYCQPCLSPVWDTALAAHALLETGEARATAAAGRGLDWLRPLQVLDVRGDWAVRRPLV

RPGGWAFQYANAYYPDVDDTAVVAAAMNRYMRAHDVPGRYDEAVARAAEWIVGMQGGDGGW

GAFEPENTHLYLNNIPFADHGALLDPPTADVSARCLSMLCQIGATPGKSEPAARALRYLLAEQMPD

GSWFGRWGTNYIYGTWSALCALNATGLAPEAPEMRRAVAWLEQIQNADGGWGEDGSSYRLDYR

GYEPAPSVASQTAWALLALMAAGAAQHAAVARGIDYLLRTQQSGGLWHEPRFTAVGFPRVFYLR

YHGYARYFPLWALARYRNLQRGGAHQVPWGL
                                                       >seq_ID 79
MRIGTTTNPSMPFPLSSSGAVFYREVNELREVQQEINRIQAFLLQRQQEDGTWRFCLESSPMTDS

HMIILLRTLGIHDERLMEKLTAHITALQHDNGAWKLYPDEQEGHLSTTIDSYYALLLSGKYTKNEPR

MALARSFILEKGGLTQANMLTKFATALTGQYQWPSHFLVPVEIALLPPSFPVSFYDFVGYARVHLA

PMMIVADRNYVKKPDNAPDLSDLYADTPISRGLYPHRFLENFLKEGQSFLATIHDSLQQLPFLPGQ

LHKLALRRLEQYILARIEPDGTLYNYSTSTFFMIFALLARGFSPKDPLIQKAMQGLTGSVYDYENGA

HLQLATSAVWDTALLTFSLQKSGLSPTHPAIQKANRYLLRKQQHTYGDWKIRNPNGKPGGWGFS

DYNTMNPDIDDTTAALRSLRLLARTDVTAATAWKRGLEWLLSMQNDDGGWPAFERNTDADFIRHL

PIEGADTVSTDPSSADLTGRTLEFLGNYAGRTLTDLHVEKGVRWLLKHQESDGSWYGRWGIAYLY

GTWAAITGLMAVGFSPTEPAIQKAVAWLVANQNPDGGWGESCQSDLKKTYVPLGASTPSQTAWA

IDALIAVSSKPTAELQRGIRYLLTHNQANDWTTRYPTGGGRPGGTYFAYHSYRWIWPLLALSHYQV

KYANT
                                                       >seq_ID 70
MLLYDKVHEEIERRTTALQTMQRQDGTWQFCFEGALLTDCHMIFLLKLLGRNDEIEPFVKRLVSLQ

TNEGTWKLYEDEKGGNLSATIQAYAALLASEKYSKEDMNMRRAEMFIKEHGGVSRAHFMTKFLLA

IHGEYEFPALFHFPTPILFLQDDSPLSIFGLSSSARIHLIPMMICMNKRFRVEKKLLPNLNHIAGGGG

QWFREERSPLIQSFLGDVKKVISYPLSLHHKGYEEVERFMKERIDENGTLYSYASATFYMIYALLAL

GHSIQSPIIEKAVTGLKSYIWKMDRGSHLQNSPSTVWDTALLSYSLQEAKVTNENKMIQRATEYLL

QKQQTKKVDWSVHASSLVAGGWGFSDVNTTIPDIDDTTAALRALARSRGNDRVDDAWGRGVEW

VKGLQNNDGGWGAFERGVTSKLLSNLPIENASDMITDPSTPDITGRVLELFGTYAPNELLEEQKKK

AIKWLMDVQEQNGSWYGKWGICYIYGTWATMTGLRALGVPSTHPALKKAASWLEHLQHEDGGW

GESCQSSVEKKFISLPFSTPSQTAWALDALISYYDQETPIIRKGISYLLAQSTMNEKYPTGTGLPGG

FYIRYHSYGHIYPLLALAHYVKKYRK
                                                      >seq_ID 140
MAGERSALITALKRSQAADGSWRFPFETGISTDAYMIILLRTLDINDEPLIQALVERIESRQEANGAW

KLFADEGDGNVTATVEAYYALLYSGYRQPTDRHMQKAKRRILDMGGLDRVHLFTKVMLALTGQYP

WPGRFPLPLEFFLLPPSFPLNMYDLSVYGRANMIPLLIAADSRYSRKTDKSPDLSDLFASRGDWG

MPESRSLLTYVKRSLIGLPAQLHQAAKQRAVRYLFEHIEPDGTLYSYFSSTFLFIFALLALGYRNDD

PRIRQAVRGLRSLRTTIDGHVHLQYTTASVWNTALASYTLQEAGVPMTDRAIEKANRYLLSRQNVR

YGDWAVHNPYSTPGGWGFSDVNTMNPDVDDTTAALRAIRQAAAKETAFRHAWDRANQWLFSM

QNDDGGFAAFEKNVSSRFWRYLPIEGAEFLLMDPSTADLTGRTLEYFGTFAGLTKDQRAVSRAVD

WLLSHQERNGSWYGRWGICYIYGTWAAITGLTAVGVPAHHPALQKAVRWLLSIQNDDGGWGES

CKSDGAKTYVPLGDSTPVHTAWALDALVAAAERPTLEMKAGFRALFRLLHHPDWTASYPVGQGM

AGAFYIHYHSYRYIFPLLALAHYEQKFGPLDD
```

```
                                                          >seq_ID 137
MAGERSALITALKRSQAADGSWRFPFETGISTDAYMIILLRTLDINDEPLIQALVERIESRQEANGAW

KLFADEGDGNVTATVEAYYALLYSGYRQPTDRHMQKAKRRILDMGGLDRVHLFTKVMLALTGQYP

WPGRFPLPLEFFLLPPSFPLNMYDLSVYGRANMIPLLIAADSRYSRKTDKSPDLSDLFASRGDWG

MPESRSLLTYVKRSLIGLPAQLHQAAKQRAVRYLFEHIEPDGTLYSYFSSTFLFIFALLALGYRNDD

PRIRQAVRGLRSLRTTIDGHVHLQYTTASVWNTALASYTLQEAGVPMTDRAIEKANRYLLSRQNVR

YGDWAVHNPYSTPGGWGFSDVNTMNPDVDDTTAALRAIRQAAAKETAFRHAWDRANQWLFSM

QNDDGGFAAFEKNVSSRFWRYLPIEGAEFLLMDPSTADLTGRTLEYFGTFAGLTKDQRAVSRAVD

WLLSHQERNGSWYGRWGICYIYGTWAAITGLTAVGVPAHHPALQKAVRWLLSIQNDDGGWGES

CKSDGAKTYVPLGDSTPVHTAWALDALVAAAERPTLEMKAGFRALFRLLHHPDWTASYPVGQGM

AGAFYIHYHSYRYIFPLLALAHYEQKFGPLDD

>seq_ID 136
MVADERSALIDALKRSQSVDGSWRFPFETGISTDAYMIILLRTLGIHDEPLIQALVERIESRQDANGA

WKLFADEGDGNVTATVEAYYALLYSGYRKKTDSHMQKAKARILEVGGLERVHLFTKVMLALTGQH

SWPRRFPLPLVFFLLPPSFPLNMYDLSVYGRANMVPLLVVAERRYSRKTDNSPDLSDLAASRNDW

RLPDTEALWSYVKRSLTGLPAWLHRAAEQRAVRYMLEHIEPDGTLYSYFSSTFLLIFALLALGYPKD

DPHIARAVRGLRSLRTEIDGHTHMQYTTASVWNTALASYALQEAGVPPTDRTIEKANRYLLSRQHI

RYGDWAVHNPYGVPGGWGFSDVNTMNPDVDDTTAALRAIRRAAAKETAFRHAWDRANRWLFS

MQNDDGGFAAFEKNVGKRFWRYLPIEGAEFLLMDPSTADLTGRTLEYFGTFAGLTKDHSAIARAID

WLLDHQEADGSWYGRWGICYVYGTWAAVTGLSAVGVPIDHPAMQKAVRWLLSIQNDDGGWGE

SCKSDGAKTYVPLGASTPVHTAWALDALIAAAERPTPEMKAGVRALVRMLHHPDWTASYPVGQG

MAGAFYIHYHGYRYIFPLLALAHYEQKFGPFVD

>seq_ID 49
MLLYEKVYEEIARRTTALQTMQRQDGTWRFCFEGAPLTDCHMIFLLKLLGRDKEIEPFVKRLASLQ

TNEGTWKLYEDEVGGNLSATIQSYAALLASEKYTKEDANMKRAEMFINERGGVARAHFMTKFLLAI

HGEYEYPSLFHLPTPIMFLQNDSPLSIFELSSSARIHLIPMMLCLNKRFRVGKKLLPNLNHIAGGGGE

WFREDRSPVFQTLLSEVKKIITYPLSLHHKGYEEVERFMKERIDENGTLYSYATASFYMIYALLALG

HSIQSPIIQKAITGIASYIWKMERGSHLQNSPSTVWDTALLSYALQEAQVPKASKVIQNASAYLLRKQ

QTKKVDWSVHAPNLFPGGWGFSDVNTMIPDIDDTTAVLRALARSRGDENVDNAWKRAVNWVKG

LQNNDGGWGAFEKGVTSRILANLPIENASDMITDPSTPDITGRVLEFFGTYAQNELPEKQKQSAIN

WLMNVQEENGSWYGKWGICYIYGTWAVLTGLRSLGIPSSDPSLKRAALWLEHIQHEDGGWGESC

QSSVEKRFVTLPFSTPSQTAWALDALISYYEKETPIIRKGISYLLSNPYVNEKYPTGTGLPGGFYIRY

HSYAHIYPLLTLAHYTKKYRK

>seq_ID 62
MNIVIRISKGWVSNLLLDEKAHEEIVRRATALQTMQWQDGTWRFCFEGAPLTDCHTIFLLKLLGRD

KEIEPFVERVASLQTNEGTWKLYEDEVGGNLSATIQSYAALLASKKYTKEDANMKRAENFIQERGG

VARAHFMTKFLLAIHGEYEYPSLFHVPTPIMFLQNDSPFSIFELSSSARIHLIPMMLCLNKRFRVGKK

LLPNLNHIAGGGGEWFREDRSPVFQTLLSDVKQIISYPLSLHHKGYKEIERFMKERIDENGTLYSYA

TASFYMIYALLALGHSLQSSMIQKAIAGITSYIWKMERGNHLQNSPSTVWDTALLSYALQEAQVSKD

NKMIQNATAYLLKKQHTKKADWSVHAQALTPGGWGFSDVNTTIPDIDDTTAVLRALARSRGNKNID

NAWKKGVNWIKGLQNNDGGWGAFEKGVTSKLLAKLPIENASDMITDPSTPDITGRVLEFFGTYAQ
```

-continued

NELPEKQIQRAINWLMNVQEENGSWYGKWGICYIYGTWAVMTGLRSLGIPSSNPSLTRAASWLEH

IQHEDGGWGESCHSSVEKRFVTLPFSTPSQTAWALDALISYYDTETPAIRKGVSYLLSNPYVNERY

PTGTGLPGAFYIRYHSYAHIYPLLTLAHYIKKYRK

>seq_ID 59
METLIDPEISRLTQRLLEDQEEDGAWRYCFENSLMTDAYMIVLIRSLGIKKERLVQELADRLLSQQE

EKGFWKIYRDEVEGNLSATVEAYFALLWSGAVKEKDENMVKARDCILSGGGLDKVHSMTKFMLAA

HGQYPWDRFFPVPVEVILLPTYFPVSFTDFSAYARVHLAPLLLLKSERYIRKTSTTPDLSYLLKDQE

DFSFFREEERSFIEYVTSGVEAIAAFPANLNDLAKKTALNYMLARLEPDGSLYSYFSSSFYMIIALLS

QGYSRKDPLVVNAIKALISYQCKGDGYPHIQNSPSTIWDTALISHALQSSGVDSRNAQILKASHYLY

RHQHTQKGDWASEAPQTAPGGWGFSESNTINPDVDDTTAALRALKLDAYTDPVKRMAWNRGVK

WALSMQNKDGGWPAFEKNKNKDILSWVPMDGAEDAALDRSCADLTGRTLEFLGNDAGMGRENS

QVLKGIEWLMNNQENDGSWYGKWGICYIYGTWAALTGMMAAGMSADHQSIIKAIKWLYQIQNSD

GGWGESCRSDKERKYISLGASTPSQTAWALDALISINDHPTKEIDRGIESLVRLLNTDDWRKEYPT

GAGLPGRFYIHYHSYPYIWPLLALSNYKTKFLEVR

>seq_ID 51
MVLYGRVCAEIERTITALHTMQQQDGAWRFCFEGSPLTDCHMIFLLRLLEKEEEIEPFVARLTSIQT

NEGTWKLYEDERAGNVSTTIQAYAALLASGMYTKEDVNMKRAEAFIQERGGIARSHFMTKFLLALH

GGYEYPRMFYFPTPILFLPEDSPLSIFELSSSARIHLIPMMICMNKRFTVSKTILPNLDHISGSSKSEW

FREDRSSLFETILGEVKKFVTYPLSLHHKGDKEAERFMIERIDRNGTLYSYASATFYMIYALLALGHH

IQSPLIQQAVAGLRTYKWHMEAGIHLQNSPSTVWDTALLSYALQEANVNESTPMIQTATEYIWQRQ

HHEKKDWSLHAPTLSPGGWGFSDVNTTIPDVDDTTAALRALARSRKRNRRIEEAWKKGVNWVKG

LQNKDGGWAAFEKGVTNRFLTHLPLENSGDMMTDPSTADITGRVLEFFGTYAPNELQDHQKNRAI

TWLMDVQENNGSWYGKWGVSYIYGTWAALTGLRAVGVANTHPALKKAVMWLERIQHRDGGWG

ESCRSSIEKRFVPLSFSTPSQTAWAIDALISYYDEETPVIRKGISYLLEHAASHQEYPTGTGLPNGFY

IRYHSYSYMYPLLTFAHYINKYRK

>seq_ID 32
MLLYEKAHEEIVRRATALQTMQWQDGTWRFCFEGAPLTDCHMIFLLKLLGRDKEIEPFVERVASLQ

TNEGTWKLHEDEVGGNLSATIQSYAALLASKKYTKEDANMKRAENFIQERGGVARAHFMTKFLLAI

HGEYEYPSLFHLPTPIMFLQNDSPFSIFELSSSARIHLIPMMLCLNKRFRVGKKLLPNLNHIAGGGG

EWFREDRSPVFQTLLSDVKQIISYPLSLHHKGYEEIERFMKERIDENGTLYSYATASFYMIYALLALG

HSLQSSMIQKAIAGITSYIWKMERGNHLQNSPSTVWDTALLSYALQEAQVSKDNKMIQNATAYLLK

KQHTKKADWSVHAPALTPGGWGFSDVNTTIPDIDDTTAVLRALARSRGNKNIDNAWKKGGNWIK

GLQNNDGGWGAFEKGVTSKLLAKLPIENASDMITDPSTPDITGRVLEFFGTYAQNELPEKQIQRAIN

WLMNVQEENGSWYGKWGICYLYGTWAVMTGLRSLGIPSSNPSLTRAASWLEHIQHEDGGWGES

CHSSVEKRFVTLPFSTPSQTAWALDALISYYDTETPAIRKGVSYLLSNPYVNERYPTGTGLPGAFYI

RYHSYAHIYPLLTLAHYIKKYRK

>seq_ID 31
MSTIHENVRSRQKKTISLLRETQNADGSWSFCFEGPILTNAFLILLLTSLGDNDKELIAELAEGIRAK

QRPDGTFANYPDDRKGNVTATVQGYAGLLASGLYSRSEAHMIQAERFIISNGGLRNVHFMTKWML

AANGLYPWPALHLPLSFLVIPPTFPLHFYQFSTYARIHFVPMAVTLNKRFSLKNPNVSSLAHLDRHM

TKNPFTWLRSDQDENRDLSSLFAHWKRLLQIPAAFHQLGLRTAKTYMLDRIEEDGTLYSYASATIF

MVYGLLALGVSRHSPVLRKALAGTKALLTSCGNIPYLENSTSTVWDTALLNYALMKSGISDNDQMI

-continued

```
TSAARFLRERQQKKVADWAVHNPHAEPGGWGFSNINTNNPDCDDTAAVLKAIPRKLYPASWERG

LSWLLSMQNSDGGFSAFEKNVNHPLVRLLPLESAEEAAIDPSTSDLTGRVLHCLGEAGLSSDHPQI

EKAVQWLIRHQEEDGSWYGRWGVCYIYGTWAALTGMKACGVSQNHPAVKKAIRWLKSIQNEDG

SWGESCKSAEEKTYVPLSYGTLVQTAWAAEALLQYEKTHHQAVTKGISFLIENRHYEGAAFSYPT

GIGLPKQFYIRYHSYPYVFSLLALSTFMKMSEKEEEK
```

>seq_ID 48
```
MLLYEKAHEEIARRATALQTMQRQDGTWRFCFEGAPLTDCHMIFLLKLLGRDKEIEPPFVKRLASLQ

TNEGTWKLYEDEVGGNLSATIQSYAALLASKKYTKEDANMKRAENFIKERGGVARAHFMTKFLLAI

HGEYEYPSLFHLPTPIMFLQNDSPLSIFELSSSARIHLIPMMVCLNKRFRVGKKLLPNLNHIAGGGG

EWFREDRSPLFQTLLSDVKQIISYPLSLHHKGYEEVERFMKERIDENGTLYSYATASFYMIYALLAL

GHSLQSSLIQKAIAGITSYIWKMERGSHLQNSPSTVWDTALLSYALQEAHVPKDHKMIQQTITYLLK

KQHTKKADWSVHALALTPGGWGFSDVNTTIPDVDDTTAVLRALARSRGNENIDNAWKKGVNWIK

GLQNNDGGWGAFEKGVTSKLLANLPIENASDMITDPSTPDITGRVLELFGTYTQNELPKKQKQSAI

NWLMNVQERNGSWYGKWGICYIYGTWAVMTGLRSLGIPSNNPSLKRAALWLEHIQHEDGGWGE

SCQSSVEKRFVTLPFSTPSQTAWALDALISYYDKETPTIRKGVSYLLANPYVNEKYPTGTGLPGGF

YIRYHSYAQIYPLLTLAHYTKKYQK
```

>seq_ID 34
```
MNIVIRISKGWVSNLLLYEKVHEEIARRTTALQSMQRQDGTWRFCFEGAPLTDCHMIFLLKLLGRD

KEIEPFVKRLASLQTNEGTWKLYEDEVGGNLSATIQSYAALLASEKYTKEDANMKRAEMFINERGG

VARAHFMTKFLLAIHGEYEYPSLFHLPTPIMFLQNDSPLSIFELSSSARIHLIPMMLCLNKRFRVGKK

LLPNLNHIAGGGGEWFREDRSPVFQTLVSDVKKIITYPLSLHHKGYEEVERFMKERIDENGTLYSY

ATASFYMIYALLALGHSLQSSMIQKAIAGITSYMWKMESGNHVQNSPSTVWDTALLSYALQEAHVL

KDNKMLQNATAYLLKKQHTKKADWSVHAPALTPGGWGFSDVNTTVPDVDDTTAVLRVLARSRGN

EKVDHAWQKGINWVKGLQNNDGGWGAFEKGVTSHILANLPIENASDMITDPSTPDITGRVLEFFG

TYAQNELPEKQKQSAINWLMNVQEENGSWYGKWGICYIYGTWAVLTGLRSLGIPSSDPSLKRAAL

WLEHIQHEDGGWGESCQSSVEKRFVTLPFSTPSQTAWALDALISYYDKETSVIRKGISYLLSNPYIN

ETYPTGTGLPGGFYIRYHSYAHIYPLLTLAHYAKKYRK
```

>seq_ID 47
```
MLLYEKVHEEIVRRATALQTMQWQDGTWRFCFEGAPLTDCHMIFLLKLLGREKEIEPFVERIASLQ

TNEGTWKLYEDEVGGNLSATIQSYAALLASKKYTKEDANMKRAENFIKERGGVARAHFMTKFLLAI

HGGYEYPSLFHLPTPIMFLQNDSPLSIFELSSSARIHLIPMMLCLNKRFRVGKKLLPNLNHIAGGGG

EWFREDRSPVFQTLISDVKQIISYPLSLHHKGYEEIERFMKERIDENGTLYSYATASFYMIYALLALG

HSPQSSMIQKAIAGLTSYIWKMGRGSHLQNSPSTVWDTALLSYALQEARVSKDNKMIQNATAYLLK

KQHTKKADWSVHAPALIPGGWGFSDVNTTIPDIDDTTAVLRALARSRGNKNIDNAWQKGVNWIKG

LQNNDGGWGAFEKGVTSKLLANLPIENASDMITDPSTPDITGRVLEFFGTYAQNGLPEKQKQSAIN

WLMNAQEENGSWYGKWGICYIYGTWAVMTGLRSLGIPSSNPSLKRAASWLEYIQHEDGGWGES

CHSSVEKRFVTLPFSTPSQTAWALDALISYYDTETPAIRKGVSYLLSNPYVNERYPTGTGLPGAFYI

RYHSYAHIYPLLTLAHYLKKYRK
```

>seq_ID 52
```
MRSILEDVKAFRQKTLAELQNRQRSDGSWRFCFEGPVMTDSFFILMLTSLGDQDSSLIASLAERIR

SRQSEDGAFRNHPDERAGNLTATVQGYTGMLASGLYDRKAPHMQKAEAFIKDAGGLKGVHFMTK

WMLAANGLYPWPRAYIPLSFLLIPSYFPLHFYHFSTYARIHFVPMAITFNRRFSLKNNQIGSLRHLDE

AMSKNPLEWLNIRAFDERTFYSFNLQWKQLFQWPAYVHQLGFEAGKKYMLDRIEEDGTLYSYASA
```

-continued

TMFMIYSLLAMGISKNAPVVKKAVSGIKSLISSCGKEGAHLENSTSTVWDTALISYAMQESGVPEQ
HSSTSSAADYLLKRQHVKKADWAVSNPQAVPGGWGFSHINTNNPDLDDTAAALKAIPFQRRPDA
WNRGLAWLLSMQNKDGGFAAFEKDVDHPLIRNLPLESAAEAAVDPSTADLTGRVLHLLGLKGRFT
DNHPAVRRALRWLDHHQKADGSWYGRWGVCFIYGTWAALTGMKAVGVSANQTSVKKAISWLKS
IQREDGSWGESCKSCEAKRFVPLHFGTVVQSSWALEALLQYERPDDPQIIKGIRFLIDEHESSRER
LEYPTGIGLPNQFYIRYHSYPFVFSLLASSAFIKKAEMRETY

>seq_ID 188
MRSELLQLQSADGSWRLCFDSGTMPDSYFIIILRMLGYSQDEALIRQIASRILSRQLPNGTWKIYPD
EEDGNLDATAEAYFALLYSGFLTKLDPRMQLAKQFILSKGGLSKIRSLLTQAIFAAAGQASWPKSM
RIPLEVFFSDNGIGIDLFSLSGHARVHIVPIIMLANAQFVQHSASMPDLSDLFAGSSKRFENDSPWIA
ALATLIGSLSLSELLPFESPTPQEKAVQFLFDRLEPDGTLLTYTTATMFMILVLLMLGYSSSSPLIHR
MVSGIHSVICANSHVQIASSEVWDTAMLVHALRKAGVNPTSTALENAGAYLRQRQQTQLGDWAIR
NPGTPAGGWGFSNVNTLYPDVDDTTAALRAIQPYSSRTPELQADWQRGLNWVLTMRNDNGGWP
AFERQGSRLPITFFNFEGAKDIAVDPSTVDLTSRTLQFLGQELGMNAGNSWIESTLRWVLSQQES
NGSWYGRWGITYVHGTSAALQGLTAVGIAEDHPAVKKGVDWLLQVQNEDGGWGESCISDKVRR
YVPLNFSTPSQTAWALDGLTAALPKPTPALERGVDALLQSLDRHDWTYTYPTGGALPGSVYAHYA
SNNYIWPLLALSNIWQKYS >seq_ID 60
MGTLQEKVRRFQKKTITELRDRQNADGSWTFCFEGPIMTNSFFILLLTSLDEGENEKELISSLAAGI
HAKQQPDGTFINYPDETRGNLTATVQGYVGMLASGCFHRTEPHMKKAEQFIISHGGLRHVHFMTK
WMLAANGLYPWPALYLPLSLMALPPTLPIHFYQFSSYARIHFAPMAVTLNQRFVLINRNISSLHHLD
PHMTKNPFTWLRSDAFEERDLTSILLHWKRVFHAPFAFQQLGLQTAKTYMLDRIEKDGTLYSYASA
TIYMVYSLLSLGVSRYSPIIRRAITGIKSLVTKCNGIPYLENSTSTVWDTALISYALQKNGVTETDGSV
TKAADFLLERQHTKIADWSVKNPNSVPGGWGFSNINTNNPDCDDTTAVLKAIPRNHSPAAWERGV
SWLLSMQNNDGGFSAFEKNVNHPLIRLLPLESAEDAAVDPSTADLTGRVLHFLGEKVGFTEKHQHI
QRAVKWLFEHQEQNGSWYGRWGVCYIYGTWAALTGMHACGVDRKHPGIQKALRWLKSIQNDD
GSWGESCKSAEIKTYVPLHRGTIVQTAWALDALLTYENSEHPSVVKGMQYLTDSSSHSADSLAYP
AGIGLPKQFYIRYHSYPYVFSLLAVGKYLDSIEKETANET >seq_ID 56
MQDFKTKVNVYMDELHMQMQHRQREDGAFVFCFEGSMMTNAFLIMLLKAVGDTDQALVHQLAE
AIREKQNEDGSFSLYHDQAGHVTATVQGYCGMLVSGRYQQDEPHMEKAARYIRSKGGLKDVHF
MTKWMLAVNGMHPWPYFYAPLSFLLIPTYFPLHFYHLSAYARIHFVPMMIALNKRYTSHEQFPSLS
HLDANMSKNPFDWFMAREERSTHHFLAYMRSYTALDSRFDFFGYEAAKRYMFDRLEKDGTLYSY
LSASIFMVYALMSLGYSPGHHLILKAVKGMKQLVTDCGGKKYAENSTSTVWDTALVSYASQRAGR
TQDDPVIKKSFTYLLNRQQMKKADWAIHNRHAAPGGFGFSDLNTNNPDCDDTQIVLKAIPQTYAPV
QWKRGFDWLLSMQNRDGGFSAFEKNQDHFLLRHLPLESAEDAAIDPSTPDITGRVLHLIASEEND
KSPLMQRQKDHCVKWLLDHQEKDGSWYGRWGVCYIYGTWAALTGLKASGIPSSHPAVQKACRF
LKTIQLEDGSFGESCKSSEVKRYVPLPFGTVVQTAWAAEALLQYVQPDDKSILKAISFLIQHQHSSK
ALHYPVGIGLPKQFYITYHSYPFVFPMMACSTFLEEMRRKNE >seq_ID 58
MKNRNKGAGCMQLVKSEIERLKQQLLSEQTPDGSWNHPFDTGCMTDIYMIVLLRTLEEEDEEELIK
ELAKGILSRQGKDGAWRLFHDHHEGSLSLTIEAYYALLYSGYYEKNHPALVKARRVITKGGGLKKA

```
GMYTKIMLALTGQYPWPLLFPVPMEVILLPRSFPLNMYDISVFGRSNLIPVILLGNKKFSRKTALSPD

LGDLSVRDDDDPWPELRSAEWRSLTSFLAAGVKALVGIPRQIRAWSIEKAREYMQSHTEPDGTLY

NYFSSTFYMIFALLALGGGPEEPAIRNAVAGLKRMTVKADGRTHIQYTTAAVWNTALISHALQEAG

VPPKENAIQKANQYLAGQQHRRFGDWIVHNTKAEPGGWGFSRFNTINPDVDDTTAALRSLYQPA

REKPHYDDIWKKGLLWTLSMQNRDGGWPAFERNVDKKLLHLLPIQGAEFILTDPSTADLTGRTLEF

LGKAGYADASLPPIKKAVKWLKKHQEPNGSWYGRWGICYIYGTWAAVTGMAAVGVTLEDKSMKK

GIDWLLSIQNEDGGWGESCRSDMEKKYIPLKESTLTQTAWAVDALAAAGMADSTPSRKGAAFLVR

EGKRKDWTADYPMGQGMANFFYIHYHSYRCIWPLLALSHYIEKSEAPD
```

>seq_ID 57
```
MQDFKTKVNEYIDELHMQLQRRQREDGAFVFCFEGPMMTNAFLIMLLKAVGDSDQALVHQLAEAI

REKQNEDGSFSLYHDQAGHVTATVQGYCGMLVSGRYQQDEPHMEKAAHFIRSNGGLKDVHFMT

KWMLAVNGMHPWPYFYAPLSFLLIPTYFPLHFYHLSAYARIHFVPMMIALNKRYTSHEQFPSLAHL

DANMSKNPFDWFMAREERSTHHFLAYMRSYTALDSRLDFFGYEAAKRYMFDRLEKDGTLYSYLS

ASIFMVYALMSLGYSPGHHLILKAVKGMKQLVTDCGGRKYAENSTSNVWDTALVSYASQQAGRT

QDDPVIKKSFTYLLNRQQMKKADWAIHNRHAAPGGFGFSDLNTNNPDCDDTQIVLKAVPQTYAPV

QWKRGFDWLLSMQNQDGGFSAFEKNQNHFLLRHLPLESAEDAAIDPSTPDIAGRVLHLIALEENS

MSPLMQRQKDHCVKWLLDHQEKNGSWFGRWGVCYIYGTWAALTGLKTAGISSSHSAVQKACRF

LKTIQLEDGSFGESCKSAEVKRYVPLPFGTVVQTAWAAEALLQYVQPDDKVILKAISFLIQHQSSE

ALHYPVGIGLPKQFYITYHSYPFVFPMMACSTFLEEMRRKNE
```

>seq_ID 61
```
MGTLQEKVRRFQKKTITELRDRQNADGSWTFCFEGPIMTNSFFILLLTSLDEGENEKELISSLAAGI

HAKQQPDGTFINYPDETRGNLTATVQGYVGMLASGCFHRTEPHMKKAEQFIISHGGLRHVHFMTK

WMLAANGLYPWPALYLPLSLMALPPTLPIHFYQFSSYARIHFAPMAVTLNQRFVLINRNISSLHHLD

PHMTKNPFTWLRSDAFEERDLTSILLHWKRVFHAPFAFQQLGLQTAKTYMLDRIEKDGTLYSYASA

TIYMVYSLLSLGVSRYSPIIRRAITGIKSLVTKCNGIPYLENSTSTVWDTALISYALQKNGVTETDGSV

TKAADFLLERQHTKIADWSVKNPNSVPGGWGFSNINTNNPDCDDTTAVLKAIPRNHSPAAWERGV

SWLLSMQNNDGGFSAFEKNVNHPLIRLLPLESAEDAAVDPSTADLTGRVLHFLGEKVGFTEKHQHI

QRAVKWLFEHQEQNGSWYGRWGVCYIYGTWAALTGMHACGLTESIPVYKRLCVGSNPYKMMTE

AGENPAKAPKSKHMYRFIEEPLYKRPGL
```

>seq_ID 50
```
MAEAISYPRRVHIITTKFPVNFYDFSVFGRSNIAPILLLADSKFQIPKTTETPDISHLYVRELYWWSED

RGWNGFTKAINKGVNNLIGLPNELHTLGRKQAENYMLDRLEDDGTLLSYYSSTFFMIYALLSVGYT

KDHKVIKKAARGLLSMNTTVKDTIHIQYTTAHIWNTSLISHALQTAGASPDDTMVMRANHYLLQRQ

HTKFGDWAIYQPNLGPGGWGFSHSNTFNPDVDDTTASLRSIQNSLHSHPNYQSSWYRGLSFTLG

MQNQDGGFPAFEKGVDKTFLHLLPVQGAEFLLTDPSTPDLTGRTLEFLGESAHLYKDSGAIKRGV

NWLIENQRRDGSWYGRWGICYIYGTWAALTGLQAVGVSKEHPSVQEGIDWLKSIQQDDGGWGE

SCESDSQKTYIPLSKSTVTQTAWAVDALIAYEKEETVEIKKGMEYLLENWNHEDWTMDYPMGQG

MAKAFYIHYHSYRYVFPLLTMGHYMRKFM
```

>seq_ID 199
```
MSETISCQRIQAAYQRSRAELLSLRNSIGHWTGELSTSALSTATAIMALEMIRRKRLPADLSLNTYI

DNGIRWLAEHQNSDGGWGDTVKSFSNISTTMLCHAVFHATKSTEQYVSHVVNARQYIDRVGGVE

AVVARYGKDKTFSVPILTHCALAGLVKWKTIPALPFELACLPARFYKTVRLPVVSYALPALIAIGQVR

HHFCKPRNPITRLIRKLAVKRSLKKLISIQPSNGGFLEAAPLTSFVTMSLAGMGLTDHPVVQKGLQF
```

```
LLDSVRPDGSWPIDTNLATWTTTLSVNALEGTLAEFEKTPIREWLLQQQYKELHPYTSAEPGGWA

WTDLPGGVPDADDTPGAILALLNLQPDEPDTQQPADLQVALRNGVKWLLDLQNSNGGWPTFCRG

WGALPFDQSAADISAHVIRALQAWLQTEPESAEAELRLRAERAVRKCFKYLATVQRPDGSWLPLW

FGNQHVENDENPVYGTARVLAAYAQGEQCGSIQAEQGILFLKSVQNLDGGWGGATSAPSSVEET

ALAVDTLLALGLEPADPVVAQGLNWLSGRVENGTYTETTPIGFYFAKLWYFEQLYPIIFTVSALHRA

ETVLKKSADDNLRLSLEEEDYPIMSVKEK
```

>seq_ID 75
```
MDQDRLQRCYAIARDDLLAQRNGQGHWTGELSTSALSTATAVSALQLVVRHDPAQSERLMPLIEG

GVRYLTEHQNPDGGWGDTDRSYSNIATTMLAVAALTIAERREALFEQLAFAENYIEAQGGIPGLRR

RYGKDKTFAVPILTNYALAGLVDWREVSPLPFELACLPQKFYKLVKLPVVSYAIPALVAIGQARYFH

RPPFNPLMRGLRGAAVKKSLAVLERMQPASGGYLEAAPLTSFVVMSLASIGNASHPVAQNGVQFL

VDSVREDGSWPIDSNLANWVTTLSISALATGGDDIAELDCLPWVLANQYQETHPFTGADPGGWG

WTDLSGSVPDADDTPGAMLAIAHFFHSPRADNETRRQIASAAISGARWLLDLQNSDGGWPTFCA

GWGTQPFDRSGSDLTAHAIRALHAWRSELGDLPVERAIERGLRYLQKQQRDDGSWLPLWFGNQ

DIHDDENPIYGTVKVLLAYRDLGKMSSETAQRGAAWLAARQNEDGGFGGGPSISTLCGGPGESS

VEETALAIEALFAAENSNISAEIVPPAVGWLCQRVEEGSYVNCTPIGFYFSKLWYYEKLYPRVMTVT

SLGAALQANASVPPAPETVTTSSDH
```

>seq_ID 325
```
MATSDPSLAEAIQNTRAHLLSLRNARGHWEGHLSNSALSTATAIVALHLVDAPLHSARIAQGVRWL

VLHQNKDGGWGDTTLSKSNLSTTLLCWSALSLCEPDRTEPIQHCEAWIKERTGSLEPEVICRAVVA

RYGKDKTFSVPILMLCAIGGRLGPEKEAWSRVLALPFELAAMPREWFGAIGLPVVSYALPALIAIGY

ARFYHAPPSLLNPLHALRKALWPRISPMLKLLQPSTGGYLEATPLTSFVTMALASAGEKFHPCVPE

AVRFLEDSQRPDGSWPIDINLATWGTTLSTKALTATSEGREALDIPALKSWLLEQQYQEIHPFTNA

APGGWAWTDLPGGVPDADDTSGALVALWHLCEDEAERQALAPAVAKGVQWLMDLQNRDGGIPT

FCRGWGTLPFDRSTPEITAHALHAWGLWQVVLPEELQQEVSLRIPRAIAFIARPPSRGAPGFNHVP

LWFGNEHAKEEENHVYGTAQIMNHLLSSGLNTPEIKVILETGHRNLLAWQQLDGGWSGSETGPAS

LEETAVSVAALALHTLHAGNRTRSSAEDAVAKGTQWLVQHTATGTTFPSAPIGLYFARLWYHEQL

YPVIWTLGALHAVETLSAAALPLRARASAPPQHPGVVRTKPIHIAPPSDP
```

>seq_ID 135
```
MIPAERLRTAYRTARAALLAERVPEGHWVGELSTSALSTATAVMALHLVNPFTHRELIDAGRKWLA

EHQNADGGWGDTVKSFSNISTTMLCRAAFKLAGEKEYPETVQRVEEYLSRNAGALPTARAAAIRA

RYGKDHTFSVPILMTCAVAKLVPWDEVPRLPFELACLPQSWYRFAKLPVVSYALPALIAIGQCIHHH

RRSQNPIRNTVRRLARGLSLKVLRRIQPTSGGYLEATPLTSFVVMALSSIRRRRAAAEQQVIDEGV

RFLVASVRPDGSWPIDTNLATWVTTLSVNALATAGDLEALDTKEQILAWLLKQQYKERHPYTGADP

GGWAWTDLPGGVPDCDDTPGALIALAHLDPKSDPQAVLSGLRWVLRLQNGDGGAPTFCRGWGT

LPFDRSGADLTAHSVRSLASWYRVWGAGPPPIEHLRHRLKDLEFPLSGLFWDVARRNPRFVRYLK

KQQRSDGSWLPLWFGNQHAPDDINPVYGTARVLAAYRDLELKDAPECRRGIEFLLSVQNADGGW

GGAKGCPSSVEETALAVEVLLDLADGDAVQKGVAWLAEAVESDRFRDASPIGFYFAKLWYFEKLY

PIIFTVAALGRAVKITSPAPAAESA
```

>seq_ID 115
```
METLSRSRLEAALAKATQALLTELNPAGHWSGELSSSALSTATAIVALGAVDREQQRELIAGGMR

WLAQHQNADGGWGDTVKSRSNISTTALCWAAVSTSTEHAESAAKAEAWLTRAAGSMAQLVPAIE
```

-continued

```
ARYGKDRTFSVPILMHLAICGRVSWSQIPALPFELAALPHQLFGALQLPVVSYALPALIAIGQAIHHH

APPTNPLLNGLRKSARARTLEVLESIQPQNGGFLEATPLTSFVTMALASAGEAQHPVARRGVSFLQ

ASVQRDGSWAIDTNLATWVTTLSIKALAHQPGALSPERALTLREWLLGQQYVVEHPYTHAAPGG

WAWTDLPGGVPDADDTPGALLALLHLGVVDAPTRQAGQIGVRWLLDLQNRDGGIPTFCRGWGAL

PFDRSSPDLTAHTLRAWTAWLPQLDESLKRRTLRAVTKAIHFLATHQRTDGSWLPLWFGNEHAPD

DENPLYGTAKVVIALRELLNRDFTLPNGMLERALCWLVERQDISGGWSGAKNGPVSVEETALAVE

ALAGTGHVSATDRGAAWLTEQIEADTWREPAPIGFYFAKLWYYERLYPQIWTVGALGRVAALRVG

ESESDTPAGLHRATSET
```

>seq_ID 208
```
MMAVVENSVSEVLDRRELRGTLDLLRGELLAQRTKDGHWTGELSASALSTATAISAMSAAVRSGK

LAGADKAALLEQIQSGRRWLADQQNDDGGFGDTDRSHSNIATSYLVLAAWTLSDQVTGETTDAN

AISRLRNWIQLAGELDGLRRRYGKDKTFVVPILTNMAIAGLVPWKKVSALPFEAAVVPQSMYRFVG

MPVVSYAVPALVAIGQVKFLEGGGCLPPWSLVRRAAIEPSMKVLRSMQPSSGGYLEATPLTAFVV

MSLSASGRADHEVTQNGLRFLRDSMLPDGSWPIDTNLANWATSLATTALTMDPDDDRSWSTNEL

IQWQRGCQYQERHPFTGADPGGWGWTDLTGSVPDADDTPGAIISLRMQATTRPDPLCDDYSRD

WPASDSSGSVSANALDTWKACDRGVDWLLGLQNRDGGWPTFCRGWGKLPFDRSSNDLTAHAL

RAIACLPKRESAKRSRAVQRGLRFLRKNQQADGSWLPLWFGNQDRPEEDNPIYGTSRVLVDVSP

ALGHDAISRGLYYLINSQNSDGGWGGGESVRETFGLPEGFISSVEETALAVEALVSWWGRIPGNE

GGQAAENDIPDGSPWDASMRSALRAAILSGTRWLIDAVQRERHQVAWPIGFYFAKLWYYERLYPL

VYTTAALGRVMQRDELLR
```

>seq_ID 247
```
MEIQDEVDLLEPQESLTASADSAVDRALFWLLDAQYEDGYWAGILESNACMEAEWLLCFHVLGIA

NHPMSRGLVQGLLQRQRADGSWDVYYGARAGDINTTVEVYAALRCQGYAADHPDIKRARDWIQL

QGGVKQVRVFTRFWLALIGEWPWEETPNLPPEILFFPRWFPFNIYHFAAWARATLVPLCILSARRM

VVPLNKKSCLQELFPEDRSAVVALGKKAGAWSTFFYHADRALKKYQRTFKRPPGRQQAIKMCLE

WILRRQDADGAWGGIQPPWIYSLMALKAEGYPVTHPVMAKGLAALDAHWSYERPGGARFVQAC

ESPVWDTLLSSFALLDCGFSCTSSSELRKAVDWILDQQVLLPGDWQQKLPTVSPGGWAFERANV

HYPDVDDTAVALIVLAKVRPDYPDTARVNLAIERGLNWLFAMQCRNGGWGAFDKDNDKDLLTKIP

FSDFGETIDPASVDVTAHVLEALGLLGYRTTHPAVAKALEFIRSEQENDGCWFGRWGVNYIYGTAA

VLPALASLNMNMNQEFIRRAANWILGKQNNDGGWGESCASYMDDTQRGRGPSTASQTAWAMM

SLLAVDGGTYAESLLRAEAYLKTTQTPEGTWDEPYYTGTGFPGYGIGRREIKRQRSLQQHAELSR

GFMINYNLYRHYFPLMALGRLAALRGA
```

>seq_ID 148
```
MTSPFKHPISHALTSFNGIVTEPEQSVEQKAGAKVHQFPASLWKSKPGKAKSPLDIAIEGCRDFFF

REQLPKGYWWAELESNVTITAEYIMLFNFLSLVDHERQRKMSNYLLSKQTEEGFWTIYYGGPGDL

STTVEAYFALKLTGYPADHPAMVKARAFILEKGGVIKSRVFTKIFLALFGEFDWLGVPSMPVELNLL

PNWAYVNVYEFSSWARATIIPLSIVMLKRPVHKLPPSQRVQELFVRPPRAIDYTFTKEDGIFTWKNF

FIGLDHMLKVYERSPVRPFKKRAMGKAEEWVLEHQEETGDWGGIQPAMLNAVLALSALGYDNGH

PAVAHGLKALENFCIESDEQIVLQSCISPVWDTALALKALVDAGVPSDHPSLVKGAQWLLEREVRR

PGDWRVKSPDLEPGGWAFEFLNDWYPDVDDSGFVMIALKGVEVKDRKAMNAAVKRGIDWCLGM

QSKNGGWGAFDKDNTRHILNKIPFADLEALIDPPTADLTGRMLELMGTFGYAKTYPAAQRALKFLK

ENQEPEGPWWGRWGVNYLYGTWSVLCGLAAIGEDLEQPYIKKAVNWIKSRQNMDGGWGETCE
```

-continued

SYHDPTLAGMGESTASQTGWALLGLMAAGEVHSATVVRGVQYLISTQSQDGTWDETQYTGTGF

PKYFMIKYHIYRNCFPLMALGTYRTLTGGTA

>seq_ID 149
MTSPFKHPISNALTSFNGNFAEPEQCVEQQTGAKVHHLPASIWKRKMGKAKSPLDVAIEGSRDFF

FQEQLPKGYWWAELESNVTITAEYIMLFHFLGLVDRERQRKMSNYLLSKQTEEGFWPIYYGGPGD

LSTTIEAYFALKLSGYPADHPALAKARAFILEQGGVVKSRVFTKIFLALFGEFEWQGVPSMPVELNL

LPDWAYINIYEFSSWARATIVPLSVVMHSRPVRRVPPSARVQELFVRQPTAADYSFAKNDGIFTWE

NFFLGLDRVLKVYEKSPLRPFKNMALAKAEEWVLEHQEPTGDWGGIQPAMLNAVLALNVLGYQN

DHPAVEQGLRALANFCIETEDQLVLQSCVSPVWDTALALKALLDAGVPPDHPSLVKGAQWLLDKE

VTRPGDWRVKSPALEPGGWAFEFLNDWYPDVDDSGFVMIALKGIQVKDRKSMDAAIKRGINWCL

GMQSKNGGWGAFDKDNTRHVLNKIPFADLEALIDPPTADLTGRMLELMGTFNYPITLPAAQRAIEF

LKKNQEPEGPWWGRWGVNYLYGTWSVLCGLAAIGEDMDQPYIRKAVNWIKSRQNIDGGWGETC

QSYHDRTLAGVGESTPSQTGWALLGLLAAGEMHSATVVRGVQYLISTQNSDGTWDEQQYTGTG

FPKYFMIKYHIYRNCFPLMALGTYRTLTRTQP

>seq_ID 216
MTDVLTRELSPNSTRDRVRSCVSSARQYLLSLQHEEGWWKGELDTNVTMEAEDLLLRQFLGISDE

QVTQETARWIRSCQREDGTWATFHGGPPDLSTTVEAYVALRLAGDAMDAAHLRKAREYILDSGGI

ESTRVFTRIWLALFGEWPWSRLPVLPPEMMLLPDWFPLNIYDWASWARQTVVPLTIVGSLRPTRD

LGFSVRELRTGIQRRDLESPLSWAGVFHGLDSVLHRLEKLPLKPLRKVALARAEQWILDRQESDG

GWGGIQPPWVYSILALHLRGYPLDHPVLRKALDGLDGFTIRHRTENGWIRKLEACQSPVWDTALA

MTALLDSGTPPNDPALVRAADWILRQEIRVSGDWRVRRPALEPSGWAFEFANDHYPDTDDTAEV

VLGLQRVRHPEPHRVNAAVERATAWLVGMQSSDGGWGAFDADNTRTLCEKLPFCDFGAVIDPPS

ADVTAHIVEMLAARGMADSESARRGVRWLLEHQEVDGSWFGRWGANHVYGTGAVVPALVACGI

SPQHEAVRAAVQWLVAHQNADGGWGEDLRSYVDRTWVGRGTSTPSQTAWALLALLAAGERGE

VVRRGVEWLMAAQRPDGGWDEPQYTGTGFPGDFYISYHMYRIVFPLTALGRYLGRGGDVGTG

>seq_ID 229
MTATTDGSTGASLRPLAASASDTDITIPAAAAGVPEAAARATRRATDFLLAKQDAEGWWKGDLET

NVTMDAEDLLLRQFLGIQDEETTRAAALFIRGEQREDGTWATFYGGPGELSTTIEAYVALRLAGDS

PEAPHMARAAEWIRSRGGIASARVFTRIWLALFGWWKWDDLPELPPELIYFPTWVPLNIYDFGCW

ARQTIVPLTIVSAKRPVRPAPFPLDELHTDPARPNPPRPLAPVASWDGAFQRIDKALHAYRKVAPR

RLRRAAMNSAARWIIERQENDGCWGGIQPPAVYSIALYLLGYDLEHPVMRAGLESLDRFAVWRE

DGARMIEACQSPVWDTCLATIALADAGVPEDHPQLVKASDWMLGEQIVRPGDWSVKRPGLPPGG

WAFEFHNDNYPDIDDTAEVVLALRRVRHHDPERVEKAIGRGVRWNLGMQSKNGAWGAFDVDNT

SAFPNRLPFCDFGEVIDPPSADVTAHVVEMLAVEGLAHDPRTRRGIQWLLDAQEADGSWFGRWG

VNYVYGTGSVIPALTAAGLPTSHPAIRRAVRWLESVQNEDGGWGEDLRSYRYVREWSGRGASTA

SQTGWALMALLAAGERDSKAVERGVAWLAATQREDGSWDEPYFTGTGFPWDFSINYNLYRQVF

PLTALGRYVHGEPFAKKSRAADAPAEAAPAEVKGS

>seq_ID 113
MTDVIDKAVAATGPADPSQGAAATLQAAADHLLGLQDDAGWWKGELETNVTMDAEDLLLRQFLGI

RTEEVTREAGDWIRSQQRADGTWANFFDGPADLSTTIEAYTALRMAGDAKDAEHMRAARTYILDS

GGIEASRVFTRIWLALFGEWQWSDLPVMPPELIYLPKWFPLNVYDWACWARQTVVPLTIVNALRP

VRPLGFDLKELRTGRRAPAQRGLFSTLDRALHVYERKPLRSVRDAALRRSADWIIARQEADGSWG

GIQPPWVYSLMALNLLGYGVDHPVMRKGIEGLDRFTIRDERGRRLEACQSPVWDTVLAMTALRDA

-continued

ELPENHPALVKAADWVLGEEITNPGDWSVRRPRVAPGGWAFEFDNDGYPDVDDTAEVVLALNRV

AHPDAPAAIRRGVDWLEGMACKDGGYGAFDADNTRTLALKLPFCDFGAVIDPPTADVTAHTLEAY

AALGLANSRASQRALEWLVKAQERDGSWFGRWGANHVYGTGAVVPAMVAVGVDPEDEMIRRAV

RWLEEHQNDDGGWGEDLRSYRDKSWIGRGVSTASQTAWALLALLAAGEERGTAVEQGVRFLIRT

QRADGTWDEDHYTGTGFPGDFYLNYHLYRLVFPISALGRYVRAVGAAGDGGDAGHAGHAGTVS

>seq_ID 236
MTATTDGGGAITGGADPRHDSTAAPAAAAAGPSGGGTGLPEGVREAVDRATAELLARQDPAGW

WKGDLQTNVTMDAEDLLLRQFLGIRDEAVTRAAALFIRGEQQGDGTWATFHGGPPELSATIEAYV

ALRLAGDPPDAPHMTRASAWIRAHGGIAAARVFTRIWLALFGWWSWDRLPELPPELVFLPPWVPL

NIYDFGCWARQTIVPLTVVSALRPVRSAPFALDELHTDARDPVPAKPLPPLASWDGAFQRMDKAL

HLYRRVAPRRLRKAAMAAAGRWIVERQENDGCWGGIQPPAVYSVIALHLLGYDLGHPVMRAGLE

SLDRFAVWREDGARMVEACQSPVWDTCLAAIALADAGLPPDHPALVRAADWMLGEEIRRPGDW

AVRRPGLAPGGWAFEFHNDNYPDIDDTAEVVLALRRIRHPQPGGVEAAIARGVSWTLGMQSKNG

AWGAFDADNTSPFPNRLPFCDFGEVIDPPSADVTAHVVEMLAAEGRAADPRARRGIAWLLAEQEP

DGPWFGRWGTNYVYGTGSVVPALTAAGIAPSHPAVRRAVRWLESVQNEDGGWGEDQRSYRDR

SWAGKGASTASQTAWALMALLSAGERDGDAVARGLAYLVETQRPDGTWDEPYFTGTGFPWDFS

INYHLYRQVFPLTALGRYLHGEPFGPERRNVPPAGES

>seq_ID 134
MSLTSDPSPATPATQPTSARPGSLSDRRSRSGGSAVAGPVLVTTRPVAPVAKSGAVTPTATSGAV

TSTATSGPALLPDLATDLADPTGPLAGAASATVRAAGGAGTRTQQTGQLGSTELAGPQADQVAD

RAAAVLGRARDHLLGLQSEAGWWKGELETNVTMDAEDLMLRQFLGILPPELAAETGRWIRSKQQ

DDGGWPTFHGGPSDLSTTFEAYVGLRLAGDLPDAPHMLAAASFVRAHGGLAATRVFTRIWMALF

GEWPWDEVPVLPPELVLLPSWVPLNVYDFGCWARQTVVALTIVGHFRPVRSLGFSIDELRVAAVR

PDRAPLVSWTGVFQRLDAGLRRYQRHPVKTLRELALRRATEWVLARQEADGGWGGIQPPWVYSI

MALHLMGYSMDHPVLVAALDGLETFTVREQVREGDEVVTVRRLEACQSPVWDTALAVVALADAG

LDARHPAMRKAGEWLVREEVTVPGDWRVRRPNLEPGGWAFEFANDIYPDVDDTAEVVLAVRRLL

GSGWDDVDPTFAKQARASVERAVNWSVGMRSANGAWGAFDADNVRELATKIPFCDFGEVIDPP

SADVTAHMVEMLADLGRADHPVTQRAVRWLLDDQEPGGSWFGRWGVNHVYGTGAVVPALISAG

VAADHPAIRSAVRWLVAHQHPDGGWGEDLRSYQDDAWVGRGEPTASQTAWALLALLAADPMNE

AVGRGVRWLCDTQLPNGTWDEPYYTGTGFPWDFSINYHLYRLVFPLTALGRYVTLTGRSAA

>seq_ID 225
MTATTDGSTGAALPPRVTAASDTDTDIPVAAGVPDIAARAMRRATDFLLSRQSDQGWWKGDLET

NVTMDAEDLLLRQFLGIRDEGTTRAAALFIRGEQREDGTWATFHGGPGDLSATIEAYVALRLAGDP

PDAPHLARASAWIREQGGIAASRVFTRIWLALFGWWKWEDLPELPPELIWFPAWVPLNIYDFGCW

ARQTIVPLTIVSAERPVRPAPFPLDELHTDPARPNPPRALAPVTGWDGAFQRLDKALHVLRGAVPR

RLRRAAMNTAARWIIERQENDGCWGGIQPPAVYSIIALHLLGYDLNHPVMRAGLESLDRFAVWRE

DGARMIEACQSPVWDTCLATIALADAGLPADHPQLVKAADWMLGEQIVRPGDWSVRRPHLPPGG

WAFEFHNDNYPDIDDTAEVVLALRRVAHHDPERVDNAIGRGVRWNLGMQSRNGAWGAFDVDNT

SPFPNRLPFCDFGEVIDPPSADVTAHVVEMLAAEGLAHDPRTRRGVQWLLAEQEPNGSWFGRW

GVNYLYGTGSVVPALTAAGISGSHPAIRRAVAWLESVQNDDGGWGEDLRSYRDARGWSGRGAS

TASQTAWALMALLAAGERESRAVERGVEWLAATQHEDGSWDEPYFTGTGFPWDFSINYHLYRQ

VFPLTALGRYVNGEPLAGKPRAAGAATAREDTGQEQSLAEAKGS

-continued

>seq_ID 223
MTATTDGSTGAANITGAPADDPTDTRTAANDVTDIARRAAERSVEHLLGRQDEQGWWKGDLATN
VTMDAEDLLLRQFLGIQDPATTRAAALFIRGEQLGDGTWNTFYGGPGDLSATIEAYVALRLAGDRP
DEPHMARASGWIRDQGGIAAARVFTRIWLALFGWWKWDDLPELPPELMFFPKWVPLNIYDFGCW
ARQTIVPLTIVSAKRPVRPAPFALDELHTDPDHPNPPRKLAPPTSWDGLFQRLDKGLHLYHKVAPR
PLRRIAMNVAARWIIERQENDGCWGGIQPPAVYSVIALHLLGYDLDHPVMKAGLASLDRFAVHRED
GARMIEACQSPVWDTCLATIALADAGLRPDHPALVKAADWMLAEEITRPGDWSVRKPELAPGGW
AFEFHNDNYPDIDDTAEVVLALRRVRHPDPARLEAAIARGVRWNLGMQSRNGAWGAFDADNTSP
FPNRLPFCDFGEVIDPPSADVTGHVVEMLAVEGLANHPRTREGIEWLLAEQEACGAWFGRWGVN
YVYGTGSVVPALITAGLPAGHPAIRRAVDWLESVQNDDGGWGEDLRSYQEEKWIGHGESTASQT
AWALLALLAAGRRDTASVTRGVTWLTEAQQADGSWDEPYFTGTGFPWDFSINYHLYRQVFPLTA
LGRYVHGDPFADRTDAAEGV >seq_ID 226
MTATTDGSTGAALPPRVTAASENDTDIPEAAGVPDIAAHAMRRATDFLLSRQDDQGWWKGDLET
NVTMDAEDLLLRQFLGIRDEDTTRAAALFIRGEQREDGTWATFHGGPGELSTTIEAYVALRLAGDP
PEAPHMARASAWIRERGGIAAARVFTRIWLALFGWWKWEDLPELPPELIWFPSWVPLNIYDFGCW
ARQTIVPLTIVSAKRPVRPAPFPLDELHTDPRRPRPPRPHAPPNTWDGAFQRLDRALHALRRAVP
RRVRQAAMNAAARWIIERQENDGCWGGIQPPAVYSVIALHLLGYDLRHPVMRAGLESLDRFAVW
REDGARMIEACQSPVWDTCLAAIALADAGLPADHPSLVKAADWMLGEQIVRPGDWSVRRPHLPP
GGWAFEFHNDNYPDIDDTAEVVLALRRVRHHDPERMDSAIGRGVRWSLGMQSKNGAWGAFDVD
NTSPFPNRLPFCDFGEVIDPPSADVTAHVVEMLAVEGLAHDPRTRRGIQWLLAEQEPDGSWFGR
WGVNYLYGTGSVVPALAAAGIPGSHPAIRRAVAWLEKVQNDDGGWGEDLRSYRHVREWSGRGA
STASQTAWALMALLAAGERDSGAVERGVAWLAATQREDGSWDEPYFTGTGFPWDFSINYHLYR
QVFPLTALGRYVHGEPFSKKQTAARNGSAQPLAGVKGSR >seq_ID 219
MDPALSRAVDWLLEHQDPAGWWCGEFETNVTITAEHILLLRFLGLDPSPLRDAVTRYLLGQQRED
GSWALYYEGPADLSTSIEAYAALKVLGLDPTSEPMRRALQVIHDLGGVAQARVFTRIWLAMFGQY
PWDGVPSMPPELIWLPPSAPFNLYDFACWARATITPLLIILARRPVRPLGCDLGELVLPGSEHLLTR
VPGSGPFWWGDKVLKRYDHLVRHPGRDACQRIVEWIIARQEADGSWGGIQSAWVMSLIALHLE
GLPLDHPVMRAGLAGFDRVALEDERGWRLQASTSPVWDTAWAVLALRRRAGLPREHPRLALAVD
WLLQEQIPGGGDWQVRTGTIPGGGWAFEFDNDHYPDIDDTAVVVLALLEAGHEDRVRNAVERAA
RWILAMRSTDGGWGAFDRDNAREVIHRLPIADFGTLIDPPSEDVTAHVLEMLARLSFPSTDPVVAR
GLEFLQQTQRPDGAWFGRWGVNYIYGTWCAVSALTAFADTDATARAMVPRAVAWLLDRQNADG
GWGETCGSYEDPNLAGVGRSTPSQTAWAVLALQAAGLGQHPACRRGLDFLRERQVGGTWEER
EHTGTGFPGDFFINYHLYRHVFPTMALAGAATGMDSPR >seq_ID 220
FLGIRDEATTRSAALFIRGEQREDGTWATFHGGPPDLSTTVEAYVALRLAGDSPDAPHMTRAAHW
VRSQGGIAEARVFTRIWLALFGWWPWDRLPELPPELIFLPPWAPLNIYDFGCWARQTIVPLTVVSA
KRPVRPAPFPLDELHTDPADPAPRARFAPLASWNGAFQRLDRALHAYRKVAPRALRRAAMATAG
RWIVERQENDGCWGGIQPPAVYSMIALHLLGYDLGHPVMRAGLESLDRFTLTREDGSRMVEACQ
SPVWDTCLATIALADAGVPADHPQLVRAADWMLDEQIERPGDWSVRRPHLAPGGWAFEFHNDN
YPDIDDTAEVVLALRRVRHPDTARMERAISLGVRWNLGMQSKNGAWGAFDVDNTSSLPNRLPFC -continued

DFGEVVDPPSADVTAHVVEMLAAEGLAADPRTRRAVDWLLAEQEPSGAWFGRWGVNYLYGTGS

AVPALVDAGLPTTHPAIRRAVAWLESVQNDDGGWGEDLRSYREQGRMARGASTASQTGWALMA

LLAAGERESRAARRGVTFLAETQHEDGSWEEPYYTGTGFPWDFSINYHLYRQVFPLTALGRYTR

GAAPEGA

>seq_ID 125
MQTQNRVTSTQKVELSNLTQAIIASQNYILSRQYPEGYWWGELESNITLTAETVLLHKIWKTDKTRP

FHKVETYLRRQQNEQGGWELFYGDGGELSTSVEAYMALRLLGVTPEDPALIRAKDFILSKGGISKT

RIFTKFHLALIGCYDWKGIPSIPPWIMLFPDNFPFTIYEMSSWARESTVPLLIVFDKKPIFEIEPAFNLD

ELYAEGVENVKYALPRNHNWSDIFLGLDKLFKWTEKNNLVPFHKKSLQAAEKWMLNHQQESGDW

GGIMPPMVNSLIAFKVLNYDVADPSVQRGFEAIDRFSIEEEDTYRVQACVSPVWDTAWVIRALVDS

GLKPDHPSLVKAGEWLLDKQILEYGDWAIKNKQGKPGGWAFEFINRFYPDLDDSAVVVMALNGIK

LPDENRKKAAINRCLEWMATMQCKPGGWAAFDVDNDQAWINEIPYGDLKAMIDPNTADVTARVL

EMVGSCGLKMDENRVQKALFYLEKEQESDGSWFGRWGVNYIYGTSGVLSALAVIAPNTHKPQME

KAVNWLISCQNEDGGWGETCWSYNDSSLKGTGISTASQTAWAIIGLLDAGEALETLATDAIKRGID

YLLATQTPDGTWEEAEFTGTGFPCHFYIRYHLYRHYFPLIALGRYWKIGLKTPSVIPLN

>seq_ID 228
MLARRATDRAVRHLLSRQDEQGWWKGDLETNVTMDAEDLMLRHFLGIQNPDVLDAAGRYIRSQQ

AADGTWATFHGGPPELSATVEAYVALRLAGDPPDAPHMAAASAWVRNNGGVASSRVFTRIWLAL

FGWWRWEDLPELPPEIIYFPPWLPLNLYDFGCWARQTIVPLTVVSAKRPVRPAPFSLDELHADPR

RPNPPRPAAPLASWDGAFQRLDRALHLYRKVALRPLRRAALRSCARWIVERQENDGCWGGIQPP

AVYSVIALHLLGYDLDHPVMRAGLESLDRFAVWREDGSRMIEACQSPVWDTCLAVIALADAGLAP

DHPALVKSADWMLAEEIDRPGDWSVKRPRLAPGGWAFEFDNDNYPDIDDTAEVILALRRVDHPRP

ERIAAAVRRGVRWTLGMQSRNGAWGAFDVDNTSPLPNRLPFCDFGEVIDPPSADVTAHVVEMLA

HEGGARDPRTRRAVGWLLAEQEPSGAWFGRWGTNYVYGTGSVVPALVAAGLPATHPAIRRAVR

WLESVQNEDGGWGEDQRSYPDPEWIGHGASTASQTAWALLALLAAGERESKAVERGVGWLAAT

QDQDGSWDEPYFTGTGFPWDFSINYHLYRLVFPLTALGRYVSGEATGARPRRT

>seq_ID 241
MTATTDGSTGALPPRADAASEHDIETPEAAGVREAAVRAARRATDFLLSRQDAQGWWKGDLETN

VTMDAEDLMLRQFLGVLDEKTAQAAALFIRGEQREDGTWASFYGGPGELSTTIEAYVALRLAGDA

PDSPHLAKASAWIREQGGIAAARVFTRIWLALFGWWKWEDLPELPPELIWFPKWVPLNIYDFGCW

ARQTIVPLTIVSAKRPVRPAPFPLDELHTDPARPNPPRPLAPAFSWDGAFQRMDKGLHALRKVAP

RGLRRAAMNAAARWIIERQENDGCWGGIQPPAVYSIIALHLLGYDLQHPVMREGLASLDRFAVWR

EDGARMVEACQSPVWDTCLAAIALVDAGLPADHPQLVKAADWMLGEEIVRPGDWSVRRPGLPP

GGWAFEFHNDNYPDIDDTAEVILALRRITHHDPVRVDKAVGRGVRWTLGMQSKNGAWAAFDVDN

TSPFPNRLPFCDFGEVIDPPSADVTAHVIEMLAVEGLAHDPRTRRGIEWLLAEQEPDGSWFGRWG

VNYVYGTGSVVPALVAAGLPGAHPAIRRAVSWLESVQNDDGGWGEDLRSYKYVKEWSGRGAST

ASQTAWALMALLAAGERDSKAVERGVEWLAATQREDGSWDEPYFTGTGFPWDFSINYHLYRQV

FPLTALGRYVHGEPFADRLKGS

>seq_ID 238
MHEGEAMTATTDGSTGAATPPATTASAPLHLSPEARETHEATARATRRAVDFLLARQSDEGWWK

GDLATNVTMDAEDLLLRQFLGIRDEATTRAAALFIRGEQQEDGTWNTFYGGPGDLSATIEGYVALR

LAGDSPEAPHMRKASAFVRAQGGVARARVFTRIWLALFGWWKWEDLPEMPPELMFFPKWAPLNI

YDFGCWARQTIVPLTVVCAQRPVRPAPFALEELHTDPADPDPAQPAPPVVSWDNVFHKLDKLLHG

-continued

YRRIAPRRVREAAMRAAATWIVERQENDGCWGGIQPPAVYSIMALNLLGYDLDHPVLRAGLASLD
RFAVWREDGARMIEACQSPVWDTCLATVALADAGVPADHPQMIKAADWMLAEQIVRPGDWVVR
RPDLPPGGWAFEFHNDNYPDIDDTAEVVLALRRVAHPDATRVDKAVRRAVDWNVGMQSKNGAW
GAFDADNTSPFPNRLPFSDFGEVIDPPSADVTAHVVEMLAEEGLAHHPRTRRGIEWLLKNQEGNG
SWFGRWGVNYVYGTGAVVPALVAAGLPASHPAIRRSVSWLGQVQNEDGGWGEDLRSYQDSAW
HGRGHSTASQTAWALLALLAAGERETEQVRRGIAYLVETQTEDGTWDEPWFTGTGFPWDFTINY
HLYRQVFPVTALGRYLNGTGPGEN

>seq_ID 237
MRRRRSPRGPGAGPEADYGPARASAPDRLRGDAARGDAARRVQDATARAIRNLLGRQDPAGW
WKGDLETNVTMDAEDLLLRQFLGIRDEAVTQAAALFIRREQREDGTWATFHGGPPELSATIEAYVA
LRLAGDAPDAPHMATASAWIRAHGGLAAARVFTRIWLALFGWWDWENLPELPPELVLLPPWVPL
NIYDFGCWARQTIVPLTVVSAMRPVRPAPFALDELHTDARVPVPPRRMAPPTTWNGAFQWMDRA
LHVYRRFAPRRLREAAMASAGRWIIERQENDGCWGGIQPPAVYSVIALHLLGYDLGHPVMRAGLE
SLDRFAVWREDGSRMIEACQSPVWDTCLAAIALADAGVRPDHPALVKAADWMLGEEIVRTGDWA
VRRPGLAPGGWAFEFHNDTYPDIDDTAEVVLALRRIRHPDPARVEAAIARGVSWNLGMQSRGGA
WGAFDADNTSPFPNRLPFCDFGEVIDPPSADVTAHVVEMLAAEGRAADPRTRRGIAWLLAEQEPE
GPWFGRWGTNYVYGTGSVVPALTAAGLSPGHPAIRRAVLWLESVQNPDGGWGEDQRSYQDRA
WAGKGESTPSQTAWALMALLSAGERDAKTVERGIAYLVETQLADGGWDEPHFTGTGFPWDFSIN
YHLYRHVFPLTALGRYLYGEPFGHDGRHIGAHLGDRTGVPAEGV >seq_ID 239
MDFLLDRQSDEGWWKGDLATNVTMDAEDLLLRQFLGIRDEATTQAAALFIRGEQQEDGTWNTFY
GGPGDLSATIEGYVALRLAGDSPEAPHMRKASAFVRARGGVARARVFTRIWLALFGWWKWEDLP
EMPPELMFFPKWAPLNIYDFGCWARQTIVPLTVVCAQRPVRPAPFALEELHTDPADPNPAQPAPP
VASWDNVFHKLDKMLHGYRKVAPRRVREAAMRAAATWIVERQENDGCWGGIQPPAVYSIIALHLL
GYDLDHPVLRAGLESLDRFAVWREDGARMIEACQSPVWDTCLATVALADAGVPADHPQMIRAAD
WMLAEQIVRPGDWVVRRPDLPPGGWAFEFHNDNYPDIDDTAEVVLALRRVAHPDATRVDKAVRR
AVDWNAGMQSKNGAWGAFDADNTSPFPNRLPFSDFGEVIDPPSADVTAHVVEMLAEEGLAHHP
RTRRGIEWLLENQEANGSWFGRWGVNYVYGTGAVVPALVAAGIPAAHPAIRRSVSWLGQVQNED
GGWGEDLRSYQDTAWHGRGHSTASQTAWALLALLAAGERDSEQVRRGIAYLVETQTEDGTWDE
PWFTGTGFPWDFTINYHLYRQVFPVTALGR >seq_ID 235
MTQTVPRTAASAPAARTAADTVAAAVQFLRREQDRAGWWKGELATNVTMDAEDLLLRHFLGILTP
QIAEESARWIRSQQRADGTWANFPDGPADLSTTVEAWVALRLAGDPADAPWLATAAEWIREHGG
IEATRVFTRIWLAMVGQWSWDDLPSLPPELIFLPSWFPLNVYDFACWARQTIVPLTIVGILRPARKL
PFDVAELRTGKRPPKPRAPWTWDGVFQNLDTALHAYAKLPLNPVRKLALKQAAEWILARQEADG
SWGGIQPPWVYSILALHLLGYSLDHPALKAGIAGLDGFTIREKTDQGWVRRLEACQSPVWDTALA
MTALLDAGVSPGDESLVRAAEWMLGEEIRVPGDWAVRRPSLKPGGFAFEFANDGYPDTDDTAEV
VLALRRMGKPDHLRIREAVDRSVAWLEGMQSSDGGWGAFDADNTQVLTTRLPFCDFGAVIDPPS
ADVTAHVVEMLAAEGKADTRECRRGIRWLWDNQEADGSWFGRWGANYVYGTGAVVPALVAAG
VPGTDPRIRRAVRWLAEHQNDDGGWGEDLRSYDDRSWAGRGDSTPSQTAWALLALLAAGERES
TVVARGVEWLCERQRPDGGWDEDKHTGTGFPGDFYLSYHLYRVVFPLSALGRYVRGGS

```
>seq_ID 159
MSGQSNFTGGKKMTPAEGSSSPAPALLEKAAPSIELDERSDPLSRTLARAVSWLVAAQDGAGHW
VAPLEADATIPSEYVFLHEVLGRPLDPVRRDKIVRAILSVQGKEGAWPLFHDGDPDISATVKAYQAL
KLCGFDPSHPALVRAREWVLSQGGAGKVNVFTRIALAIFGQYSWTKIPALPAEMVLLPSWFPFSIY
SVSYWSRTVIVPLLFIYHHKPLVRLSPERGISELFDPARPDGESFAPSPDFFSLRNLFLLLDKVLQV
WNRHPPGFLRKKALSFAMEWMVPRLKGEGGLGAIYPAMANSAVALSLEGYELDHPLMQRVLASI
DDLLIEGEKEVLVQPCVSPVWDTALAMGALIEAGISPDSPTVDRAMEWFCAREVRTRGDWAIRAP
DCEPGGWAFQFENDYYPDVDDTAMVLMGMAKILPARPDLAARMEGVFRRATLWVMAMQGTDG
GWGAFDRDNDLLFLNHIPFADHGALLDPSTADLTGRVLELLGALGYGPDFPPAARAIRYLRREQEE
DGSWFGRWGVNYIYGTWSVVAGLKSIGVPMSEPWVMRSMEFLLARQNPDGGWGEDCLSYASR
DFAGRGASTPSQTAWALIALLHGGHAGHMAVRQGVDYLIQQMTPEGTWNEELFTGTGFPRVFYL
RYHMYRHYFPLWALALYRNMTERGRALGHERVDFWKTAPYAPIARSV
>seq_ID 232
MTATTDGSTGALPPRAPSASDTDHGTPVAAGVQEAALHAVGRATDFLLSRQDAQGWWKGDLET
NVTMDAEDLLLRQFLGIRDDATTRAAALFIRGEQRPDGTWATFYGGPPDLSATVEAYVALRLAGD
DPAAPHMAKASAWIRARGGIAAARVFTRIWLALFGWWKWDDLPEMPPEIVYFPTWMPLNIYDFGC
WARQTIVPLTVVSAKRPVRPAPFPLDELHTDPGRPNPPRPLDRLGSWEGAFQRLDRALHGYHKV
ALKRLRRAAMNRAARWIVERQENDGCWGGIQPPAVYSVIALHLLGYDLGHPVMRAGLESLDRFAV
WREDGARMIEACQSPVWDTCLATIALADAGLPPDHPQLVKAADWMLGEEIVRPGDWSVKRPQLP
PGGWAFEFHNDNYPDIDDTAEVVLALRRVRHPDPERVERAVRRGVRWTLGMQSGNGAWAAFDA
DNTSPFPNRLPFCDFGEVIDPPSADVTAHVVEMLAAEGLSHDPRTRRGIEWLLAEQEPGGAWFG
RWGVNYVYGTGSVVPALVTAGLPAAHPAIRRAVAWLETVQNDDGGWGEDLRSYPDPAEWGGK
GASTASQTAWALLALLAAGERDGKATERGVAWLARTQREDGSWDEPYFTGTGFPWDFSINYHLY
RQVFPLTALGRYVHGEPAVLKPGTR
>seq_ID 224
MTATTDGSTGAANLRAAAASDPTESTSAAPDMMAVARHAAERSVEHLLGRQDEQGWWKGDLAT
NVTMDAEDLLLRQFLGIQDPETVKAAARFIRGEQLGDGTWNTFYEGPPDLSATVEAYVALRLAGD
RPDDPHMIRAAGWVREQGGIAESRVFTRIWLALFGWWKWDDLPELPPELMFFPKWVPLNIYDFG
CWARQTIVPLTIVSAKRPVRPAPFALDELHTDPACPNPSRPTAPAASWDGVFQRLDKALHLYHKV
APRRLRRIAMNEAARWIIERQENDGCWGGIQPPAVYSVIALHLLGYDLDHPVMRAGLESLDRFAV
WREDGARMIEACQSPVWDTCLATIALADAGVSPDHPALVRAADWMLGEEIVRPGDWAVRKPGLA
PGGWAFEFHNVNYPDIDDTAEVALALRRVRHPDPARVDAAIERGVRWNLGMQSRNGAWGAFDA
DNTSPFPNRLPFCDFGEVIDPPSADVTGHVVEMLAVEGRAHDPRTRRGVEWLLAEQEASGAWFG
RWGVNYIYGTGSVVPALIAAGLPAAHPSVRRAVDWLRSVQNDDGGWGEDLRSYREEKWIGHGS
STASQTGWALLALLAAGERETRSVERGVAWLAATQQADGSWDEPHFTGTGFPWDFSINYHLYRQ
VFPLTALGRYVYGDPFATATAIGAGTGKGA
>seq_ID 243
MSISALQTDRLSQTLTQSVVAAQQHLLSIQNPEGYWWANLESNASITAEVVLLHKIWGTLDSQPLA
KLENYLRAQQKTHGGWELYWNDGGELSTSVEAYMGLRLLGVPASDPALVKAKQFILHRGGVSKT
RIFTKPHLALIGCYRWQGLPSLPAWVMQLESPFPFSIYELSSWARGSTVPLLIVFDKKPVYPLQPSP
TLDELFTESAENVRWELEEKGDWSDAFLWLDKAFKLAESVDLVPFREESIRKAEKWVLERQEPSG
DWGGIIPAMLNSMLALRALGYSVSDPVVRRGFQAIDNFMVESETECWAQPCISPVWDTGLAVRSL
```

-continued

TDSGLSPNHPALVKAGEWLLDKQILSYGDWSVKNPQGQPGGWAFEFENSFYPDVDDTAVVAMAL

QDITLPNEPLKRRAIARAVRWIATMQCKTGGWAAFDINNDQDWLNDIPYGDLRAMIDPSTADITGR

VLEMHGRFAADLDLANSYAADLSPYRLSRGLNYLIKEQELDGSWFGRWGVNYIYGTGQALSALALI

APERCRIQIERGIAWFVSVQNADGGWGETCESYKDKSLKGKGISTASQTAWALLGLLDVSFCLDP

AAKIAVDRGIQYLVSTQSEGTWQEESFTGTGFPQHFYLRYRLYCHYFPLMALGRYQRVINSSAGI

>seq_ID 197
MTSGTFGAKRVDLLAAFEHSAPAEKTRETCVGLQTAIARTRQYLLDQQHSEGFFVAELEGDTILES

EYILLLAFLNEGQSPDAQAAARYLLTKQNTDGSWSNFPGGPIDVSCAVKAYLALRITGHAADEPALI

RAREAILQAGGVERVNSFTRFYLAMLGLIPYSLCPAVPPEVVLLPDWFPINLSQMSAWSRTIVVPLS

LLWAFQPAVELNDADGHQITIEELYASPEKQLPRFIRGVNHESNSNGWMNWSRFFFRVDQCLKSI

ESYGIKPLRSRAVRKCVQWILDRQEMSDGLGAIFPPIVWTLIGLKCAGFDDQHPMVQKQRDELNR

LMLREQDALRLQPCLSPVWDTAISIIALRESGVEPDHPALSKARNWLLSKEVRHAGDWSKAHPET

PVSGWYFEFNNEFYPDVDDTAMVLIALASTLPEEATPLAISHGVLPVQTGWSAESTSRVQALKQLE

NHRPVLEAMGRGVQWLKALQSKDGGWGAFDSDINKELLTKVPFADHNAMLDETNADISARVLEA

YAAVGISFNDPSVQRALEFIWNDQEDDHAWYGRWGVNYIYGTWQVLVGLTAIGISAHDPRLVRAA

GWLKSKQQACGGWGETPATYDNPTLRGQGTPTASQTAWAVLGLIAAGEQNSIECQRGVEFLLKT

QKHNGTWDEEEFTGTGFPRVFYLRYHYYPLYFPLMALGRFARAGGRVNFAG

>seq_ID 158
MTTNAAATSARSGEDAIRQVSGQQLETAIASARNSLLALQRPDGHFVFELEADATIPAEYVLMRHY

LAEPVDAVLEEKIARYLRRIQSDDGGWPLFRDGASNISASVKAYYALKMIGDAPNAPHMQKARAWI

LAQGGASHSNVFTRNLLALFGAIPWSGVPVMPVEIMLLPKWFPFHIDKISYWARTVLIPLTVLNALK

PVARNPKGVGIAELFVTPPDQVRNWPKGPHQKFPWSQVFGGIDRVLRLFEPAFPKSLRKKSIDKA

VAFATERLNGEDGLGGIFPAMVNALLVYDALGYPHDHPDYVTARGSIEKLLVIKDDEAYCQPCLSP

VWDTALAVHALMESGVAQADQNVDRALAWLKPLQVLDTVGDWAASRPGVRPGGWAFQYANAY

YPDVDDTAVVVMAMDRAAGGDAAKRDHYRESMARGREWVAGVQSKNGGWGAFDADNTYEYL

NQIPFSDHGALLDPPTADVSARCVSMLAQLGERRETSPVLDKAMRYLESTQEKDGSWYGRWGM

NYIYGTWSVLCALNAAGVAPSAPSMRKAADWLLSIQNSDGGWGEDGESYSLDYKGYEPAPSTAS

QTAWALMGLMAAGEVDHPAVQRGVAYLAAKQGSDGFWGEERFTATGFPRVFYLRYHGYSKFFP

LWALARYRNLNAANSKSVLVGM

>seq_ID 77
MAADGSALSESRLSSEALDRAVLSAHTALSQAQQDDGHWVYELEADATIPAEYILLEHFMDRIDDA

LEQKIAIYLRRIQSEEHGGWPLYHNGKFDLSATVKAYFALKAVGDDINAPHMQRAREAILDHGGAE

RSNVFTRSQLALFGEVPWRATPVMPVELMLLPAKAFFSVWNMSYWSRTVIAPLLVLAALRPVAAN

PRQVHVRELFVTPPEKVQDWIRGPYRSAWGYVFKGLDSVLRPVVPFIPEKTHKKAIQAALDFIEPR

LNGKDGLGAIYPAMANVVMMYRAMGVPDEDPRAKTAWEAVQALIVEKDDEAYCQPCVSPIWDTG

LSGHAMIEAASGPNGIAPEKTVAELKKASAWLRSKQILNVKGDWAVRNPNLAPGGWAFQYGNDY

YPDVDDTAVVGMLLHREGDPTNAEAIERARTWIVGMQSTDGGWGAFDIDNNKDVLNHIPFADHG

ALLDPPTADVTARCISFLAQLRNPEDEPVIQRGLEYLRKEQEKDGSWFGRWGTNYIYGTWSALCA

LNAAGVSHDDPAVVKAVEWLRSVQRADGGWGEGCESYEGGPHGTYGESLPSQTAWAVLGLMA

AGRRDDPAVTRGIAWLADQQDANGEWHEDPYNAVGFPKVFYLRYHGYKQFFPLMALARYRNLE

SSNTRRVSFGF

>seq_ID 6
MTVSTSSAFHHSSLSDDVEPIIQKATRALLEKQHQDGHWVFELEADATIPAEYILLKHYLGEPEDLEI

EAKIGRYLRRIQGEHGGWSLFYGGDLDLSATVKAYFALKMIGDSPDAPHMLRARNEILARGGAMR

ANVFTRIQLALFGAMSWEHVPQMPVELMLMPEWFPVHINKMAYWARTVLVPLLVLQALKPVARNR

RGILVDELFVPDVLPTLQESGDPIWRRFFSALDKVLHKVEPYWPKNMRAKAIHSCVHFVTERLNGE

DGLGAIYPAIANSVMMYDALGYPENHPERAIARRAVEKLMVLDGTEDQGDKEVYCQPCLSPIWDT

ALVAHAMLEVGGDEAEKSAISALSWLKPQQILDVKGDWAWRRPDLRPGGWAFQYRNDYYPDVD

DTAVVTMAMDRAAKLSDLHDDFEESKARAMEWTIGMQSDNGGWGAFDANNSYTYLNNIPFADH

GALLDPPTVDVSARCVSMMAQAGISITDPKMKAAVDYLLKEQEEDGSWFGRWGVNYIYGTWSAL

CALNVAALPHDHLAIQKAVAWLKNIQNEDGGWGENCDSYALDYSGYEPMDSTASQTAWALLGLM

AVGEANSEAVTKGINWLAQNQDEEGLWKEDYYSGGGFPRVFYLRYHGYSKYFPLWALARYRNLK

KANQPIVHYGM

>seq_ID 89
MNDLTNSSAPGARPDDATPSAAGPTPAEAAGGAVAPSRAVQPADTQTAATGAAGAAAAVGATPA

ELAATAPASSGTPAGASAAPAPSGTPSVDAPAELASAAPAPSGATPAATATAATAPAPARAASIDA

PALAAADLDAAITRATDALLAAQQADGHWIYELEADSTIPAEYVLLVHYLGETPNLELERKIARYLRR

VQLPGGGWPLFTDGAPDVSASVKAYFALKMIGDDANAEHMVRARNAIHAMGGAEMSNVFTRIQL

ALFGVVPWFAVPMMPVEIMLLPQWFPFHLSKVSYWARTVTVPLLVLSAKRPLARNPRGVRVDELF

VAPPVNAGLLPRAGHQSPAWFACFRLLDGLLRLTDGLFPRYTRERAIRQALQFVDERLNGEDGLG

AIYPAMANSVMMYAALGYPEDHPNRATARRAIEKLLVIHDDEAYCQPCLSPVWDTSLAAHALLETG

EPRAEAAAIRGLDWLRPLQILDVRGDWISRRPDVRPGGWAFQYANPHYPDVDDTAVVTLAMDRV

AKLAQTDAYRDAIARAREWVVGMQSSDGGWGAFEPENTHQYLNSIPFSDHGALLDPPTADVSGR

CLSMLAQLGETAANSAPARRALDYLLAEQGADGSWYGRWGMNYIYGTWSALGALNAAGLPFDD

PRVKRAAQWLLSIQNPDGGWGEDGDSYKLDYRGYERAASTASQTAWALLGLMAAGEVEHPAVA

RGIAWLAAQQREHGLWDEARFTATGFPRVFYLRYHGYRKFFPLWALARYRNLRRTGTRRVTVGM

>seq_ID 201
MLPYNQNSYKEALHGGHAAHNPPTLEEAIKRSQEFLLAHQHPEGFWWGDLECNVTSASHTLILYKI

LGIADRYPLHKFEKYLRRMQCSHGGWEMSFGDGGYLSATIEAYICLRLLNVPQSDPALQRALKNIL

ARGGVTKARVFTKVCLALLGGFDWAALPSLPPWLMLFPAWFPWNIYEAASWARGCVVPLIVLLEK

KPVFQVKPEVSFDELYVEGRAHACKALPFSAHDWVSNIFVAADRAFKLMERFGAVPFRQWSIKEA

KKWVLDRQEEMGDFIGYNPPMLYFAVCLKLWGYEVTDPLLQRALLAHKKLTVETEDECWLQSSQ

SPVWDTALVIPALVESGLPPDHPALQKAGQWLLEKQILKHGDWALKTGGGRMQDDIGGGWAFQF

VNSWYPDVDDSAAVVIALNCIKMPDEDVKNGAIARCLKWIAFMQGRNGGWAAFDRDSNQRWMD

ATPFSDIEAMLDVSTADVTARVLEMVGLMRLKHAAQPANNSLGKAHRHISTESIARGVDYLTKEQE

KEGCWWGRWGVNYIYGTRGALMGLSQVAAKTHKKEIARGAAWLVKVQNKKNEKKQGAQDGGW

GEACFSYDDPATKGQNSRSTASQTGWAMQGLLAAGEVLGRKYEMEAVEEGVQFLLDTQRKDGS

WSEAEFTGGGFPKHYYLKYHYFAQHFPLSALARYRARLLQLSRPKNQA

>seq_ID 183
MDGSQRISDMSQQPEGIAVSDEISSAYSVSSLNQDEINVDELENKLTQARSAMLSLQKPDGHWCF

PLEADCTIPAEYILMMHFMDEIDVILENKIARFIREKQDLTHGGWPLYYGGAFDISCTIKSYYALKLVG

DSPDAAHMVRAREAILERGGAAKANVFIRLLLAMYEQIPWSGVPVVPTELMLLPSWFPPFHISKVSY

WSRTVMIPLSILCTIKARAINPRNVDIRELFIVPPEQEKNYFPQADTWLKRAFMLVERVLSRVEPKLP

-continued

QAIRQYSIRKAENWTLERLNGECGIGAIFPAMVNAHESLALLGYAYDHPSRVQCRNALRGLLVDEG

ERAWCQPCTSPVWDTVLTCLALQEDPAADQGPVLKALDWLVDQQVLDEPGDWRDKRPDLLGGG

WAFQYANPHYPDLDDTAAVAWALDQSDAQRYQKPLDRAANWLAGMQSRNGGFAAFDIDNTYHY

LNEIPFADHGALIDPPTSDVTARCVGLLGKYGKHQREVWRGISFLLREQEKNGSWFGRWGTNYIY

GTWSVLEAFQLANFDMQHTSVRRAVKWLESVQRVDGGWGETNDSYLDIQLAGQFPQTSTTFQT

AWAVLGLMAAGEVNSKSVRRGINYLLHNQADDHLWEDPWFTAPGFPRVFYLRYHGYSKFFPIWA

LVRYRALTKERVS

>seq_ID 102
MNDLSQTQPLDAVLPEAADAASNLAEAAVVANAPAVADALATATPSPMQTAGASPLDVSITRATD

AILAAQQPDGHWIYELEADATIPAEYVLLVHYLGETPNLELEQKIARYLRRIQLPNGGWPLFTDGAL

DISASVKAYFALKMIGDPVDAEHMVRARDAILAHGGAEHANVFTRILLALFGVVSWRAVPMMPVEI

MLLPMWFPFHLSKVSYWARTVIVPLLVLNAKRPLARNPRKVRIDELFRGAPVNTGMNERAPHQHA

GWFGFFRCVDTVLRAVDGLLPKASRERAIRAAVAFVDERLNGEDGLGAIFPAMANSVMMYDVLGY

PADHPNRAIARKSLDKLLVIKEDEAYCQPCLSPVWDTSLVAHALLETREARAEQAAERGLAWLRPL

QILDVRGDWISRRPNVRPGGWAFQYNNAHYPDVDDTAVVAMAMHRSAALTKSDVDREAIARARE

WVVGMQSSEGGWGAFEPENTQYYLNNIPFSDHAALLDPPTADVSGRCLSMFAQIGELPQNSEPA

QRAFDYMLQEQESDGSWYGRWGLNYIYGTWTALCSLNAAGMSHDDPRMRRAVQWLVSIQNED

GGWGEGGESYKLDYRGYERAPSTASQTAWALLGLMAAGEVDHDAVARGIDYLQREQREHGLW

DETRFTATGFPRVFYLRYHGYRKFFPLWALARFRHLKRNGLTRVTVGM

>seq_ID 90
MIRPMKNSDLPLPSLLDAAILRGRDALAQRQSADGSWCFELESDATITAEYILMMHFMGKIDEARQ

ARMARYLRGIQRLATHGAWDLYVDGAPDVSCSVKAYFALKAAGDSEDAPHMARARETILKLGGAA

KSNVFTRILLATFGQVPWRATPFMPVEFVLFPKWVPISMYKVAYWARTTMVPLLVLCSLKARAKNP

RNVSIRELFVTAPEAERHYFARGGFVRNLFLGIDRALRPLDALIPKALRRRAIRHAEAWCAERMNG

EDGMGGIFPPIVYSYQMMDVLGYPEDHPLRRDCENALDKLLVERPDGSVYCQPCLSPVWDTAWS

TMALEQARAVPDPRDAPPVSDAQLQRCIAASYEWLAGKQVTQVRGDWVENAPAATPAGGWAFQ

YENPYYPDIDDSAVVAAMLHRRGRLLARSTGTDPYAQVVARGLDWMRGLQSRNGGFAFDADC

DRLYLNLIPFADHGALLDPPTEDVSGRVLLCLGVTGRDEDKPALARAIEYVKRMQRADGCWWGR

WGTNYIYGTWSVLAGLALAGENPSQPYIARAIAWLRACQNADGGWGETNDSYLDPALAGTNGGE

SASNVTAWALLAQMAFGDWQSESVQRGIRYLLSVQQADGFWWHRSHNAPGFPRIYYLKYHGYT

AYFPLWALARYRRLSQAGAARDVTDGAALAAS

>seq_ID 167
MREAAVSKVETLQRPKTRDVSLDDVERGVQSATRALTEMTQADGHICFELEADATIPSEYILFHQF

RGTEPRPGLEAKIGNYLRRTQSKVHGGWALVHDGPFDMSASVKAYFALKMIGDDIEAPHMRAVR

KAILQRGGAANANVFTRILLALYGEVPWVAVPVMPVEVMHLPKWFPFHLDKVSYWARCTMVPLFV

IQAKKPRAKNPRGVGVAELFVTPPDSVRTWPGSPHATWPWTPIFGGIDRVLQKTQDHFPKVPRQ

RAIDKAVAWVSERLNGEDGLGAIFPAMVNSVLMYEVLGYPPEHPQVKIALEAIEKLVAEKEDEAYV

QPCLSPVWDTALNSHAMLEAGGHQAEANARAGLDWLKPLQILDIKGDWAETKPNVRPGGWAFQ

YANPHYPDLDDTAVVVMAMDRAQRQHGLVSGMPDYSESIARAREWVEGLQSADGGWAAFDAD

NNHHYLNHIPFSDHGALLDPPTADVTARVVSMLSQLGETRATSRALDRGVTYLLNDQEKDGSWY

```
GRWGMNFIYGTWSVLCALNAAGVDPQSPEIRKAVAWLIRIQNPDGGWGEDASSYKLNPEFEPGY

STASQTAWALLALMAAGEVDDPAVARGVNYLVRTQGQDGLWSEERYTATGFPRVFYLRYHGYPK

FFPLWAMARFRNLKRGNSRQVQFGM
```

>seq_ID 133
```
MTTTDETALAAGTPKAAFAPAPRGAADDLVARTVAVEAPPSPAPASDDTLARAVAHLKSLQDEAG

WWKGDLETNTTMDSEDLMLRHWLGIWNPEQAERTARFIRSKQYADGSWPIYHAGPGDLNATVES

YVALRMVGDSPQDPHMRAAAAWARARGGVPATRIFTRIWLALFGWWRWEDLPVLPPELIFVPAK

MPLSIYKFASWGRQTIVAIMVLMAHRPAGTPPFPIAELFPPPATKKKAAAQRKAQKKAGHAGGPTA

WRDSSIDDMFTEPAPGTDTLRQPAALAIGPARPAPAKGRRGKGQPAAPDVMGRAKDGGGPGLPL

PARLVSRVGFRTRRALRQAALDHVNWNLLFGGIDRFLHVYHRHPIRPVRSLALGLAERWIVVRQE

ADGCFGGIQPPTVYSIMALRVLGYPMDHPVMTAALRSLDEYSVTLPDGARMQEACQSPVWDTCL

ATIALADAGVPRDDPSLVRAADWMLAEEVRERRGDWSVPIPDVPTGGWSFEFDNDTYPDVDDSA

EVMLALMRVAHPRPEKVVAATYRGLQWVFGMQCADGGWGAFDVDNAGELVYKIPFADFGMLTD

PPSADVTAHVVELLGELGLGDDPRTKRGVEWLLHSQEADGSWYGRWGVNHLYGTGGVVPALRA

AGLPASHPAIQRAADWLVAKQNPDGGWGESCYSYDEMSTAGVGVSTASQTAWALLALIAAGRVG

DGVTGEAAARGVAWLAETQTAEGTWDEDYFTGTGFAGYFYINYHLYRLVWPVMALGRYQAALAG

KGH
```

>seq_ID 7
```
MNPVVHNLTRPHRSAEPRPSALQRSIAAAQAALLQHQAADGHWCFEFEADCTIPAEYILMMHYMD

ERDAALEAKMAAYLRRKQENHGGWSLYHGGHFDMSASVKAYFALKLAGDDPEAAHMRRARSAIL

AHGGAERANVFTRITLALFGQVPWRAVPFIPVEILLFPRWFPMHIYKVASWSRTVMVPLFILCSLKP

QAKNPLGVHIRELFTRPPEDIDDYFAHALQGWVSRIFLWFDRLGRALESWIPQALRRRAIARAEAW

FIERLNGEDGLNGIFPAMVNAHEALALLGYAAEHPYRQQTRAALTKLVVERAGEAYCQPCVSPVW

DTCLALHALLEADGDVSEAARRSMQWLLDRQITDAPGDWRERRPHLAGGGWAFQYANPYYPDL

DDDTAAVAWALARARRPEDRPAVERAANWLAGMQSRNGGFGAYDVDNTYYYLNEIPFADHKALLD

PPTADVSGRVLAFLAILDREQDAPVRARLIQYLLREQEPSGAWFGRWGTNYIYGTWSVLMGMAEL

RDPGAEVRDAMARAAHWLRSVQQDDGGWGESNDSYADPGLAGLGQESTAAQTAWACLALMAA

GDSDSESLRRGIQWLQRHQEQPGDWQDPYFNAPGFPRVFYLTYHGYKIYFPLWALARYRNITER

HCA
```

>seq_ID 190
```
MALSNGEIREEIQRLSEELIQRQEPDGSWRFCFENGITIDACTIILLRTLNVDKEELIRQLHDRIVAAQ

QPEGCWRWYHDDKEGHLSATVEAYYALLCSGYSRPEDEPIQRAKRYILDRGGIGQARSLFTKAIL

AATGQRKWPASLSLIPIEILLLPESLPLNFYDFSGYSRVHLVPLLIMAERNFRTRSVRTPDLSELFLD

ARNGEEDPLTLTPESREPLKLIQSGLAHLVGTPRRIRQAAVNRAEQYMLDRIEGDGTLYTYASCTV

LMVFALLALGYEPQHPVIQRAVEGLSQMKFTVDSTGQGGTRYVTIQNSPSTVWDTALISYALQEAG

VSSSHPAIQRAADYLRNRQHRRPGDWQIHNPGIVPGGWGFSETNTFVPDVDDTTAALRALSALH

GSEPAVLGAWNRGLNWVWSMQNNDGGWPAFEKNTNKEMLTWLAIEGAKSAATDPSEADLTGR

TLEYLGNFAKLSVRQDWVARGADWLLSHQEADGSWYGRWGICYIYGTWAALTGLMAVGMPADH

PGIAKAANWLIRIQNADGGWGESCRSDQVRRYVPLHASTPSQTAWALDALIAVHDRRAPEIERGV

ARLIALLHEDDWPSTYPTGAGLPGYFYVHYHSYRYIWPLLALSHYVNKYGDSSP
```

```
                                                                >seq_ID 45
MSGVLLYDKVREEIERRTTALQTMQRQDGTWSFCFEGALLTDCHMIFLLKLLGRNDEIEPFVKRLA

SLQTNEGTWKLYEDENGGNLSATIQAYAALLASEKYSKEDINMRRAEMFIKEHGGVSRAHFMTKF

LLAIHGEYEFPTLFHFPTPILFLQDDSPLSIFELSSSARIHLIPMMICMNKRFRVEKKLLPNLNHIAGE

GGQWFREERSPLFQSFVGDVKKVIAYPLSLHHKGYEEVERFIGERIDENGTLYSYASATFYMIYALL

ALGHSIQSPIIEKAVIGLKSYIWKMDRGSHLQNSPSTVWDTALLSYSLQEANVMKENKMIQKATEYL

LQRQQTKRMDWSVHAPSIMAGGWGFSDVNTTIPDVDDTTAALRALARSRGSSRVDSAWERGVE

WLKGLQNNDGGWGAFERGVTSRILANLPIENASDMITDPSTPDITGRVLEFFGTYAPNELPEEQKK

KAVKWLMDVQELNGSWYGKWGICYIYGTWAAMTGLRALGVPSSHPSLKKAASWLEHLQYEDGG

WGESCQSSVEKKFISLPFSTPSQTAWALDALISYYDQETPIIRKGISYLLAQPTMNEKYPTGTGLPG

GFYIRYHSYGHIYPLLALAHYIKKYKK

>seq_ID 53
MSGVLLYDKVHEEIERRTTALQTMQRQDGTWQFCFEGALLTDCHMIFLLKLLGRNDEIEPFVKRLV

SLQTNEGTWKLYEDEKGGNLSATIQAYAALLASERYSKEAMNMRRAEMFIKEHGGVSRAHFMTKF

LLAIHGEYEFPALFHFPTPILFLQDDSPLSIFGLSSSARIHLIPMMICMNKRFRVEKKLLPNLNHIAGG

GGQWFREERSPLFQSFLGDVKKVISYPLSLHHKGYEEVERFMKERIDENGTLYSYASATFYMIYAL

LALGHSIQSPIIEKAVTGLKSYIWKMDRGSHLQNSPSTVWDTALLSYSLQEAKVTNENKMIQRATEY

LLQKQQTKKVDWSVHASSLVAGGWGFSDVNTTIPDIDDTTAALRALARSRGNDRVDDAWGRGVE

WVKGLQNNDGGWGAFERGVTSKLLSNLPIENASDMITDPSTPDITGRVLELFGTYAPNELLEEQKK

KAIKWLMDVQEQNGSWYGKWGICYIYGTWATMTGLRALGVPSTHPALKKAASWLEHLQHEDGG

WGESCQSSVEKKFISLPFSTPSQTAWALDALISYYDQETPIIRKGISYLLAQSTMNEKYPTGTGLPG

GFYIRYHSYGHIYPLLALAHYVKKYRK

>seq_ID 44
MSGVLLYDKVHEEIERRTTALQTMQRQDGTWQFCFEGALLTDCHMIFLLKLLGRNDEIEPFVKRLA

SLQTNEGTWKLYEDEKGGNLSATIQAYAALLASEKYSKEDMNMRRAEMFIKEHGGVSRAHFMTKF

LLAIHGEYEFPALFHFPTPILFLQDDSPLSIFGLSSSARIHLIPMMICMNKRFRVEKKLLPNLNHIAGG

GGQWFREERSPLFQSLLGDVKKVISYPLSLHHKGYEEVERFMKERIDENGTLYSYASATFYMIYAL

LALGHSIQSPIIEKAVTGLKSYIWKMDRGSHLQNSPSTVWDTALLSYSLQEAKVTNENKMIQRATEY

LLQKQQTKKVDWSVHASSLVAGGWGFSDVNTTIPDIDDTTAALRALARSRGNDRVDDAWGRGVE

WVKGLQNNDGGWGAFERGVTSKLLSNLPIENASDMITDPSTPDITGRVLELFGTYAPNELLEEQKK

KAIKWLMDVQEQNGSWYGKWGICYIYGTWATMTGLRALGVPSTHPSLKKAASWLEHLQHEDGG

WGESCQSSVEKKFISLPFSTPSQTAWALDALISYYDQETPIIRKGITYLLAQSTMNEKYPTGTGLPG

GFYIRYHSYGHIYPLLALAHYVKKYRK

>seq_ID 64
MSNLLLYEKVHEEIARRTTALQTMQRQDGTWRFCFEGAPLTDCHMIFLLKLLGRDKEIEPFVKRLA

SLQTNEGTWKLYEDEAGGNLSATIQSYAALLASEKYTKEDANMKRAEMFINERGGVARAHFMTKF

LLAIHGEYEYPSLFHLPTPIMFLQNDSPLSIFELSSSARIHLIPMMLCLNKRFRVGKKLLPNLNHIAGG

GGEWFREDRSPVFQTLLSDVKKIITYPLSLHHKGYEEVERFMKERIDENGTLYSYATASFYMIYALL

ALGHSIQSPIIEKAITGITSYIWKMERGSHLQNSPSTIWDTALLSYALQEAVPKASKVIHNASAYLLR

KQQTKKVDWSVHAPDLFPGGWGFSDVNTTIPDIDDTTAALRALARSRGNENVDNAWKRAVNWVK

GLQNNDGGWGAFEKGVTSRILANLPIENASDMITDPSTPDITGRVLEFFGTYTQNELPEKQKQSAI

NWLMNVQEENGSWYGKWGICYIYGTWAVMTGLRSFGIPSSNPSLKRAALWLEHIQHEDGGWGE
```

SCQSSVEKRFVTLPFSTPSQTAWALDALISYYDKETPVIRKGISYLLSNSYINEKYPTGTGLPGGFYI

RYHSYAHIYPLLTLAHYAKKYKK

>seq_ID 68

MLLYEKVHEEIARRTTALQTMQRQDGTWRFCFEGAPLTDCHMIFLLKLLGKDKEIEPFVKRLASLQ

TNEGTWKLYEDEVGGNLSATIQSYAALLASEKYTKEDVNMKRAEMFINEHGGVARAHFMTKFLLAI

HGEYEYPSLFHLPTPIMFLQNDSPLSIFELSSSARIHLIPMMLCLNKRFRVGKKLLPNLNHIAGGGGE

WFREDRSPVFQTLVSDVKKIITYPLSLHHKGYEEVERFMKERIDENGTLYSYATASFYMIYALLALG

HSIQSPIIQKAITGITSYIWKMERGSHLQNSPSTVWDTALLSYALQEAQVPKASKVIHNASAYLLRKQ

QTKKVDWSVHAPDLFPGGWGFSDVNTTIPDIDDTTAALRALARSRGNENVDTAWKRAVNWVKGL

QNNDGGWGAFEKGVTSRILANLPIENASDMITDPSTPDITGRVLEFFGTYTQNELPEKQKQSAINW

LMNVQEENGSWYGKWGICYIYGTWAVLTGLRSLGIPSSDPSVKRAALWLEHIQHEDGGWGESCQ

SSVEKRFVTLPFSTPSQTAWALDALISYYDKETPVIRKGISYLLSNSYINEKYPTGTGLPGGFYIRYH

SYAHIYPLLTLAHYAKKYRK

>seq_ID 41

MSNLLLYEKVHEEIARRTTALQTMQRQDGTWQFCFEGAPLTDCHMIFLLKLLGRDKEIEPFVKRLA

SLQTNEGTWKLYEDEMGGNLSATIQSYAALLASEKYTKEDANMKRAEMFINERGGVARAHFMTKF

LLAIHGEYEYPSLFHLPTPIMFLQNDSPLSIFELSSSARIHLIPMMLCLNKRFRVGKKLLPNLNHIAGG

GGEWFREDRSPVFQTLVSDVKKIITYPLSLHHKGYEEVERFMKERIDENGTLYSYATASFYMIYALL

ALGHSIQSPIIQKAITGITSYIWKMERGSHLQNSPSTVWDTALLSYVLQEAQVPKASKVIHNASAYLL

RKQQTKKVDWSVHAPDLFPGGWGFSDVNTTIPDIDDTTAALRALARSRGNENVDTAWKRAVNWV

KGLQNNDGGWGTFEKGVTSRILANLPIENASDMITDPSTPDITGRVLEFFGTYTQNELPEKQKQSAI

NWLMNVQEENGSWYGKWGICYIYGTWAVLTGLRSLGIPSSDPSVKRAALWLEHIQHEDGGWGE

SCQSSVEKRFVTLPFSTPSQTAWALDALISYYDKETPVIRKGISYLLSNSYINEKYPTGTGLPGGFYI

RYHSYAHIYPLLTLAHYAKKYRK

>seq_ID 66

MSNLLLYEKVHEEIARRTTALQTMQRQDGTWQFCFEGAPLTDCHMIFLLKLLGRDKEIEPFVKRLA

SLQINEGTWKLYEDEMGGNLSATIQSYAALLASEKYTKEDANMKRAENFIKERGGVARAHFMTKF

LLAIHGEYEYPSLFHLPTPIMFLQNDSPLSIFELSSSARIHLIPMMLCLNKRFRVGKKLLPNLNHIAGG

GGEWFREDRSPVFQTLASDVKKIITYPLSLHHKGYEEVERFMKERIDENGTLYSYATASFYMIYALL

ALGHSIQSPIIEKAIMGITSYIWKMERGSHLQNSPSTIWDTALLSYALQEAQVPKASKVIQNASAYLL

RKQQTKKVDWSVHAPDLFPGGWGFSDVNTTIPDIDDTTAVLRALARSRGNENVDNAWKRAVNW

VKGLQNNDGGWGAFEKGVTSRILANLPIENASDMITDPSTPDITGRVLEFFGTYGQNELPEKQKQS

AINWLTNAQEENGSWYGKWGICYIYGTWAVLTGLRSLGIPSSDPSLKRAALWLEHIQHEDGGWGE

SCHSSVEKRFVTLPFSTPSQTAWALDALISYYDKETPVIRKGISYLLSNPYINEKYPTGTGLPGGFYI

CYHSYAHIYPLLTLAHYAKKYRK

>seq_ID 138

MVADERSALIDALKRSQSVDGSWRFPFETGISTDAYMIILLRTLGIHDEPLIQALVERIESRQDANGA

WKLFADEGDGNVTATVEAYYALLYSGYRKKTDSHMQKAKARILEVGGLERVHLFTKVMLALTGQH

SWPRRFPLPLVFFLLPPSFPLNMYDLSVYGRANMVPLLVVAERRYSRKTDNSPDLSDLAASRNDW

RLPDTEALWSYVKRSLTGLPAWLHRAAEQRAVRYMLEHIEPDGTLYSYFSSTFLLIFALLALGYPKD

DPHIARAVRGLRSLRTEIDGHTHMQYTTASVWNTALASYALQEAGVPPTDRTIEKANRYLLSRQHI

RYGDWAVHNPYGVPGGWGFSDVNTMNPDVDDTTAALRAIRRAAAKETAFRHAWDRANRWLFS

MQNDDGGFAAFEKNVGKRFWRYLPIEGAEFLLMDPSTADLTGRTLEYFGTFAGLTKDHSAIARAID

```
WLLDHQEADGSWYGRWGICYVYGTWAAVTGLSAVGVPIDHPAMQKAVRWLLSIQNDDGGWGE

SCKSDGAKTYVPLGASTPVHTAWALDALIAAAERPTPEMKAGVRALVRMLHHPDWTASYPVGQG

MAGAFYIHYHGYRYIFPLLALAHYEQKFGPFVD
```

>seq_ID 69
```
MLLYEKVHEEIARRTTALQTMQRQDGTWRFCFEGAPLTDCHMIFLLKLLGRDKEIEPFVKRLASLQ

TNEGTWKLYEDEVGGNLSATIQSYAALLASEKYTKEDANMKRAEMFINERGGVARAHFMTKFLLA

VHGEYEYPSLFHLPTPIMFLQNDSPLSIFELSSSARIHLIPMMLCLNKRFRVGKKLLPNLNHIAGGGG

EWFREDRSPVFQTLLSEVKKIITYPLSLHHKGYEAVERFMKERIDENGTLYSYATASFYMIYALLAL

GHSIQSPIIQKAITGITSYIWKMERGSHLQNSPSTVWDTALLSYALQEAQVPKASKGIQNASAYLLR

KQQTKKVDWSVHAPDLFPGGWGFSDVNTTIPDIDDTTAVLRALARSRGNENVDNSWKRAVNWVK

GLQNNDGGWGAFEKGVTSRILANLPIENASDMIPDPSTPDITGRVLEFFGTYAQNELPEKQKQSAI

NWLMNIQEEENGSWYGKWGICYIYGTWAVLTGLRSLGIPSSDPSLKRAALWLEHIQHEDGGWGES

CQSSVEKRFVTLPFSTPSQTAWALDALISYYEKETPVIRKGISYLLSNPYVNEKYPTGTGLPGGFYI

RYHSYTHIYPLLTLAHYAKKYRK
```

>seq_ID 67
```
MSNLLLYEKVHEEIARRTTALQTMQRQDGTWRFCFEGAPLTDCHMIFLLKLLGRDKEIEPFVKRLA

SLQTNEGTWKLYEDEVGGNLSATIQSYAALLASEKYTKEDANMKRAEMFINERGGVARAHFMTKF

LLAIHGEYEYPSLFHLPTPIMFLQNDSPLSIFELSSSARIHLIPMMLCLNKRFRVGKKLLPNLNHIAGG

GGEWFREDRSPVFQTLLSEVKKIITYPLSLHHKGYEEVERFMKERIDENGTLYSYATASFYMIYALL

ALGHSIQSPIIQKAITGIASYIWKMERGSHLQNSPSTVWDTALLSYALQEAQVPKASKVIQNASAYLL

RKQQTKKVDWSVHAPNLFPGGWGFSDVNTMIPDIDDTTAVLRALARSRGDENVDNAWKRAVNW

VKGLQNNDGGWGAFEKGVTSRILANLPIENASDMITDPSTPDITGRVLEFFGTYAQNELPEKQKQS

AINWLMNVQEENGSWYGKWGICYIYGTWAVLTGLRSLGIPSSDPSLKRAALWLEHIQHEDGGWG

ESCQSSVEKRFVTLPFSTPSQTAWALDALISYYEKETPIIRKGISYLLSNPYVNEKYPTGTGLPGGF

YIRYHSYAHIYPLLTLAHYTKKYRK
```

>seq_ID 35
```
MSNLLLYEKAHEEIVRRATALQTMQWDGTWRFCFEGAPLTDCHMIFLLKLLGRDKEIEPFVERVA

SLQTNEGTWKLYEDEVGGNLSATIQSYAALLASKKYTKEDANMKRAENFIQERGGVARAHFMTKF

LLAIHGEYEYPSLFHLPTPIMFLQDDAPFSIFELSSSARIHLIPMMLCLNKRFRVGKKLLPNLNHIAGG

GGEWFREDRSPVFQTLLSDVKQIISYPLSLHHKGYEEIERFMKERIDENGTLYSYATASFYMIYALL

ALGHSLQSSMIQKAIAGITSYIWKMERGNHLQNSPSTVWDTALLSYALQEAQVSKDNKMIQNATAY

LLKKQHTKKADWSVHAPALTPGGWGFSDVNTTIPDIDDTTAVLRALARSRGNKNIDNAWKKGGN

WIKGLQNNDGGWGAFEKGVTSKLLAKLPIENASDMITDPSTPDITGRVLEFFGTYAQNELPEKQIQ

RAINWLMNVQEENGSWYGKWGICYIYGTWAVMTGLRSLGIPSSNPSLKRAASWLEHIQHEDGGW

GESCHSSVEKRFVTLPFSTPSQTAWALDALISYYDTETPAIRKGVSYLLLNPYVNERYPTGTGLPG

AFYIRYHSYAHIYPLLTLAHYLKKYRK
```

>seq_ID 43
```
MNALLLYEKVHEEIARRTTALQTMQRQDGTWRFCFEGAPLTDCHMIFLLKLLGRDKEVEPFVKRLA

SLQTNEGTWKLYDDEMGGNLSATIQSYAALLASKKYTKEDANMKRAEMFITERGGVARAHFMTKF

LLAIHGEYEYPSLFHLPTPIMFLQNDSPLSIFELSSSARIHLIPMMLCLNKRFRVGKKLLPNLNHIAGG

GGEWFREDQSPMFQTLLGNVKQIISYPLSLHHKGNEEVERFMKERIDENGTLYSYASASFYMIYAL

LALGHSIQSPMIQKAITGITSYIWKMERGNHLQNSPSTVWDTALLSYALQEARVSKESKMIQNASAY
```

-continued

LLKKQHKKKADWSVHAPVLIPGGWGFSDVNTTVPDVDDTTAVLRALAQSRGNGNVDDAWKKGT
NWIKGLQNNDGGWGAFEKGVTSKLLANLPIENASDMITDPSTPDITGRVLEFFGTYTQNELPEKQK
QSAINWLMNEQEENGSWYGKWGICYIYGTWAVMTGLRALGITSAHPSLKRATLWLEHIQHEDGG
WGESCQSSVEKRFATLPFSTPSQTAWALDALISYYDKETPAIRKGISYLLANPYVNEKYPTGTALP
GGFYIHYHSYAHIYPLLTLAHYAKKYKK

>seq_ID 33
MNIVIRISKGWVSNLLLYEKVHEEIARRTTALQTMQRQDGTWQFCFEGAPLTDCHMIFLLKLLGRD
KEIEPFVKRLASLQTNEGTWKLYEDEVGGNLSATIQSYAALLASKKYTKEDANMKRAEMFINERGG
VARAHFMTKFLLAIHGEYEYPSLFHLPTPIMFLQNDSPLSIFELSSSARIHLIPMMVCLNKRFQVGKK
LLPNLNHIAGGGGEWFREDRSPMFQTLLSDVKQIISYPLSLHHKGYEEVERFMKERIDENGTLYSY
ATASFYMIYALLALGHSLQSSMIQKAIAGITSYIWKMEKGNHLQNSPSTVWDTALLSYTLQEAHASK
DNKMIQHAAAYVLKKQHTKKADWSVHAPGLIPGGWGFSDVNTTIPDVDDTTAVLRALARSRGNEN
VDNAWKKGVNWVKGLQNNDGGWGAFEKGVTSNLLANLPIENASDMITDPSTPDITGRVLELFGTY
AQNELPEKQKQSAINWLMNVQEENGSWYGKWGICYIYGTWAVMTGLRSLGIPSSNPSMKRAALW
LEHIQHEDGGWGESCQSSVEKRFITLPFSTPSQTAWALDALISYHDEETPAIRKGISYLLANPYVNE
KYPTGTGLPGGFYIHYHSYAYIYPLLTLAHYIKKYRK >seq_ID 36
MSNLLLYEKVHEEIARRATALQTMQRQDGTWRFCFEGAPLTDCHMIFLLKLLGRDKEIEPFVKRLA
SLQTNEGTWKLYEDEVGGNLSATIQSYAALLASQKYTKEDANMKRAENFIKERGGVARAHFMTKF
LLAIHGEYEYPSLFHVPTPIMFLQNDSPLSIFELSSSARIHLIPMMVCLNKRFRVGKKLLPNLNHIAG
GGGEWFREDRSPLFQTLLSDVKQIISYPLSLHHKGYEEVERFMKERIDENGTLYSYATASFYMIYAL
LALGHSLQSSMIQKAIAGITSYIWKMERGSHLQNSPSTVWDTALLSYALQEAVPKDHKMIQQTITY
LLKKQHTKKADWSVHAPALTPGGWGFSDVNTTVPDVDDTTAVLRVLARSRENEKVNNAWQKGID
WVKGLQNNDGGWGAFEKGVTSKLLANLPIENASDMITDPSTPDITGRVLELFGTYTQNELPEKQK
QSAINWLMNAQEENGSWYGKWGICYIYGTWAVMTGLRSLGIPSNNPSLKRAALWLEHIQHEDGG
WGESCQSSMEKRFITLPFSTPSQTAWALDALISYYDTETPAIRKGISYLLANPYVNEKYPTGTGLPG
GFYIRYHSYAQIYPLLTLAHYTKKYRK >seq_ID 42
MSNLLLYEKVHEEIARRTTALQTMQRQDGTWRFCFEGAPLTDCHMIFLLKLLGRDKEIEPFVKRLA
SLQTNEGTWKLYEDEVGGNLSATIQSYAALLASEKYTKEDANMKRAEMFINERGGVARAHFMTKF
LLAIHGEYEYPSLFHLPTPIMFLQNDSPLSIFELSSSARIHLIPMMLCLNKRFRVGKKLLPNLNHIAGG
GGEWFREDRSPVFQTLVSDVKKIITYPLSLHHKGYEEVERFMKERIDENGTLYSYATASFYMIYALL
ALGHSIQSPIIEKAIMGITSYIWKVERGSHLQNSPSTIWDTALLSYALQEAQVPKASKVIQNASAYLL
RKQQTKKVDWSVHAPDLFPGGWGFSDVNTTIPDIDDTTAVLRALARSRGNEHVDNAWKRAVNW
VKGLQNNDGGWGAFEKGVTSRILANLPIENASDMITDPSTPDITGRVLEFFGTYTQNELPEKQKQS
AINWLMNVQEENGSWYGKWGICYIYGTWAVLTGLRSLGIPSSDSSLKRAVLWLEHIQHEDGGWG
ESCQSSVEKRFVTLPFSTPSQTAWALDALISYYDKETPVIRKGISYLSNPYINEKYPTGTGLPGGF
YIRYHSYAHIYPLLTLAHYAKKYRK >seq_ID 65
MSNLLLYEKVYEEIARRTTALQTMQRQDGTWRFCFEGAPLTDCHMIFLLKLLGRDKEIEPFVKRLA
SLQTNEGTWKLYEDEVGGNLSATIQSYAALLASEKYTKEDANMKRAEMFINERGGVARAHFMTKF
LLAIHGEYEYPSLFHLPTPIMFLQNDSPLSIFELSSSARIHLIPMMLCLNKRFRVGKKLLPNLNHIAGG
GGEWFREDRSPVFQTLVSDVKKIITYPLSLHHKGYEEVERFMKGRIDENGTLYSYATASFYMIYALL

```
ALGHSIQSPIIEKAIMGITSYIWKMERGSHLQNSPSTIWDTALLSYALQEAQVPKVSKVIQNASAYLL

RKQQTKKVDWSVHAPDLFPGGWGFSDVNTTIPDIDDTTAVLRALARSRGNENVDNAWKRAVNW

VKGLQNNDGGWGAFEKGVTSRILANLPIENASDMITDPSTPDITGRVLEFFGTYTQNELPEKQKQS

AINWLMNVQEENGSWYGKWGICYIYGTWAVLTGLRSLGIPSSDSSLKRAVLWLEHIQHEDGGWG

ESCQSSVEKRFVTLPFSTPSQTAWALDALISYYDKETPVIRKGISYLLSNPYINEKYPTGTGLPGGF

YIRYHSYAHIYPLLTLAHYAKKYRK

>seq_ID 39
MNNLLLYEKVHEEIARRATALQTMQQQDGTWRFCFEGAPLTDCHMIFLLKLLGRDKEIEPFVKRLA

SLQTNEGTWKLYEDEVGGNLSATIQSYAALLASKKYTKEDANMKRAENFIKERGGVARAHFMTKF

LLAIHGEYEYPSLFHLPTPIMFLQNDSHLSIFELSSSARIHLIPMMLCLNKRFRVGKKLLPSLNHIAGG

GGEWFREDRSPLFQTLVSDVKQIISYPLSLHHKGYEEVERFMKERIDENGTLYSYATASFYMIYALL

ALGHSLQSTMIQKAITGITSYIWKMESGNHLQNSPSTVWDTALLSYALQEAHVPKDNKMIQHAATY

LLKKQHTQKADWSVHAPALTPGGWGFSDVNTTIPDVDDTTAVLRALARSRGNEKVDNAWPKGIN

WVKGLQNNDGGWGAFEKGVTSNILANLPIENASDMITDPSTPDITGRVLEFFGKYAQNELPEKQK

QSAINWLMNVQEENGSWYGKWGICYIYGTWAVMTGLRSLGIPSSNPSMKRAALWLEHIQHEDGG

WGESCHSSVEKRFVTLPFSTPSQTAWALDALISYYDKETSIIRKGISYLLANPYVNEKYPTGTGLPG

GFYIRYHSYAHIYPLLTLAHYIKKYRK

>seq_ID 63
MSNLLLYEKAHEEIARRATALQTMQREDGTWRFCFEGAPLTDCHMIFLLKLLGRDKEIEPFVKRLA

TLQTNEGTWKLYEDEVGGNLSATIQSYAALLASGKYTKEDANMKRAENFIKERGGVARAHFMTKF

LLAIHGEYEYPSLFHVPTPIMFLQNDSPLSIFELSSSARIHLIPMMLCLNKRFRVGKKLLPNLNHIAGG

GGEWFREERSPLFQTLLSDVKQIISYPLSLHHKGYEEVERFMKERIDENGTLYSYATASFYMIYALL

ALGHSLQSSMIQKAIAGITSYIWKMESGNHVQNSPSTVWDTALLSYALQEAHVPKDNKMLQNATA

YLLKKQHTKKADWSVHAPALTPGGWGFSDVNTTVPDVDDTAVLRVLARSKGNEKLDHAWQKGI

NWVKGLQNNDGGWGAFEKGVTSRILANLPIENASDMITDPSTPDITGRVLEFFGTYAQNELPEKQ

KQSAINWLMNAQEENGSWYGKWGICYIYGTWAVMTGLRSFGIPSSNPSLKRAALWLEHIQHKDG

GWGESCHSSVEKRFVTLPFSTPSQTAWALDALISYYDTETPVIRKGISYLLANPYVNEKYPTGTGL

PGGFYIRYHSYAHIYPLLTLTHYIKNIENKPRDISRFIFLGSRSLLKRIRLCFPYFSVDWRF

>seq_ID 37
MSNLLLYEKAHEEIARRATALQTMQREDGTWRFCFEGAPLTDCHMIFLLKLLGRDKEIEPFVKRLA

SLQTNEGTWKLYEDEVGGNLSATIQSYAALLASGKYTKEDANMKRAENFIKERGGVARAHFMTKF

LLAIHGEYEYPSLFHVPTPIMFLQNDSPLSIFELSSSARIHLIPMMLCLNKRFRVGKKLLPNLNHIAGG

GGEWFREERSPLFQTLLSDVKQIISYPLSLHHKGYEEVERFMKERIDENGTLYSYATASFYMIYALL

ALGHSLQSSMIQKAIAGITSYIWKMESGNHVQNSPSTVWDTALLSYALQEAHVPKDNKMLQNATA

YLLKKQHTKKADWSVHAPALTPGGWGFSDVNTTVPDVDDTAVLRVLARSKGNEKLDHAWQKGI

NWVKGLQNNDGGWGAFEKGVTSRILANLPIENASDMITDPSTPDITGRVLEFFGTYAQNELPEKQ

KQSAINWLMNAQEENGSWYGKWGICYIYGTWAVMTGLRSFGIPSSNPSLKRAALWLEHIQHKDG

GWGESCHSSVEKRFVTLPFSTPSQTAWALDALISYYDTETPVIRKGISYLLANPYVNEKYPTGTGL

PGGFYIRYHSYAHIYPLLTLTHYIKKYRK

>seq_ID 46
MLLYEKVHEEVKEKMAALQAMQQQDGTWRFCFEGSPLTDCYMIFLLTLLGQDQEIEPFVARLAAL

QTNEGTWKLYEDEPDGNLSATIQAYAALLVSKMYKKEDINMKRAEVFIRKQGGITKAHFMTKFLLA
```

-continued

LHGGYEYPPLFHFPTPILFLSEDSPLSIFELSSSARIHLIPMMLCMNKRFTVSKKMLPNLDYISGGSK

EQWFREERSPLFQTLLRDVTKFLSYPLSLHYKGDKAAERFMIERIDTNGTLYSYASATFYMIYALLA

LGHSIQSPLISNAVLGLKTYVWNMDRWAHLQNSPSTVWDTALLSYSLQEARVPHDNEMIQKAINYL

LQKQHKEKKDWSVHAPTLDAGGWGFSDVNTTIPDVDDTTAVLRALAGSRQGNPKVESAWRKGIE

WVKGLQNSDGGWAAFEKGVTSKVLTHLPLDNSGDMITDPSTVDITGRVLEFFGTYAPNELQGDQ

KDRAIRWLIYTQEKNGSWHGKWGVCYIYGTWAALTGLRAVGVPSNHIALQKAATWLESIQHSDGG

WGESCRSSVEKKFISLPFSTPSQTAWALDALIACYDSETPTIRKGISYLLKHSTKHQEYPTGTALAN

GFYIRYHSYHHIFPLLTFAHYIKKYRK

>seq_ID 40
MSNLLLYEKVHEEIARRTTALQTMQRRDGTWRFCFEGAPLTDCHMIFLLKLLGRDKEIEPFVKRLA

SLQTNEGTWKLYEDEVGGNLSATIQSYAALLASKKYTKEDANMKRAEMFINERGGVARAHFMTKF

LLAVHGEYEYPSLFHLPTPIMFLQSDSPLSIFELSSSARIHLIPMMLCLNKKFRIRKKLLPNLNHISGG

GGEWFRGNRSPLFQTLVSDVKQIISYPLSLHHKGNEEVERFMKERIDENGTLYSYATASFYMIYAL

LALGHSLQSTMIQKAITGITSYIWNMESGNHLQNSPSTVWDTALLSYALQEAHVPKDTNMLQHATA

YLLKKQHTKKADWSVHAPALAPGGWGFSDVNTTIPDVDDTTAVLRALARSRGSEKVDYVWEKGIN

WVKGLQNNDGGWGAFEKGVTSNLLANLPIENASDMITDPSTPDITGRVLELFGTYAQNELPEKQT

QSAINWLMNVQEKNGSWYGKWGICYIYGTWAVMTGLRSLGIPSSNPSLKRAALWLEHIQHEDGG

WGESCHSSVEKRFVTLPFSTPSQTAWALDALISYYDKETPAIRKGISYLLANRYVNEKYPTGTGLP

GGFYICYHSYAHIYPLLTLAHYIKKYRK

>seq_ID 38
MSNLLLYEKAHEEIARRATALQSMQWQDGTWRFCFEGAPLTDCHMIFLLKLLGRDKEIEPFVKRLA

SLQTNEGTWKLYEDEVGGNLSATIQSYAALLASGKYTKEDANMKRAENFIKERGGVARAHFMTKF

LLAVHGEYEYPSLFHLPTPIMFLQNDSPLSIFELSSSARIHLIPMMLCLNKRFRVGKKLLPNLNHIAG

GGGEWFREERSPLFQTLVSDVKQIISYPLSLHHKGYEEVERFMKERIDENGTLYSYATASFYMIYA

LLALGHSLQSSIIQNAITGITSYIWKMESGNHLQNSPSTVWDTALLSYALQEAHVPKDNKMLQNATA

YLLKKQHTKKADWSVHASALTPGGWGFSDVNTTVPDVDDTTAVLRVLARSRGNEKVDHAWQKGI

NWVKGLQNNDGGWGAFEKGVTSNILAKLPIENASDMITDPSTPDITGRVLEFFGTYAQNELPEKQK

QSAINWLMNVQEENGSWYGKWGICYIYGTWAVMTGLRSFGIPSSNPSLKRAALWLEHIQHKDGG

WGESCHSSVEKRFVTLPFSTPSQTAWALDALISYYDTETPIIRKGISYLLANPYVNEKYPTGTGLPG

GFYIRYHSYAHIYPLLTLAHYIKKYRK

>seq_ID 55
MLLYEKVRQEVERKVTALRTMQYQDGAWRFCFEGSPLTDCHMIFLLRLLGQNGEMEPFVTRVAS

LQTNEGTWKLYEDESVGNLSTTINAYVALLASGRYTKEDINMKRAEAFIRRQGGITKAHFMTKFLLA

LHGGYEYPSLFHFPTPMLFLPEDSPLSIFELSSSARIHLIPMMICMNKRFTVSKTILPNLDYISGGSKK

QWFREERSSLFQRLLGDVKKFLSYPLSLQHKGYKEAERFMIERIETNGTLYSYASATFYMIYALLAL

GHSIQSPLISNAVLGLKSYIWNMNKGTHLQNSPSTVWDTALLSYSLQEAGVPNDNQMIQKATDYLL

QKQHKEKKDWSVHAPSLDAGGWGFSDVNTTIPDIDDTTAALRAIARSREGNQRIEEAWRKGIEWV

KGLQNIDGGWAAFERGVTSHFLTHLPLDNAGDMTTDPSTSDITGRVLEFFGTYAPHQLKDDQKDR

AIKWLMQAQEKNGSWYGKWGVCYIYGTWAALTGLRAVGVPSNHTALQKAATWLERIQHNDGGW

GESCRSSIEKHFISLPFSTPSQTAWALDALITFYDTETPVIRKGISYLLAHLNQNQDYPTGIGLPDGF

YIRYHSYHHIFPILTFAHYIKKYMK

```
>seq_ID 54
MLLYEKVRQEVERKVTALRTTQYQDGAWRFCFEGSPLTDCHMIFLLRLLGQNGEMEPFVTRVASL
QTNEGTWKLYEDESVGNLSTTINAYVALLASGRYTKEDINMKRAEAFIRRQGGITKAHFMTKFLLAL
HGGYEYPSLFHFPTPMLFLPEDSPLSIFELSSSARIHLIPMMICMNKRFTVSKTIFPNLDYISGGSKK
QWFREERSPLFQTLLGDVKKFLSYPLSLQHKGYKEAERFMIERIETNGTLYSYASATFYMIYALLAL
GHSIQSPLISNAVLGLKSYIWNMNKGTHLQNSPSTVWDTALLSYSLQEAGVPNDNQMIQKATDYLL
QKQHKEKKDWSVHAPSLDAGGWGFSDVNTTIPDIDDTTAALRAIARSREGNQRIEEDWRKGIEWV
KGLQNIDGGWAAFERGVTSHFLTHLPLDNAGDMTTDPSTSDITGRVLEFFGTYAPHQLKDDQKDR
AIKWLMQAQEKNGSWYGKWGVCYIYGTWAVLTGLRAVGVPSNHTALQKAATWLERIQHNDGGW
GESCRSSIEKHFISLPFSTPSQTAWALDALITFYDTETPVIRKGISYLLAHLNQNQDYPTGIGLPDGF
YIRYHSYHHIFPILTFAHYIKKYMK >seq_ID 189
MRSELLQLQSADGSWRLCFDSGTMPDSYFIIILRMLGYSQDEALIRQIASRILSRQLPNGTWKIYPD
EEDGNLDATAEAYFALLYSGFLTKLDPRMQLAKQFILSKGGLSKIRSLLTQAIFAAAGQASWPKSM
RIPLEVFFSDNGIGIDLFSLSGHARVHIVPIIMLANAQFVQHSASMPDLSDLFAGSSKRFENDSPWIA
ALATLIGSLSLSELLPFESPTPQEKAVQFLFDRLEPDGTLLTYTTATMFMILVLLMLGYSSSSPLIHR
MVSGIHSVICANSHVQIASSEVWDTAMLVHALRKAGVNPTSTALENAGAYLRQRQQTQLGDWAIR
NPGTPAGGWGFSNVNTLYPDVDDTTAALRAIQPYSSRTPELQADWQRGLNWVLTMRNDNGGWP
AFERQGSRLPITFFNFEGAKDIAVDPSTVDLTSRTLQFLGQELGMNAGNSWIESTLRWVLSQQES
NGSWYGRWGITYVHGTSAALQGLTAVGIAEDHPAVKKGVDWLLQVQNEDGGWGESCISDKVRR
YVPLNFSTPSQTAWALDGLTAALPKPTPALERGVDALLQSLDRHDWTYTYPTGGALPGSVYAHYA
SNNYIWPLLALSNIWQKYS >seq_ID 200
MALPFNQDSYKGDDEADVSKGAAKSPPSLEEAIQRSQEFLLAQQFPEGFWFGELEANVTIISHTVI
LYKLLGIEENFPMYKFERYLRRMQCSHGGWEIAYGIGSYLSATIEAYIALRLLNVPQSDPALQKALR
VILDSGGVTKARIFTKICLALLGSFDWRGIPSLPPWLILCPTWFPLSIYEVSSWARGCIVPLLVILDKK
PVFKVSPEVSFDELYAEGREHACKIIPISGDWTSKFFITVDRVFKMMERLRVVPFRQWGIREAEKWI
LERQEESGDYVNIFPAMFYSVMCMKVLGYETTDPVVQRALLGFKGFTIETADECKVQSTVSPIWDT
AFIVRALVDSGIPPDHPALQKAGQWLLQKQILKHGDWAFKDRQNPVNQRGFACLQRDSQIETADE
CRVQSTLSPVWDTAFVVKALVDSGIPPNHPALQKAGQWLLQNQTLTHGDWAFKTQSGHLAAGG
WAFQSHNRWYPDADDSAAVMMALDCIELPDEDVKNGAIARGLKWISALQSRNGGWAGYDKNCD
QQWINKVPFNDLNGILDVPTADVTARVLEMVGRLSRLGAVGTPYSPRHCTLVESIPHLLLPETIARG
LAYLRREQEGEGCWWGKWGVNYIYGTCGALLALSQVAPTTHQEEIARGAKWLAQVQNRCDKQK
AAQGPRDGGWGESCFSYDDPALKGQNDASTASQTAWAVQGLLAAGDALGKYEVEAIEQGVQYL
LATQRKDGTWHEAHFTGSCFAQHFYVRYHYYAQHFPLSALGLYRTRILQHQ >seq_ID 139
MVADERSALIDALKRSQSVDGSWRFPFETGISTDAYMIILLRTLGIHDEPLIQALVERIESRQDANGA
WKLFADEGDGNVTATVEAYYALLYSGYRKKTDSHMQKAKARILEVGGLERVHLFTKVMLALTGQH
SWPRRFPLPLVFFLLPPSFPLNMYDLSVYGRANMVPLLVVAERRYSRKTDNSPDLSDLAASRNDW
RLPDTEALWSYVKRSLTGLPAWLHRAAEQRAVRYMLEHIEPDGTLYSYFSSTFLLIFALLALGYPKD
DPHIARAVRGLRSLRTEIDGHTHMQYTTASVWNTALASYALQEAGVPPTDRTIEKANRYLLSRQHI
RYGDWAVHNPYGVPGGWGFSDVNTMNPDVDDTTAALRAIRRAAAKETAFRHAWDRANRWLFS
```

-continued

```
MQNDDGGFAAFEKNVGKRFWRYLPIEGAEFLLMDPSTADLTGRTLEYFGTFAGLTKDHSAIARAID

WLLDHQEADGSWYGRWGICYVYGTWAAVTGLSAVGVPIDHPAMQKAVRWLLSIQNDDGGWGE

SCKSDGAKTYVPLGASTPVHTAWALDALIAAAERPTPEMKAGVRALVRMLHHPDWTASYPVGQG

MAGAFYIHYHGYRYIFPLLALAHYEQKFGPFVD
```

>seq_ID 13
```
MAQMASSLGSPRLLLRMGREAAQQQHLASGTEVQKALRLAVGHSLDLQRTDGAWCGEVHSNAT

FTAQYVFLQQQIGLPLDPTEIEGLSRWLFSQQNEDGSWGLGPGLGGDVSITTETYLALKILGVSPE

DPRMAAARTSIIKAGSLPATRMFTRVFLASFGLIPWSAVPPLPAELILLPTLFPVNIYNLSSWARATC

VPLLLIRHHEPLHSLPNGRHAENDFLDELWTKDIPRDFCYTTPLSRMWRLGDYAGIFFTSADHGFR

FLGQYFNSPLRNLSRRKIINWILDHQEQSGEWAGYWPPQHNNIWALSLEGYSLDHPVLRRGIAAV

KSFVLHDATGMRAQVTVSQVWDTALMSIALSDSAPSTGIISPTQAIDWLMHHEVASHRGDWRVLR

PKLATGGFCFEEFNTLYPDVDDTAAVIMALIKSNPAHLISGCVRQCFGMMMAGRHGYSLDCQLET

RLRASSQLAIAYLLGCQENNGSWWGRWGVNYLYGTSNVLCGLAYYYDRSSLSKGDGKSNSNIVS

AVDRASEWLKARQHSNGGWGEGLESYDNAQLAGCGQPTASQSAWVTMALLNYLSPTDEVIQRG

VSYLVRNQVKYGDESRATWPLERYTATGFPGHLYMEYDYYRHYFPIMALGRYVNKLSGSHKLL
```

>seq_ID 198
```
MEDLTQKLQQALQLASRALLNERVRPGLAHWEGELSTSALSTATAVMALFQYAKCQQASGRLQK

VFDGKSEGDWRLIEQGLAWLLQHQLADGGWGDTDKSISNISTTMLAHATLVACREAVRQKSLVLN

ASDIDAAIERSGRLIEELGGIQAIRDRYGKDHTFSVPILTHAALAGLVSWNEIPALPYELALLPHRFFE

VIQLPVVSYALPALIAIGQTLHLRQRTWNPWWWVRRAAIPGTLQKLQSIQPESGGFLEATPLTSFVT

MCLASVGRVDHPVTQAGLKFIRDSVRPDGSWPIDTNLATWVTTLSINHLGAEAFSSDEREALMRW

LLQQQYRTMHPYTNAAPGGWAWTNLSGGVPDADDTPGAMLALMELDRVSVSSQESLSIEQALY

QAALWLIKLQNRDGGWPTFCRGWGALPFDRSSNDITAHCLRALIQYERRLNDVTVDATGDTTSRP

LAVEVPSPKLREQMQRSIQQGFEYLEKTQREDGSWLPLWFGNQHSPDDENPLYGTARVLLAYAD

AGLEGSSAALRGCDWLVRHQHADGAWGPGTSIETADTSDAESDVEGEPASIEETALALMALCRF

DATHNVLHRGASWLITKVENETWREPTPIGFYFAKLWYYEKLYPQVFTVGALKALALRLGSALTTV

SENEPAPSSAEPPIPPIATDRVADSMHLQRTSPSINLANGGITLA
```

>seq_ID 252
```
SPVWDTVLTLLALDDCGYNDCYSEEVDKAVQWVLDQQVLSKGDWSVKLPNVEPGGWAFEYANT

RYPDTDDTAVALIVLSQFKDDPKWKERGINQAIERGVNWLFEMQCKNGGWGAFDKDNDKTLLTKI

PFCDFGEALDPPSVDVTAHIVEAFGKLGYSKDHPKIAHAIEYLKEEQEADGAWFGRWGVNYVYGT

GAVLPALEAIGEDMSQPYIRKAANWLVLHQNEDGGWGE
```

>seq_ID 253
```
SPVWDTVLTLLAFDDCDKNEAYQASVEKAVQWTLDNQVLRKGDWSVKLPDVEPGGWAFEYANT

FYPDTDDTAVALIVLSQFRDVEKWQEAGIEKAIERGVNWLFAMQSKNGGWGAFDKDNDNNFITKI

PFCDFGEALDPPSVDVTAHCIEAFGKLGLSRARPEIARGLDYLKSEQEADGAWFGRWGVNYVYG

TGAVLPALEAIGEDMSQPYIRKAANWLILRQNEDGGWGE
```

>seq_ID 257
```
SPVWDTXLTLLALDDCDLNERQSKEVEKAVQWVLNQQVLRPGDWCVKVPKVQPGGWAFEYKNY

FYPDTDDTAVALIVLSQFRDDPKWQEKNIEQAIDRGLNWLIGMQCKGGGWGAFDKDNDKTYLTKI

PFCDFGEALDSPSVDVTAHIVEAFGKLGLGKSHPAMIRAIDYLKAEQEQDGAWFGRWGVNYIYGT

GAVLPALEAIGEDMRAPYIAKACDWLIAVQQEDGGWGE
```

-continued

```
>seq_ID 254
SPVWDTLLTLLAYDDSGQNERKADEVEKAVDWVLAXQVLRPGDWKVKAPNLEPGGWAFEYANY
FYPDTDDTAVALIVLSQFRNDAAWKEKGIEQAIEKGVNWLFGMQCKGGGWGAFDKDNDKQFLTKI
PFCDFGEALDPPSVDVTAHIVEAFGKLKFSKDHPNIRRAIDYMKDEQEADGAWFGRWGVNYIYGT
GAVLPALEAIGEDMFAPCIGRACDWLVSRQNDDGGWGE >seq_ID 255
SPVWDTLLTLLAYDNSGHNARKASEVEKAVDWVLAQQVLRPGDWNVKAPNLEPGGWAFEYANY
FYPDTDDTAVALIVLSQFRNDAAWKDKGIEQAIEKGVNWLFGMQCKGGGWGAFDKDNDRQFLTKI
PFCDFGEALDPPSVDVTAHIVEAFGKLKFSKDHPNIRRAIDYTKDEQEDDGAWFGRWGVNYIYGT
GAVLLALEAIGEDMSAPYIGRACDWLVSRQNDDGGWGE >seq_ID 256
SPVWDTLLTLLAIEDSGQSVKRAQEVEKAVDWVLSQQVLRPGDWKVRAPHLEPGGWAFEYANYF
FPDTDDTAVALIVLSQFRNDAAWKAKGIETAIEKGVNWLLGMQCKGGGWGAFDKDNDKTYLTKIP
FCDFGEALDPPSVDVTAHIVEAFGKLGFSKDHPNIARAIEYLKSEQESDGXWFGRWGVNYVYGVG
AVLPALEAIGEDMSAPYIGRACDWLVSKQNSDGGWGE >seq_ID 258
SPVWDTVLTMLAIHDCGADKQYAPQMDKAIDWLLANEVRHKGDWAVKLPDVEPGGWAFEYSNA
CYPDLDDTAVALIVLAPYRNDPKWQARDIEGAVERAVDWTLAMQCKNGGWGAFGKDNDKAILTKI
PFCDFGEALDPPSVDVTAHVLEALAALGYDNSHPAVARAIRYLRDEQEPDGSWWGRWGVNYIYG
TAAVLPALKAMGVDMNEPFVHKAADWIGSVQNEDGGWGE >seq_ID 302
SPVWDTSLVLVAMQEAGVPVDHPALVKAAQWLLDREVRLKGDWRVKSPDLEPGGWAFEFLNDW
YPDVDDSGFVMLALKDIKVRDKKQKSQAIKRGIAWCLGMQSANGGWGAFDKDNTKYLLNKIPFAD
LEALIDPPTADLTGRMLELMGTFNYPKSHVAVVRALGFLKSVQEPEGPWWGRWGVNYIYGTWSV
LGGLDAIGEDMSQPYIRKAVNWLKSKQNLDGGWGEVCETYEDRSLMGCGPSTPSQTSWALLSLF
SAGEINAKAVLRGIKYLVETQNQDGSWDEDAYTGTGFP >seq_ID 271
SPVWDTAISVISLAXSGMERGHPALVRAAXWLMSKEIKTAGDWKVTNPAGPVGGWAFEFNNAFY
PDIDDSAMVMMALRHVHLDEHTAHRREKACLRGLNWLLSMQSRTGGWAAFDKDNTKVIMTKIPF
ADHNAMIDPPWADITGRVLEFLGYIGYDQSYPAVARAARFLREEQEEDGSWFGRWGVNYIYGTW
QVLRGLAAIDEDMSQPYIRRAAEWLRSVQPPDGGWGETCATYHDPSLKGKGPATPAQTAWAVM
GLMAAGIYDESVSRGIDYLVRTQRPDGTWDETEYTGTGFP >seq_ID 299
SPVWDTALVLVAMQEAGVPVDHPALIKSAQWLLDLEVRRKGDWHVKSPDLEPGGWAFESLNDW
YPDVDDSGFVMLFIKDIKVRDKKLKDQAIKCGIAWCLGMQSENGGWGAFDKDNTKHLLNKIPFADL
EALIDPPTADLTGRMLELMGNFNYPKSHQAAVKALDFLKVEQEPEGPWWGRWGVNYIYGTWSVL
CGLEAIGEDMSQPYIKKAVNWLKSKQNLDGGWGEVCDSYADRSLMGCGPSTASQTSWALLSLFA
AGEVSSKAALRGVEYLLSTQKLDGTWDEDAFTGTGFP >seq_ID 314
SPVWDTALAVRALAAAGVPPEHPAMVKASEWLLTQQIFKPGDWSIKCPDLPPGGWAFEFVNNWY
PDVDDSSMVLVALKDGLADAAKHQAALQRGINWCLGMQSKNGGFASFDKDNTKEWLNSLPFGDL
KALVDPPTEDITARILEMMGAFGHGLDHPVAARALAYLHQTQRPEGPWWGRWGVNYIYGTWSVL
VALKRIGEDMSRPYVRRAVDWVKAHQNPDGGWGEFCESYRNPELMGKGPSTASQTAWALLGLF
AAGEVHAPEVTAGVDYLVKTQDSLGRWDEEQFTGTGFP
```

```
                                                       >seq_ID 251
SPVWDTVLTMLSVQDCDADENSENAPAIEKAIEWLLANEVRTGGDWQEKVKGVEPGGWAFEYKN

ASYPDTDDTAVAMMALAPYRTEEKWKKKGLPEALKRAAEWNIAMQCSNGGWGAFDKDNDKTILC

KIPFCDFGEALDPPSVDVTAHVLEGLAALDYPPEHPAIQRAVQFIKDEQEPDGSWWGRWGVNFIY

GTAAALPALKAVGEDMRAPYIDRAAKWIVDHQNEDGGWGE

>seq_ID 312
SPVWDTALAVRALAAAGVPPEHPAMVQASEWLLTQQIFKPGDWSVKCPDLPPGGWAFEFVNNW

YPDVDDSSMVLVALKDGLADAAKHQAALQRGINWCLGMQSKNGGFASFDKDNTKEWLNAIPFGD

LKALVDPPTEDITARILEMMGAFGHGLDHPVAVRAMAYLHETQRPEGPWWGRWGVNYIYGTWSV

LVALKRIGEDMSRPYVRRAVDWVKAHQNLDGGWGECCESYRNPELMGRGPSTASQTAWALLGL

FASGEVHTPEVKAGVDYLVKTQNSLGRWDEEQFTGTGFP

>seq_ID 250
SPMWDTVLTTLAVQDAGVDQEPEFKPAMERTLEWLLKNEVRTGGDWQQKTRGVEPGGWAFEY

ANASYPDNDDTAVALIVLAPFRHDPKWQARGIQHVIDRAVNWMFAMQCDNGGWAAFDLDNDKAI

LTRIPFCDFGEALDPPSVDVTAHVLEALAALGYSREHPAVRRAIAFLKEDQEPDGSWFGRWGVNFI

YGTAAALPALKAMDEDMTQDWITRAADWMRSRQNDDGGWGE

>seq_ID 260
SPVWDTVLTLLAIQDADKQDDMAAEVDRAIGWLLSKEVRTNGDWSVKLPDVEPGGWAFEHENAR

YPDTDDTAVAVMVLAPYRHHPKWRKRGLPEALDRAISWMRAMQCRNGGWGAFDKDNDNAFLC

VIPFCDXGEALDPPSIDVTAHALEAFAAMGFGPEDTTVARALDYMSKEQEADGSWWGRWGVNYI

YGTAAALPAYKAFGQDMRDPKLMKAADYLRAKQNADGGWGE

>seq_ID 259
SPVWDTVLTLLAMEDCEATEEHAAAIEQAIEWLLENEVRTPGDWQMKVPDADPGGWAFEYANAA

YPDVDDTAVAILVLARYRDDPKWQAKGLPQAIDRAVAWVLAMQCSNGGWAAFDKDNDKSILCKIP

FCDFGEALDPATVDVTAHVLEALAAVGYGPDHPAVRRGLDFLYAEQEADGSWWGRWGVNYVYG

TGAALPAFKAIGADMRDPRMLKAADWILRCQNKDGGWGE

>seq_ID 261
SPVWDTVLTLLAIQDADKQEEMAGEIDKAIGWLLSKEVRTKGDWSVKLPRVEPGGWAFEHENARY

PDIDDTAVAIMVLAPYRDHPKWKKRGLPEALDRAIAWMRAMQCRGGGWGAFDKDNDKQILCTIPF

CDFGEALDPPSIDVTAYALEAFAAMGYGPDDKTVARALKYMSKEQEADGSWWGRWGVNYIYGTA

AALPAYKALGQDMRDPGLMKAADYLRDKQNADGGWGE

>seq_ID 262
SPVWDTVLTLLAMQDADRTDKHKAAVDKAIQWVLDQEVRTPGDWCVQTPDVEPGGWAFEYENA

RYPDVDDTAVAIMVLAPYQDDPKWRKRGLPDALARAIAWIRAMQCKNGGWGAFDRDNDNSMLT

VIPFCDFGEALDPPSVDVTAHALEAFHMMGYGPEDPTVARALAYLDAEQEQDGSWWGRWGVNFI

YGTSAALPALKAMGRDMRDPRYTKAADYLRAVQNDDGGWGE

>seq_ID 275
SPVWDTLLALLALQDCDRELTAEMSRALDWVLANEVRYHGDWTKKVKGVEPSGWAFERANLNY

PDIDDTAVALIVLARLPRAWLDEPRIRATIDRVLGWTLAMQSSNGGWAAFDKDNDRPIITKIPFCDF

GEALDPPSADVTAHVLEALGLLGFDRRHPAVERGLRFLRSEQEADGSWFGRWGVNYVYGTAAVL

PGLAAIGEDMTQDYIRRANDWLIAHQNPDGGWGE
```

```
                                                         >seq_ID 280
SPVWDTLLSLVALQDCGKELTPARERALEWILGREIRTRGDWAKKVKNVEASGWAFERANLHYPD

IDDTAVALIMLARLPRAWLDQPRIRAVIDRALGWTLAMQSSSGGWAAFDKDNDRLIITKIPFCDFGE

ALDPPSADVTAHVLEALGILGFDRQHAAVRHGLKFLRSEQEADGSWFGRWGVNHVYGTGAVLPA

LAAIGEDMAQDYVRRAADWLVAHQNADGGWGE
                                                         >seq_ID 277
SPVWDTLLALLAMQDCERELTPQMERALDWVLANEVRYYGDWSKKVRGVEPSGWAFERANLNY

PDIDDTVVALIVLARLPRALLDQPRIRAVIDRALGWTLAMQSSNGGWAAFDKDNDHLIITKIPFCGFG

EALDPPSADVTAHVLEALGLLGFDRHHPAVARGYQFLRKEQEADGSWFGRWGVNHIYGTAAVLP

ALAAIGEDMSQPYIRAAAEWIIAHQNADGGWGE
                                                         >seq_ID 300
SPVWDTALVLVAMQXAGVPVXHPALVKSAQWLLDLEVXXKGDWQVKSPELEPGGWAFXFLNDW

YPDVDDSGFVMLSIKXIKVRDKKHKEQAIKRGISWCLGMQSDNGGWAAFDKNNTKYLLNKIPFAXL

EALIDPPTAXLTGRMLELMGNFNYPKTHKAAVQALEFLXMEXEPXGPWWGRWGVNYIYGTWSVL

CGLEAIGEDMAQPYIKKSINWLKSKQNMDGGWGEVCESYGDRSLMGCGPSTASQTSWALLSLFA

AGEVHSKAATRGIEYLLATQKLDGTWDEDAYTGTGFP
                                                         >seq_ID 279
SPVWDTLLXLLAMQDCERESTPSMERALDWXXANEVRYYGDWSKKVRGVEPSGWAFXRANLNY

PDIDDTDVALIVLARLPRALLDQSRVHAVIDRALGWTLXMQSSNGGWAAFDKDNNHLIITKIPFCDF

XEALDPPSADVTAHVLEALGLLGFNRNHPAVERGYRFLRSEQETDGSWFGRWGVNHVYGTXAVL

PALAAIGEDMTQPYIRSAAEWIIAHQNADGGWGE
                                                         >seq_ID 264
SPVWDTLLTLEALLDCNLSPKTFTGMQAAVDWILSKQIVTPGDWQIKVPGVSCGGWAFERANTFY

PDMDDTAVAMIVLARIRRYYNDSSRIDRALACATDWILSMQCSNGGWAAFDLDNTNDLVTRIPFSD

FGEMLDPPSVDVTAHVVEALGCLGRTRNDPAVARAVAYILDEQEPEGSWFGRWGVNHIYGTGAV

LPALAAVGTDMSAGYITRAADWVATHQNADGGWGE
                                                         >seq_ID 19
GGWMFQASISPIWDTGLTVLALRSAGLPPDHPALIKAGEWLVSKQILKDGDWKVRRRKAKPGGW

AFEFHCENYPDVDDTAMVVLALNGIQLPDEGKRRDALTRGFRWLREMQSSNGGWGAYDVDNTR

QLTNRIPFCNFGEVIDPPSEDVTAHVLECFGSFGYDEAWKVIRKAVEYLKAQQRPDGSWFGRWG

VNYVYGIGAVVPGLKAVGVDMREPWVQKSLDWLVEHQNEDGGWGE
                                                         >seq_ID 278
SPVWDTLLSLLAMQDCERGFTPSMERALDWVLANEVRYYGDWSKKVRGVEPSGWAFERANLNY

PDIDDTAVALIVLARLPRAQLDQPRIREVIDRALGWTLAMQSSNGGWAAFDKDNDHLIITKIPFCDF

GEALDPPSADVAAHVLEALGLLGFERKHPAVERGLKFIRSEQEADGSWFGRWGVNHIYGTAAVLP

ALXAIGEDM
                                                         >seq_ID 315
SPVWDTALAVRALAAAGLPPDHPFMTQATSWLLTQQIFKPGDWCIKCPDLPPGGWAFXFHNNWY

PDVDDSSMVLVALKDGLPDTARHQAALQRGINWCLGMQSKNGGFASFDKDNTKEWLNALPFGDL

KALVDPPTEDITARILEMMGAFGHGLDHPTADRALAFLRRTQHPEGPWWGRWGVNYLYGTWSVL

VALKRIGXDMSRPYVQRAVNWIKSHQNPDGGWGEVCESYRHPELMGQGPSTASQTAWALLGLL

AAGEIQAAEVKAGVDYLVKTQNAQGRWDEKYFTGNWLP
                                                         >seq_ID 297
SPVWDTALVLQAMQEASIPLDHPALVKAAQWLLDREVRIKGDWKIKSPGLEPGGWAFEFQNDWY

PDVDDSAAVLIAIKDIQVKNNKAKQGAVRRGIDWCLGMQSKNGGWAFDKDNTKHLLNKIPFADL
```

EALIDPPTADLTGRMLELMGNFGYDKHHPQAVHALEFLKKEQEPEGPWFGRWGVNYIYGTWYVLI

GLEAIGEDMNQPYIKKAANWIKSRQNIDGGWGE

>seq_ID 17

QASISPVWDTGLAVLALRAAGLPADHDRLVKAGEWLLDRQITVPGDWVVKRPNLNPGGFALQFD

NVYYPDVDDTAVVIWALNTLRLPDERRRRDAMTKGFRWIVGMQSSNGGWGAYDVDNTSDLPNHI

PFCDFGEVTDPPSEDVTAHVLECFGSFGYDDAWKVIQRAVAYLKREQKPDGSWFGRWGVNYIYG

TGAVVSALKAVGIDMREPYIQKALDWVEQHQNPDG

>seq_ID 303

SPVWDTALVLVAMQEAGVPLDHPALVKAAQWLLDREVRIKGDWRIKSPDIEPGGWAFEFLNDWY

PDVDDSGFVMLAIKDVKVRDKKKKEQAIKRGINWCLGMQSANGGWGAFDKDNTKYLLNKIPFADL

EALIDPPTADLTGRMLELLGTFNFPKDHHAIERALEFIQLEQEPEGPWWGRWGVNYIYGTWSVISG

LEAIGEDMSQPYIRKTVNWLKSKQNMDGGWGE

>seq_ID 298

SPVWDTTLVLVAMQEAGVPVDHPALVKSAQWLLDLEVRRKGDWQVKSPDVEPGGWAFEFMND

WYPDVDDSGFVMLAIXNIRVRDKKHQEQAIKRGIAWCLEMQSENGGWGAFDKDNTKYLLNKIPFA

DLEALIDPPTADLTGRMLELMGNFDYSASYPAAVRALEFLKKEQEPEGPWWGRWGVNYIYGTWS

VLCGLEAIGEDMSQPYIRKAVNWLKSKQNLDGGWGE

>seq_ID 301

SPVWDTALALVAMQEAGVPKDHPALVKAAQWLLDLEVRRKGDWQIKSPELEPGGWAFEFLNDW

YPDVDDSGFVIMAIRDIKAPDKKHKEQAIKRGIAWCLGMQSKNGGWGAFDKDNTKHLLNKIPFADL

EALIDPPTADLTGRMLELMGSFDYPMDHPAAARALEFLKKEQEPEGPWWGRWGVNYIYGTWSVL

CGLESIGEDMSQPYIKKAVNWLKSKQNMDGGWGE

>seq_ID 276

SPVWDTLLTLLAMEDCDRGLTPSMQRALEWVLAQEVRYAGDWSKKVKGVEPSGWAFERANLNY

PDIDDTAVALIVLARLPRAWLDEPRIRATIDRVLGWTLAMQSSNGGWAAFDKDNDRPIITKIPFCDF

GEALDPPSADVTAHVLEALGLPGFDRRHPAVERGYKFLRSEQEADGSWFGRWGVNHIYGTAAVL

PALASIXEDM

>seq_ID 283

SPVWDTCLTSNALVESGGDTSAPHVHRSVQWLLNQEIRNHGDWSVKAPKVGPSGWAFEFANKV

YPDVDDAAEVIIALANYSNDSGTAPPDAIARGVRWISGMQSSNGGWGSFDKNNTSFFVTRLPFFD

FGEVIDPPSVDVTAHVIEALAVAGWQEKASKQIQKALDYIWSEQEADGPWFGRWGINYIYGTCAVL

SALEAIGYDMADARVVKALKWIEECQNADGGWGE

>seq_ID 307

SPVWDTPWMIEALLETGVPPGDPALLRAGRWLMSKQITGVRGDWAMKSPKGKPGGWAFEFEND

YYPDVDDTIQVLTALCKLSIPWREKEKAVMQGIDWLISMQNDDGGWGAFDRNQTRWIVNRIPFSD

HKACLDPSSPDITGRMVEFLMRRNYSTSHPSVKKALKYIRETQEDFGAWFARWGINYIYGTWCVL

TALAAMGIGHTDSRVAKAVAWLSSVQRPDGGFSEAADTYHPHKPFESYSESVPSQSAWALMGLV

AGGAVHSPAAARAACYLINNRNLNNGWDERHYTGTGFP

>seq_ID 267

SPVWDTAISVIALAESGLHRGHPSLVQATEWLVANEIRRGGDWQVKNPTAPISGWAFEFKNDFYP

DVDDTAMVLLALRHVHLYNDDVSQDREKSYLRGLNWMLSMQCKNGGWAAFDRDNVKTIFEKIPF

ADHNAMIDPPSVDITGRVLELLGYVGYDKSYPCVTKALEYIKKDQEADGSWYGRWGVNYIYGTWQ

VLRGLAAIGEDMQSEYVQKAVRWMKSVQNPDGGWGE

-continued

```
>seq_ID 309
SPVWDTVLSITALADADLPRTHPAMRRAVAWVLGKQVLCEGDWRVKNRRGEPGGWSFEFNNNF
YQDNDDTAAVLIALHKARLPDEAKGEAMQRGLRWLLSMQCDDGGWSAFDVNNNKRLLNKIPFAD
LESMLDPSTCDLTGRTLEALGSIGFPFTHRIVQHAVRFIRQHQEADGAWYGRWGVNYIYGTCHVL
CGLLSVGEDMHQPYVQRAVQWLIEHQNADGGWGE >seq_ID 202
MVYSYEMMVLLDYPEDHPLRVECKAALKKLVVHRDDGSSYCQPCLSPVWDTAWSVMALEQAPS
DARTETAIARAYDWLTDRQVLDLRGDWENNAAPSTPPGGWAFQYENPYYPDIDDSAVVLAMLHA
RGKRTGQPGRYEMPVARCLDWIIGLQSRNGGFGAFDANCDRDFLNAIPFADHGALLDPPTEDVS
GRVLLALGITERPQDATARERCIQYLRDTQQPDGSWWGRWGTNYIYGTWSVLAGLGLAGVDRKL
PMVRNGLQWLRGKQNADGGWGETNDSYARPELAGKHEDGSMAEQTAWAMLGQMAVGEGDAD
SVHRGAAYLLDAQNEDGFWMHPYHNAPGFPRIFHLKYHG >seq_ID 306
SPVWDTPWTVMALLEAGVPSNDPALLRSGRWLLAKQITDTKGDWAIKNKNTAPGGWSFEFENKY
FPDVDDTIEVLHCLHKLAIPWREKEKPCRLGIDWLLSMQNDDGGWGAFDKNQKRQVVNRIPFSDH
GACLDPSSPDITGRMIEFLATQKFNSEYESVKRALKYIWKTQEDFGGWHARWGINYIYGTWCVLT
GLRAIGFNMTDRRVQKALNWLESIQNKDGGFGESPASYEECRYIPWKESVPSQTAWALMALVAG
GGAGSAPAENAATFLINYRNSNGVWDEECYTGTGFP >seq_ID 281
SPVWDTLLTLLAYQDCELEMNDSAGRALDWILSQENSYRGDWAHRNKKLEPSGWAFERANLHYP
DIDDTSVALIVLARLPQAVRSRPDIKSAIDRALAWTLGMQCRNGGWAAFDRDNDKLIITMIPFCDFS
EALDPPSADVTAHVVEAMAHLGFDRSHKAVEKAYQYLLAEQEDDGSWFGRWGVNHIYGTAAVLP
ALAALGEDATVPHVKRAADWISAHQNTDGGWGE >seq_ID 310
SPVWDTALAVRALAAAGLPPEHPAMVKASEWLLTQQIFKPGDWSVKCPDLPPGGWAFEFVNNW
YPDVDDSSMVLVALKEGLADAAKHQAALQRGINWCLGMQSKNGGFASFDKDNTKEWLNAIPFGD
LKALVDPPTEDITARILEMMGAFGHGLDHPVAVRGLAYLHQTQRPEGPWWGRWGVNYIYGTWSV
LVALKRIGEDMSRPYVRRAVDWVKAHQNPDGGWGE >seq_ID 311
SPVWDTALAVRALAAAGLPPEHPAMVKASEWLLTQQIFKPGDWSVKCPDLPPGGWAFEFVNNW
YPDVDDSSMVLVALKDGLVDAAKHQAALQRGINWCLGMQSKNGGFASFDKDNTKEWLNAIPFGD
LKALVDPPTEDITARILEMMGAFGHGLDHPVAVRALAYLHQTQRPEGPWWGRWGVNYIYGTWSV
LVALKRIGEDMNRPYVRRAVDWVKAHQNLDGGWGE >seq_ID 290
SPIWDTAKAVNALHESGLPSDHPQLKAAARWLVEKEVRKPGDWKMRVPHVDVGGWPFQFRNEF
YPDVDDTAAVVMALGRVDERDVPGIKDSITRGINWVTQMQCSCGGWAAFDVDVKREFLTKVPYA
DHNAMLDPPCPDITGRCLEMYGRFPGVRKDADVQRVIEKGIEYLKKTQEPDGSWYGRWGVNYIY
GTWQSLKGLAAVGEDPSQPYIQKAAHFLKTHQNSDGGWGE >seq_ID 292
SPVWDTAKAVNALHESGLPSDHPQLKAAARWLVEKEVRKPGDWKMRVPHVDVGGWPFQFRNE
FYPDVDDTAAVVMALGRVDERDVPGIKDSITRGINWVTQMQCSCGGWAAFDVDVKREFLTKVPY
ADHNAMLDPPCPDITGRCLEMYGRFPEVRKDANVQNVIAKGIEYLKKTQEPDGSWYGRWGVNYI
YGTWQSLKGLAAVGEDPSQPYIQKAAHFLKTHQNSDGGWGE
```

```
                                                              >seq_ID 293
SPVWDTCLSLAALTEAGAQNDHPAVKQAVEWLLDHQIFVEGDWCAQASGLEPGGWAFQYENDK

YPDVDDTGMVLMSLLRAGVHDKEHKRKRVNQALNWVLGMQNPDGSWGAFDIENNYEYLNKIPFA

DHGALVDPGTADLTARCVELLAMLGYDATFPPVKRALEFLEHDQEEDGSWYGRWGVNYIYGTWS

VLCALGAIGEDVAKPYVRKSVQWLQDTQNEDGGWGE

>seq_ID 313
SPIWDTALAVRALTAAGMPPEHPAMVKASEWLLTQQIFKPGDWSVKCPDLPPGGWAFEFVNNWY

PDVDDSSMVLVALKEGLADTAKHQAALQRGINWCLGMQSKNGGFASFDKDNTKEWLNAIPFGDL

KALVDPPTEDITARILEMMGAFGHGLDHPVAVRALAYLHETQRPGGPWWGRWGVNYLYGTWSVL

VALKRIGEDMSRPYVRRAVDWVKDHQNLDGGWGE

>seq_ID 304
SPVWDTPWMVMALLEAGVPTDXPGLLRAGRWLISKQITGVHGDWAVKNRHALPGGWSFEFEND

YFPDVDDTIEVLHVIHRLAIPWEEKSECCRLGLDWLLSMQNDDGGWGAFDRNQTLVMVNRIPFSD

HAACLDPSSPDIVGRVLEFLASRSFSREHPAVKRALDYIWREQSPFGGWWARWGIDYLYGTWCV

LTGLRAIGWDMEDPRVRKAVAWLESVARPDGGYGESPESYRDHSYVEWKRSVPSQTAWALMGL

VAGGVGHGKAARGAADYLLTSRNAQGGWDEMDYTGTGFP

>seq_ID 291
SPMWDTAKAVNALHESGLPSDHPQLKAAARWLVEKEVQKPGDWKMRVPYVDVGGWPFQFRNE

FYPDVDDTAAVVMALGRVDERDVPGIKDSITRGINWVTQMQCSCGGWAAFDVDVKREFLTKVPY

ADHNAMLDPPCPDITGRCLEMYGRFPEVRKDVDVQRVIEKGIEYLKKTQEPDGSWYGRWGVNYI

YGTWQSLKGLAAVGEDPSQPYIQKAAHFLKTHQNSDGGWGE

>seq_ID 318
SPVWDTGLALHALLESGMDPDDPAIAKAMHWLDEREITDVAGDWAEQRPGLAPGGWAFQYRND

HYPDVDDTAVVGMAMHRANPQARPETLERTRAWIEGMQSQNGGWGAFDADNTHYHLNHIPFAD

HGAMLDPPTADVSARCLGMLSQMGYDRDHPSIQRAIAYLKNDQEEDGSWFGRWGTNYIYGTWS

VLSALNAAGEDMSQPYIRKAVDYLTNFQREDGGWGE

>seq_ID 294
SPVWDTCLSLAALTEAGAQNDHPAVKQAVEWLLDHQIFVEGDWCDQAPGLEPGGWAFQYENNK

YPDVDDTGMVLMSLLRAGVHDKEHKRKRVNQALNWVLGMQNPDGSWGAFDIENNYEYLNRIPFA

DHGALVDPGTADLTARCVELLAMLGYDATFPPVKRALEFLEQDQEEDGSWYGRWGVNYIYGTWS

VLCALGATGEDVAKPYVRKSVQWLQDTQNEDGGWGE

>seq_ID 320
SPVWDTCLGLHALLEAGEPREAPSVKKAVDWLLEREITETYGDWVWRRPHLKPSGWAFQYWNN

YYPDVDDTAVVVMALDRVGDPRCRPAIERACEWIIGMQSTSGGWGSFDPENEFTYLNHIPFADHG

ALLDPPTVDVTARCISMLAQVGYRHDHPAIRKSVXFILREQEKDGSWYGRWGTNYVYGTWSALSA

LNAVGEDMSSPVVRKGVAWLEAFQQPDGGWGE

>seq_ID 295
SPVWDTCLSLTAMTESGAHPEHPAVKQAVEWLLDQQIFVKGDWADQAKNLEPGGWAFQFENDR

CPDVDDTGMVLMALLRAGVQDKEHKIKRINQAVNWVLGMQNPDGSWGAFDIGNDHEYLNNIPFA

DHGALVDPGTADLTARCVELLAMLGYPDFPPIQRAVAFLERDQEEFGAWYGRWGVNYIYGTWS

VLSAIGILGEDYAKPYVRKAVEWLKEIQNDDGGWGE
```

```
                                                              >seq_ID 324
SPVWDTSLAAHALLEAGEPNDPEVIGLLDWLKDKQILTTVGDWSARRPNLRPGGWAFQYENPHY

PDVDDTAVVAMAMHRQGDPKYAEAIARACEWLAGMQSSSGGWGAFDPENEHFYLNSIPFADHG

ALLDPPTVDVTARCVGCLAQVDAERFASEIQAGIDYIKREQEEDGSWFGRWGANYVYGTWSALV

ALNKAGEDMNTPYIRRAVDWLKARQRPDGGWGE
                                                              >seq_ID 296
SPVWDTCLSLNALTEADMPANDPRVRAAVQWLFDRQIFVRGDWSENAPELEPGGWAFQYENDK

YPDVDDTGMVLMSLLRANAHEHDAQRKRMNQALNWVLGMQNSDGSWGAFDIDNHYTYLNNIPF

ADHGALVDPGTADLTGRCIELFGMLGYDKNFTPARRGIEFLKRDQHPCGGWYGRWGVNYLYGT

WSVLTALGAIGEARDAPYLRRAVEWLYSVQNDDGGWGE
                                                              >seq_ID 305
SPVWDTPWMVMALLEAGCPANDPXLIRAGRWLKAKXITEVRGDWAVKNRKALPGGWSFEFEND

YFPDVDDTIEVLSVIHRLSIPWNEKAKSCRLGLEWXLSMXNRDGGWGAFDREQXFKVVNRIPFSD

HAACLDPSSPDITGRMVEFLASXNFSKGHVAVRRALDYIWKQQAXFGGWWARWGIDYLYGTWC

VLTGLASLGFXMDDPRARKAADWLESIQHADGGFGESPESYREDSFVDWKRSVPSQTAWALMG

LVAAGRASGAAAQRAAAWLLDNRNTNGSWDEQDYTGTGFP
                                                              >seq_ID 282
SPMWDTSLAAHALMEADGRGDPKDNPRLISAMDWLADKQILDHVGDWAVRRPDVRPGGWAFQY

ENPDYPDVDDTAVVVMAMHRADPERYEMSIDRACEWLVGMQSKNGGWGAFEPENEHYYLNSIP

FADHGALLDPPTVDVTARCVGALAQVDRDRYAAEIANGIRSIRREQEDDGSWFGRWGANYVYGT

WSALVALKGAGEDMQQPYIRRAVDWLKARQRSDGGWGE
                                                              >seq_ID 316
SPVWDTAWAVIGLCESGMERTHPAVRSAIRWLYSMQILRPGDWAVKNPLTEPGGWAFEFHNDFY

PDNDDTAAVLMGLLFSDLNDEENHRAFERGVRWLLSMQNNDSGWGAFERNVDNKIFDQIPFNDQ

KNMLDPSTADVTGRVVELLGRIGRRLGGSFSDEPYVRQAIEFLKNEQEPEGCWFGRWGVNYIYG

TWSVLVALEAIGESMRAPYIRKAVNWVKKVQNPDGGWGE
                                                              >seq_ID 266
SPIWDTGIVLHSLVESGVSPDHEALLRSVSWLLAKEVTHEGDWKVKCPDAPVGGWYFEYANEFN

PDCDDTAKVLMATSRFSSVDFPDAGRLRDARNRGLQWLLHMQNKDGGWAAFDKGCDNELLTYI

PFADHNAMIDPSTEDITGRVLETLAREGFDNTHPVVKRAIQYLHKTQDAEGPWYGRWGSNFIYGT

WLVLQGLKAVGEDMTXPRYQRAANWLLNVQNXNGSWGE
                                                              >seq_ID 323
SPMWDTSLAAHAFLESGDREDPRLIRALDWLVDKQILDHVGDWAVRRPGLRPGGWAFQYENPD

YPDVDDTAVVAMAMHRTDPERYAENIDRACEWLAGMQSKNGGWGAFDPENEHYYLNSIPFADH

GALLDPPTVDVTARCIGCLAQVDAEAFADNIKRGIGFIKREQEPDGSWFGRWGANYIYGTWSALV

ALKGAGEDMSQPYIRKSVAWLKGRQGPDGGWGE
                                                              >seq_ID 274
SPVWDTILSMQALLDTKEVFQPSPTLKKAMEWLLEQQVRAWGDWKVYVSDARGGGWAFQRANS

FYPDVDDTIMVMMALRNVSPRGESKVVDEAIERALFWVLGMQCEDGGWAAFDRDNAKAFLTKVP

FADHNAMIDPSTADLTSRTFEMFAMIAPEVFTIHHPVVRRGLEFLKKDQCKDGSWFGRWGVNYMY

GTWQVLRGLRLIGEDMSKGYVRKGVEWFKSVQLEDGGWGE
```

```
>seq_ID 284
SPVWDTVAQLHALIASGLARRDEALRRAASWLLTRQSRTHGDWSGRNPAEPGGFYFEFRNEFYP
DVDDTAMALMVLTQAEANVATDVQHAAIARALAWMLGMQNRDGGWAAFDRDNDKHFLTQVPFA
DHNAMIDPSTADITGRVLGALSHVPSYGPDHPSVRRAIAFLQRDQEPDGSWYGRWGVNYLYGTG
QVLRGLRAIGFDMQQPFVRRAARFLSAHQNDDGGWGE >seq_ID 285
SPVWDTAITIIALAESGLPKNHPAFEQAATWLEKKEIRFKGDWAVRMPGVEPSGWAFEHENKYYP
DTDDTMMVLMALRHVQSRNSAERCEQFDRALKWLLAFQCQDGGWAAFDKDVTASWLEHVPFAD
HNAILDPTCSDLTARVLELLGSISFDRQSAIVRRAVAMMRRTQETDGSWYGRWGVNYIYGTWQAL
RGLAAIGENMDQEWIRRGRDWLESCQNDDGGWGE >seq_ID 308
SPVWDTAIAGYALGESGCAPQSALRRMADWLLTKEVRRKDDWSVKRPDVEPSGWYFEFANEFY
PDTDDTAMVLLSLLHGRATNPAAQEACAKRAVNWLLAMQSKDGGWAAFDVDNDWKPLSYVPFA
DHNAMLDPSCPDITGRVLEALCKYGVSQEHPAVLRAIDYLIQTQEQDGSWHGRWGVNYVYGTFL
ALRGLKAAGVSDREAYVLRAGEWLDLIQNPDGGWGE >seq_ID 288
SPVWDTAITAVSLAESGLEPDHPALQKSAEWLLDKEVRIQGDWAIKNRHGEASGWAFEFNNEFYP
DVDDTLKVLLALRLIKTRDEETKREAMERALGWVMSFQCSDGGWAAFDKDVTQRWLEDVPFADH
NAILDPTCSDITARCLELLGKMGCTSDHPAVRRALRMVRETQEPDGTWWGRWGVNYIYGTWQIL
RGLSALKIDMNQDWIVRAKEWLESCQNPDGGWGE >seq_ID 287
SPVWDTAITSVALTSSGVKPDHPQIQKAADWLLDREVVMRGDWKVKNPYPHASGWAFEFNNDFY
PDADDTFKVLLALMKMKSSDPERQRKIMDRALDWARSFQCKDGGFAAFDKDVTKKWLEHVPFAD
HNAILDPSCSDITARGLECMGKLGWPRTDRVIRRAIRYLKKTQEEDGSWWGRWGVNYIYGTWQS
LRGLEAIGEDMNQDWVVRARNWLESCQNPDGGWGE >seq_ID 289
SPIWDTAIVTMAIAESGQDPNDPRLQKAADWLLEREIGFRGDWRENCDFPEATGWAFEFNNDWY
PDVDDTFQVILGLKPLSASDSRRQEQTLDRAIRWCRAMQCREGGFAAFDKDINDAWLNEVPFADH
NAILDPPCSDITGRALETLSLMGFDREDPVVRRARQYLMETQLEDGSWFGRWGVNYIYGTGHALR
GLHAIGEDINGSAMQRARNWLENCQNDDGGWGE >seq_ID 286
SPVWDTAINVISLAESGLLSDHPALQKAADWLVNKEVRFRGDWSVNNSYPQVSGWAFEYNNVYY
PDTDDTAMVLMALRLIRPKDPQALNELFRRALDWQLSFQCRDGGWAAFDKNVTTPWLEDMPFAD
HNAILDPTCSDLTARTLELLGYTGFDPKAQSVRDALQYLIDTQDEDGSWYGRWGVNYIYGTWQVL
RGLRAMGQDMTQDWILRGRDWLESCQNSDGGWGE >seq_ID 270
SPVWDTALAMSALLEGDTAPDDEALQRGCRWLLGKEVRHRGDWQVNVGAEPGGWFFEYENEF
YPDCDDTAEVLAVLERVRLSDPEEDQRRRDALDRALAWQLGMQSTNGGWGAFDKDCDHRILELV
PFADHNAMIDPPTVDVTSRSIEAALAMGVPASDAAIRRAVRFLYSEQEADGSWYGRWGSNYLYGT
WLALCALRSAGEDLTSPAVQRAVEWLLSVQQEDGGWGE >seq_ID 322
SPVWDTGIAAHALGEAGHASAMQSTADWLLTKEVRRKGDWSVKRPDVEPSGWYFEFANEFYPDI
DDTAQVLLGLAHAKASDPAKQKACMDRAVAWLLAMQGSDGGWAAFDVDNNWEFLSSVPFADHN
AMLDPTCPDITGRVLEALAACGVPNSHPAVKRGVEFLRNSVEKDGSWYGRWGVNYIYGTYLALR
GLRASGEDDREAHILRAGEWLRAIQNADGGWGE
```

```
                                                         >seq_ID 263
SPVWDTSLILNALLAGSEKTETDPKILKAGQWLLDREVREIGDWKIKNNRGPVGGWYFEYANEFYP

DCDDTAEVITVLNQMQFSDPEKEKAKQVAQQRGLDWLLSMQNKDGGWPAFDKNCDKQSLTYMP

FADHNAMIDPSYEDITGRTLEALASLGFSEDDPIVRRAVDFLKSKQLPDGTWYGRWGCNFLYGTW

LAISGLYHAGEDLNEERYQSLLSWLEQCQNEDGGWGE

>seq_ID 268
SPVWDTCLILNSMLEHLEPDHPRVQKAAEWLLSKEVTEPGDWQVKCPEAPVGGWYFEYANEFYP

DCDDTAEVLAALQRVQFTDADREAQKRGAIQRGLGWLLAMQNQDGGXAAFDRECTREALTYVPF

ADHNAMIDPSNGDITGRVLKALDYAGYSPDDPIVRGGVDFLLANQEPDGTWYGRWGCNHLYGSW

LVVWGLKHAGVNLQQTQFTQVMSWLESCQNADGGWGE

>seq_ID 265
SPVWDTTNAMTAVLDAGLPGNHPAVLRAARWLLSKEVRMPGDWRLWYKNGEPGGWFFEYNNE

FYPDADDTAEALHCLCRVVFDCEDEMDRCRAAIKRGLNWQFACQNPDGGWPAFDKECDDEYLT

FIPFADHNAMIDPSCCDITGRSLQALSKLGYTTNDVDVKRAIDYLLDAQEDDGTWYGRWGINYIYG

TWLAVQGLRAIGVDLSEKRFQKVTKWLRKKQNPDGGWGE

>seq_ID 269
SPVWDTCLILNSLLEHLEPDHPRLQHAAEWLLSKEVTEPGDWQVKCPEAPIGGWYFEYANEFYPD

CDDTAEVLAALQRVRFSDADREAQKHAAIERGLGWLLAMQNGDGGWAAFDRECTREALTYVPFA

DHNAMIDPSNGDITGRVLKALDYSGRSPQDPVVQGGVHFLLANQEPDGTWYGRWGCNHLYGSW

LAIWGLKHAGVDSQQSQFMRLLSWLESCQNPDGGWGE

>seq_ID 319
SPVWDTSLSAHALMEAGLEENDKRLEGLLDWLKDLQILDVKGDWVARRPDVRPGGWAFQYRND

HYPDVDDTAVVAMAMHRQGDEKYKEAIDRAAEWIVGMQSSSGGWGAFDPENEHFYLNSIPFADH

GALLDPPTEDVTARCVGFLAQLDPDAYAEPIKRGVEFLKRTQQEDGSWWGRWGANFVYGTWSV

LCALNAAGEDPKSPYIQKAVAWLKSRQREDGGWGE

>seq_ID 321
SPVWDTGIACQALQEVGGPAADAGVQRALDWLVERQLRDEPGDWRRDRPDLEGGGWAFQYNN

PHYPDLDDTSMVAWVMQVADHGRYREEIRRAAKWVVGMRSEGGGFASFEVDNTYYYLNHIPFA

DHGXLLDPPTXDVTARCIAVLAITDRAQHETVIREAIDFLFVDQEEDGSWFGRWGTDYIYGTWSVL

SXLDVVGFDMRDARVRXSVEWLFXQQNPDGGWGE

>seq_ID 272
SPVWDTGLVALALQEVDKHNSQDALQRNLKQAYSWLLSKQLKDEPGDWRISKPTLTGGGWAFQF

NNPHYPDVDDTAVVAFALAQAEHTELDESIHLATRWIEGMQSQNGGYGAFDVDNTFYYLNEIPFA

DHGALLDPPTADVSARCAMLMARVAKDHEEYLPALERTIQYLRSEQEADGSWFGRWGTNYVYGT

WSVLLGLEQTNVPKTDPLFTKAAQWLKSVQRPDGGWGE

>seq_ID 273
SPVWDTGLVALALPEVDKHNSQDALQPNLKQAYSWLLSKQLKDQPGDWRISKPTLTGGGWAFQF

NNPHYPDVHDTAVLAFALAQAEHTELDESIHLATRWIEGMQSQNGGYGAFDVDNTFYYLNEIPFA

DHGALLDPPTADVSARCAMLMARVAKGHEEYLPALERTIQYLRSEQEADGSWFGRWGTNYVYGT

WSVLLGLEQTNVPKTDPLFTKAAQWLKSVQRPDGGWGE

>seq_ID 317
SPVWDTILGMIGLVDCGHDGKDPLLVTARDWIVKRQLLVNYGDWKVYNPNGPSGGWSFEYDNS

WYPDVDDTAAIVIGFLKQDYEFRHSEVVKRACDWIASMQNQXGGWAAFDINNDKTFLNEIPFSDM

ESLCDPSSPDVVGRVLEAFGILNDPKYAEVCRRGIEYLRRTQESEGSWFGRWGVNYVYGTSNVL

CSLKRQDVAXKDPMVTRALTWLKKVQNKDGGWGE
```

```
>seq_ID 215
MGRQTRNLTRREPAAEAEERGFRLLDAHRRADSSWVGELSSSALATAMSALALRLLGHPAESGP

VAGGLAWLAATRNPDGGWGDAPGEPSNMNATSIAAAALARCAPRRYREEVAGGRRWVEEHGG

FAALNDPRTTTLSGPGRTLWALAGLVPPERVRKLPTEMILLPRRIRRTVSTTFPAFLSLSLLHERFR

PSPRWRRPLRRRAEREALAWLRRAQGPNGSYEESAFLTSLIAAALTAAGAEGGDIVRRALPFVLR

SRRPDGSWPIDRDLENFDTTQAILAHHEAGRPLREAGRVREWLLDNQFRRPFFPTSSPPGGWAW

AYPAGWPDTDDTACALRSLRLLGVPAGHPSIRLGLRWLYRMQNRDGSWPTFVRGSRMPFDHGC

PYITSQVLSALALMGPEARRGAPLRRALAYLRRAQRPDGSLGSLWFRPHTRGTAAAVEAFSDLGL

SGDPLVGRAARWLAEHQNPDGGWGDGHGAPSTAEETAWASAALLRLGGGEAARKGVRWLVEH

QDPGGWKPAVIGLYYASLSYSDTFYALSYPLVALARHRRLSR
                                                                >seq_ID 191
MIKKILVLILLMVVVTSKVDIERVQTVIRDAREICWNELTDNEWVYPTYLGTLFLSEYYFELKALGIQN

SQFEESKFTQILLGSQLPDGSWVQVEDAYIQTGQLDATIFNYWYLKAVGIDIHTDTMKKAQEWIKA

NGGIEKAQTMTKFKLAMFGQYPWKKLFKIPLILFYKKFNPLYIKDITAQWVYPHMTALAYLQNQRIIF

NVAVSISELYKNKAPKIKNHQKKGRPSFFINNLVQEMLKLRQPMGSFGGYTVSTLLSMLALNDYTG

RTNKHKSEISDALKKGLDFVEFNYFNFRQAYHGSLDDGRWWDTILISWAMLESGEDKEKVRPIVE

NMLQKGVQPNGGIEYGYDFGYAPDADDTGLLLQVLSYYGTDYADAMDKGAEFVYSVQNTDGGFP

AFDKGKMGKNPLYKYAFKIAGIADSAEIFDPSSPDVTAHILEGLISSDRSNYDVVVKSLKYFMDTQE

NFGSWEGRWGINYIYAAGAVLPALKKMNNGWAKAVNWLVSKQNADGGFGETTLSYRDPKKYNGI

GVSTVTQTSWGLLGLLAVEDHYDVKEAIEKARDGEFKDISVVGTGHRGLLYLQYPSYARSFPVISL

GRFLDQQR
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10717973B2). An electronic copy of the "Sequence Listing" will also be available from the USPTO upon request and payment of the fee set forth in 37 CFR 1.19(b)(3).

The invention claimed is:

1. A method of production of isopulegol of general formula (I)

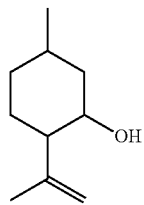

(I)

comprising cyclizing citronellal of general formula (II)

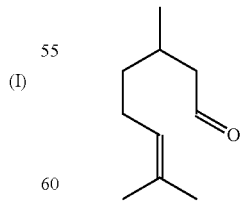

(II)

to isopulegol of formula (I) by means of an enzyme mutant with cyclase activity which is a mutant of a wild-type enzyme comprising the amino acid sequence of SEQ ID NO: 209 with a mutation at a position corresponding to position F445 of the amino acid sequence of SEQ ID NO: 209, wherein up to 10% of the amino acid residues in said enzyme mutant are altered relative to SEQ ID NO: 209 by deletion, insertion, substitution, addition, inversion, or a combination thereof, and wherein said enzyme mutant catalyzes at least the cyclization of a citronellal isomer to at least one isopulegol isomer, or in the presence of a microorganism expressing said enzyme mutant.

2. A method for enzymatic or biocatalytic cyclization or conversion of compounds of general formula IV

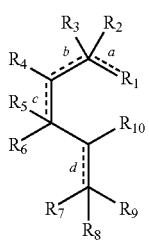

(IV)

in which

"a", "b", "c" and "d", in each case independently of one another, represent a single or double C—C bond, with the proviso that cumulative double bonds are excluded; and with the following provisos:

$R_1$ is defined as:
(1) when "a" is a double bond:
$R_1$ is selected from the group consisting of:
oxo (=O), and
CH—(CH$_2$)$_n$—Z,
in which n is 0, 1 or 2 and
Z is OH, CHO; C(O)C$_1$-C$_4$-alkyl; COOH, C(CH$_2$)—CH=CH$_2$;
C(OH)(CH$_3$)—CH=CH$_2$; C(CH$_3$)=CH—CH=CH$_2$; or a radical of the formula C(CH$_3$)=CH—CH$_2$Y
in which
Y is OH, CH$_2$OH, COOH, or CH$_2$C(O)CH$_3$; or
(2) when "a" is a single bond:
$R_1$ is selected from the group consisting of:
CH$_3$; CHO; CH$_2$CH$_2$OH; CH=CH$_2$; CH$_2$C(O)OH; CH$_2$CHO; and
C$_3$H$_6$CH(CH$_3$)CHO;
and, when "a" is a double bond, it has E or Z configuration;

$R_2$ and $R_3$ are defined as:
(1) when "a" and "b" are each a single bond:
$R_2$ and $R_3$ independently of one another are H, C$_1$-C$_4$-alkyl, or OH, or $R_2$ and $R_3$ together are a methylene (=CH$_2$) or oxo (=O) group; or
(2) when "a" or "b" is a double bond, one of the radicals $R_2$ and $R_3$ is absent and the other of the two radicals is H, C$_1$-C$_4$-alkyl, or OH;

$R_4$ is H or hydroxy-C$_1$-C$_4$-alkyl;

$R_5$ and $R_6$ are defined as:
(1) when "c" is a single bond:
$R_5$ and $R_6$ are each H, or $R_5$ and $R_6$ together are an oxo (=O) group; or
(2) when "c" is a double bond, one of the radicals $R_5$ and $R_6$ is absent and the other of the two radicals is H;

$R_7$, $R_8$, and $R_9$ are defined as:
(1) when "d" is a single bond:
two of the radicals $R_7$, $R_8$ and $R_9$ in each case independently of one another are H or C$_1$-C$_4$-alkyl, and the other of the radicals is OH; or
(2) when "d" is a double bond, one of the radicals $R_7$, $R_8$ and $R_9$ is absent and the other of the two radicals in each case independently of one another are H or C$_1$-C$_4$-alkyl;

$R_{10}$ is H or hydroxy-C$_1$-C$_6$-alkyl or mono- or polyunsaturated C$_2$-C$_6$-alkenyl;

comprising reacting a compound of the formula IV in stereoisomerically pure form, or a stereoisomer mixture thereof:

a) using an enzyme mutant with cyclase activity which is a mutant of a wild-type enzyme comprising the amino acid sequence of SEQ ID NO: 209 with a mutation at a position corresponding to position F445 of the amino acid sequence of SEQ ID NO: 209, wherein up to 10% of the amino acid residues in said enzyme mutant are altered relative to SEQ ID NO: 209 by deletion, insertion, substitution, addition, inversion, or a combination thereof; or b) in the presence of a microorganism expressing said enzyme mutant,
wherein the microorganism comprises:
i) at least one nucleic acid sequence coding for said enzyme mutant;
ii) at least one expression cassette comprising said at least one nucleic acid sequence; or
iii) at least one vector comprising, under the control of at least one regulatory element, said at least one nucleic acid sequence or said at least one expression cassette.

3. The method of claim 2, comprising converting a compound selected from the group consisting of:
a) compounds of formula IVa

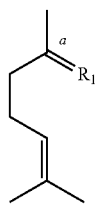

(IVa)

in which $R_1$
i) is defined as:
(1) when "a" is a double bond:
$R_1$ is selected from
oxo (=O), or
CH—(CH$_2$)$_n$—Z,
in which n is 0, 1 or 2 and
Z is OH, CHO, C(O)C$_1$-C$_4$-alkyl; COOH, C(CH$_2$)—CH=CH$_2$;
C(OH)(CH$_3$)—CH=CH$_2$; C(CH$_3$)=CH—CH=CH$_2$; or a radical of the formula C(CH$_3$)=CH—CH$_2$Y
in which
Y is OH, CH$_2$OH, COOH, or CH$_2$C(O)CH$_3$; or
(2) when "a" is a single bond:
$R_1$ is selected from
CH$_3$; CHO; CH$_2$CH$_2$OH; CH=CH$_2$; CH$_2$C(O)OH; CH$_2$CHO or C$_3$H$_6$CH(CH$_3$)CHO;

and, when "a" is a double bond, it has E or Z configuration; or
ii) is a radical of the formula
CH—(CH$_2$)$_n$—Z
in which
n=0 and Z=CHO or COOH;
n=1 and Z=OH; or
n=2 and Z=C(O)CH$_3$; COOH, C(CH$_2$)—CH═CH$_2$; C(CH$_3$)═CH—CH═CH$_2$;
iii) is a radical of the formula C(CH$_3$)═CH—CH$_2$Y
in which Y is OH, CH$_2$OH, COOH, or CH$_2$C(O)CH$_3$;
and "a" optionally has E or Z configuration;
b) compounds of formula IVb

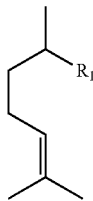

(IVb)

in which R$_1$ is defined as above or is CH$_2$CHO; and
c) compounds of formula IVc

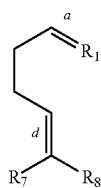

(IVc)

in which
R$_1$ is defined as above, or is CH—CHO; and one of the radicals R$_7$ and R$_8$ is H and the other is C$_1$-C$_4$-alkyl, or wherein R$_7$ is ethyl and the double bonds "a" and "d" have Z configuration.

4. The method of claim 2, in which the compound of formula IV is selected from citronellal, citral, farnesol, homofarnesol, homofarnesol derivatives, homofarnesylic acid, geranylacetone, melonal, nonadienal, and trimethyldecatetraene.

5. The method of claim 2 for the cyclization of terpenes and/or terpenoids, and for the conversion of compounds of the general formula IV, comprising utilizing:
(a) said enzyme mutant;
(b) a nucleic acid coding for said enzyme mutant;
(c) an expression construct comprising said nucleic acid;
(d) a recombinant vector comprising, under the control of at least one regulatory element, at least one of the nucleic acid of (b) or at least one of the expression construct of (c); or
(e) a recombinant microorganism comprising the nucleic acid of (b), the expression construct of (c), or the recombinant vector of (d).

6. The method of claim 5 for the conversion of citronellal to isopulegol, or for the conversion of squalene to hopene.

7. The method of claim 1, wherein up to 5% of the amino acid residues in said enzyme mutant are altered relative to SEQ ID NO: 209 by deletion, insertion, substitution, addition, inversion, or a combination thereof.

8. The method of claim 1, wherein said mutation at the position corresponding to position F445 of the amino acid sequence of SEQ ID NO: 209 is a substitution selected from the group consisting of F445N, F445Q, F445L, F445M, F445E, F445G, F445S, F445V, F445T, F445C, F445I and F445A.

9. The method of claim 1, wherein said enzyme mutant is a single mutant comprising F445X, with X=N, Q, L, M, E, G, S, V, T, C, 1, or A, of the amino acid sequence of SEQ ID NO: 209.

10. The method of claim 2, wherein up to 5% of the amino acid residues in said enzyme mutant are altered relative to SEQ ID NO: 209 by deletion, insertion, substitution, addition, inversion, or a combination thereof.

11. The method of claim 2, wherein said mutation at the position corresponding to position F445 of the amino acid sequence of SEQ ID NO: 209 is a substitution selected from the group consisting of F445N, F445Q, F445L, F445M, F445E, F445G, F445S, F445V, F445T, F445C, F445I and F445A.

12. The method of claim 2, wherein said enzyme mutant is a single mutant comprising F445X, with X=N, Q, L, M, E, G, S, V, T, C, 1, or A, of the amino acid sequence of SEQ ID NO: 209.

* * * * *